(12) United States Patent
Chen et al.

(10) Patent No.: US 9,138,436 B2
(45) Date of Patent: Sep. 22, 2015

(54) INHIBITORS OF BRUTON'S TYROSINE KINASE

(75) Inventors: Wei Chen, Fremont, CA (US); David J. Loury, San Jose, CA (US); Tarak D. Mody, Sunnyvale, CA (US); Longcheng Wang, Palo Alto, CA (US)

(73) Assignee: PHARMACYCLICS LLC, Sunnyvale, CA (US)

( * ) Notice: Subject to any disclaimer, the term of this patent is extended or adjusted under 35 U.S.C. 154(b) by 169 days.

(21) Appl. No.: 13/549,267

(22) Filed: Jul. 13, 2012

(65) Prior Publication Data

US 2013/0018032 A1 Jan. 17, 2013

Related U.S. Application Data

(60) Provisional application No. 61/507,482, filed on Jul. 13, 2011.

(51) Int. Cl.
*C07D 487/04* (2006.01)
*A61K 31/519* (2006.01)
*A61K 31/52* (2006.01)
*C07D 473/34* (2006.01)

(52) U.S. Cl.
CPC .............. *A61K 31/52* (2013.01); *C07D 473/34* (2013.01); *C07D 487/04* (2013.01)

(58) Field of Classification Search
CPC ........................... A61K 31/519; C07D 487/04
USPC ........................................ 544/262; 514/262.1
See application file for complete search history.

(56) References Cited

U.S. PATENT DOCUMENTS

| 6,326,469 | B1 | 12/2001 | Ullrich et al. |
| 7,711,492 | B2 | 5/2010 | Staudt et al. |
| 2008/0214501 | A1 | 9/2008 | Pan et al. |
| 2011/0086866 | A1 | 4/2011 | Chen et al. |
| 2012/0053189 | A1* | 3/2012 | Loury ........................ 514/262.1 |

FOREIGN PATENT DOCUMENTS

| EP | 2201840 | 6/2010 |
| WO | WO2001/019829 | 3/2001 |
| WO | WO-2008121742 A2 | 10/2008 |
| WO | WO-2011055215 A2 | 5/2011 |

OTHER PUBLICATIONS

Arnold et al., Pyrrolo[2,3-d]pyrimidines containing an Extended 5-substituent as Potent and Selective Inhibitors of lck I, Bioorganic & Medicinal Chemistry Letters, 10:2167-2170 (2000).

Burchat et al., Pyrazolo[3,4-d]pyrimidines Containing an Extended 3-Substituent as Potent Inhibitors of Lck—a selectivity Insight, Bioorganic & Medicinal Chemistry Letters 12: 1687-1690 (2002).
Compagno et al., (2009), Nature 459:712-721.
Davis et al., (2001), Journal of Experimental Medicine 194:1861-1874.
Davis et al., Chronic active B-cell receptor signalling in diffuse large B-cell lymphoma, Nature, 463:88-92 (Jan. 7, 2010).
Horning et al., The natural history of initially untreated low-grade non-Hodgkin's lymphomas, (1984) N. Engl. J. Med. 311:1471-1475.
Klein et al., Germinal centres:role in B-cell physiology and malignancy., (2008), Nature Reviews Immunology 8:22-23.
Kuzmic et al. (2000), High-throughput screening of enzyme inhibitors: simultaneous determination of tight-binding inhibition constants and enzyme concentration, Anal. Biochem. 286:45-50.
Lentz et al., (2008), Oncogenic CARD11 mutations in human diffuse large B cell lymphoma, Science 319:1676-1679.
Marcotte et al, Structures of human Bruton's tyrosine kinase in active and inactive conformations suggest a mechanism of activation for TEC family kinases., Protein Science. 2010, 19:429-439.
Nandakumar et al. Collagen type II-specific monoclonal antibody-induced arthritis in mice: description of the disease and the influence of age, sex, and genes, (2003), Am. J. Pathol 163:1827-1837.
National Cancer Institute sponsored study of classifications of non-Hodgkin's lymphomas: summary and description of a working formulation for clinical usage. The Non-Hodgkin's Lymphoma Pathologic Classification Project., The Non-Hodgkin's Lymphoma Pathologic Classification Project, Cancer 49(1982):2112-2135.
Nisitani et al., In situ detection of activated Bruton's tyrosine kinase in the Ig signaling complex by phosphopeptide-specific monoclonal antibodies., (1999), PNAS USA 96:2221-2226.
Pagel et al., Induction of apoptosis using inhibitors of lysophosphatidic acid acyltransferase-beta and anti-CD20 monoclonal antibodies for treatment of human non-Hodgkin's lymphomas, (2005), Clin Cancer Res 11(13) 4857-4866.
Pan et al., Discovery of Selective Irreversible Inhibitors for Bruton's Tyrosine Kinase, ChemMedChem. 2007, 2:58-61.
PCT/US/2012/046779 International Search Report and Written Opinion dated Mar. 28, 2013.
Srinivasan et al., PI3 kinase signals BCR-dependent mature B cell survival, (2009), Cell 139:573-586.
Garske et al. Chemical genetic strategy for targeting protein kinases based on covalent complementarity. PNAS USA 108(37):15046-15052 (2011).

\* cited by examiner

*Primary Examiner* — Susanna Moore
(74) *Attorney, Agent, or Firm* — Wilson Sonsini Goodrich & Rosati

(57) ABSTRACT

Described herein are kinase inhibitor compounds, methods for synthesizing such inhibitors, and methods for using such inhibitors in the treatment of diseases. Further described herein are methods, assays and systems for determining an appropriate inhibitor of a protein, including a kinase.

6 Claims, No Drawings

INHIBITORS OF BRUTON'S TYROSINE KINASE

RELATED APPLICATIONS

The present application claims the benefit of priority from U.S. Provisional Patent Application No. 61/507,482 filed Jul. 13, 2011, which is herein incorporated by reference in its entirety.

FIELD OF THE INVENTION

Described herein are kinase inhibitor compounds, methods for synthesizing such inhibitors, and methods for using such inhibitors in the treatment of diseases.

BACKGROUND OF THE INVENTION

A kinase, alternatively known as a phosphotransferase, is a type of enzyme that transfers phosphate groups from high-energy donor molecules, such as ATP, to specific target molecules; the process is termed phosphorylation. Protein kinases, which act on and modify the activity of specific proteins, are used to transmit signals and control complex processes in cells. Up to 518 different kinases have been identified in humans. Their enormous diversity and role in signaling makes them attractive targets for drug discovery.

SUMMARY OF THE INVENTION

Described herein are inhibitors of Bruton's tyrosine kinase (Btk). Also described herein are methods for synthesizing such inhibitors, methods for using such inhibitors in the treatment of diseases (including diseases wherein inhibition of Btk provides therapeutic benefit to a patient having the disease). Further described are pharmaceutical formulations that include an inhibitor of Btk.

In one aspect, provided herein are compounds of Formula (I) having the structure:

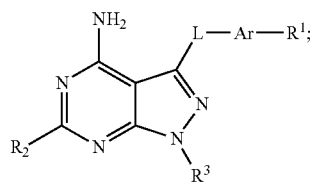

Formula (I)

wherein:
  $R^1$ is L-Ar², OR$^b$, or NR$^b$R$^b$;
  L is each independently CR$^a$R$^a$, O, S, NR$^b$, N—OR$^b$, C=O, C=S, C=N—R$^b$, or C=N—OR$^b$;
  $R^a$ is each independently H, $C_1$-$C_6$ alkyl, $C_1$-$C_6$ heteroalkyl, halogen, OR$^b$, or NR$^b$R$^b$;
  $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
  $R^1$ is L-Ar², OR$^b$, or NR$^b$R$^b$;
  $R^2$ is H, OR$^b$, NR$^b$R$^b$, halogen, $C_1$-$C_6$ alkyl, $C_1$-$C_6$ heteroalkyl, $C_3$-$C_6$ cycloalkyl, or $C_2$-$C_6$ heterocycloalkyl;
  $R^3$ is optionally substituted alkyl, —(C=O)$C_1$-$C_6$ alkyl, —(C=O)OR$^b$, —(C=O)NR$^b$R$^b$, —(C=O)SR$^b$, optionally substituted cycloalkyl, optionally substituted heterocycloalkyl, optionally substituted aryl, or optionally substituted heteroaryl;
  Ar and Ar² are each independently $C_5$-$C_{12}$ aryl or heteroaryl optionally substituted with halogen, OR$^b$, NR$^b$R$^b$, $C_1$-$C_6$ alkyl, $C_1$-$C_6$ heteroalkyl, $C_3$-$C_6$ cycloalkyl, or $C_2$-$C_6$ heterocycloalkyl;
  or a pharmaceutically acceptable salt, solvate, N-oxide, or prodrug thereof.

In one aspect, provided herein are compounds of Formula (II) having the structure:

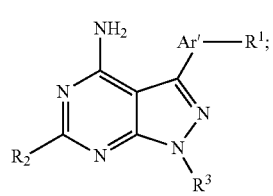

Formula (II)

wherein:
  $R^1$ is L-Ar²;
  L is each independently CR$^a$R$^a$, O, S, NR$^b$, N—OR$^b$, C=O, C=S, C=N—R$^b$, or C=N—OR$^b$;
  $R^2$ is H, OR$^b$, NR$^b$R$^b$, halogen, $C_1$-$C_6$ alkyl, $C_1$-$C_6$ heteroalkyl, $C_3$-$C_6$ cycloalkyl, or $C_2$-$C_6$ heterocycloalkyl;
  $R^3$ is optionally substituted alkyl, —(C=O)$C_1$-$C_6$ alkyl, —(C=O)OR$^b$, —(C=O)NR$^b$R$^b$, —(C=O)SR$^b$, optionally substituted cycloalkyl, optionally substituted heterocycloalkyl, optionally substituted aryl, or optionally substituted heteroaryl;
  $R^a$ is each independently H, $C_1$-$C_6$ alkyl, $C_1$-$C_6$ heteroalkyl, halogen, OR$^b$, or NR$^b$R$^b$;
  $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
  Ar' is selected from furan, thiophene, oxazole, isoxazole, oxadiazole, thiazole, isothiazole, thiadiazole, imidazole, triazole, pyrazole, thiodiazole, tetrazole, pyridine, pyrimidine, and pyrazine;
  Ar² is $C_5$-$C_{12}$ aryl or heteroaryl optionally substituted with halogen, OR$^b$, NR$^b$R$^b$, $C_1$-$C_6$ alkyl, $C_1$-$C_6$ heteroalkyl, $C_3$-$C_6$ cycloalkyl or $C_2$-$C_6$ heterocycloalkyl; or a pharmaceutically acceptable salt, solvate, N-oxide, or prodrug thereof.

In one aspect, provided herein are compounds of Formula (III) having the structure:

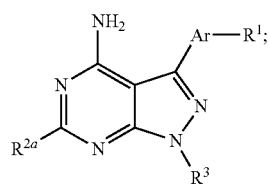

Formula (III)

wherein:
  $R^1$ is L-Ar²;
  L is CR$^a$R$^a$, O, S, NR$^b$, N—OR$^b$, C=O, C=S, C=N—R$^b$, or C=N—OR$^b$;
  $R^a$ is each independently H, $C_1$-$C_6$ alkyl, $C_1$-$C_6$ heteroalkyl, halogen, OR$^b$, or NR$^b$R$^b$;
  $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
  $R^{2a}$ is OR$^b$, NR$^b$R$^b$, halogen, $C_1$-$C_6$ alkyl, $C_1$-$C_6$ heteroalkyl, $C_3$-$C_6$ cycloalkyl, or $C_2$-$C_6$ heterocycloalkyl;
  $R^3$ is optionally substituted alkyl, —(C=O)$C_1$-$C_6$ alkyl, —(C=O)OR$^b$, —(C=O)NR$^b$R$^b$, —(C=O)SR$^b$, optionally substituted cycloalkyl, optionally substituted heterocycloalkyl, optionally substituted aryl, or optionally substituted heteroaryl;

Ar and $Ar^2$ are each independently $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl; or a pharmaceutically acceptable salt, solvate, N-oxide, or prodrug thereof.

In one aspect, provided herein are compounds of Formula (IV) having the structure:

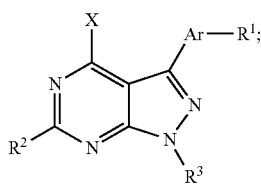

Formula (IV)

wherein:

X is hydrogen, hydroxy, alkoxy, thiol, halogen or $C_1$-$C_6$ alkyl;

$R^1$ is L-$Ar^2$;

L is $CR^aR^a$, O, S, $NR^b$, N—$OR^b$, C=O, C=S, C=N—$R^b$, or C=N—$OR^b$;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;

$R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl;

$R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl;

Ar and $Ar^2$ is each independently $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl;

or a pharmaceutically acceptable salt, solvate, N-oxide, or prodrug thereof.

In one aspect, provided herein are compounds of Formula (V) having the structure:

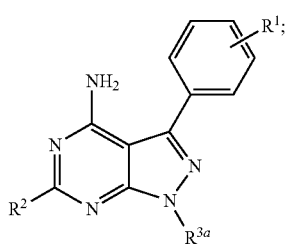

Formula (V)

wherein:

$R^1$ is L-$Ar^2$;

L is $CR^aR^a$, O, S, $NR^b$, N—$OR^b$, C=O, C=S, C=N—$R^b$, or C=N—$OR^b$;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;

$R^2$ is H, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;

$R^{3a}$ is selected from

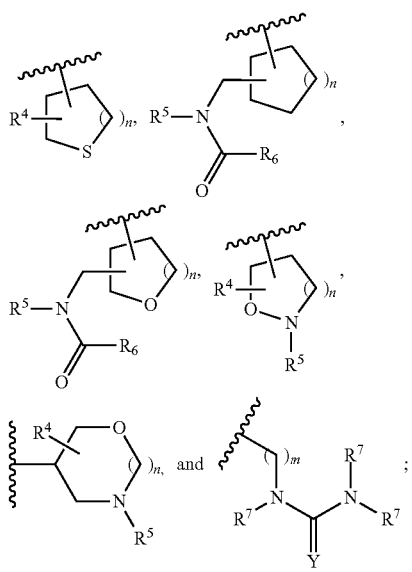

$R^4$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group;

$R^5$ is H, optionally substituted $C_1$-$C_6$ alkyl, —(C=O)$C_1$-$C_6$ alkyl, —(C=O)$OR^b$, —(C=O)$NR^bR^b$, —(C=O)$SR^b$, cycloalkyl, heterocycloalkyl, aryl, or heteroaryl;

$R^6$ is optionally substituted $C_1$-$C_6$ alkyl or $NR^S$;

$R^7$ is each independently hydrogen, optionally substituted $C_1$-$C_6$ alkyl, optionally substituted cycloalkyl, optionally substituted heterocycloalkyl, optionally substituted aryl, or optionally substituted heteroaryl;

$Ar^2$ is $C_5$-$C_{12}$ aryl or heteroaryl optionally substituted with halogen, hydroxy, amine, or $C_1$-$C_6$ alkyl;

n is an integer from 0 to 3;

m is an integer from 0 to 6;

Y is O, S or $NR^b$;

or a pharmaceutically acceptable salt, solvate, N-oxide, or prodrug thereof.

In one aspect, provided herein are compounds of Formula (VI) having the structure:

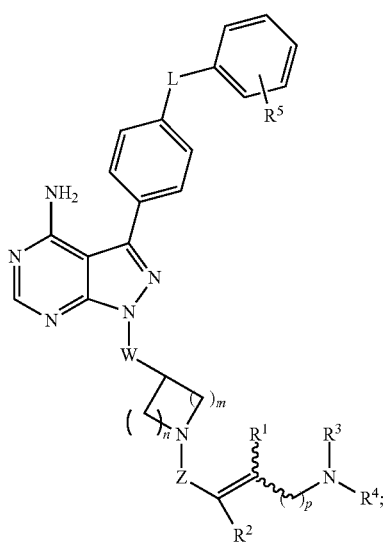

Formula (VI)

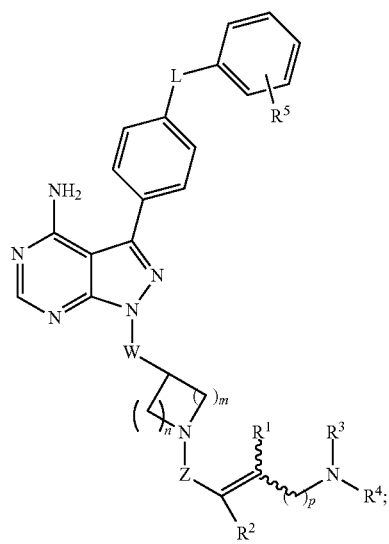

Formula (VIA)

wherein:

L is $CR^aR^a$, O, S, $NR^b$, N—$OR^b$, C=O, C=S, C=N—$R^b$ or C=N—$OR^b$;

W is a bond or optionally substituted $C_1$-$C_3$ alkyl;

Z is C=O, $SO_2$ or SO;

$R^1$ and $R^2$ are each independently H or $C_1$-$C_3$ alkyl, wherein $R^1$ and $R^2$ have a cis or trans relationship; or $R^1$ and $R^2$ join together to form a bond;

n and p are each independently an integer from 0 to 3;

m is an integer from 1 to 3;

$R^3$ is H, substituted or unsubstituted $C_1$-$C_3$ alkyl, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^5$ is H, OH, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;

or a pharmaceutically acceptable salt, solvate, N-oxide, or prodrug thereof.

In one aspect, provided herein are compounds of Formula (VIA) having the structure:

wherein:

L is $CR^aR^a$, O, S, $NR^b$, N—$OR^b$, C=O, C=S, C=N—$R^b$ or C=N—$OR^b$;

W is a bond or optionally substituted $C_1$-$C_3$ alkyl;

Z is C=O, $SO_2$ or SO;

$R^1$ and $R^2$ are each independently H or $C_1$-$C_3$ alkyl, wherein $R^1$ and $R^2$ have a cis or trans relationship; or $R^1$ and $R^2$ join together to form a bond;

n and p are each independently an integer from 0 to 3;

m is an integer from 1 to 3;

$R^3$ is H, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^5$ is H, OH, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl or $C_2$-$C_6$ heterocycloalkyl;

or a pharmaceutically acceptable salt, solvate, N-oxide, or prodrug thereof.

In one aspect, provided herein are compounds of Formula (VII) having the structure:

Formula (VII)

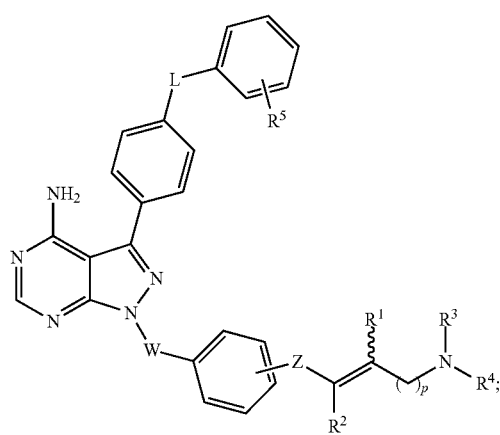

wherein:

L is $CR^aR^a$, O, S, $NR^b$, N—$OR^b$, C=O, C=S, C=N—$R^b$ or C=N—$OR^b$;

W is a bond or optionally substituted $C_1$-$C_3$ alkyl;

Z is $NR^cC$=O, $SO_2$ or SO;

$R^1$ and $R^2$ are each independently H or $C_1$-$C_3$ alkyl, wherein $R^1$ and $R^2$ have a cis or trans relationship; or $R^1$ and $R^2$ join together to form a bond;

p is an integer from 0 to 3;

$R^3$ is H, substituted or unsubstituted $C_1$-$C_3$ alkyl, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^5$ is H, OH, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl or $C_2$-$C_6$ heterocycloalkyl;

$R^c$ is H or $C_1$-$C_6$ alkyl;

or a pharmaceutically acceptable salt, solvate, N-oxide, or prodrug thereof.

In one aspect, provided herein are compounds of Formula (VIII) having the structure:

Formula (VIII)

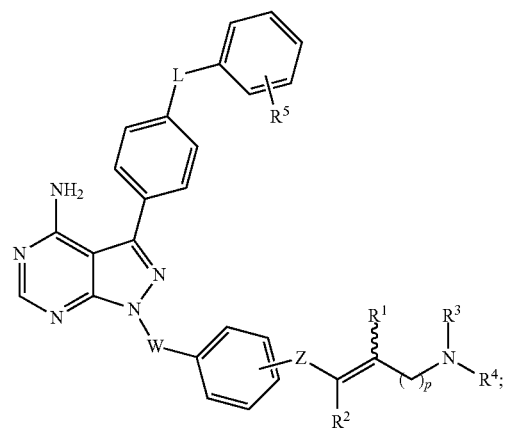

wherein:

L is $CR^aR^a$, O, S, $NR^b$, N—$OR^b$, C=O, C=S, C=N—$R^b$ or C=N—$OR^b$;

W is a bond or optionally substituted $C_1$-$C_3$ alkyl;

Z is $NR^cC$=O, $SO_2$ or SO;

$R^1$ and $R^2$ are each independently H or $C_1$-$C_3$ alkyl, wherein $R^1$ and $R^2$ have a cis or trans relationship; or $R^1$ and $R^2$ join together to form a bond;

p is an integer from 0 to 3;

$R^3$ is H, substituted or unsubstituted $C_1$-$C_3$ alkyl, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^5$ is H, OH, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl or $C_2$-$C_6$ heterocycloalkyl;

$R^c$ is H or $C_1$-$C_6$ alkyl;

or a pharmaceutically acceptable salt, solvate, N-oxide, or prodrug thereof.

In one aspect, provided herein are compounds of Formula (IX) having the structure:

Formula (IX)

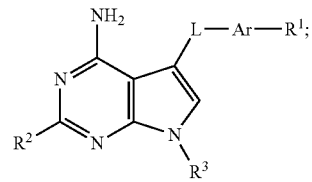

wherein:

L is each independently $CR^aR^a$, O, S, $NR^b$, N—$OR^b$, C=O, C=S, C=N—$R^b$, or C=N—$OR^b$;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;

$R^1$ is L-$Ar^2$, $OR^b$, or $NR^bR^b$;

$R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl;

$R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl;

Ar and $Ar^2$ are each independently $C_5$-$C_{12}$ aryl or $C_5$-$C_{11}$ heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl; or a pharmaceutically acceptable salt, solvate, N-oxide, or prodrug thereof.

In one aspect, provided herein are compounds of Formula (X) having the structure:

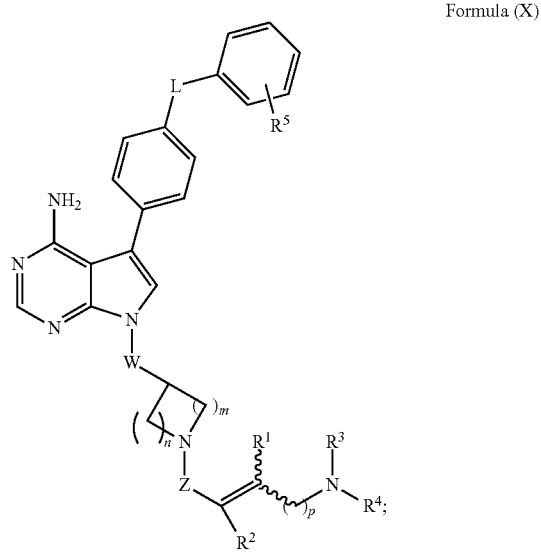

Formula (X)

wherein:

L is $CR^aR^a$, O, S, $NR^b$, N—$OR^b$, C=O, C=S, C=N—$R^b$ or C=N—$OR^b$;

W is a bond or optionally substituted $C_1$-$C_3$ alkyl;

Z is C=O, $SO_2$ or SO;

$R^1$ and $R^2$ are each independently H or $C_1$-$C_3$ alkyl, wherein $R^1$ and $R^2$ have a cis or trans relationship; or $R^1$ and $R^2$ join together to form a bond;

n and p are each independently an integer from 0 to 3;

m is an integer from 1 to 3;

$R^3$ is H, substituted or unsubstituted $C_1$-$C_3$ alkyl, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^5$ is H, OH, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl or $C_2$-$C_6$ heterocycloalkyl;

or a pharmaceutically acceptable salt, solvate, N-oxide, or prodrug thereof.

In one aspect is a pharmaceutical composition comprising a compound having the structure of Formula (I), (IA), (II), (III), (IV), (V), (VI), (VIA), (VIB), (VII), (VIII), (IX), (X), (XI), (XII), (XIII), or (XIV), or a pharmaceutically acceptable salt or solvate thereof; and a pharmaceutically acceptable excipient, binder or carrier. In another aspect is a pharmaceutical composition comprising a compound having the structure of Formula (VI) or a pharmaceutically acceptable salt or solvate thereof; and a pharmaceutically acceptable excipient, binder or carrier.

In certain embodiments, provided herein is a pharmaceutical composition containing: i) a physiologically acceptable carrier, diluent, and/or excipient; and ii) one or more compounds provided herein.

Other objects, features and advantages of the methods and compositions described herein will become apparent from the following detailed description. It should be understood, however, that the detailed description and the specific examples, while indicating specific embodiments, are given by way of illustration only. The section headings used herein are for organizational purposes only and are not to be construed as limiting the subject matter described.

DETAILED DESCRIPTION OF THE INVENTION

The methods described herein include administering to a subject in need a composition containing a therapeutically effective amount of one or more Btk inhibitor compounds described herein. Without being bound by theory, the diverse roles played by Btk signaling in various hematopoietic cell functions, e.g., B-cell receptor activation, suggests that small molecule Btk inhibitors are useful for reducing the risk of or treating a variety of diseases affected by or affecting many cell types of the hematopoetic lineage including, e.g., autoimmune diseases, heteroimmune conditions or diseases, inflammatory diseases, cancer (e.g., B-cell proliferative disorders), and thromboembolic disorders. Further, the Btk inhibitor compounds described herein can be used to inhibit a small subset of other tyrosine kinases that share homology with Btk by having a cysteine residue (including a Cys 481 residue) that can form a covalent bond with the inhibitor. Thus, a subset of tyrosine kinases other than Btk are also expected to be useful as therapeutic targets in a number of health conditions.

In some embodiments, the methods described herein can be used to treat an autoimmune disease, which includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

In some embodiments, the methods described herein can be used to treat heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In further embodiments, the methods described herein can be used to treat an inflammatory disease, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In yet other embodiments, the methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In further embodiments, the methods described herein can be used to treat thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Hematological Malignancies

Disclosed herein, in certain embodiments, is a method for treating a hematological malignancy in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

In some embodiments, the hematological malignancy is a chronic lymphocytic leukemia (CLL), small lymphocytic lymphoma (SLL), high risk CLL, or a non-CLL/SLL lymphoma. In some embodiments, the hematological malignancy is follicular lymphoma, diffuse large B-cell lymphoma (DLBCL), mantle cell lymphoma, Waldenstrom's macroglobulinemia, multiple myeloma, marginal zone lymphoma, Burkitt's lymphoma, non-Burkitt high grade B cell lymphoma, or extranodal marginal zone B cell lymphoma. In some embodiments, the hematological malignancy is acute or chronic myelogenous (or myeloid) leukemia, myelodysplastic syndrome, or acute lymphoblastic leukemia. In some embodiments, the hematological malignancy is relapsed or refractory diffuse large B-cell lymphoma (DLBCL), relapsed or refractory mantle cell lymphoma, relapsed or refractory follicular lymphoma, relapsed or refractory CLL; relapsed or refractory SLL; relapsed or refractory multiple myeloma. In some embodiments, the hematological malignancy is a hematological malignancy that is classified as high-risk. In some embodiments, the hematological malignancy is high risk CLL or high risk SLL.

B-cell lymphoproliferative disorders (BCLDs) are neoplasms of the blood and encompass, inter alia, non-Hodgkin lymphoma, multiple myeloma, and leukemia. BCLDs can originate either in the lymphatic tissues (as in the case of lymphoma) or in the bone marrow (as in the case of leukemia and myeloma), and they all are involved with the uncontrolled growth of lymphocytes or white blood cells. There are many subtypes of BCLD, e.g., chronic lymphocytic leukemia (CLL) and non-Hodgkin lymphoma (NHL). The disease course and treatment of BCLD is dependent on the BCLD subtype; however, even within each subtype the clinical presentation, morphologic appearance, and response to therapy is heterogeneous.

Malignant lymphomas are neoplastic transformations of cells that reside predominantly within lymphoid tissues. Two groups of malignant lymphomas are Hodgkin's lymphoma and non-Hodgkin's lymphoma (NHL). Both types of lymphomas infiltrate reticuloendothelial tissues. However, they differ in the neoplastic cell of origin, site of disease, presence of systemic symptoms, and response to treatment (Freedman et al., "Non-Hodgkin's Lymphomas" Chapter 134, Cancer Medicine, (an approved publication of the American Cancer Society, B.C. Decker Inc., Hamilton, Ontario, 2003).

Non-Hodgkin's Lymphomas

Disclosed herein, in certain embodiments, is a method for treating a non-Hodgkin's lymphoma in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

Further disclosed herein, in certain embodiments, is a method for treating relapsed or refractory non-Hodgkin's lymphoma in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV). In some embodiments, the non-Hodgkin's lymphoma is relapsed or refractory diffuse large B-cell lymphoma (DLBCL), relapsed or refractory mantle cell lymphoma, or relapsed or refractory follicular lymphoma.

Non-Hodgkin lymphomas (NHL) are a diverse group of malignancies that are predominately of B-cell origin. NHL may develop in any organs associated with lymphatic system such as spleen, lymph nodes or tonsils and can occur at any age. NHL is often marked by enlarged lymph nodes, fever, and weight loss. NHL is classified as either B-cell or T-cell NHL. Lymphomas related to lymphoproliferative disorders following bone marrow or stem cell transplantation are usually B-cell NHL. In the Working Formulation classification scheme, NHL has been divided into low-, intermediate-, and high-grade categories by virtue of their natural histories (see "The Non-Hodgkin's Lymphoma Pathologic Classification Project," Cancer 49 (1982):2112-2135). The low-grade lymphomas are indolent, with a median survival of 5 to 10 years (Horning and Rosenberg (1984) N. Engl. J. Med. 311:1471-1475). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

A non-limiting list of the B-cell NHL includes Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lympoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma. Additional non-Hodgkin's lymphomas are contemplated within the scope of the present invention and apparent to those of ordinary skill in the art.

DLBCL

Disclosed herein, in certain embodiments, is a method for treating a DLCBL in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

As used herein, the term "Diffuse large B-cell lymphoma (DLBCL)" refers to a neoplasm of the germinal center B lymphocytes with a diffuse growth pattern and a high-intermediate proliferation index. DLBCLs represent approximately 30% of all lymphomas and may present with several morphological variants including the centroblastic, immunoblastic, T-cell/histiocyte rich, anaplastic and plasmoblastic subtypes. Genetic tests have shown that there are different subtypes of DLBCL. These subtypes seem to have different outlooks (prognoses) and responses to treatment. DLBCL can affect any age group but occurs mostly in older people (the average age is mid-60s).

Disclosed herein, in certain embodiments, is a method for treating diffuse large B-cell lymphoma, activated B cell-like subtype (ABC-DLBCL), in an individual in need thereof, comprising: administering to the individual an irreversible Btk inhibitor in an amount from 300 mg/day up to, and including, 1000 mg/day. The ABC subtype of diffuse large B-cell lymphoma (ABC-DLBCL) is thought to arise from post germinal center B cells that are arrested during plasmatic differentiation. The ABC subtype of DLBCL (ABC-DLBCL) accounts for approximately 30% total DLBCL diagnoses. It is considered the least curable of the DLBCL molecular subtypes and, as such, patients diagnosed with the ABC-DLBCL typically display significantly reduced survival rates compared with individuals with other types of DLCBL. ABC-DLBCL is most commonly associated with chromosomal translocations deregulating the germinal center master regulator BCL6 and with mutations inactivating the PRDM1 gene, which encodes a transcriptional repressor required for plasma cell differentiation.

A particularly relevant signaling pathway in the pathogenesis of ABC-DLBCL is the one mediated by the nuclear factor (NF)-κB transcription complex. The NF-κB family comprises 5 members (p50, p52, p65, c-rel and RelB) that form homo- and heterodimers and function as transcriptional factors to mediate a variety of proliferation, apoptosis, inflammatory and immune responses and are critical for normal B-cell development and survival. NF-κB is widely used by eukaryotic cells as a regulator of genes that control cell proliferation and cell survival. As such, many different types of human tumors have misregulated NF-κB: that is, NF-κB is constitutively active. Active NF-κB turns on the expression of genes that keep the cell proliferating and protect the cell from conditions that would otherwise cause it to die via apoptosis.

The dependence of ABC DLBCLs on NF-kB depends on a signaling pathway upstream of IkB kinase comprised of CARD11, BCL10 and MALT1 (the CBM complex). Interference with the CBM pathway extinguishes NF-kB signaling in ABC DLBCL cells and induces apoptosis. The molecular basis for constitutive activity of the NF-kB pathway is a subject of current investigation but some somatic alterations to the genome of ABC DLBCLs clearly invoke this pathway. For example, somatic mutations of the coiled-coil domain of CARD11 in DLBCL render this signaling scaffold protein able to spontaneously nucleate protein-protein interaction with MALT1 and BCL10, causing IKK activity and NF-kB activation. Constitutive activity of the B cell receptor signaling pathway has been implicated in the activation of NF-kB in ABC DLBCLs with wild type CARD11, and this is associated with mutations within the cytoplasmic tails of the B cell receptor subunits CD79A and CD79B. Oncogenic activating mutations in the signaling adapter MYD88 activate NF-kB and synergize with B cell receptor signaling in sustaining the survival of ABC DLBCL cells. In addition, inactivating mutations in a negative regulator of the NF-kB pathway, A20, occur almost exclusively in ABC DLBCL.

Indeed, genetic alterations affecting multiple components of the NF-κB signaling pathway have been recently identified in more than 50% of ABC-DLBCL patients, where these lesions promote constitutive NF-κB activation, thereby contributing to lymphoma growth. These include mutations of CARD11 (~10% of the cases), a lymphocyte-specific cytoplasmic scaffolding protein that—together with MALT1 and BCL10—forms the BCR signalosome, which relays signals from antigen receptors to the downstream mediators of NF-κB activation. An even larger fraction of cases (~30%) carry biallelic genetic lesions inactivating the negative NF-κB regulator A20. Further, high levels of expression of NF-κB target genes have been observed in ABC-DLBCL tumor samples. See, e.g., U. Klein et al., (2008), *Nature Reviews Immunology* 8:22-23; R. E. Davis et al., (2001), *Journal of Experimental Medicine* 194:1861-1874; G. Lentz et al., (2008), *Science* 319:1676-1679; M. Compagno et al., (2009), Nature 459:712-721; and L. Srinivasan et al., (2009), *Cell* 139:573-586).

DLBCL cells of the ABC subtype, such as OCI-Ly10, have chronic active BCR signalling and are very sensitive to the Btk inhibitor described herein. The irreversible Btk inhibitor described herein potently and irreversibly inhibits the growth of OCI-Ly10 ($EC_{50}$ continuous exposure=10 nM, $EC_{50}$ 1 hour pulse=50 nM). In addition, induction of apoptosis, as shown by capsase activation, Annexin-V flow cytometry and increase in sub-G0 fraction is observed in OCILy10. Both sensitive and resistant cells express Btk at similar levels, and the active site of Btk is fully occupied by the inhibitor in both as shown using a fluorescently labeled affinity probe. OCI-Ly10 cells are shown to have chronically active BCR signalling to NF-kB which is dose dependently inhibited by the Btk inhibitors described herein. The activity of Btk inhibitors in the cell lines studied herein are also characterized by comparing signal transduction profiles (Btk, PLCγ, ERK, NF-kB, AKT), cytokine secretion profiles and mRNA expression profiles, both with and without BCR stimulation, and observed significant differences in these profiles that lead to clinical biomarkers that identify the most sensitive patient populations to Btk inhibitor treatment. See U.S. Pat. No. 7,711,492 and Staudt et al., Nature, Vol. 463, Jan. 7, 2010, pp. 88-92, the contents of which are incorporated by reference in their entirety.

Follicular Lymphoma

Disclosed herein, in certain embodiments, is a method for treating a follicular lymphoma in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

As used herein, the term "follicular lymphoma" refers to any of several types of non-Hodgkin's lymphoma in which the lymphomatous cells are clustered into nodules or follicles. The term follicular is used because the cells tend to grow in a circular, or nodular, pattern in lymph nodes. The average age for people with this lymphoma is about 60.

CLL/SLL

Disclosed herein, in certain embodiments, is a method for treating a CLL or SLL in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

Chronic lymphocytic leukemia and small lymphocytic lymphoma (CLL/SLL) are commonly thought as the same disease with slightly different manifestations. Where the cancerous cells gather determines whether it is called CLL or SLL. When the cancer cells are primarily found in the lymph nodes, lima bean shaped structures of the lymphatic system (a system primarily of tiny vessels found in the body), it is called SLL. SLL accounts for about 5% to 10% of all lymphomas. When most of the cancer cells are in the bloodstream and the bone marrow, it is called CLL.

Both CLL and SLL are slow-growing diseases, although CLL, which is much more common, tends to grow slower. CLL and SLL are treated the same way. They are usually not considered curable with standard treatments, but depending on the stage and growth rate of the disease, most patients live longer than 10 years. Occasionally over time, these slow-growing lymphomas may transform into a more aggressive type of lymphoma.

Chronic lymphoid leukemia (CLL) is the most common type of leukemia. It is estimated that 100,760 people in the United States are living with or are in remission from CLL. Most (>75%) people newly diagnosed with CLL are over the age of 50. Currently CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes). Though CLL progresses slowly in most cases, it is considered generally incurable. Certain CLLs are classified as high-risk. As used herein, "high risk CLL" means CLL characterized by at least one of the following 1) 17p13-; 2) 11q22-; 3) unmutated IgVH together with ZAP-70+ and/or CD38+; or 4) trisomy 12.

CLL treatment is typically administered when the patient's clinical symptoms or blood counts indicate that the disease has progressed to a point where it may affect the patient's quality of life.

Small lymphocytic leukemia (SLL) is very similar to CLL described supra, and is also a cancer of B-cells. In SLL the abnormal lymphocytes mainly affect the lymph nodes. However, in CLL the abnormal cells mainly affect the blood and the bone marrow. The spleen may be affected in both conditions. SLL accounts for about 1 in 25 of all cases of non-Hodgkin lymphoma. It can occur at any time from young adulthood to old age, but is rare under the age of 50. SLL is considered an indolent lymphoma. This means that the disease progresses very slowly, and patients tend to live many years after diagnosis. However, most patients are diagnosed with advanced disease, and although SLL responds well to a variety of chemotherapy drugs, it is generally considered to be incurable. Although some cancers tend to occur more often in one gender or the other, cases and deaths due to SLL are evenly split between men and women. The average age at the time of diagnosis is 60 years.

Although SLL is indolent, it is persistently progressive. The usual pattern of this disease is one of high response rates to radiation therapy and/or chemotherapy, with a period of disease remission. This is followed months or years later by an inevitable relapse. Re-treatment leads to a response again, but again the disease will relapse. This means that although the short-term prognosis of SLL is quite good, over time, many patients develop fatal complications of recurrent disease. Considering the age of the individuals typically diagnosed with CLL and SLL, there is a need in the art for a simple and effective treatment of the disease with minimum side-effects that do not impede on the patient's quality of life. The instant invention fulfills this long standing need in the art.

Mantle Cell Lymphoma

Disclosed herein, in certain embodiments, is a method for treating a Mantle cell lymphoma in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

As used herein, the term, "Mantle cell lymphoma" refers to a subtype of B-cell lymphoma, due to CD5 positive antigen-naive pregerminal center B-cell within the mantle zone that surrounds normal germinal center follicles. MCL cells generally over-express cyclin D1 due to a t(11:14) chromosomal translocation in the DNA. More specifically, the translocation is at t(11;14)(q13;q32). Only about 5% of lymphomas are of this type. The cells are small to medium in size. Men are affected most often. The average age of patients is in the early 60s. The lymphoma is usually widespread when it is diagnosed, involving lymph nodes, bone marrow, and, very often, the spleen. Mantle cell lymphoma is not a very fast growing lymphoma, but is difficult to treat.

Marginal Zone B-cell Lymphoma

Disclosed herein, in certain embodiments, is a method for treating a marginal zone B-cell lymphoma in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

As used herein, the term "marginal zone B-cell lymphoma" refers to a group of related B-cell neoplasms that involve the lymphoid tissues in the marginal zone, the patchy area outside the follicular mantle zone. Marginal zone lymphomas account for about 5% to 10% of lymphomas. The cells in these lymphomas look small under the microscope. There are 3 main types of marginal zone lymphomas including extranodal marginal zone B-cell lymphomas, nodal marginal zone B-cell lymphoma, and splenic marginal zone lymphoma.

MALT

Disclosed herein, in certain embodiments, is a method for treating a MALT in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

The term "mucosa-associated lymphoid tissue (MALT) lymphoma", as used herein, refers to extranodal manifestations of marginal-zone lymphomas. Most MALT lymphoma are a low grade, although a minority either manifest initially as intermediate-grade non-Hodgkin lymphoma (NHL) or evolve from the low-grade form. Most of the MALT lymphoma occur in the stomach, and roughly 70% of gastric MALT lymphoma are associated with *Helicobacter pylori* infection. Several cytogenetic abnormalities have been identified, the most common being trisomy 3 or t(11;18). Many of these other MALT lymphoma have also been linked to infections with bacteria or viruses. The average age of patients with MALT lymphoma is about 60.

Nodal Marginal Zone B-Cell Lymphoma

Disclosed herein, in certain embodiments, is a method for treating a nodal marginal zone B-cell lymphoma in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

The term "nodal marginal zone B-cell lymphoma" refers to an indolent B-cell lymphoma that is found mostly in the lymph nodes. The disease is rare and only accounts for 1% of all Non-Hodgkin's Lymphomas (NHL). It is most commonly diagnosed in older patients, with women more susceptible than men. The disease is classified as a marginal zone lymphoma because the mutation occurs in the marginal zone of the B-cells. Due to its confinement in the lymph nodes, this disease is also classified as nodal.

Splenic Marginal Zone B-Cell Lymphoma

Disclosed herein, in certain embodiments, is a method for treating a splenic marginal zone B-cell lymphoma in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

The term "splenic marginal zone B-cell lymphoma" refers to specific low-grade small B-cell lymphoma that is incorporated in the World Health Organization classification. Characteristic features are splenomegaly, moderate lymphocytosis with villous morphology, intrasinusoidal pattern of involvement of various organs, especially bone marrow, and relative indolent course. Tumor progression with increase of blastic forms and aggressive behavior are observed in a minority of patients. Molecular and cytogenetic studies have shown heterogeneous results probably because of the lack of standardized diagnostic criteria.

Burkitt Lymphoma

Disclosed herein, in certain embodiments, is a method for treating a Burkitt lymphoma in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

The term "Burkitt lymphoma" refers to a type of Non-Hodgkin Lymphoma (NHL) that commonly affects children. It is a highly aggressive type of B-cell lymphoma that often starts and involves body parts other than lymph nodes. In spite of its fast-growing nature, Burkitt's lymphoma is often curable with modern intensive therapies. There are two broad types of Burkitt's lymphoma—the sporadic and the endemic varieties:

Endemic Burkitt's lymphoma: The disease involves children much more than adults, and is related to Epstein Barr Virus (EBV) infection in 95% cases. It occurs primarily is equatorial Africa, where about half of all childhood cancers are Burkitt's lymphoma. It characteristically has a high chance of involving the jawbone, a rather distinctive feature that is rare in sporadic Burkitt's. It also commonly involves the abdomen.

Sporadic Burkitt's lymphoma: The type of Burkitt's lymphoma that affects the rest of the world, including Europe and the Americas is the sporadic type. Here too, it's mainly a disease in children. The link between Epstein Barr Virus (EBV) is not as strong as with the endemic variety, though direct evidence of EBV infection is present in one out of five patients. More than the involvement of lymph nodes, it is the abdomen that is notably affected in more than 90% of the children. Bone marrow involvement is more common than in the sporadic variety.

Waldenstrom Macroglobulinemia

Disclosed herein, in certain embodiments, is a method for treating a Waldenstrom macroglobulinemia in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

The term "Waldenstrom macroglobulinemia", also known as lymphoplasmacytic lymphoma, is cancer involving a subtype of white blood cells called lymphocytes. It is characterized by an uncontrolled clonal proliferation of terminally differentiated B lymphocytes. It is also characterized by the lymphoma cells making an antibody called immunoglobulin M (IgM). The IgM antibodies circulate in the blood in large amounts, and cause the liquid part of the blood to thicken, like syrup. This can lead to decreased blood flow to many organs, which can cause problems with vision (because of poor circulation in blood vessels in the back of the eyes) and neurological problems (such as headache, dizziness, and confusion) caused by poor blood flow within the brain. Other symptoms can include feeling tired and weak, and a tendency to bleed easily. The underlying etiology is not fully understood but a number of risk factors have been identified, including the locus 6p21.3 on chromosome 6. There is a 2- to 3-fold risk increase of developing WM in people with a personal history of autoimmune diseases with autoantibodies and particularly elevated risks associated with hepatitis, human immunodeficiency virus, and rickettsiosis.

Multiple Myeloma

Disclosed herein, in certain embodiments, is a method for treating a myeloma in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

Multiple myeloma, also known as MM, myeloma, plasma cell myeloma, or as Kahler's disease (after Otto Kahler) is a cancer of the white blood cells known as plasma cells. A type of B cell, plasma cells are a crucial part of the immune system responsible for the production of antibodies in humans and other vertebrates. They are produced in the bone marrow and are transported through the lymphatic system.

Leukemia

Disclosed herein, in certain embodiments, is a method for treating a leukemia in an individual in need thereof, comprising: administering to the individual a composition containing a therapeutic amount of at least one compound having the structure of Formula (I), (IA), (II), (III), (IV), (V), (VI), (VIA), (VIB), (VII), (VIII), (IX), (X), (XI), (XII), (XIII), or (XIV).

Leukemia is a cancer of the blood or bone marrow characterized by an abnormal increase of blood cells, usually leukocytes (white blood cells). Leukemia is a broad term covering a spectrum of diseases. The first division is between its acute and chronic forms: (i) acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children; (ii) chronic leukemia is distinguished by the excessive build up of relatively mature, but still abnormal, white blood cells. Typically taking months or years to progress, the cells are produced at a much higher rate than normal cells, resulting in many abnormal white blood cells in the blood. Chronic leukemia mostly occurs in older people, but can theoretically occur in any age group. Additionally, the diseases are subdivided according to which kind of blood cell is affected. This split divides leukemias into lymphoblastic or lymphocytic leukemias and myeloid or myelogenous leukemias: (i) lymphoblastic or lymphocytic leukemias, the cancerous change takes place in a type of marrow cell that normally goes on to form lymphocytes, which are infection-fighting immune system cells; (ii) myeloid or myelogenous leukemias, the cancerous change takes place in a type of marrow cell that normally goes on to form red blood cells, some other types of white cells, and platelets.

Within these main categories, there are several subcategories including, but not limited to, Acute lymphoblastic leukemia (ALL), Acute myelogenous leukemia (AML), Chronic myelogenous leukemia (CML), and Hairy cell leukemia (HCL).

Symptoms, diagnostic tests, and prognostic tests for each of the above-mentioned conditions are known in the art. See, e.g., *Harrison's Principles of Internal Medicine©,*" 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of Btk inhibitor compounds for treating any of the foregoing diseases.

For example, dosing of Btk inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), *Am. J. Pathol* 163:1827-1837.

In another example, dosing of Btk inhibitors for the treatment of B-cell proliferative disorders can be examined in, e.g., a human-to-mouse xenograft model in which human B-cell lymphoma cells (e.g. Ramos cells) are implanted into immunodefficient mice (e.g., "nude" mice) as described in, e.g., Pagel et al. (2005), Clin Cancer Res 11(13):4857-4866.

Animal models for treatment of thromboembolic disorders are also known.

The therapeutic efficacy of the compound for one of the foregoing diseases can be optimized during a course of treatment. For example, a subject being treated can undergo a diagnostic evaluation to correlate the relief of disease symptoms or pathologies to inhibition of in vivo Btk activity achieved by administering a given dose of an Btk inhibitor. Cellular assays known in the art can be used to determine in vivo activity of Btk in the presence or absence of an Btk inhibitor. For example, since activated Btk is phosphorylated at tyrosine 223 (Y223) and tyrosine 551 (Y551), phospho-specific immunocytochemical staining of P-Y223 or P-Y551-positive cells can be used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor inhibitor compound that is administered to a subject can be increased or decreased as needed so as to maintain a level of Btk inhibition optimal for treating the subject's disease state.

Compounds disclosed herein can irreversibly inhibit Btk and may be used to treat mammals suffering from Bruton's tyrosine kinase-dependent or Bruton's tyrosine kinase mediated conditions or diseases, including, but not limited to, cancer, autoimmune and other inflammatory diseases. Compounds disclosed herein have shown efficacy in a wide variety of diseases and conditions that are described herein.

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry terms are found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients. Standard techniques are optionally used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such optionally vary. It is also to be understood that the terminology used herein is for the purpose of describing particular embodiments only, and is not intended to limit the scope of the methods and compositions described herein, which will be limited only by the appended claims.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group includes a monoradical or a diradical (i.e., an alkylene group), and if a "lower alkyl" having 1 to 6 carbon atoms.

As used herein, $C_1$-$C_x$ includes $C_1$-$C_2$, $C_1$-$C_3$ ... $C_1$-$C_x$.

The "alkyl" moiety optionally has 1 to 10 carbon atoms (whenever it appears herein, a numerical range such as "1 to 10" refers to each integer in the given range; e.g., "1 to 10 carbon atoms" means that the alkyl group is selected from a moiety having 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups are optionally substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

An "alkoxy" group refers to a (alkyl)O— group, where alkyl is as defined herein.

"Alkoxyalkyl" refers to an alkyl radical, as defined herein, substituted with an alkoxy group, as defined herein.

The term "ester" refers to a chemical moiety with formula —COOR, where R is selected from among $C_1$-$C_4$alkyl, phenyl or benzyl. Any hydroxy, or carboxyl side chain on the compounds described herein can be esterified. The procedures and specific groups to make such esters are found in sources such as Greene and Wuts, Protective Groups in Organic Synthesis, 3$^{rd}$ Ed., John Wiley & Sons, New York, N.Y., 1999, which is incorporated herein by reference for this disclosure.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "carbonyl" as used herein refers to a group containing a moiety selected from the group consisting of —C(O)—, —S(O)—, —S(O)2—, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "halo" or, alternatively, "halogen" or "halide" means fluoro, chloro, bromo and iodo.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

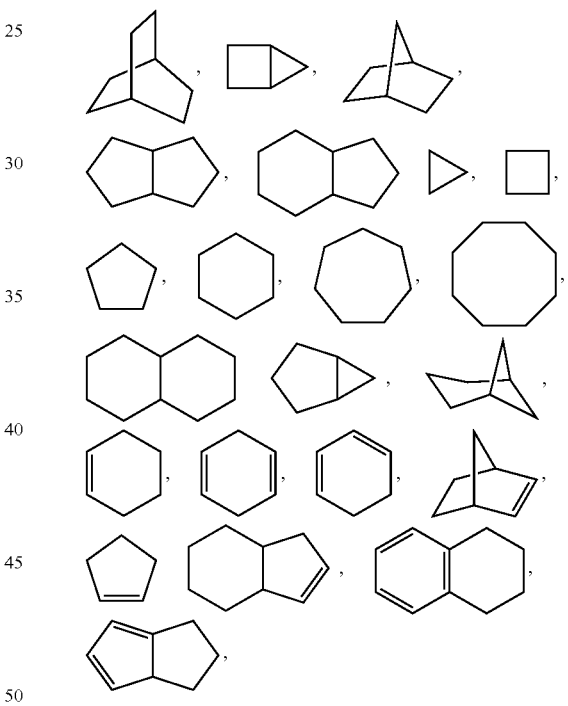

and the like. Depending on the structure, a cycloalkyl group can be a monoradical or a diradical (e.g., an cycloalkylene group). The cycloalkyl group could also be a "lower cycloalkyl" having 3 to 8 carbon atoms The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

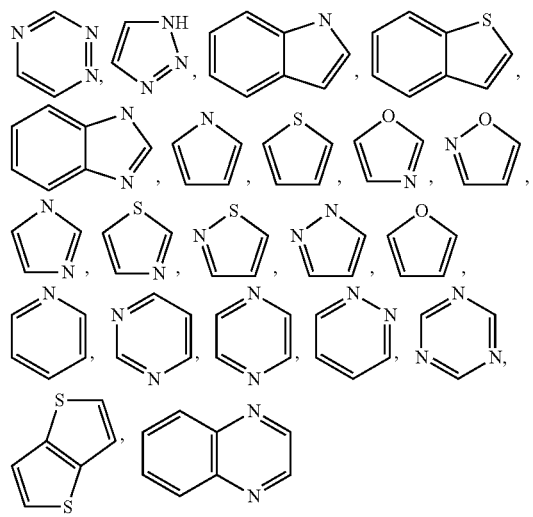

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

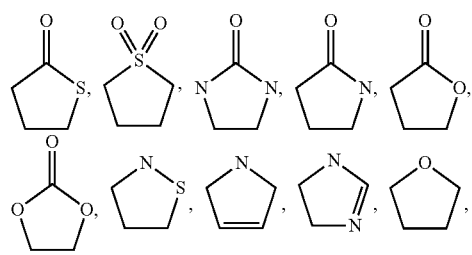

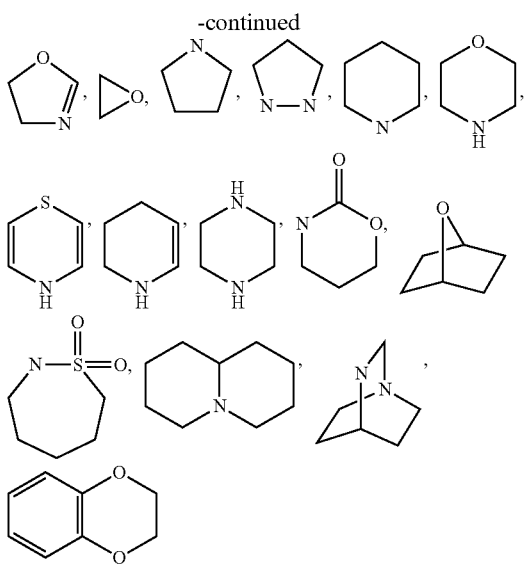

and the like.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "SH" group is also referred to either as a thiol group or a sulfhydryl group.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of Formula (I), dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which compounds disclosed herein, such as, compounds of Formula (I), are absorbed into the general circulation when the pharmaceutical composition is taken orally as compared to intravenous injection.

"Blood plasma concentration" refers to the concentration of compounds disclosed herein, such as, compounds of Formula (I), in the plasma component of blood of a subject. It is understood that the plasma concentration of compounds of Formula (I), may vary significantly between subjects, due to variability with respect to metabolism and/or possible interactions with other therapeutic agents. In accordance with one embodiment disclosed herein, the blood plasma concentration of the compounds of Formula (I), does vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of a compound of Formula (I), is expected to vary from subject to subject.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139.), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEELYS-SARQ").

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case is optionally determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the of Formula (I), age, weight, general condition of the subject, the condition being treated, the severity of the condition being treated, and the judgment of the prescribing physician.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350. See also the sequence alignments of tyrosine kinases (TK) published on the world wide web at kinase.com/human/kinome/phylogeny.html.

The terms "inhibits", "inhibiting", or "inhibitor" of a kinase, as used herein, refer to inhibition of enzymatic phosphotransferase activity.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "plasma half life," as used herein refers to half-life in rat, dog or human as determined by measure drug concentration over time in plasma following a single dose and fitting data to standard pharmacokinetic models using software such as WinNonLin to determine the time at which drug has been 50% eliminated from plasma.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like.

As used herein, the term "selective binding compound" refers to a compound that selectively binds to any portion of one or more target proteins.

As used herein, the term "selectively binds" refers to the ability of a selective binding compound to bind to a target protein, such as, for example, Btk, with greater affinity than it binds to a non-target protein. In certain embodiments, specific binding refers to binding to a target with an affinity that is at least about 10, about 50, about 100, about 250, about 500, about 1000 or more times greater than the affinity for a non-target.

As used herein, the term "selective modulator" refers to a compound that selectively modulates a target activity relative to a non-target activity. In certain embodiments, specific modulator refers to modulating a target activity at least about 10, about 50, about 100, about 250, about 500, about 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

Inhibitor Compounds

In the following description of Btk compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. In addition, nucleic acid and amino acid sequences for Btk (e.g., human Btk) are known in the art as disclosed in, e.g., U.S. Pat. No. 6,326,469. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

The Btk inhibitor compounds described herein are selective for Btk and kinases having a cysteine residue in an amino acid sequence position of the tyrosine kinase that is homologous to the amino acid sequence position of cysteine 481 in Btk.

Cellular functional assays for Btk inhibition include measuring one or more cellular endpoints in response to stimulating a Btk-mediated pathway in a cell line (e.g., BCR activation in Ramos cells) in the absence or presence of a range of concentrations of a candidate Btk inhibitor compound. Useful endpoints for determining a response to BCR activation include, e.g., autophosphorylation of Btk, phosphorylation of a Btk target protein (e.g., PLC-γ), and cytoplasmic calcium flux.

High throughput assays for many acellular biochemical assays (e.g., kinase assays) and cellular functional assays (e.g., calcium flux) are well known to those of ordinary skill in the art. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of Btk compounds without undue effort.

Btk inhibitor compounds can be used for the manufacture of a medicament for treating any of the foregoing conditions (e.g., autoimmune diseases, inflammatory diseases, allergy disorders, B-cell proliferative disorders, or thromboembolic disorders).

In some embodiments, the Btk inhibitor compound used for the methods described herein inhibits Btk or a Btk homolog kinase activity with an in vitro $IC_{50}$ of less than 10 µM. (e.g., less than 1 µM, less than 0.5 µM, less than 0.4 µM, less than 0.3 µM, less than 0.1 µM, less than 0.08 µM, less than 0.06 µM, less than 0.05 µM, less than 0.04 µM, less than 0.03 µM, less than less than 0.02 µM, less than 0.01 µM, less than 0.008 µM, less than 0.006 µM, less than 0.005 µM, less than 0.004 µM, less than 0.003 µM, less than less than 0.002 µM, less than 0.001 µM, less than 0.00099 µM, less than 0.00098 µM, less than 0.00097 µM, less than 0.00096 µM, less than 0.00095 µM, less than 0.00094 µM, less than 0.00093 µM, less than 0.00092, or less than 0.00090 µM).

In one embodiment, the Btk inhibitor compound selectively inhibits an activated form of its target tyrosine kinase (e.g., a phosphorylated form of the tyrosine kinase). For example, activated Btk is transphosphorylated at tyrosine 551. Thus, in these embodiments the Btk inhibitor inhibits the target kinase in cells only once the target kinase is activated by the signaling events.

In the following description of kinase inhibitor compounds suitable for use in the methods described herein. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

Described herein are compounds of any of Formula (I), (IA), (II), (III), (IV), (V), (VI), (VIA), (VIB), (VII), (VIII), (IX), (X), (XI), (XII), (XIII), or (XIV). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by any of Formula (I), (IA), (II), (III), (IV), (V), (VI), (VIA), (VIB), (VII), (VIII), (IX), (X), (XI), (XII), (XIII), or (XIV) are also provided.

In one aspect, provided herein are compounds of Formula (I) having the structure:

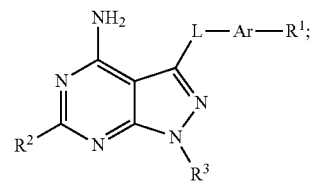

Formula (I)

wherein:
L is each independently $CR^aR^a$, O, S, $NR^b$, N—$OR^b$, C=O, C=S, C=N—$R^b$, or C=N—$OR^b$;
$R^a$ is each independently H, $C_1$-$C_6$ alkyl, $C_1$-$C_6$ heteroalkyl, halogen, $OR^b$, or $NR^bR^b$;
$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
$R^1$ is L-$Ar^2$, $OR^b$, or $NR^bR^b$;
$R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl;
$R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl;
Ar and $Ar^2$ are each independently $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl;
or a pharmaceutically acceptable salt, solvate, N-oxide, or prodrug thereof.

In one embodiment is a compound of Formula (I) wherein L is $CH_2$ or C=O. In another embodiment is a compound of Formula (I) wherein Ar is phenyl. In yet another embodiment is a compound of Formula (I) wherein $R^2$ is H and $R^3$ is optionally substituted cycloalkyl. In a further embodiment is a compound of Formula (I) wherein $R^1$ is O-Ph.

For any and all of the embodiments, substituents are selected from among from a subset of the listed alternatives. For example, in some embodiments, $R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl; wherein $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, $R^2$ is H, OH, $NH_2$, halogen or $C_1$-$C_6$ alkyl. In some embodiments, $R^2$ is F, Cl, Br or I. In other embodiments, $R^2$ is methyl, ethyl, n-propyl, iso-propyl, n-butyl, sec-butyl, iso-butyl, n-pentyl, or hexyl. In yet other embodiments, $R^2$ is H, OH, or $NH_2$. In other embodiments, $R^2$ is H.

In some embodiments, $R^1$ is O—$Ar^2$ wherein $Ar^2$ is $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl; and $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, $R^1$ is O—$Ar^2$ wherein $Ar^2$ is $C_5$-$C_{12}$ aryl or heteroaryl optionally substituted with halogen, hydroxy, amine, or $C_1$-$C_6$ alkyl. In other embodiments, $Ar^2$ is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In other embodiments, $Ar^2$ is phenyl, pyridinyl, furanyl, thiophenyl or quinolinyl. In certain embodiments, $Ar^2$ is phenyl or pyridinyl.

In some embodiments, $R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl. In other embodiments, $R^3$ is methyl, ethyl, n-propyl, iso-propyl, n-butyl, iso-butyl, and tert-butyl. In yet other embodiments, $R^3$ is —C=O-Me, —(C=O)Et, or —(C=O)Bu. In other embodiments, $R^3$ is —COOH, —COOMe, —COOEt, —COOPr or —COOBu. In yet other embodiments, $R^3$ is —$CONH_2$, —CONHMe, —CONHEt or —CONHBu. In other embodiments, $R^3$ is —C=O—SMe, —(C=O)SEt or —C=O—SPr. In yet other embodiments, $R^3$ is optionally substituted cyclobutyl, cyclopentyl, cyclohexyl, or the like. In yet other embodiments, $R^3$ is optionally substituted azetidinyl, pyrrolidinyl, piperidinyl or the like. In yet other embodiments, $R^3$ is optionally substituted phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like.

In another embodiment is a compound of Formula (I) wherein $R^3$ is optionally substituted with at least one substituent selected from halogen, —CN, —$NO_2$, —OH, —$OCF_3$, —$OCF_2H$, —$OCH_2F$, —$CF_3$, —$SR^8$, —S(=O)$R^9$, —S(=O)$_2R^9$, —$NR^{10}$S(=O)$_2R^9$, —S(=O)$_2$N($R^{10}$)$_2$, —$OR^{10}$, —C(=O)$R^9$, —OC(=O)$R^9$, —$CO_2R^{10}$, —N($R^{10}$)$_2$, —C(=O)N($R^{10}$)$_2$, —$NR^{10}$C(=O)$R^{10}$, —$NR^{10}$C(=O)$OR^{10}$, —$NR^{10}$C(=O)N($R^{10}$)$_2$, substituted or unsubstituted alkyl, substituted or unsubstituted heteroalkyl, substituted or unsubstituted cycloalkyl or substituted or unsubstituted heterocycloalkyl; wherein $R^8$ is H or substituted or unsubstituted alkyl; $R^9$ is substituted or unsubstituted alkyl, substituted or unsubstituted cycloalkyl, substituted or unsubstituted heterocycloalkyl, substituted or unsubstituted aryl or substituted or unsubstituted heteroaryl; and each $R^{10}$ is independently H, substituted or unsubstituted alkyl, substituted or unsubstituted cycloalkyl, substituted or unsubstituted heterocycloalkyl, substituted or unsubstituted aryl or substituted or unsubstituted heteroaryl, or two $R^{10}$ together with the atoms to which they are attached form a heterocycle. In one embodiment, $R^3$ is substituted with halogen, —CN, —$NO_2$, —OH, —$OCF_3$, —$OCF_2H$, —$OCH_2F$, —$CF_3$, —SH. In another embodiment is a compound of Formula (I) wherein $R^3$ is substituted with —S(=O)$R^9$, —S(=O)$_2R^9$, —$NR^{10}$S(=O)$_2R^9$, —S(=O)$_2$N($R^{10}$)$_2$, —C(=O)$R^9$, —$CO_2R^{10}$, —C(=O)N($R^{10}$)$_2$. In another embodiment, $R^9$ is an unsubstituted or substituted alkyl selected from methyl, ethyl, n-propyl, iso-propyl, n-butyl, iso-butyl or tert-butyl. In another embodiment, is a compound of Formula (I) wherein $R^9$ is a substituted or unsubstituted cycloalkyl. In a further embodiment, the cycloalkyl is selected from cyclopropyl, cyclobutyl, cyclopentyl, cyclohexyl or cycloheptyl. In another embodiment $R^9$ is a substituted or unsubstituted heterocycloalkyl. In another embodiment, $R^9$ is a substituted or unsubstituted aryl. In a further embodiment, the aryl is a phenyl group. In a further embodiment, the aryl is a naphthalene group. In yet a further embodiment, $R^9$ is a substituted or unsubstituted heteroaryl. In yet another embodiment the heteroaryl is selected from pyrrole, furan, thiophene, pyrazole, imidazole, isoxazole, oxazole, isothiazole, thiazole, 1,2,3-triazole, 1,3,4-triazole, 1-oxa-2,3-diazole, 1-oxa-2,4-diazole, 1-oxa-2,5-diazole, 1-oxa-3,4-diazole, 1-thia-2,3-diazole, 1-thia-2,4-diazole, 1-thia-2,5-diazole, 1-thia-3,4-diazole, tetrazole, pyridine, pyridazine, pyrimidine, and pyrazine.

In some embodiments, L is each independently $CR^aR^a$, O, S, $NR^b$, C=O, C=S, C=N—$R^b$ or C=N—$OR^b$ wherein $R^a$ is each independently H, $C_1$-$C_6$ alkyl, $C_1$-$C_6$ heteroalkyl, halogen, $OR^b$, or $NR^bR^b$; and $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, L is each independently $CR^aR^a$, O, S, $NR^b$, C=O, C=S, C=N—$R^b$ or C=N—$OR^b$ wherein $R^a$ is each independently H, $C_1$-$C_6$ alkyl, or halogen; and $R^b$ is each independently H or $C_1$-$C_6$ alkyl. In other embodiments, L is $CH_2$, O, S, NH, C=O, C=S, C=N—H or C=N—OH. In other embodiments, L is —CH(Me) or —CH(Cl). In yet other embodiments, L is C=N-Me, C=N—OMe, C=N-Et, C=N—OEt, C=N-$^n$Pr, or C=N—$O^n$Pr.

In some embodiments, Ar is $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl; and $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, Ar is $C_5$-$C_{12}$ aryl or heteroaryl optionally substituted with halogen, hydroxy, amine, or $C_1$-$C_6$ alkyl. In other embodiments, Ar is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In certain embodiments, Ar is phenyl, or pyridinyl optionally substituted with amine or hydroxy. In certain embodiments, Ar is phenyl, or pyridinyl optionally substituted with methyl, ethyl, propyl, or the like.

In another aspect, provided herein are compounds of Formula (II) having the structure:

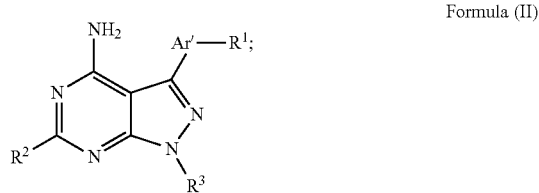

Formula (II)

wherein:
$R^1$ is L-Ar$^2$;
L is each independently $CR^aR^a$, O, S, $NR^b$, N—$OR^b$, C=O, C=S, C=N—$R^b$, or C=N—$OR^b$;
$R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl;
$R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl;
$R^a$ is each independently H, $C_1$-$C_6$ alkyl, $C_1$-$C_6$ heteroalkyl, halogen, $OR^b$, or $NR^bR^b$;
$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
Ar' is selected from furan, thiophene, oxazole, isoxazole, oxadiazole, thiazole, isothiazole, thiadiazole, imidazole, triazole, pyrazole, thiodiazole, tetrazole, pyridine, pyrimidine, and pyrazine;
Ar$^2$ is $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl or $C_2$-$C_6$ heterocycloalkyl; or a pharmaceutically acceptable salt, solvate, N-oxide, or prodrug thereof.

In one embodiment is a compound of Formula (II) wherein Ar' is oxazole, isoxazole, or oxadiazole. In another embodiment is a compound of Formula (II) wherein $R^2$ is H. In yet another embodiment is a compound of Formula (II) wherein $R^2$ is H and $R^3$ is optionally substituted cycloalkyl. In a further embodiment is a compound of Formula (II) wherein $R^1$ is O-Ph.

In some embodiments, $R^1$ is O—Ar$^2$ wherein Ar$^2$ is $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl; and $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, $R^1$ is O—Ar$^2$ wherein Ar$^2$ is $C_5$-$C_{12}$ aryl or heteroaryl optionally substituted with halogen, hydroxy, amine, or $C_1$-$C_6$ alkyl. In other embodiments, Ar$^2$ is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In other embodiments, Ar$^2$ is phenyl, pyridinyl, furanyl, thiophenyl or quinolinyl. In certain embodiments, Ar$^2$ is phenyl or pyridinyl.

In some embodiments, $R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl; wherein $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, $R^2$ is H, OH, $NH_2$, halogen or $C_1$-$C_6$ alkyl. In other embodiments, $R^2$ is F, Cl, Br or I. In other embodiments, $R^2$ is methyl, ethyl, n-propyl, iso-propyl, n-butyl, sec-butyl, iso-butyl, n-pentyl, or hexyl. In yet other embodiments, $R^2$ is H, OH, or $NH_2$. In other embodiments, $R^2$ is H.

In some embodiments, $R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl. In other embodiments, $R^3$ is methyl, ethyl, n-propyl, iso-propyl, n-butyl, iso-butyl, and tert-butyl. In yet other embodiments, $R^3$ is —C=O-Me, —(C=O)Et, or —(C=O)Bu. In other embodiments, $R^3$ is —COOH, —COOMe, —COOEt, —COOPr or —COOBu. In yet other embodiments, $R^3$ is —CONH$_2$, —CONHMe, —CONHEt or —CONHBu. In other embodiments, $R^3$ is —C=O—SMe, —(C=O)SEt or —C=O—SPr. In yet other embodiments, $R^3$ is optionally substituted cyclobutyl, cyclopentyl, cyclohexyl, or the like. In yet other embodiments, $R^3$ is optionally substituted azetidinyl, pyrrolidinyl, piperidinyl or the like. In yet other embodiments, $R^3$ is optionally substituted phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like.

In another embodiment is a compound of Formula (II) wherein $R^3$ is optionally substituted with at least one substituent selected from halogen, —CN, —NO$_2$, —OH, —OCF$_3$, —OCF$_2$H, —OCH$_2$F, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —OR$^{10}$, —C(=O)R$^9$, —OC(=O)R$^9$, —OC(=O)R$^9$, CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted heteroalkyl, substituted or unsubstituted cycloalkyl or substituted or unsubstituted heterocycloalkyl; wherein $R^8$ is H or substituted or unsubstituted alkyl; $R^9$ is substituted or unsubstituted alkyl, substituted or unsubstituted cycloalkyl, substituted or unsubstituted heterocycloalkyl, substituted or unsubstituted aryl or substituted or unsubstituted heteroaryl; and each $R^{10}$ is independently H, substituted or unsubstituted alkyl, substituted or unsubstituted cycloalkyl, substituted or unsubstituted heterocycloalkyl, substituted or unsubstituted aryl or substituted or unsubstituted heteroaryl, or two $R^{10}$ together with the atoms to which they are attached form a heterocycle. In one embodiment, $R^3$ is substituted with halogen, —CN, —NO$_2$, —OH, —OCF$_3$, —OCF$_2$H, —OCH$_2$F, —CF$_3$, —SH. In another embodiment is a compound of Formula (II) wherein $R^3$ is substituted with —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —CO$_2$R$^{10}$, —C(=O)N(R$^{10}$)$_2$. In another embodiment, $R^9$ is an unsubstituted or substituted alkyl selected from methyl, ethyl, n-propyl, iso-propyl, n-butyl, iso-butyl or tert-butyl. In another embodiment, is a compound of Formula (II) wherein $R^9$ is a substituted or unsubstituted cycloalkyl. In a further embodiment, the cycloalkyl is selected from cyclopropyl, cyclobutyl, cyclopentyl, cyclohexyl or cycloheptyl. In another embodiment $R^9$ is a substituted or unsubstituted heterocycloalkyl. In another embodiment, $R^9$ is a substituted or unsubstituted aryl. In a further embodiment, the aryl is a phenyl group. In a further embodiment, the aryl is a naphthalene group. In yet a further embodiment, $R^9$ is a substituted or unsubstituted heteroaryl. In yet another embodiment the heteroaryl is selected from pyrrole, furan, thiophene, pyrazole, imidazole, isoxazole, oxazole, isothiazole, thiazole, 1,2,3-triazole, 1,3,4-triazole, 1-oxa-2,3-diazole, 1-oxa-2,4-diazole, 1-oxa-2,5-diazole, 1-oxa-3,4-diazole, 1-thia-2,3-diazole, 1-thia-2,4-diazole, 1-thia-2,5-diazole, 1-thia-3,4-diazole, tetrazole, pyridine, pyridazine, pyrimidine, and pyrazine.

In some embodiments, Ar' is selected from furan, thiophene, oxazole, isooxazole, oxadiazole, thiazole, isothiazole, and thiadiazole. In other embodiments, Ar' is oxazole, isooxazole or oxadiazole.

In one aspect, provided herein are compounds of Formula (III) having the structure:

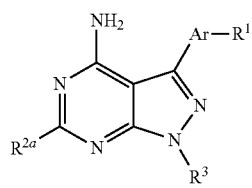

Formula (III)

wherein:
wherein:
R$^1$ is L-Ar$^2$;
L is CR$^a$R$^a$, O, S, NR$^b$, N—OR$^b$, C=O, C=S, C=N—R$^b$, or C=N—OR$^b$;
R$^a$ is each independently H, C$_1$-C$_6$ alkyl, C$_1$-C$_6$ heteroalkyl, halogen, OR$^b$, or NR$^b$R$^b$;
R$^b$ is each independently H, C$_1$-C$_6$ alkyl, C$_2$-C$_6$ heteroalkyl, C$_3$-C$_6$ cycloalkyl, or C$_2$-C$_6$ heterocycloalkyl;
R$^{2a}$ is OR$^b$, NR$^b$R$^b$, halogen, C$_1$-C$_6$ alkyl, C$_1$-C$_6$ heteroalkyl, C$_3$-C$_6$ cycloalkyl, or C$_2$-C$_6$ heterocycloalkyl;
R$^3$ is optionally substituted alkyl, —(C=O)C$_1$-C$_6$ alkyl, —(C=O)OR$^b$, —(C=O)NR$^b$R$^b$, —(C=O)SR$^b$, optionally substituted cycloalkyl, optionally substituted heterocycloalkyl, optionally substituted aryl, or optionally substituted heteroaryl;
Ar and Ar$^2$ are each independently C$_5$-C$_{12}$ aryl or heteroaryl optionally substituted with halogen, OR$^b$, NR$^b$R$^b$, C$_1$-C$_6$ alkyl, C$_1$-C$_6$ heteroalkyl, C$_3$-C$_6$ cycloalkyl, or C$_2$-C$_6$ heterocycloalkyl; or a pharmaceutically acceptable salt, solvate, N-oxide, or prodrug thereof.

In one embodiment is a compound of Formula (III) wherein Ar is phenyl. In another embodiment is a compound of Formula (III) wherein R$^{2a}$ is CH$_3$ or OH. In yet another embodiment is a compound of Formula (III) wherein R$^3$ is optionally substituted cycloalkyl. In a further embodiment is a compound of Formula (III) wherein R$^1$ is O-Ph.

In some embodiments, R$^{2a}$ is OR$^b$, NR$^b$R$^b$, halogen, C$_1$-C$_6$ alkyl, C$_1$-C$_6$ heteroalkyl, C$_3$-C$_6$ cycloalkyl, or C$_2$-C$_6$ heterocycloalkyl. In some embodiments, R$^{2a}$ is OH, NH$_2$, halogen, or C$_1$-C$_6$ alkyl. In other embodiments, R$^{2a}$ is OH, NH$_2$, F, Cl, Br or I. In yet other embodiments, R$^{2a}$ is methyl, ethyl, n-propyl, iso-propyl, n-butyl, iso-butyl, and tert-butyl.

In some embodiments, R$^1$ is O—Ar$^2$ wherein Ar$^2$ is C$_5$-C$_{12}$ aryl or heteroaryl optionally substituted with halogen, OR$^b$, NR$^b$R$^b$, C$_1$-C$_6$ alkyl, C$_1$-C$_6$ heteroalkyl, C$_3$-C$_6$ cycloalkyl, or C$_2$-C$_6$ heterocycloalkyl; and R$^b$ is each independently H, C$_1$-C$_6$ alkyl, C$_2$-C$_6$ heteroalkyl, C$_3$-C$_6$ cycloalkyl, or C$_2$-C$_6$ heterocycloalkyl. In some embodiments, R$^1$ is O—Ar$^2$ wherein Ar$^2$ is C$_5$-C$_{12}$ aryl or heteroaryl optionally substituted with halogen, hydroxy, amine, or C$_1$-C$_6$ alkyl. In other embodiments, Ar$^2$ is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In other embodiments, Ar$^2$ is phenyl, pyridinyl, furanyl, thiophenyl or quinolinyl. In certain embodiments, Ar$^2$ is phenyl or pyridinyl.

In some embodiments, R$^3$ is optionally substituted alkyl, —(C=O)C$_1$-C$_6$ alkyl, —(C=O)OR$^b$, —(C=O)NR$^b$R$^b$, —(C=O)SR$^b$, optionally substituted cycloalkyl, optionally substituted heterocycloalkyl, optionally substituted aryl, or optionally substituted heteroaryl. In other embodiments, R$^3$ is methyl, ethyl, n-propyl, iso-propyl, n-butyl, iso-butyl, and tert-butyl. In yet other embodiments, R$^3$ is —C=O-Me, —(C=O)Et, or —(C=O)Bu. In other embodiments, R$^3$ is —COOH, —COOMe, —COOEt, —COOPr or —COOBu. In yet other embodiments, R$^3$ is —CONH$_2$, —CONHMe, —CONHEt or —CONHBu. In other embodiments, R$^3$ is —C=O—SMe, —(C=O)SEt or —C=O—SPr. In yet other embodiments, R$^3$ is optionally substituted cyclobutyl, cyclopentyl, cyclohexyl, or the like. In yet other embodiments, R$^3$ is optionally substituted azetidinyl, pyrrolidinyl, piperidinyl or the like. In yet other embodiments, R$^3$ is optionally substituted phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like.

In another embodiment is a compound of Formula (III) wherein R$^3$ is optionally substituted with at least one substituent selected from halogen, —CN, —NO$_2$, —OH, —OCF$_3$, —OCF$_2$H, —OCH$_2$F, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —OR$^{10}$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted heteroalkyl, substituted or unsubstituted cycloalkyl or substituted or unsubstituted heterocycloalkyl; wherein R$^8$ is H or substituted or unsubstituted alkyl; R$^9$ is substituted or unsubstituted alkyl, substituted or unsubstituted cycloalkyl, substituted or unsubstituted heterocycloalkyl, substituted or unsubstituted aryl or substituted or unsubstituted heteroaryl; and each R$^{10}$ is independently H, substituted or unsubstituted alkyl, substituted or unsubstituted cycloalkyl, substituted or unsubstituted heterocycloalkyl, substituted or unsubstituted aryl or substituted or unsubstituted heteroaryl, or two R$^{10}$ together with the atoms to which they are attached form a heterocycle. In one embodiment, R$^3$ is substituted with halogen, —CN, —NO$_2$, —OH, —OCF$_3$, —OCF$_2$H, —OCH$_2$F, —CF$_3$, —SH. In another embodiment is a compound of Formula (III) wherein R$^3$ is substituted with —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —CO$_2$R$^{10}$, —C(=O)N(R$^{10}$)$_2$. In another embodiment, R$^9$ is an unsubstituted or substituted alkyl selected from methyl, ethyl, n-propyl, iso-propyl, n-butyl, iso-butyl or tert-butyl. In another embodiment, is a compound of Formula (III) wherein R$^9$ is a substituted or unsubstituted cycloalkyl. In a further embodiment, the cycloalkyl is selected from cyclopropyl, cyclobutyl, cyclopentyl, cyclohexyl or cycloheptyl. In another embodiment R$^9$ is a substituted or unsubstituted heterocycloalkyl. In another embodiment, R$^9$ is a substituted or unsubstituted aryl. In a further embodiment, the aryl is a phenyl group. In a further embodiment, the aryl is a naphthalene group. In yet a further embodiment, R$^9$ is a substituted or unsubstituted heteroaryl. In yet another embodiment the heteroaryl is selected from pyrrole, furan, thiophene, pyrazole, imidazole, isoxazole, oxazole, isothiazole, thiazole, 1,2,3-triazole, 1,3,4-triazole, 1-oxa-2,3-diazole, 1-oxa-2,4-diazole, 1-oxa-2,5-diazole, 1-oxa-3,4-diazole, 1-thia-2,3-diazole, 1-thia-2,4-diazole, 1-thia-2,5-diazole, 1-thia-3,4-diazole, tetrazole, pyridine, pyridazine, pyrimidine, and pyrazine.

In some embodiments, Ar is $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl; and $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, Ar is $C_5$-$C_{12}$ aryl or heteroaryl optionally substituted with halogen, hydroxy, amine, or $C_1$-$C_6$ alkyl. In other embodiments, Ar is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In certain embodiments, Ar is phenyl, or pyridinyl optionally substituted with amine or hydroxy. In certain embodiments, Ar is phenyl, or pyridinyl optionally substituted with methyl, ethyl, propyl, or the like.

In one aspect, provided herein are compounds of Formula (IV) having the structure:

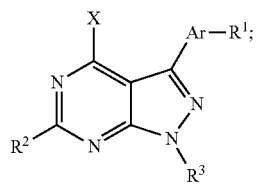

Formula (IV)

wherein:
X is hydrogen, hydroxy, alkoxy, thiol, halogen or $C_1$-$C_6$ alkyl;
$R^1$ is L-$Ar^2$;
L is $CR^aR^a$, O, S, $NR^b$, N—$OR^b$, C=O, C=S, C=N—$R^b$, or C=N—$OR^b$;
$R^a$ is each independently H, $C_1$-$C_6$ alkyl, $C_1$-$C_6$ heteroalkyl, halogen, $OR^b$, or $NR^bR^b$;
$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
$R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl;
$R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl;
Ar and $Ar^2$ are each independently $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl;
or a pharmaceutically acceptable salt, solvate, N-oxide, or prodrug thereof.

In some embodiments, $R^1$ is O—$Ar^2$ wherein $Ar^2$ is $C_5$-$C_{12}$ aryl or heteroaryl optionally substituted with halogen, hydroxy, amine, or $C_1$-$C_6$ alkyl. In other embodiments, $Ar^2$ is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In other embodiments, $Ar^2$ is phenyl, pyridinyl, furanyl, thiophenyl or quinolinyl. In certain embodiments, $Ar^2$ is phenyl or pyridinyl.

In some embodiments, $R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl. In other embodiments, $R^3$ is methyl, ethyl, n-propyl, iso-propyl, n-butyl, iso-butyl, and tert-butyl. In yet other embodiments, $R^3$ is —C=O-Me, —(C=O)Et, or —(C=O)Bu. In other embodiments, $R^3$ is —COOH, —COOMe, —COOEt, —COOPr or —COOBu. In yet other embodiments, $R^3$ is —CONH$_2$, —CONHMe, —CONHEt or —CONHBu. In other embodiments, $R^3$ is —C=O—SMe, —(C=O)SEt or —C=O—SPr. In yet other embodiments, $R^3$ is optionally substituted cyclobutyl, cyclopentyl, cyclohexyl, or the like. In yet other embodiments, $R^3$ is optionally substituted azetidinyl, pyrrolidinyl, piperidinyl or the like. In yet other embodiments, $R^3$ is optionally substituted phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like.

In another embodiment is a compound of Formula (IV) wherein $R^3$ is optionally substituted with at least one substituent selected from halogen, —CN, —NO$_2$, —OH, —OCF$_3$, —OCF$_2$H, —OCH$_2$F, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —OR$^{10}$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted heteroalkyl, substituted or unsubstituted cycloalkyl or substituted or unsubstituted heterocycloalkyl; wherein $R^8$ is H or substituted or unsubstituted alkyl; $R^9$ is substituted or unsubstituted alkyl, substituted or unsubstituted cycloalkyl, substituted or unsubstituted heterocycloalkyl, substituted or unsubstituted aryl or substituted or unsubstituted heteroaryl; and each $R^{10}$ is independently H, substituted or unsubstituted alkyl, substituted or unsubstituted cycloalkyl, substituted or unsubstituted heterocycloalkyl, substituted or unsubstituted aryl or substituted or unsubstituted heteroaryl, or two $R^{10}$ together with the atoms to which they are attached form a heterocycle. In one embodiment, $R^3$ is substituted with halogen, —CN, —NO$_2$, —OH, —OCF$_3$, —OCF$_2$H, —OCH$_2$F, —CF$_3$, —SH. In another embodiment is a compound of Formula (IV) wherein $R^3$ is substituted with —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —CO$_2$R$^{10}$, —C(=O)N(R$^{10}$)$_2$. In another embodiment, $R^9$ is an unsubstituted or substituted alkyl selected from methyl, ethyl, n-propyl, iso-propyl, n-butyl, iso-butyl or tert-butyl. In another embodiment, is a compound of Formula (IV) wherein $R^9$ is a substituted or unsubstituted cycloalkyl. In a further embodiment, the cycloalkyl is selected from cyclopropyl, cyclobutyl, cyclopentyl, cyclohexyl or cycloheptyl. In another embodiment $R^9$ is a substituted or unsubstituted heterocycloalkyl. In another embodiment, $R^9$ is a substituted or unsubstituted aryl. In a further embodiment, the aryl is a phenyl group. In a further embodiment, the aryl is a naphthalene group. In yet a further embodiment, $R^9$ is a substituted or unsubstituted heteroaryl. In yet another embodiment the heteroaryl is selected from pyrrole, furan, thiophene, pyrazole, imidazole, isoxazole, oxazole, isothiazole, thiazole, 1,2,3-triazole, 1,3,4-triazole, 1-oxa-2,3-diazole, 1-oxa-2,4-diazole, 1-oxa-2,5-diazole, 1-oxa-3,4-diazole, 1-thia-2,3-diazole, 1-thia-2,4-diazole, 1-thia-2,5-diazole, 1-thia-3,4-diazole, tetrazole, pyridine, pyridazine, pyrimidine, and pyrazine.

In one embodiment is a compound of Formula (IV) wherein Ar is phenyl. In another embodiment is a compound of Formula (IV) wherein X is hydroxy or alkoxy. In yet another embodiment is a compound of Formula (IV) wherein $R^3$ is optionally substituted cycloalkyl. In a further embodiment is a compound of Formula (IV) wherein $R^1$ is O-Ph.

In some embodiments, X is hydroxy, methoxy, ethoxy or butoxy. In other embodiments, X is F, Cl, Br or I. In yet other embodiments, X is methyl, ethyl, propyl, or the like.

In one aspect, provided herein are compounds of Formula (V) having the structure:

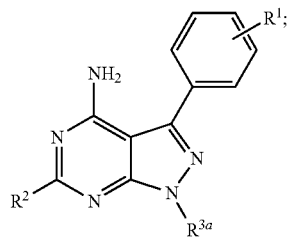

Formula (V)

wherein:
R$^1$ is L-Ar$^2$;
L is CR$^a$R$^a$, O, S, NR$^b$, N—OR$^b$, C=O, C=S, C=N—R$^b$, or C=N—OR$^b$;
R$^a$ is each independently H, C$_1$-C$_6$ alkyl, C$_1$-C$_6$ heteroalkyl, halogen, OR$^b$, or NR$^b$R$^b$;
R$^b$ is each independently H, C$_1$-C$_6$ alkyl, C$_2$-C$_6$ heteroalkyl, C$_3$-C$_6$ cycloalkyl, or C$_2$-C$_6$ heterocycloalkyl;
R$^2$ is H, OR$^b$, NR$^b$R$^b$, halogen, C$_1$-C$_6$ alkyl, C$_1$-C$_6$ heteroalkyl, C$_3$-C$_6$ cycloalkyl or C$_2$-C$_6$ heterocycloalkyl;
R$^{3a}$ is selected from

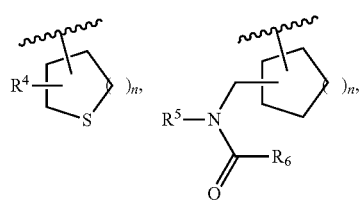

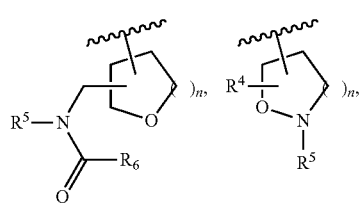

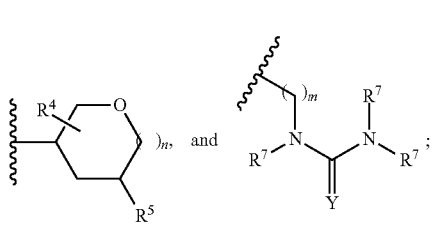

R$^4$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group;
R$^5$ is H, optionally substituted C$_1$-C$_6$ alkyl, —(C=O)C$_1$-C$_6$ alkyl, —(C=O)OR$^b$, —(C=O)NR$^b$R$^b$, —(C=O)SR$^b$, cycloalkyl, heterocycloalkyl, aryl, or heteroaryl;
R$^6$ is optionally substituted C$_1$-C$_6$ alkyl or NR$^S$;
R$^7$ is each independently hydrogen, optionally substituted C$_1$-C$_6$ alkyl, optionally substituted cycloalkyl, optionally substituted heterocycloalkyl, optionally substituted aryl, or optionally substituted heteroaryl;
Ar$^2$ is C$_5$-C$_{12}$ aryl or heteroaryl optionally substituted with halogen, hydroxy, amine, or C$_1$-C$_6$ alkyl;
n is an integer from 0 to 3;
m is an integer from 0 to 6;
Y is O, S or NR$^b$;
or a pharmaceutically acceptable salt, solvate, N-oxide, or prodrug thereof.

In one embodiment is a compound of Formula (V) wherein R$^{3a}$ is

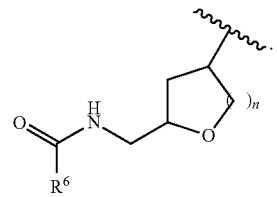

In another embodiment is a compound of Formula (V) wherein R$^{3a}$ is

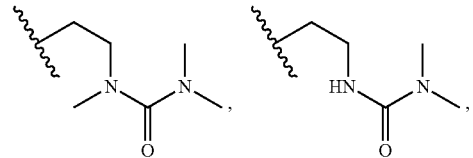

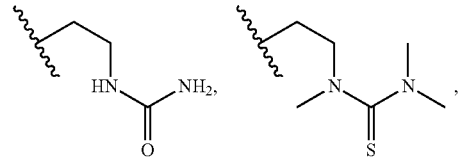

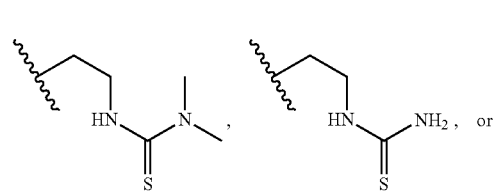

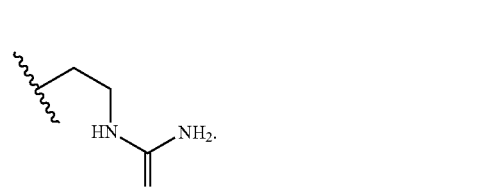

In yet another embodiment is a compound of Formula (V) wherein R$^5$ is H or CH$_3$. In a further embodiment is a compound of Formula (V) wherein R$^1$ is O-Ph.

In one aspect, provided herein are compounds of Formula (VI) having the structure:

Formula (VI)

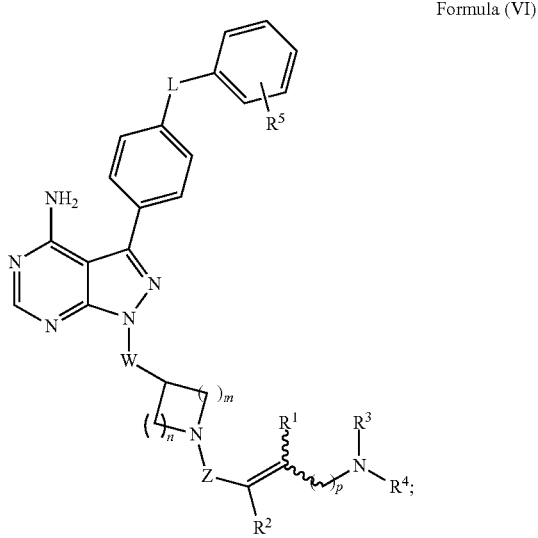

wherein:
L is CR$^a$R$^a$, O, S, NR$^b$, N—OR$^b$, C=O, C=S, C=N—R$^b$ or C=N—OR$^b$;
W is a bond or optionally substituted C$_1$-C$_3$ alkyl;
Z is C=O, SO$_2$ or SO;
R$^1$ and R$^2$ are each independently H or C$_1$-C$_3$ alkyl, wherein R$^1$ and R$^2$ have a cis or trans relationship; or R$^1$ and R$^2$ join together to form a bond;
n and p are each independently an integer from 0 to 3;
m is an integer from 1 to 3;
R$^3$ is H, substituted or unsubstituted C$_1$-C$_3$ alkyl, substituted or unsubstituted C$_3$-C$_6$ cycloalkyl, substituted or unsubstituted C$_1$-C$_6$ heteroalkyl, substituted or unsubstituted C$_2$-C$_6$ heterocycloalkyl, substituted or unsubstituted C$_6$-C$_{12}$ aryl, or substituted or unsubstituted C$_5$-C$_{11}$ heteroaryl;
R$^4$ is substituted or unsubstituted C$_3$-C$_6$ cycloalkyl, substituted or unsubstituted C$_2$-C$_6$ heterocycloalkyl, substituted or unsubstituted C$_6$-C$_{12}$ aryl, or substituted or unsubstituted C$_5$-C$_{11}$ heteroaryl;
R$^5$ is H, OH, OR$^b$, NR$^b$R$^b$, halogen, C$_1$-C$_6$ alkyl, C$_1$-C$_6$ heteroalkyl, C$_3$-C$_6$ cycloalkyl, or C$_2$-C$_6$ heterocycloalkyl;
R$^a$ is each independently H, C$_1$-C$_6$ alkyl, C$_1$-C$_6$ heteroalkyl, halogen, OR$^b$, or NR$^b$R$^b$;
R$^b$ is each independently H, C$_1$-C$_6$ alkyl, C$_2$-C$_6$ heteroalkyl, C$_3$-C$_6$ cycloalkyl, or C$_2$-C$_6$ heterocycloalkyl;
or a pharmaceutically acceptable salt, solvate, N-oxide, or prodrug thereof.

In one embodiment is a compound of Formula (VI) wherein L is CH$_2$ or C=O. In another embodiment is a compound of Formula (VI) wherein L is O. In another embodiment is a compound of Formula (VI) wherein W is a bond. In another embodiment is a compound of Formula (VI) wherein W is optionally substituted C$_1$-C$_3$ alkyl. In another embodiment is a compound of Formula (VI) wherein R$^1$ is H. In another embodiment is a compound of Formula (VI) wherein R$^2$ is H. In yet another embodiment is a compound of Formula (VI) wherein R$^1$ is H and R$^2$ is H. In another embodiment is a compound of Formula (VI) wherein R$^1$ and R$^2$ have a trans relationship. In another embodiment is a compound of Formula (VI) wherein R$^1$ and R$^2$ have a cis relationship. In another embodiment is a compound of Formula (VI) wherein m is 2. In another embodiment is a compound of Formula (VI) wherein n is 1. In another embodiment is a compound of Formula (VI) wherein n is 2. In another embodiment is a compound of Formula (VI) wherein n is 2 and m is 1. In another embodiment is a compound of Formula (VI) wherein n is 3 and m is 1. In another embodiment is a compound of Formula (VI) wherein n is 2 and m is 2. In another embodiment is a compound of Formula (VI) wherein p is 1. In another embodiment is a compound of Formula (VI) wherein R$^3$ is H. In another embodiment is a compound of Formula (VI) wherein R$^3$ is CH$_3$. In a further embodiment is a compound of Formula (VI) wherein R$^3$ is not substituted or unsubstituted C$_1$-C$_3$alkyl. In another embodiment is a compound of Formula (VI) wherein R$^3$ is H, methyl, ethyl, or isopropyl. In another embodiment is a compound of Formula (VI) wherein R$^4$ is substituted or unsubstituted C$_3$-C$_6$ cycloalkyl. In a further embodiment is a compound of Formula (VI) wherein R$^4$ is cyclopropyl, cyclobutyl, cyclopentyl or cyclohexyl. In another embodiment is a compound of Formula (VI) wherein R$^4$ is substituted or unsubstituted C$_2$-C$_6$ heterocycloalkyl. In a further embodiment is a compound of Formula (VI) wherein R$^4$ is tetrahydropyran, tetrahydrofuran, oxetane, or

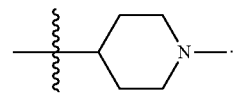

In another embodiment is a compound of Formula (VI) wherein R$^4$ is substituted or unsubstituted C$_5$-C$_{11}$ heteroaryl. In a further embodiment is a compound of Formula (VI) wherein R$^4$ is pyridyl.

In another embodiment is a compound of Formula (VI) wherein L is O, W is a bond, R$^1$ is H, R$^2$ is H, p is 1, Z is C=O, R$^3$ is H, and R$^4$ is substituted or unsubstituted C$_3$-C$_6$ cycloalkyl. In another embodiment is a compound of Formula (VI) wherein L is O, W is a bond, R$^1$ is H, R$^2$ is H, p is 1, Z is C=O, R$^3$ is H, and R$^4$ is substituted or unsubstituted C$_2$-C$_6$ heterocycloalkyl. In another embodiment is a compound of Formula (VI) wherein L is O, W is a bond, R$^1$ is H, R$^2$ is H, p is 1, Z is C=O, R$^3$ is methyl, and R$^4$ is substituted or unsubstituted C$_3$-C$_6$ cycloalkyl. In another embodiment is a compound of Formula (VI) wherein L is O, W is a bond, R$^1$ is H, R$^2$ is H, p is 1, Z is C=O, R$^3$ is methyl, and R$^4$ is substituted or unsubstituted C$_2$-C$_6$ heterocycloalkyl. In another embodiment is a compound of Formula (VI) wherein L is O, W is a bond, R$^1$ is H, R$^2$ is H, p is 1, Z is C=O, R$^3$ is ethyl, and R$^4$ is substituted or unsubstituted C$_3$-C$_6$ cycloalkyl. In another embodiment is a compound of Formula (VI) wherein L is O, W is a bond, R$^1$ is H, R$^2$ is H, p is 1, Z is C=O, R$^3$ is ethyl, and R$^4$ is substituted or unsubstituted C$_2$-C$_6$ heterocycloalkyl. In another embodiment is a compound of Formula (VI) wherein L is O, W is a bond, R$^1$ is H, R$^2$ is H, p is 1, Z is C=O, R$^3$ is H, and R$^4$ is substituted or unsubstituted C$_6$-C$_{12}$ aryl. In another embodiment is a compound of Formula (VI) wherein L is O, W is a bond, R$^1$ is H, R$^2$ is H, p is 1, Z is C=O, R$^3$ is H, and R$^4$ is substituted or unsubstituted C$_5$-C$_{11}$ heteroaryl. In another embodiment is a compound of Formula (VI) wherein L is O, W is a bond, R$^1$ is H, R$^2$ is H, p is 1, Z is C=O, R$^3$ is methyl, and R$^4$ is substituted or unsubstituted C$_6$-C$_{12}$ aryl. In another embodiment is a compound of Formula (VI) wherein L is O, W is a bond, R$^1$ is H, R$^2$ is H, p is 1, Z is C=O, R$^3$ is methyl, and R$^4$ is substituted or unsubstituted C$_5$-C$_{11}$ heteroaryl.

In one aspect, provided herein are compounds of Formula (VIA) having the structure:

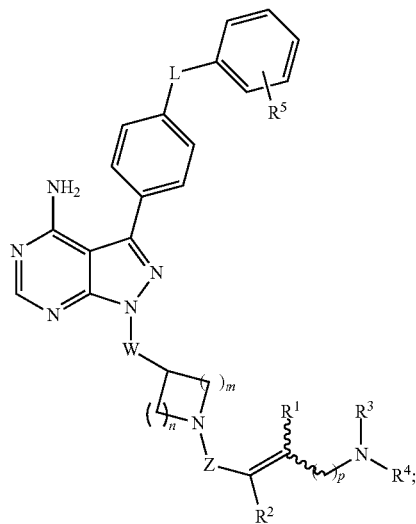

Formula (VIA)

wherein:
L is $CR^aR^a$, O, S, $NR^b$, N—$OR^b$, C=O, C=S, C=N—$R^b$ or C=N—$OR^b$;
W is a bond or optionally substituted $C_1$-$C_3$ alkyl;
Z is C=O, $SO_2$ or SO;
$R^1$ and $R^2$ are each independently H or $C_1$-$C_3$ alkyl, wherein $R^1$ and $R^2$ have a cis or trans relationship; or $R^1$ and $R^2$ join together to form a bond;
n and p are each independently an integer from 0 to 3;
m is an integer from 1 to 3;
$R^3$ is H, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;
$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;
$R^5$ is H, OH, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;
$R^a$ is each independently H, $C_1$-$C_6$ alkyl, $C_1$-$C_6$ heteroalkyl, halogen, $OR^b$, or $NR^bR^b$;
$R^b$ is each independently H, $C_1$-$C_6$ alkyl, $C_2$-$C_6$ heteroalkyl, $C_3$-$C_6$ cycloalkyl or $C_2$-$C_6$ heterocycloalkyl;
or a pharmaceutically acceptable salt, solvate, N-oxide, or prodrug thereof.

In one embodiment is a compound of Formula (VIA) wherein L is $CH_2$ or C=O. In another embodiment is a compound of Formula (VIA) wherein L is O. In another embodiment is a compound of Formula (VIA) wherein W is a bond. In another embodiment is a compound of Formula (VIA) wherein W is optionally substituted $C_1$-$C_3$ alkyl. In another embodiment is a compound of Formula (VIA) wherein $R^1$ is H. In another embodiment is a compound of Formula (VIA) wherein $R^2$ is H. In yet another embodiment is a compound of Formula (VIA) wherein $R^1$ is H and $R^2$ is H. In another embodiment is a compound of Formula (VIA) wherein $R^1$ and $R^2$ have a trans relationship. In another embodiment is a compound of Formula (VIA) wherein $R^1$ and $R^2$ have a cis relationship. In another embodiment is a compound of Formula (VIA) wherein m is 2. In another embodiment is a compound of Formula (VIA) wherein n is 1. In another embodiment is a compound of Formula (VIA) wherein n is 2. In another embodiment is a compound of Formula (VIA) wherein n is 2 and m is 1. In another embodiment is a compound of Formula (VIA) wherein n is 3 and m is 1. In another embodiment is a compound of Formula (VIA) wherein n is 2 and m is 2. In another embodiment is a compound of Formula (VIA) wherein p is 1. In another embodiment is a compound of Formula (VIA) wherein $R^3$ is H. In another embodiment is a compound of Formula (VIA) wherein $R^3$ and $R^4$ are each independently substituted or unsubstituted $C_3$-$C_6$ cycloalkyl.

In another embodiment is a compound of Formula (VIA) wherein L is O, W is a bond, $R^1$ is H, $R^2$ is H, p is 1, Z is C=O, $R^3$ is H and $R^4$ is substituted or unsubstituted $C_3$-$C_6$ cycloalkyl. In another embodiment is a compound of Formula (VIA) wherein L is O, W is a bond, $R^1$ is H, $R^2$ is H, p is 1, Z is C=O, $R^3$ is H and $R^4$ is substituted or unsubstituted $C_2$-$C_6$ heterocycloalkyl. In another embodiment is a compound of Formula (VIA) wherein L is O, W is a bond, $R^1$ is H, $R^2$ is H, p is 1,
Z is C=O, $R^3$ is H and $R^4$ is substituted or unsubstituted $C_6$-$C_{12}$ aryl. In another embodiment is a compound of Formula (VIA) wherein L is O, W is a bond, $R^1$ is H, $R^2$ is H, p is 1, Z is C=O, $R^3$ is H and $R^4$ is substituted or unsubstituted $C_5$-$C_{11}$ heteroaryl.

In another embodiment is a compound of Formula (VIA) wherein L is O, W is a bond, $R^1$ is H, $R^2$ is H, p is 1, Z is C=O, $R^3$ is substituted or unsubstituted $C_3$-$C_6$ cycloalkyl and $R^4$ is substituted or unsubstituted $C_3$-$C_6$ cycloalkyl. In another embodiment is a compound of Formula (VIA) wherein L is O, W is a bond, $R^1$ is H, $R^2$ is H, p is 1, Z is C=O, $R^3$ is substituted or unsubstituted $C_3$-$C_6$ cycloalkyl and $R^4$ is substituted or unsubstituted $C_2$-$C_6$ heterocycloalkyl. In another embodiment is a compound of Formula (VIA) wherein L is O, W is a bond, $R^1$ is H, $R^2$ is H, p is 1, Z is C=O, $R^3$ is substituted or unsubstituted $C_3$-$C_6$ cycloalkyl and $R^4$ is substituted or unsubstituted $C_6$-$C_{12}$ aryl. In another embodiment is a compound of Formula (VIA) wherein L is O, W is a bond, $R^1$ is H, $R^2$ is H, p is 1, Z is C=O, $R^3$ is substituted or unsubstituted $C_3$-$C_6$ cycloalkyl and $R^4$ is substituted or unsubstituted $C_5$-$C_{11}$ heteroaryl.

In one aspect, provided herein are compounds of Formula (VIB) having the structure:

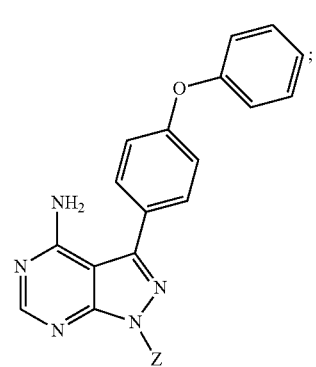

Formula (VIB)

wherein:

Z is selected from

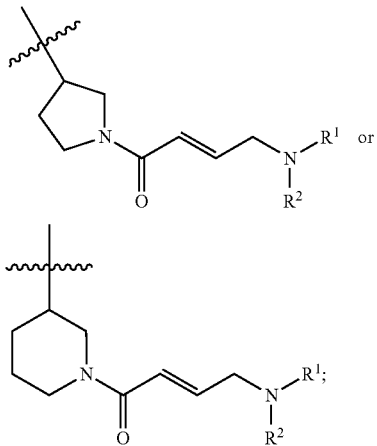

$R^1$ is $C_3$-$C_6$ cycloalkyl, pyridine, tetrahydrofuran, tetrahydropyran, or

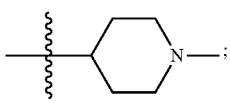 [SMILES: *C1CCN(C)CC1 ; "."]

$R^2$ is H or $CH_3$;

or a pharmaceutically acceptable salt, solvate, N-oxide, or prodrug thereof.

In some embodiments is a compound of Formula (VIB) wherein Z is

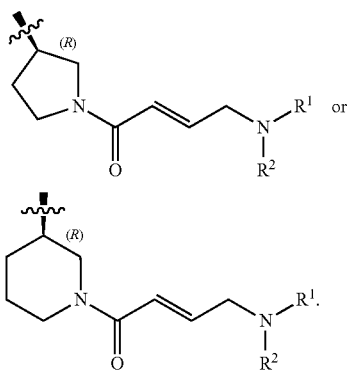

In one embodiment is a compound of Formula (VIB) wherein $R^1$ is $C_3$-$C_6$ cycloalkyl and $R^2$ is H. In another embodiment is a compound of Formula (VIB) wherein $R^1$ is $C_3$-$C_6$ cycloalkyl and $R^2$ is $CH_3$. In another embodiment is a compound of Formula (VIB) wherein $R^1$ is pyridine and $R^2$ is H. In another embodiment is a compound of Formula (VIB) wherein $R^1$ is pyridine and $R^2$ is $CH_3$. In another embodiment is a compound of Formula (VIB) wherein $R^1$ is tetrahydrofuran, tetrahydropyran or

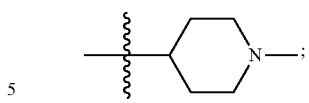

and $R^2$ is H. In yet another embodiment is a compound of Formula (VIB) wherein $R^1$ is tetrahydrofuran, tetrahydropyran or

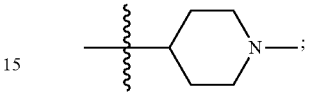

and $R^2$ is $CH_3$. In another embodiment is a compound of Formula (VIB) wherein $R^1$ is tetrahydrofuran or tetrahydropyran; and $R^2$ is H. In a further embodiment is a compound of Formula (VIB) wherein $R^1$ is tetrahydrofuran or tetrahydropyran; and $R^2$ is $CH_3$.

In certain aspect, provided here are compounds of Formula (IA) having the structure:

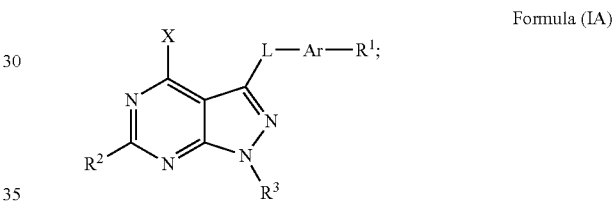

Formula (IA)

wherein:

L is each independently $CR^aR^a$, O, S, $NR^b$, N—$OR^b$, C=O, C=S, C=N—$R^b$, or C=N—$OR^b$;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;

$R^1$ is L-$Ar^2$, $OR^b$, or $NR^bR^b$;

$R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl;

$R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl;

Ar and $Ar^2$ are each independently $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl;

X is hydrogen, hydroxy, alkoxy, thiol, halogen or $C_1$-$C_6$ alkyl;

or a pharmaceutically acceptable salt, solvate, N-oxide, or prodrug thereof.

In one aspect, provided herein are compounds of Formula (VII) having the structure:

Formula (VII)

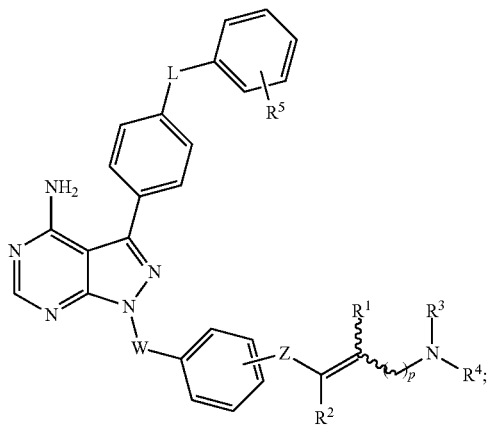

wherein:
L is CR$^a$R$^a$, O, S, NR$^b$, N—OR$^b$, C=O, C=S, C=N—R$^b$ or C=N—OR$^b$;
W is a bond or optionally substituted C$_1$-C$_3$ alkyl;
Z is NR$^c$C=O, SO$_2$ or SO;
R$^1$ and R$^2$ are each independently H or C$_1$-C$_3$ alkyl, wherein R$^1$ and R$^2$ have a cis or trans relationship; or R$^1$ and R$^2$ join together to form a bond;
p is an integer from 0 to 3;
R$^3$ is H, substituted or unsubstituted C$_1$-C$_3$ alkyl, substituted or unsubstituted C$_3$-C$_6$ cycloalkyl, substituted or unsubstituted C$_1$-C$_6$ heteroalkyl, substituted or unsubstituted C$_2$-C$_6$ heterocycloalkyl, substituted or unsubstituted C$_6$-C$_{12}$ aryl, or substituted or unsubstituted C$_5$-C$_{11}$ heteroaryl;
R$^4$ is substituted or unsubstituted C$_3$-C$_6$ cycloalkyl, substituted or unsubstituted C$_2$-C$_6$ heterocycloalkyl, substituted or unsubstituted C$_6$-C$_{12}$ aryl, or substituted or unsubstituted C$_5$-C$_{11}$ heteroaryl;
R$^5$ is H, OH, OR$^b$, NR$^b$R$^b$, halogen, C$_1$-C$_6$ alkyl, C$_1$-C$_6$ heteroalkyl, C$_3$-C$_6$ cycloalkyl or C$_2$-C$_6$ heterocycloalkyl;
R$^a$ is each independently H, C$_1$-C$_6$ alkyl, C$_1$-C$_6$ heteroalkyl, halogen, OR$^b$, or NR$^b$R$^b$;
R$^b$ is each independently H, C$_1$-C$_6$ alkyl, C$_2$-C$_6$ heteroalkyl, C$_3$-C$_6$ cycloalkyl or C$_2$-C$_6$ heterocycloalkyl;
R$^c$ is H or C$_1$-C$_6$ alkyl;
or a pharmaceutically acceptable salt, solvate, N-oxide, or prodrug thereof.

In one embodiment is a compound of Formula (VII) wherein L is CH$_2$ or C=O. In another embodiment is a compound of Formula (VII) wherein L is O. In another embodiment is a compound of Formula (VII) wherein W is a bond. In another embodiment is a compound of Formula (VII) wherein W is optionally substituted C$_1$-C$_3$ alkyl. In another embodiment is a compound of Formula (VII) wherein R$^1$ is H. In another embodiment is a compound of Formula (VII) wherein R$^2$ is H. In yet another embodiment is a compound of Formula (VII) wherein R$^1$ is H and R$^2$ is H. In another embodiment is a compound of Formula (VII) wherein R$^1$ and R$^2$ have a trans relationship. In another embodiment is a compound of Formula (VII) wherein R$^1$ and R$^2$ have a cis relationship. In another embodiment is a compound of Formula (VII) wherein p is 1. In a further embodiment is a compound of Formula (VII) wherein R$^3$ is not substituted or unsubstituted C$_1$-C$_3$alkyl. In another embodiment is a compound of Formula (VII) wherein R$^3$ is H, methyl, ethyl, or isopropyl. In another embodiment is a compound of Formula (VII) wherein R$^3$ is H. In another embodiment is a compound of Formula (VII) wherein R$^3$ is CH$_3$. In another embodiment is a compound of Formula (VII) wherein R$^4$ is substituted or unsubstituted C$_3$-C$_6$ cycloalkyl. In a further embodiment is a compound of Formula (VII) wherein R$^4$ is cyclopropyl, cyclobutyl, cyclopentyl or cyclohexyl. In another embodiment is a compound of Formula (VII) wherein R$^4$ is substituted or unsubstituted C$_2$-C$_6$ heterocycloalkyl. In a further embodiment is a compound of Formula (VII) wherein R$^4$ is tetrahydropyran, tetrahydrofuran, oxetane, or

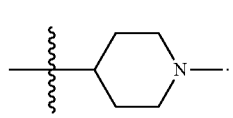

In another embodiment is a compound of Formula (VII) wherein R$^4$ is substituted or unsubstituted C$_5$-C$_{11}$ heteroaryl. In a further embodiment is a compound of Formula (VII) wherein R$^4$ is pyridyl.

In another embodiment is a compound of Formula (VII) wherein L is O, W is a bond, R$^1$ is H, R$^2$ is H, p is 1, Z is C=O, R$^3$ is H, and R$^4$ is substituted or unsubstituted C$_3$-C$_6$ cycloalkyl. In another embodiment is a compound of Formula (VII) wherein L is O, W is a bond, R$^1$ is H, R$^2$ is H, p is 1, Z is C=O, R$^3$ is methyl, and R$^4$ is substituted or unsubstituted C$_3$-C$_6$ cycloalkyl. In another embodiment is a compound of Formula (VII) wherein L is O, W is a bond, R$^1$ is H, R$^2$ is H, p is 1, Z is C=O, R$^3$ is ethyl, and R$^4$ is substituted or unsubstituted C$_3$-C$_6$ cycloalkyl. In another embodiment is a compound of Formula (VII) wherein L is O, W is a bond, R$^1$ is H, R$^2$ is H, p is 1, Z is C=O, R$^3$ is H, and R$^4$ is substituted or unsubstituted C$_2$-C$_6$ heterocycloalkyl. In another embodiment is a compound of Formula (VII) wherein L is O, W is a bond, R$^1$ is H, R$^2$ is H, p is 1, Z is C=O, R$^3$ is methyl, and R$^4$ is substituted or unsubstituted C$_2$-C$_6$ heterocycloalkyl. In another embodiment is a compound of Formula (VII) wherein L is O, W is a bond, R$^1$ is H, R$^2$ is H, p is 1, Z is C=O, R$^3$ is ethyl, and R$^4$ is substituted or unsubstituted C$_2$-C$_6$ heterocycloalkyl. In another embodiment is a compound of Formula (VII) wherein L is O, W is a bond, R$^1$ is H, R$^2$ is H, p is 1, Z is C=O, R$^3$ is H, and R$^4$ is substituted or unsubstituted C$_6$-C$_{12}$ aryl. In another embodiment is a compound of Formula (VII) wherein L is O, W is a bond, R$^1$ is H, R$^2$ is H, p is 1, Z is C=O, R$^3$ is methyl, and R$^4$ is substituted or unsubstituted C$_6$-C$_{12}$ aryl. In another embodiment is a compound of Formula (VII) wherein L is O, W is a bond, R$^1$ is H, R$^2$ is H, p is 1, Z is C=O, R$^3$ is ethyl, and R$^4$ is substituted or unsubstituted C$_6$-C$_{12}$ aryl. In another embodiment is a compound of Formula (VII) wherein L is O, W is a bond, R$^1$ is H, R$^2$ is H, p is 1, Z is C=O, R$^3$ is H, and R$^4$ is substituted or unsubstituted C$_5$-C$_{11}$ heteroaryl. In another embodiment is a compound of Formula (VII) wherein L is O, W is a bond, R$^1$ is H, R$^2$ is H, p is 1, Z is C=O, R$^3$ is methyl, and R$^4$ is substituted or unsubstituted C$_5$-C$_{11}$ heteroaryl. In another embodiment is a compound of Formula (VII) wherein L is O, W is a bond, R$^1$ is H, R$^2$ is H, p is 1, Z is C=O, R$^3$ is ethyl, and R$^4$ is substituted or unsubstituted C$_5$-C$_{11}$ heteroaryl.

In one aspect, provided herein are compounds of Formula (VIII) having the structure:

Formula (VIII)

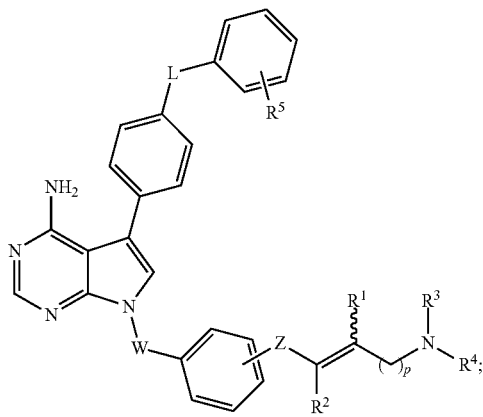

wherein:
L is $CR^aR^a$, O, S, $NR^b$, N—$OR^b$, C=O, C=S, C=N—$R^b$ or C=N—$OR^b$;
W is a bond or optionally substituted $C_1$-$C_3$ alkyl;
Z is $NR^cC$=O, $SO_2$ or SO;
$R^1$ and $R^2$ are each independently H or $C_1$-$C_3$ alkyl, wherein $R^1$ and $R^2$ have a cis or trans relationship; or $R^1$ and $R^2$ join together to form a bond;
p is an integer from 0 to 3;
$R^3$ is H, substituted or unsubstituted $C_1$-$C_3$ alkyl, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;
$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;
$R^5$ is H, OH, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;
$R^a$ is each independently H, $C_1$-$C_6$ alkyl, $C_1$-$C_6$ heteroalkyl, halogen, $OR^b$, or $NR^bR^b$;
$R^b$ is each independently H, $C_1$-$C_6$ alkyl, $C_2$-$C_6$ heteroalkyl, $C_3$-$C_6$ cycloalkyl or $C_2$-$C_6$ heterocycloalkyl;
$R^c$ is H or $C_1$-$C_6$ alkyl;
or a pharmaceutically acceptable salt, solvate, N-oxide, or prodrug thereof.

In one embodiment is a compound of Formula (VIII) wherein L is $CH_2$ or C=O. In another embodiment is a compound of Formula (VIII) wherein L is O. In another embodiment is a compound of Formula (VIII) wherein W is a bond. In another embodiment is a compound of Formula (VIII) wherein W is optionally substituted $C_1$-$C_3$ alkyl. In another embodiment is a compound of Formula (VIII) wherein $R^1$ is H. In another embodiment is a compound of Formula (VIII) wherein $R^2$ is H. In yet another embodiment is a compound of Formula (VIII) wherein $R^1$ is H and $R^2$ is H. In another embodiment is a compound of Formula (VIII) wherein $R^1$ and $R^2$ have a trans relationship. In another embodiment is a compound of Formula (VIII) wherein $R^1$ and $R^2$ have a cis relationship. In another embodiment is a compound of Formula (VIII) wherein p is 1. In a further embodiment is a compound of Formula (VIII) wherein $R^3$ is not substituted or unsubstituted $C_1$-$C_3$ alkyl. In another embodiment is a compound of Formula (VIII) wherein $R^3$ is H, methyl, ethyl, or isopropyl. In another embodiment is a compound of Formula (VIII) wherein $R^3$ is H. In another embodiment is a compound of Formula (VIII) wherein $R^3$ is $CH_3$. In another embodiment is a compound of Formula (VIII) wherein $R^4$ is substituted or unsubstituted $C_3$-$C_6$ cycloalkyl. In a further embodiment is a compound of Formula (VIII) wherein $R^4$ is cyclopropyl, cyclobutyl, cyclopentyl or cyclohexyl. In another embodiment is a compound of Formula (VIII) wherein $R^4$ is substituted or unsubstituted $C_2$-$C_6$ heterocycloalkyl. In a further embodiment is a compound of Formula (VIII) wherein $R^4$ is tetrahydropyran, tetrahydrofuran, oxetane, or

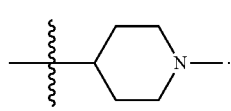

In another embodiment is a compound of Formula (VIII) wherein $R^4$ is substituted or unsubstituted $C_5$-$C_{11}$ heteroaryl. In a further embodiment is a compound of Formula (VIII) wherein $R^4$ is pyridyl.

In another embodiment is a compound of Formula (VIII) wherein L is O, W is a bond, $R^1$ is H, $R^2$ is H, p is 1, Z is C=O, $R^3$ is H, and $R^4$ is substituted or unsubstituted $C_3$-$C_6$ cycloalkyl. In another embodiment is a compound of Formula (VIII) wherein L is O, W is a bond, $R^1$ is H, $R^2$ is H, p is 1, Z is C=O, $R^3$ is methyl, and $R^4$ is substituted or unsubstituted $C_3$-$C_6$ cycloalkyl. In another embodiment is a compound of Formula (VIII) wherein L is O, W is a bond, $R^1$ is H, $R^2$ is H, p is 1, Z is C=O, $R^3$ is ethyl, and $R^4$ is substituted or unsubstituted $C_3$-$C_6$ cycloalkyl. In another embodiment is a compound of Formula (VIII) wherein L is O, W is a bond, $R^1$ is H, $R^2$ is H, p is 1, Z is C=O, $R^3$ is H, and $R^4$ is substituted or unsubstituted $C_2$-$C_6$ heterocycloalkyl. In another embodiment is a compound of Formula (VIII) wherein L is O, W is a bond, $R^1$ is H, $R^2$ is H, p is 1, Z is C=O, $R^3$ is methyl, and $R^4$ is substituted or unsubstituted $C_2$-$C_6$ heterocycloalkyl. In another embodiment is a compound of Formula (VIII) wherein L is O, W is a bond, $R^1$ is H, $R^2$ is H, p is 1, Z is C=O, $R^3$ is ethyl, and $R^4$ is substituted or unsubstituted $C_2$-$C_6$ heterocycloalkyl. In another embodiment is a compound of Formula (VIII) wherein L is O, W is a bond, $R^1$ is H, $R^2$ is H, p is 1, Z is C=O, $R^3$ is H, and $R^4$ is substituted or unsubstituted $C_6$-$C_{12}$ aryl. In another embodiment is a compound of Formula (VIII) wherein L is O, W is a bond, $R^1$ is H, $R^2$ is H, p is 1, Z is C=O, $R^3$ is methyl, and $R^4$ is substituted or unsubstituted $C_6$-$C_{12}$ aryl. In another embodiment is a compound of Formula (VIII) wherein L is O, W is a bond, $R^1$ is H, $R^2$ is H, p is 1, Z is C=O, $R^3$ is ethyl, and $R^4$ is substituted or unsubstituted $C_6$-$C_{12}$ aryl. In another embodiment is a compound of Formula (VIII) wherein L is O, W is a bond, $R^1$ is H, $R^2$ is H, p is 1, Z is C=O, $R^3$ is H, and $R^4$ is substituted or unsubstituted $C_5$-$C_{11}$ heteroaryl. In another embodiment is a compound of Formula (VIII) wherein L is O, W is a bond, $R^1$ is H, $R^2$ is H, p is 1, Z is C=O, $R^3$ is methyl, and $R^4$ is substituted or unsubstituted $C_5$-$C_{11}$ heteroaryl. In another embodiment is a compound of Formula (VIII) wherein L is O, W is a bond, $R^1$ is H, $R^2$ is H, p is 1, Z is C=O, $R^3$ is ethyl, and $R^4$ is substituted or unsubstituted $C_5$-$C_{11}$ heteroaryl.

In one aspect, provided herein are compounds of Formula (IX) having the structure:

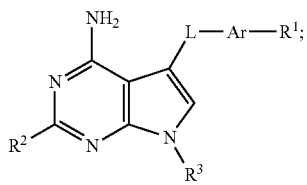

Formula (IX)

wherein:
- L is each independently $CR^aR^a$, O, S, $NR^b$, N—$OR^b$, C=O, C=S, C=N—$R^b$, or C=N—$OR^b$;
- $R^a$ is each independently H, $C_1$-$C_6$ alkyl, $C_1$-$C_6$ heteroalkyl, halogen, $OR^b$, or $NR^bR^b$;
- $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
- $R^1$ is L-$Ar^2$, $OR^b$, or $NR^bR^b$;
- $R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl;
- $R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl;
- Ar and $Ar^2$ are each independently $C_5$-$C_{12}$ aryl or $C_5$-$C_{11}$ heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl;
- or a pharmaceutically acceptable salt, solvate, N-oxide, or prodrug thereof.

In one embodiment is a compound of Formula (IX) wherein L is $CH_2$ or C=O. In another embodiment is a compound of Formula (IX) wherein Ar is phenyl. In yet another embodiment is a compound of Formula (IX) wherein $R^2$ is H and $R^3$ is optionally substituted cycloalkyl. In a further embodiment is a compound of Formula (IX) wherein $R^1$ is O-Ph.

For any and all of the embodiments, substituents are selected from among from a subset of the listed alternatives. For example, in some embodiments, $R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl; wherein $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, $R^2$ is H, OH, $NH_2$, halogen or $C_1$-$C_6$ alkyl. In some embodiments, $R^2$ is F, Cl, Br or I. In other embodiments, $R^2$ is methyl, ethyl, n-propyl, iso-propyl, n-butyl, sec-butyl, iso-butyl, n-pentyl, or hexyl. In yet other embodiments, $R^2$ is H, OH, or $NH_2$. In other embodiments, $R^2$ is H.

In some embodiments, $R^1$ is O—$Ar^2$ wherein $Ar^2$ is $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl; and $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, $R^1$ is O—$Ar^2$ wherein $Ar^2$ is $C_5$-$C_{12}$ aryl or heteroaryl optionally substituted with halogen, hydroxy, amine, or $C_1$-$C_6$ alkyl. In other embodiments, $Ar^2$ is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In other embodiments, $Ar^2$ is phenyl, pyridinyl, furanyl, thiophenyl or quinolinyl. In certain embodiments, $Ar^2$ is phenyl or pyridinyl.

In some embodiments, $R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl. In other embodiments, $R^3$ is methyl, ethyl, n-propyl, iso-propyl, n-butyl, iso-butyl, and tert-butyl. In yet other embodiments, $R^3$ is —C=O-Me, —(C=O)Et, or —(C=O)Bu. In other embodiments, $R^3$ is —COOH, —COOMe, —COOEt, —COOPr or —COOBu. In yet other embodiments, $R^3$ is —$CONH_2$, —CONHMe, —CONHEt or —CONHBu. In other embodiments, $R^3$ is —C=O—SMe, —(C=O)SEt or —C=O—SPr. In yet other embodiments, $R^3$ is optionally substituted cyclobutyl, cyclopentyl, cyclohexyl, or the like. In yet other embodiments, $R^3$ is optionally substituted azetidinyl, pyrrolidinyl, piperidinyl or the like. In yet other embodiments, $R^3$ is optionally substituted phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like.

In another embodiment is a compound of Formula (IX) wherein $R^3$ is optionally substituted with at least one substituent selected from halogen, —CN, —$NO_2$, —OH, —$OCF_3$, —$OCF_2$H, —$OCH_2$F, —$CF_3$, —$SR^8$, —S(=O)$R^9$, —S(=O)$_2R^9$, —$NR^{10}$S(=O)$_2R^9$, —S(=O)$_2$N($R^{10}$)$_2$, —$OR^{10}$, —C(=O)$R^9$, —OC(=O)$R^9$, —$CO_2R^{10}$, —N($R^{10}$)$_2$, —C(=O)N($R^{10}$)$_2$, —$NR^{10}$C(=O)$R^{10}$, —N$R^{10}$C(=O)$OR^{10}$, —$NR^{10}$C(=O)N($R^{10}$)$_2$, substituted or unsubstituted alkyl, substituted or unsubstituted heteroalkyl, substituted or unsubstituted cycloalkyl or substituted or unsubstituted heterocycloalkyl; wherein $R^8$ is H or substituted or unsubstituted alkyl; $R^9$ is substituted or unsubstituted alkyl, substituted or unsubstituted cycloalkyl, substituted or unsubstituted heterocycloalkyl, substituted or unsubstituted aryl or substituted or unsubstituted heteroaryl; and each $R^{10}$ is independently H, substituted or unsubstituted alkyl, substituted or unsubstituted cycloalkyl, substituted or unsubstituted heterocycloalkyl, substituted or unsubstituted aryl or substituted or unsubstituted heteroaryl, or two $R^{10}$ together with the atoms to which they are attached form a heterocycle. In one embodiment, $R^3$ is substituted with halogen, —CN, —$NO_2$, —OH, —$OCF_3$, —$OCF_2$H, —$OCH_2$F, —$CF_3$, —SH. In another embodiment is a compound of Formula (IX) wherein $R^3$ is substituted with —S(=O)$R^9$, —S(=O)$_2R^9$, —$NR^{10}$S(=O)$_2R^9$, —S(=O)$_2$N($R^{10}$)$_2$, —C(=O)$R^9$, —$CO_2R^{10}$, —C(=O)N($R^{10}$)$_2$. In another embodiment, $R^9$ is an unsubstituted or substituted alkyl selected from methyl, ethyl, n-propyl, iso-propyl, n-butyl, iso-butyl or tert-butyl. In another embodiment, is a compound of Formula (IX) wherein $R^9$ is a substituted or unsubstituted cycloalkyl. In a further embodiment, the cycloalkyl is selected from cyclopropyl, cyclobutyl, cyclopentyl, cyclohexyl or cycloheptyl. In another embodiment $R^9$ is a substituted or unsubstituted heterocycloalkyl. In another embodiment, $R^9$ is a substituted or unsubstituted aryl. In a further embodiment, the aryl is a phenyl group. In a further embodiment, the aryl is a naphthalene group. In yet a further embodiment, $R^9$ is a substituted or unsubstituted heteroaryl. In yet another embodiment the heteroaryl is selected from pyrrole, furan, thiophene, pyrazole, imidazole, isoxazole, oxazole, isothiazole, thiazole, 1,2,3-triazole, 1,3,4-triazole, 1-oxa-2,3-diazole, 1-oxa-2,4-diazole, 1-oxa-2,5-diazole, 1-oxa-3,4-diazole, 1-thia-2,3-diazole, 1-thia-2,4-diazole, 1-thia-2,5-diazole, 1-thia-3,4-diazole, tetrazole, pyridine, pyridazine, pyrimidine, and pyrazine.

In some embodiments, L is each independently $CR^aR^a$, O, S, $NR^b$, C=O, C=S, C=N—$R^b$ or C=N—$OR^b$ wherein $R^a$ is each independently H, $C_1$-$C_6$ alkyl, $C_1$-$C_6$ heteroalkyl, halogen, $OR^b$, or $NR^bR^b$; and $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, L is each independently $CR^aR^a$, O, S, $NR^b$, C=O, C=S, C=N—$R^b$ or C=N—$OR^b$ wherein $R^a$ is each independently H, $C_1$-$C_6$ alkyl, or halogen; and $R^b$ is each independently H or $C_1$-$C_6$ alkyl. In other embodiments, L is $CH_2$, O, S, NH, C=O, C=S, C=N—H or C=N—OH. In other embodiments, L is —CH(Me) or —CH(Cl). In yet other embodiments, L is C=N-Me, C=N—OMe, C=N-Et, C=N—OEt, C=N—$^n$-Pr, or C=N—O$^n$Pr.

In some embodiments, Ar is $C_5$-$C_{12}$ aryl or $C_5$-$C_{11}$ heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl; and $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, Ar is $C_5$-$C_{12}$ aryl or heteroaryl optionally substituted with halogen, hydroxy, amine, or $C_1$-$C_6$ alkyl. In other embodiments, Ar is phenyl, pyridinyl, pyridazinyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In certain embodiments, Ar is phenyl, or pyridinyl optionally substituted with amine or hydroxy. In certain embodiments, Ar is phenyl, or pyridinyl optionally substituted with methyl, ethyl, propyl, or the like.

In one aspect, provided herein are compounds of Formula (X) having the structure:

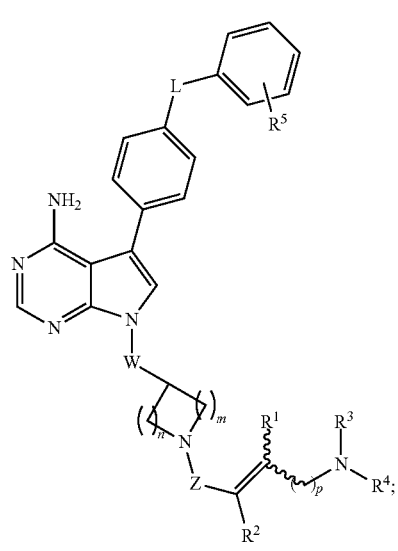

Formula (X)

wherein:
L is $CR^aR^a$, O, S, $NR^b$, N—$OR^b$, C=O, C=S, C=N—$R^b$ or C=N—$OR^b$;
W is a bond or optionally substituted $C_1$-$C_3$ alkyl;
Z is C=O, $SO_2$ or SO;
$R^1$ and $R^2$ are each independently H or $C_1$-$C_3$ alkyl, wherein $R^1$ and $R^2$ have a cis or trans relationship; or $R^1$ and $R^2$ join together to form a bond;
n and p are each independently an integer from 0 to 3;
m is an integer from 1 to 3;
$R^3$ is H, substituted or unsubstituted $C_1$-$C_3$ alkyl, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;
$R^5$ is H, OH, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;
$R^a$ is each independently H, $C_1$-$C_6$ alkyl, $C_1$-$C_6$ heteroalkyl, halogen, $OR^b$, or $NR^bR^b$;
$R^b$ is each independently H, $C_1$-$C_6$ alkyl, $C_2$-$C_6$ heteroalkyl, $C_3$-$C_6$ cycloalkyl or $C_2$-$C_6$ heterocycloalkyl;
or a pharmaceutically acceptable salt, solvate, N-oxide, or prodrug thereof.

In one embodiment is a compound of Formula (X) wherein L is $CH_2$ or C=O. In another embodiment is a compound of Formula (X) wherein L is O. In another embodiment is a compound of Formula (X) wherein W is a bond. In another embodiment is a compound of Formula (X) wherein W is optionally substituted $C_1$-$C_3$ alkyl. In another embodiment is a compound of Formula (X) wherein $R^1$ is H. In another embodiment is a compound of Formula (X) wherein $R^2$ is H. In yet another embodiment is a compound of Formula (X) wherein $R^1$ is H and $R^2$ is H. In another embodiment is a compound of Formula (X) wherein $R^1$ and $R^2$ have a trans relationship. In another embodiment is a compound of Formula (X) wherein $R^1$ and $R^2$ have a cis relationship. In another embodiment is a compound of Formula (X) wherein m is 2. In another embodiment is a compound of Formula (X) wherein n is 1. In another embodiment is a compound of Formula (X) wherein n is 2. In another embodiment is a compound of Formula (X) wherein p is 1. In another embodiment is a compound of Formula (X) wherein $R^3$ is H. In another embodiment is a compound of Formula (X) wherein $R^3$ is $CH_3$. In a further embodiment is a compound of Formula (X) wherein $R^3$ is not substituted or unsubstituted $C_1$-$C_3$alkyl. In another embodiment is a compound of Formula (X) wherein $R^3$ is H, methyl, ethyl, or isopropyl. In another embodiment is a compound of Formula (X) wherein $R^4$ is substituted or unsubstituted $C_3$-$C_6$ cycloalkyl. In a further embodiment is a compound of Formula (X) wherein $R^4$ is cyclopropyl, cyclobutyl, cyclopentyl or cyclohexyl. In another embodiment is a compound of Formula (X) wherein $R^4$ is substituted or unsubstituted $C_2$-$C_6$ heterocycloalkyl. In a further embodiment is a compound of Formula (X) wherein $R^4$ is tetrahydropyran, tetrahydrofuran, oxetane, or

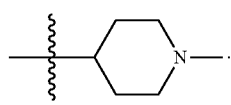

In another embodiment is a compound of Formula (X) wherein $R^4$ is substituted or unsubstituted $C_5$-$C_{11}$ heteroaryl. In a further embodiment is a compound of Formula (X) wherein $R^4$ is pyridyl. In another embodiment is a compound of Formula (X) wherein $R^3$ and $R^4$ are each independently substituted or unsubstituted $C_3$-$C_6$ cycloalkyl.

In another embodiment is a compound of Formula (X) wherein L is O, W is a bond, $R^1$ is H, $R^2$ is H, p is 1, Z is C=O, $R^3$ is H, and $R^4$ is substituted or unsubstituted $C_3$-$C_6$ cycloalkyl. In another embodiment is a compound of Formula (X) wherein L is O, W is a bond, $R^1$ is H, $R^2$ is H, p is 1, Z is C=O, $R^3$ is methyl, and $R^4$ is substituted or unsubstituted $C_3$-$C_6$ cycloalkyl. In another embodiment is a compound of Formula (X) wherein L is O, W is a bond, $R^1$ is H, $R^2$ is H, p is 1, Z is C=O, $R^3$ is ethyl, and $R^4$ is substituted or unsubstituted $C_3$-$C_6$ cycloalkyl. In another embodiment is a compound of Formula (X) wherein L is O, W is a bond, $R^1$ is H, $R^2$ is H, p is 1, Z is C=O, $R^3$ is H, and $R^4$ is substituted or unsubstituted $C_2$-$C_6$ heterocycloalkyl. In another embodiment is a compound of Formula (X) wherein L is O, W is a bond, $R^1$ is H, $R^2$ is H, p is 1, Z is C=O, $R^3$ is methyl, and $R^4$ is substituted or unsubstituted $C_2$-$C_6$ heterocycloalkyl. In another embodiment is a compound of Formula (X) wherein L is O, W is a bond, $R^1$ is H, $R^2$ is H, p is 1, Z is C=O, $R^3$ is ethyl, and $R^4$ is substituted or unsubstituted $C_2$-$C_6$ heterocycloalkyl. In another embodiment is a compound of Formula (X) wherein L is O, W is a bond, $R^1$ is H, $R^2$ is H, p is 1, Z is C=O, $R^3$ is H, and $R^4$ is substituted or unsubstituted $C_6$-$C_{12}$ aryl. In another embodiment is a compound of Formula (X) wherein L is O, W is a bond, $R^1$ is H, $R^2$ is H, p is 1, Z is C=O, $R^3$ is methyl, and $R^4$ is substituted or unsubstituted $C_6$-$C_{12}$ aryl. In another embodiment is a compound of Formula (X) wherein L is O, W is a bond, $R^1$ is H, $R^2$ is H, p is 1, Z is C=O, $R^3$ is ethyl, and $R^4$ is substituted or unsubstituted $C_6$-$C_{12}$ aryl. In another embodiment is a compound of Formula (X) wherein L is O, W is a bond, $R^1$ is H, $R^2$ is H, p is 1, Z is C=O, $R^3$ is H, and $R^4$ is substituted or unsubstituted $C_5$-$C_{11}$ heteroaryl. In another embodiment is a compound of Formula (X) wherein L is O, W is a bond, $R^1$ is H, $R^2$ is H, p is 1, Z is C=O, $R^3$ is methyl, and $R^4$ is substituted or unsubstituted $C_5$-$C_{11}$ heteroaryl. In another embodiment is a compound of Formula (X) wherein L is O, W is a bond, $R^1$ is H, $R^2$ is H, p is 1, Z is C=O, $R^3$ is ethyl, and $R^4$ is substituted or unsubstituted $C_5$-$C_{11}$ heteroaryl.

In another aspect, provided herein are compounds of Formula (XI) having the structure:

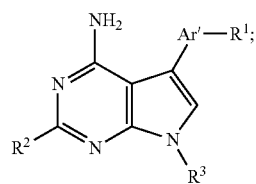

Formula (XI)

wherein:
$R^1$ is L-$Ar^2$;
L is each independently $CR^aR^a$, O, S, $NR^b$, N—$OR^b$, C=O, C=S, C=N—$R^b$, or C=N—$OR^b$;
$R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl;
$R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl;
$R^a$ is each independently H, $C_1$-$C_6$ alkyl, $C_1$-$C_6$ heteroalkyl, halogen, $OR^b$, or $NR^bR^b$;
$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
Ar' is selected from furan, thiophene, oxazole, isooxazole, oxadiazole, thiazole, isothiazole, thiadiazole, imidazole, triazole, pyrazole, thiodiazole and tetrazole, pyridine, pyrimidine, pyrazine;
$Ar^2$ is $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl or $C_2$-$C_6$ heterocycloalkyl;
or a pharmaceutically acceptable salt, solvate, N-oxide, or prodrug thereof.

In one embodiment is a compound of Formula (XI) wherein Ar' is oxazole, isooxazole, or oxadiazole. In another embodiment is a compound of Formula (XI) wherein $R^2$ is H. In yet another embodiment is a compound of Formula (XI) wherein $R^2$ is H and $R^3$ is optionally substituted cycloalkyl. In a further embodiment is a compound of Formula (XI) wherein $R^1$ is O-Ph.

In some embodiments, $R^1$ is O—$Ar^2$ wherein $Ar^2$ is $C_5$-$C_{12}$ aryl or heteroaryl optionally substituted with halogen, $OR^b$, $NR^bR^b$, $C_1$-$C_6$ alkyl, $C_1$-$C_6$ heteroalkyl, $C_3$-$C_6$ cycloalkyl, or $C_2$-$C_6$ heterocycloalkyl; and $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, $R^1$ is O—$Ar^2$ wherein $Ar^2$ is $C_5$-$C_{12}$ aryl or heteroaryl optionally substituted with halogen, hydroxy, amine, or $C_1$-$C_6$ alkyl. In other embodiments, $Ar^2$ is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In other embodiments, $Ar^2$ is phenyl, pyridinyl, furanyl, thiophenyl or quinolinyl. In certain embodiments, $Ar^2$ is phenyl or pyridinyl.

In some embodiments, $R^2$ is H, $OR^b$, $NR^bR^b$, halogen, $C_1$-$C_6$ alkyl, $C_1$-$C_6$ heteroalkyl, $C_3$-$C_6$ cycloalkyl, or $C_2$-$C_6$ heterocycloalkyl; wherein $R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, $R^2$ is H, OH, $NH_2$, halogen or $C_1$-$C_6$ alkyl. In other embodiments, $R^2$ is F, Cl, Br or I. In other embodiments, $R^2$ is methyl, ethyl, n-propyl, iso-propyl, n-butyl, sec-butyl, iso-butyl, n-pentyl, or hexyl. In yet other embodiments, $R^2$ is H, OH, or $NH_2$. In other embodiments, $R^2$ is H.

In some embodiments, $R^3$ is optionally substituted alkyl, —(C=O)$C_1$-$C_6$ alkyl, —(C=O)$OR^b$, —(C=O)$NR^bR^b$, —(C=O)$SR^b$, optionally substituted cycloalkyl, optionally substituted heterocycloalkyl, optionally substituted aryl, or optionally substituted heteroaryl. In other embodiments, $R^3$ is methyl, ethyl, n-propyl, iso-propyl, n-butyl, iso-butyl, and tert-butyl. In yet other embodiments, $R^3$ is —C=O-Me, —(C=O)Et, or —(C=O)Bu. In other embodiments, $R^3$ is —COOH, —COOMe, —COOEt, —COOPr or —COOBu. In yet other embodiments, $R^3$ is —$CONH_2$, —CONHMe, —CONHEt or —CONHBu. In other embodiments, $R^3$ is —C=O—SMe, —(C=O)SEt or —C=O—SPr. In yet other embodiments, $R^3$ is optionally substituted cyclobutyl, cyclopentyl, cyclohexyl, or the like. In yet other embodiments, $R^3$ is optionally substituted azetidinyl, pyrrolidinyl, piperidinyl or the like. In yet other embodiments, $R^3$ is optionally substituted phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like.

In another embodiment is a compound of Formula (XI) wherein $R^3$ is optionally substituted with at least one substituent selected from halogen, —CN, —$NO_2$, —OH, —$OCF_3$, —$OCF_2H$, —$OCH_2F$, —$CF_3$, —$SR^8$, —S(=O)$R^9$, —S(=O)$_2R^9$, —$NR^{10}$S(=O)$_2R^9$, —S(=O)$_2N(R^{10})_2$, —$OR^{10}$, —C(=O)$R^9$, —OC(=O)$R^9$, —$CO_2R^{10}$, —$N(R^{10})_2$, —C(=O)$N(R^{10})_2$, —$NR^{10}$C(=O)$R^{10}$, —N$R^{10}$C(=O)$OR^{10}$, —$NR^{10}$C(=O)$N(R^{10})_2$, substituted or unsubstituted alkyl, substituted or unsubstituted heteroalkyl, substituted or unsubstituted cycloalkyl or substituted or unsubstituted heterocycloalkyl; wherein $R^8$ is H or substituted or unsubstituted alkyl; $R^9$ is substituted or unsubstituted alkyl, substituted or unsubstituted cycloalkyl, substituted or unsubstituted heterocycloalkyl, substituted or unsubstituted aryl or substituted or unsubstituted heteroaryl; and each $R^{10}$ is independently H, substituted or unsubstituted alkyl, substituted or unsubstituted cycloalkyl, substituted or unsubstituted heterocycloalkyl, substituted or unsubstituted aryl or substituted or unsubstituted heteroaryl, or two $R^{10}$ together with the atoms to which they are attached form a heterocycle. In one embodiment, $R^3$ is substituted with halogen, —CN, —NO$_2$, —OH, —OCF$_3$, —OCF$_2$H, —OCH$_2$F, —CF$_3$, —SH. In another embodiment is a compound of Formula (XI) wherein $R^3$ is substituted with —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —CO$_2$R$^{10}$, —C(=O)N(R$^{10}$)$_2$. In another embodiment, $R^9$ is an unsubstituted or substituted alkyl selected from methyl, ethyl, n-propyl, iso-propyl, n-butyl, iso-butyl or tert-butyl. In another embodiment, is a compound of Formula (IX) wherein $R^9$ is a substituted or unsubstituted cycloalkyl. In a further embodiment, the cycloalkyl is selected from cyclopropyl, cyclobutyl, cyclopentyl, cyclohexyl or cycloheptyl. In another embodiment $R^9$ is a substituted or unsubstituted heterocycloalkyl. In another embodiment, $R^9$ is a substituted or unsubstituted aryl. In a further embodiment, the aryl is a phenyl group. In a further embodiment, the aryl is a naphthalene group. In yet a further embodiment, $R^9$ is a substituted or unsubstituted heteroaryl. In yet another embodiment the heteroaryl is selected from pyrrole, furan, thiophene, pyrazole, imidazole, isoxazole, oxazole, isothiazole, thiazole, 1,2,3-triazole, 1,3,4-triazole, 1-oxa-2,3-diazole, 1-oxa-2,4-diazole, 1-oxa-2,5-diazole, 1-oxa-3,4-diazole, 1-thia-2,3-diazole, 1-thia-2,4-diazole, 1-thia-2,5-diazole, 1-thia-3,4-diazole, tetrazole, pyridine, pyridazine, pyrimidine, and pyrazine.

In some embodiments, Ar' is selected from furan, thiophene, oxazole, isooxazole, oxadiazole, thiazole, isothiazole, and thiadiazole. In other embodiments, Ar' is oxazole, isooxazole or oxadiazole.

In one aspect, provided herein are compounds of Formula (XII) having the structure:

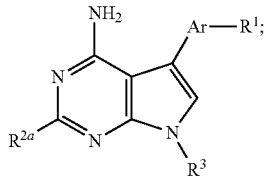

Formula (XII)

wherein:
$R^1$ is L-Ar$^2$;
L is CR$^a$R$^a$, O, S, NR$^b$, N—OR$^b$, C=O, C=S, C=N—R$^b$, or C=N—OR$^b$;
$R^a$ is each independently H, $C_1$-$C_6$ alkyl, $C_1$-$C_6$ heteroalkyl, halogen, OR$^b$, or NR$^b$R$^b$;
$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
$R^{2a}$ is OR$^b$, NR$^b$R$^b$, halogen, $C_1$-$C_6$ alkyl, $C_1$-$C_6$ heteroalkyl, $C_3$-$C_6$ cycloalkyl, or $C_2$-$C_6$ heterocycloalkyl;
$R^3$ is optionally substituted alkyl, —(C=O)$C_1$-$C_6$ alkyl, —(C=O)OR$^b$, —(C=O)NR$^b$R$^b$, —(C=O)SR$^b$, optionally substituted cycloalkyl, optionally substituted heterocycloalkyl, optionally substituted aryl, or optionally substituted heteroaryl;
Ar and Ar$^2$ are each independently $C_5$-$C_{12}$ aryl or heteroaryl optionally substituted with halogen, OR$^b$, NR$^b$R$^b$, $C_1$-$C_6$ alkyl, $C_1$-$C_6$ heteroalkyl, $C_3$-$C_6$ cycloalkyl, or $C_2$-$C_6$ heterocycloalkyl; or a pharmaceutically acceptable salt, solvate, N-oxide, or prodrug thereof.

In one embodiment is a compound of Formula (XII) wherein Ar is phenyl. In another embodiment is a compound of Formula (XII) wherein $R^{2a}$ is CH$_3$ or OH. In yet another embodiment is a compound of Formula (XII) wherein $R^3$ is optionally substituted cycloalkyl. In a further embodiment is a compound of Formula (XII) wherein $R^1$ is O-Ph.

In some embodiments, $R^{2a}$ is OR$^b$, NR$^b$R$^b$, halogen, $C_1$-$C_6$ alkyl, $C_1$-$C_6$ heteroalkyl, $C_3$-$C_6$ cycloalkyl, or $C_2$-$C_6$ heterocycloalkyl. In some embodiments, $R^{2a}$ is OH, NH$_2$, halogen, or $C_1$-$C_6$ alkyl. In other embodiments, $R^{2a}$ is OH, NH$_2$, F, Cl, Br or I. In yet other embodiments, $R^{2a}$ is methyl, ethyl, n-propyl, iso-propyl, n-butyl, iso-butyl, and tert-butyl.

In some embodiments, $R^1$ is O—Ar$^2$ wherein Ar$^2$ is $C_5$-$C_{12}$ aryl or heteroaryl optionally substituted with halogen, OR$^b$, NR$^b$R$^b$, $C_1$-$C_6$ alkyl, $C_1$-$C_6$ heteroalkyl, $C_3$-$C_6$ cycloalkyl, or $C_2$-$C_6$ heterocycloalkyl; and R$^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, $R^1$ is O—Ar$^2$ wherein Ar$^2$ is $C_5$-$C_{12}$ aryl or heteroaryl optionally substituted with halogen, hydroxy, amine, or $C_1$-$C_6$ alkyl. In other embodiments, Ar$^2$ is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In other embodiments, Ar$^2$ is phenyl, pyridinyl, furanyl, thiophenyl or quinolinyl. In certain embodiments, Ar$^2$ is phenyl or pyridinyl.

In some embodiments, $R^3$ is optionally substituted alkyl, —(C=O)$C_1$-$C_6$ alkyl, —(C=O)OR$^b$, —(C=O)NR$^b$R$^b$, —(C=O)SR$^b$, optionally substituted cycloalkyl, optionally substituted heterocycloalkyl, optionally substituted aryl, or optionally substituted heteroaryl. In other embodiments, $R^3$ is methyl, ethyl, n-propyl, iso-propyl, n-butyl, iso-butyl, and tert-butyl. In yet other embodiments, $R^3$ is —C=O-Me, —(C=O)Et, or —(C=O)Bu. In other embodiments, $R^3$ is —COOH, —COOMe, —COOEt, —COOPr or —COOBu. In yet other embodiments, $R^3$ is —CONH$_2$, —CONHMe, —CONHEt or —CONHBu. In other embodiments, $R^3$ is —C=O—SMe, —(C=O)SEt or —C=O—SPr. In yet other embodiments, $R^3$ is optionally substituted cyclobutyl, cyclopentyl, cyclohexyl, or the like. In yet other embodiments, $R^3$ is optionally substituted azetidinyl, pyrrolidinyl, piperidinyl or the like. In yet other embodiments, $R^3$ is optionally substituted phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like.

In another embodiment is a compound of Formula (XII) wherein $R^3$ is optionally substituted with at least one substituent selected from halogen, —CN, —NO$_2$, —OH, —OCF$_3$, —OCF$_2$H, —OCH$_2$F, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —OR$^{10}$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted heteroalkyl, substituted or unsubstituted cycloalkyl or substituted or unsubstituted heterocycloalkyl; wherein $R^8$ is H or substituted or unsubstituted alkyl; $R^9$ is substituted or unsubstituted alkyl, substituted or unsubstituted cycloalkyl, substituted or unsubstituted heterocycloalkyl, substituted or unsubstituted aryl or substituted or unsubstituted heteroaryl; and each $R^{10}$ is independently H, substituted or unsubstituted alkyl, substituted or unsubstituted cycloalkyl, substituted or unsubstituted heterocycloalkyl, substituted or unsubstituted aryl or substituted or unsubstituted heteroaryl, or two $R^{10}$ together with the atoms to which they are attached form a heterocycle. In one embodiment, $R^3$ is substituted with halogen, —CN, —NO$_2$, —OH, —OCF$_3$, —OCF$_2$H, —OCH$_2$F, —CF$_3$, —SH. In another embodiment is a compound of Formula (XII) wherein $R^3$ is substituted with —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —CO$_2$R$^{10}$, —C(=O)N(R$^{10}$)$_2$. In another embodiment, $R^9$ is an unsubstituted or substituted alkyl selected from methyl, ethyl, n-propyl, iso-propyl, n-butyl, iso-butyl or tert-butyl. In another embodiment, is a compound of Formula (XII) wherein $R^9$ is a substituted or unsubstituted cycloalkyl. In a further embodiment, the cycloalkyl is selected from cyclopropyl, cyclobutyl, cyclopentyl, cyclohexyl or cycloheptyl. In another embodiment $R^9$ is a substituted or unsubstituted heterocycloalkyl. In another embodiment, $R^9$ is a substituted or unsubstituted aryl. In a further embodiment, the aryl is a phenyl group. In a further embodiment, the aryl is a naphthalene group. In yet a further embodiment, $R^9$ is a substituted or unsubstituted heteroaryl. In yet another embodiment the heteroaryl is selected from pyrrole, furan, thiophene, pyrazole, imidazole, isoxazole, oxazole, isothiazole, thiazole, 1,2,3-triazole, 1,3,4-triazole, 1-oxa-2,3-diazole, 1-oxa-2,4-diazole, 1-oxa-2,5-diazole, 1-oxa-3,4-diazole, 1-thia-2,3-diazole, 1-thia-2,4-diazole, 1-thia-2,5-diazole, 1-thia-3,4-diazole, tetrazole, pyridine, pyridazine, pyrimidine, and pyrazine.

In some embodiments, Ar is $C_5$-$C_{12}$ aryl or heteroaryl optionally substituted with halogen, OR$^b$, NR$^b$R$^b$, $C_1$-$C_6$ alkyl, $C_1$-$C_6$ heteroalkyl, $C_3$-$C_6$ cycloalkyl, or $C_2$-$C_6$ heterocycloalkyl; and R$^b$ is each independently H, $C_1$-$C_6$ alkyl, $C_2$-$C_6$ heteroalkyl, $C_3$-$C_6$ cycloalkyl, or $C_2$-$C_6$ heterocycloalkyl. In some embodiments, Ar is $C_5$-$C_{12}$ aryl or heteroaryl optionally substituted with halogen, hydroxy, amine, or $C_1$-$C_6$ alkyl. In other embodiments, Ar is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In certain embodiments, Ar is phenyl, or pyridinyl optionally substituted with amine or hydroxy. In certain embodiments, Ar is phenyl, or pyridinyl optionally substituted with methyl, ethyl, propyl, or the like.

In one aspect, provided herein are compounds of Formula (XIII) having the structure:

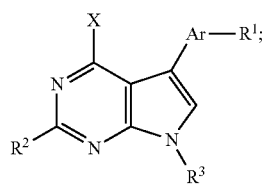

Formula (XIII)

wherein:
X is hydrogen, hydroxy, alkoxy, thiol, halogen or $C_1$-$C_6$ alkyl;
$R^1$ is L-Ar$^2$;
L is CR$^a$R$^a$, O, S, NR$^b$, N—OR$^b$, C=O, C=S, C=N—R$^b$, or C=N—OR$^b$;
R$^a$ is each independently H, $C_1$-$C_6$ alkyl, $C_1$-$C_6$ heteroalkyl, halogen, OR$^b$, or NR$^b$R$^b$;
R$^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;
$R^2$ is H, OR$^b$, NR$^b$R$^b$, halogen, $C_1$-$C_6$ alkyl, $C_1$-$C_6$ heteroalkyl, $C_3$-$C_6$ cycloalkyl, or $C_2$-$C_6$ heterocycloalkyl;
$R^3$ is optionally substituted alkyl, —(C=O)$C_1$-$C_6$ alkyl, —(C=O)OR$^b$, —(C=O)NR$^b$R$^b$, —(C=O)SR$^b$, optionally substituted cycloalkyl, optionally substituted heterocycloalkyl, optionally substituted aryl, or optionally substituted heteroaryl;
Ar and Ar$^2$ is each independently $C_5$-$C_{12}$ aryl or heteroaryl optionally substituted with halogen, OR$^b$, NR$^b$R$^b$, $C_1$-$C_6$ alkyl, $C_1$-$C_6$ heteroalkyl, $C_3$-$C_6$ cycloalkyl, or $C_2$-$C_6$ heterocycloalkyl;
or a pharmaceutically acceptable salt, solvate, N-oxide, or prodrug thereof.

In some embodiments, $R^1$ is O—Ar$^2$ wherein Ar$^2$ is $C_5$-$C_{12}$ aryl or heteroaryl optionally substituted with halogen, hydroxy, amine, or $C_1$-$C_6$ alkyl. In other embodiments, Ar$^2$ is phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like. In other embodiments, Ar$^2$ is phenyl, pyridinyl, furanyl, thiophenyl or quinolinyl. In certain embodiments, Ar$^2$ is phenyl or pyridinyl.

In some embodiments, $R^3$ is optionally substituted alkyl, —(C=O)$C_1$-$C_6$ alkyl, —(C=O)OR$^b$, —(C=O)NR$^b$R$^b$, —(C=O)SR$^b$, optionally substituted cycloalkyl, optionally substituted heterocycloalkyl, optionally substituted aryl, or optionally substituted heteroaryl. In other embodiments, $R^3$ is methyl, ethyl, n-propyl, iso-propyl, n-butyl, iso-butyl, and tert-butyl. In yet other embodiments, $R^3$ is —C=O-Me, —(C=O)Et, or —(C=O)Bu. In other embodiments, $R^3$ is —COOH, —COOMe, —COOEt, —COOPr or —COOBu. In yet other embodiments, $R^3$ is —CONH$_2$, —CONHMe, —CONHEt or —CONHBu. In other embodiments, $R^3$ is —C=O—SMe, —(C=O)SEt or —C=O—SPr. In yet other embodiments, $R^3$ is optionally substituted cyclobutyl, cyclopentyl, cyclohexyl, or the like. In yet other embodiments, $R^3$ is optionally substituted azetidinyl, pyrrolidinyl, piperidinyl or the like. In yet other embodiments, $R^3$ is optionally substituted phenyl, pyridinyl, pyridaznyl, pyrimidinyl, pyrazinyl, triazinyl, tetrazinyl, furanyl, thiophenyl, oxazolyl, thiazolyl, pyrazolyl, quinolinyl, isoquinolinyl, indolyl, benzofuranyl, benzimidazolyl, or the like.

In another embodiment is a compound of Formula (XIII) wherein $R^3$ is optionally substituted with at least one substituent selected from halogen, —CN, —NO$_2$, —OH, —OCF$_3$, —OCF$_2$H, —OCH$_2$F, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —OR$^{10}$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted heteroalkyl, substituted or unsubstituted cycloalkyl or substituted or unsubstituted heterocycloalkyl; wherein $R^8$ is H or substituted or unsubstituted alkyl; $R^9$ is substituted or unsubstituted alkyl, substituted or unsubstituted cycloalkyl, substituted or unsubstituted heterocycloalkyl, substituted or unsubstituted aryl or substituted or unsubstituted heteroaryl; and each R$^{10}$ is independently H, substituted or unsubstituted alkyl, substituted or unsubstituted cycloalkyl, substituted or unsubstituted heterocycloalkyl, substituted or unsubstituted aryl or substituted or unsubstituted heteroaryl, or two R$^{10}$ together with the atoms to which they are attached form a heterocycle. In one embodiment, $R^3$ is substituted with halogen, —CN, —NO$_2$, —OH, —OCF$_3$, —OCF$_2$H, —OCH$_2$F, —CF$_3$, —SH. In another embodiment is a compound of Formula (XIII) wherein $R^3$ is substituted with —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —CO$_2$R$^{10}$, —C(=O)N(R$^{10}$)$_2$. In another embodiment, $R^9$ is an unsubstituted or substituted alkyl selected from methyl, ethyl, n-propyl, iso-propyl, n-butyl, iso-butyl or tert-butyl. In another embodiment, is a compound of Formula (XIII) wherein $R^9$ is a substituted or unsubstituted cycloalkyl. In a further embodiment, the cycloalkyl is selected from cyclopropyl, cyclobutyl, cyclopentyl, cyclohexyl or cycloheptyl. In another embodiment $R^9$ is a substituted or unsubstituted heterocycloalkyl. In another embodiment, $R^9$ is a substituted or unsubstituted aryl. In a further embodiment, the aryl is a phenyl group. In a further embodiment, the aryl is a naphthalene group. In yet a further embodiment, $R^9$ is a substituted or unsubstituted heteroaryl. In yet another embodiment the heteroaryl is selected from pyrrole, furan, thiophene, pyrazole, imidazole, isoxazole, oxazole, isothiazole, thiazole, 1,2,3-triazole, 1,3,4-triazole, 1-oxa-2,3-diazole, 1-oxa-2,4-diazole, 1-oxa-2,5-diazole, 1-oxa-3,4-diazole, 1-thia-2,3-diazole, 1-thia-2,4-diazole, 1-thia-2,5-diazole, 1-thia-3,4-diazole, tetrazole, pyridine, pyridazine, pyrimidine, and pyrazine.

In one embodiment is a compound of Formula (XIII) wherein Ar is phenyl. In another embodiment is a compound of Formula (XIII) wherein X is hydroxy or alkoxy. In yet another embodiment is a compound of Formula (XIII) wherein $R^3$ is optionally substituted cycloalkyl. In a further embodiment is a compound of Formula (XIII) wherein $R^1$ is O-Ph.

In some embodiments, X is hydroxy, methoxy, ethoxy or butoxy. In other embodiments, X is F, Cl, Br or I. In yet other embodiments, X is methyl, ethyl, propyl, or the like.

In one aspect, provided herein are compounds of Formula (XIV) having the structure:

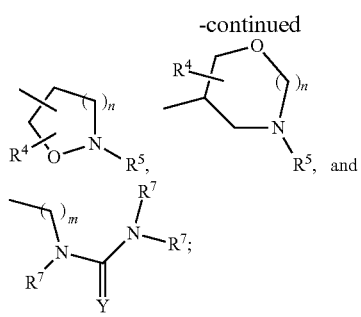

Formula (XIV)

wherein:

$R^1$ is L-$Ar^2$;

L is $CR^aR^a$, O, S, $NR^b$, N—$OR^b$, C=O, C=S, C=N—$R^b$, or C=N—$OR^b$;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl, or $C_2$-$C_6$ heterocycloalkyl;

$R^2$ is H, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;

$R^{3a}$ is selected from

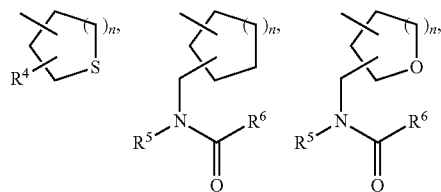

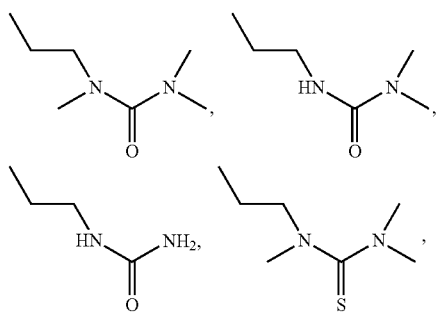

$R^4$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group;

$R^5$ is H, optionally substituted $C_1$-$C_6$ alkyl, —(C=O)$C_1$-$C_6$ alkyl, —(C=O)$OR^b$, —(C=O)$NR^bR^b$, —(C=O)$SR^b$, cycloalkyl, heterocycloalkyl, aryl, or heteroaryl;

$R^6$ is optionally substituted $C_1$-$C_6$ alkyl or $NR^S$;

$R^7$ is each independently hydrogen, optionally substituted $C_1$-$C_6$ alkyl, optionally substituted cycloalkyl, optionally substituted heterocycloalkyl, optionally substituted aryl, or optionally substituted heteroaryl;

$Ar^2$ is $C_5$-$C_{12}$ aryl or heteroaryl optionally substituted with halogen, hydroxy, amine, or $C_1$-$C_6$ alkyl;

n is an integer from 0 to 3;

m is an integer from 0 to 6;

Y is O, S or $NR^b$;

or a pharmaceutically acceptable salt, solvate, N-oxide, or prodrug thereof.

In one embodiment is a compound of Formula (XIV) wherein $R^{3a}$ is

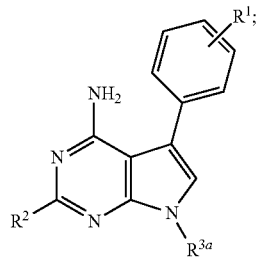

In another embodiment is a compound of Formula (XIV) wherein $R^{3a}$ is

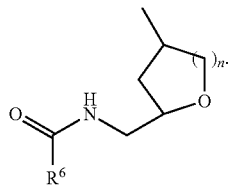

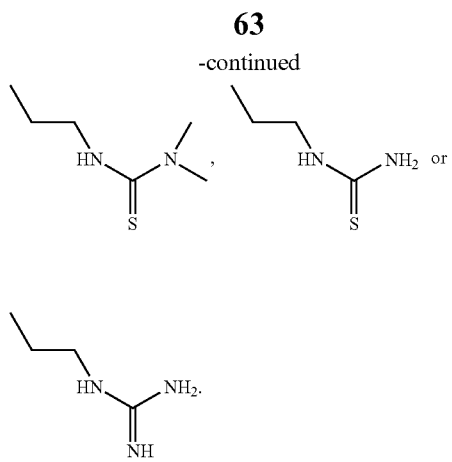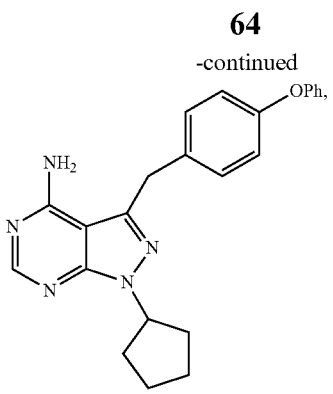
In yet another embodiment is a compound of Formula (XIV) wherein $R^5$ is H or $CH_3$. In a further embodiment is a compound of Formula (XIV) wherein $R^1$ is O-Ph.
In one embodiment is a compound having the structure selected from
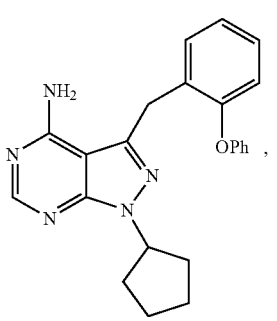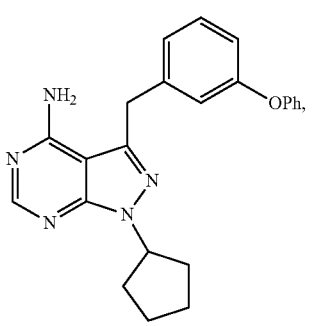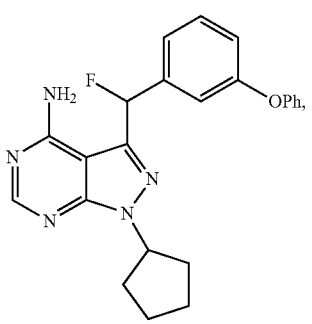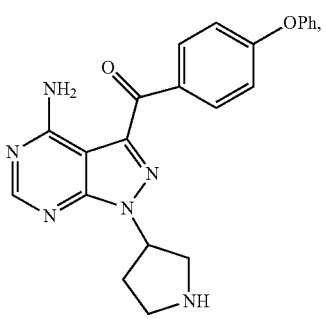

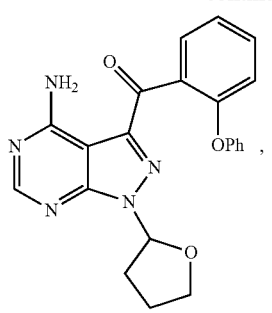
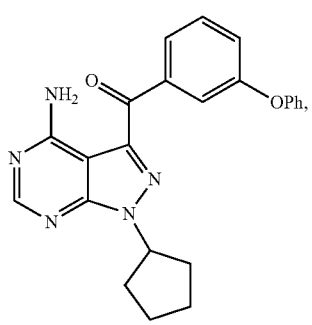
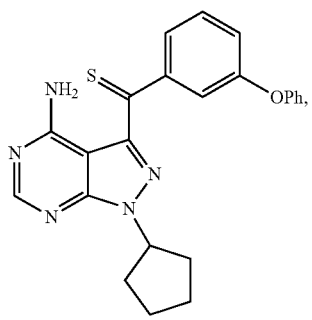
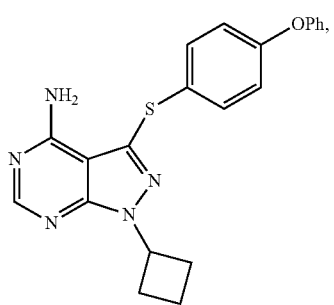
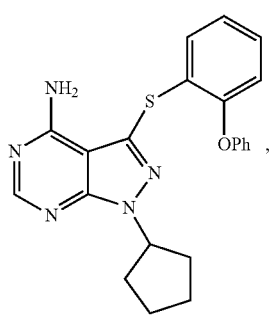
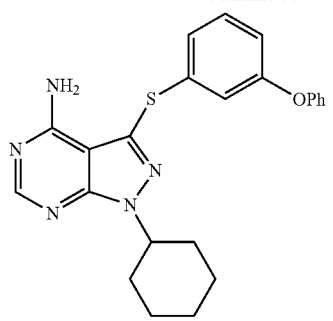
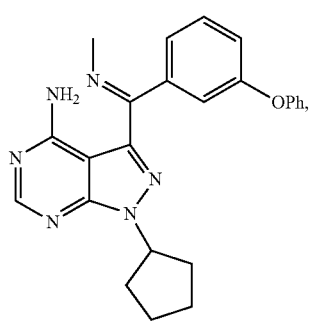
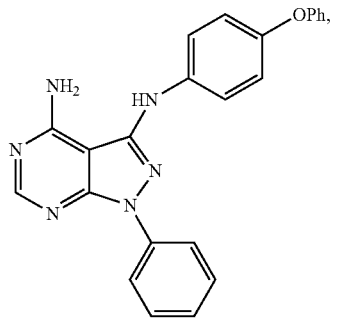
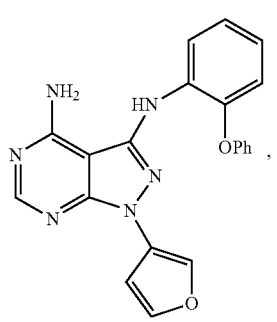
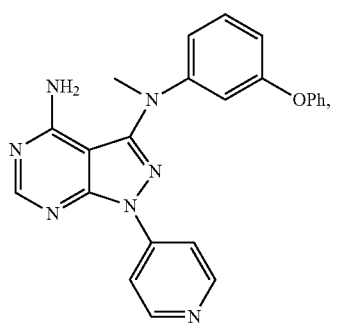

-continued
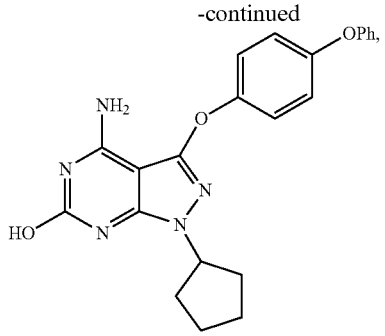
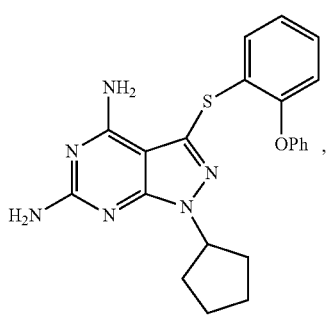
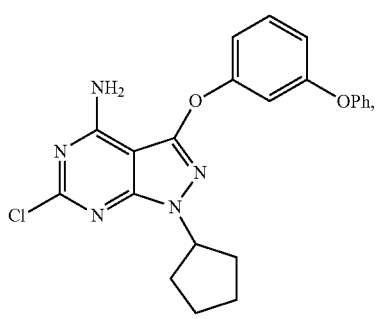
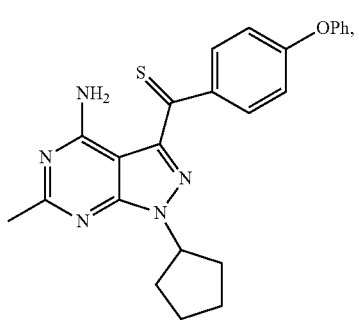
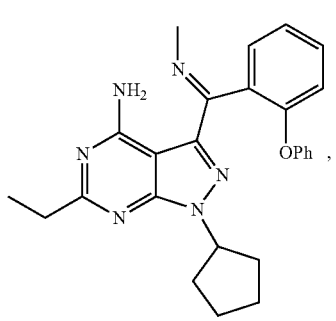
-continued
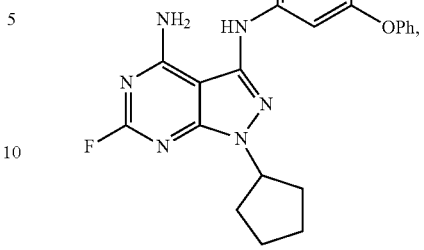
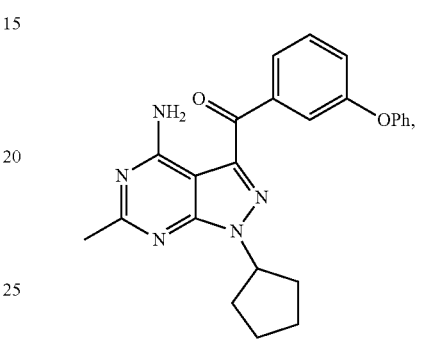
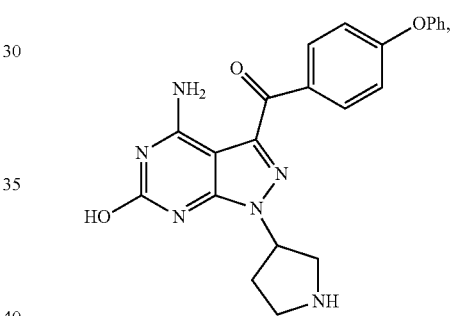
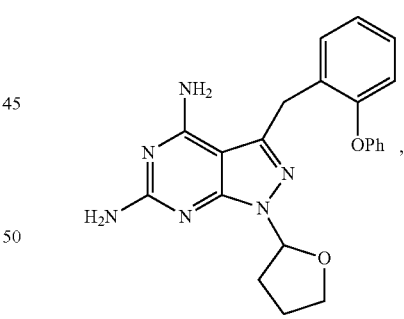
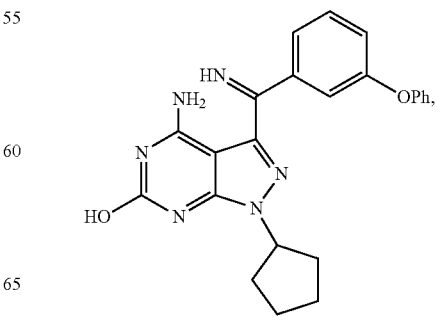

-continued
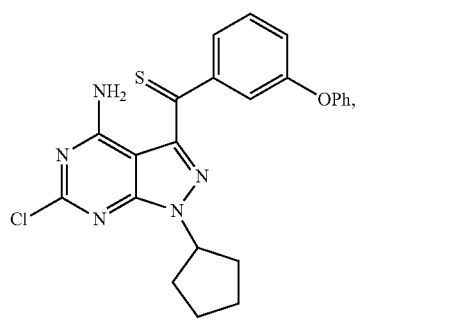
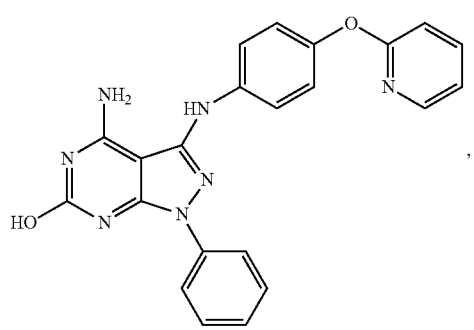
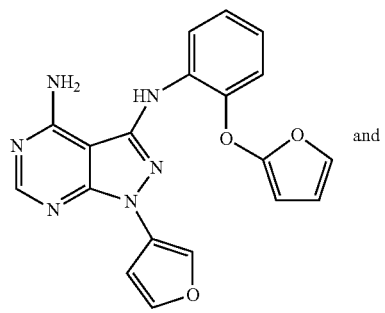
and
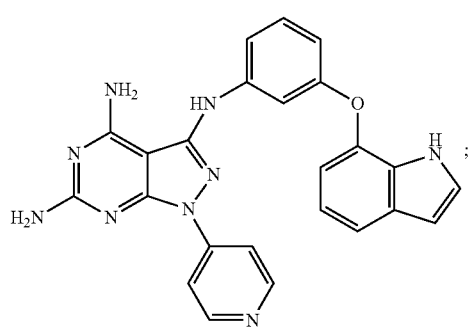
or a pharmaceutically acceptable salt, solvate, N-oxide, or prodrug thereof.
In another embodiment, provided herein is a compound selected from:
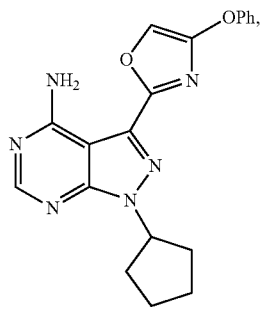
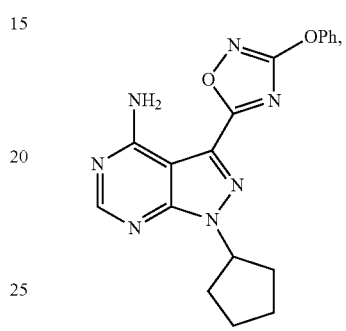
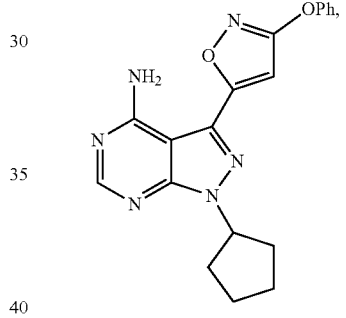
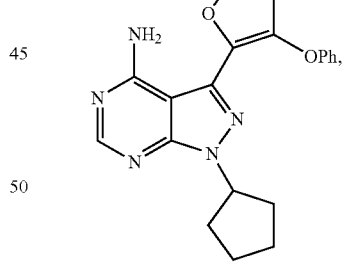
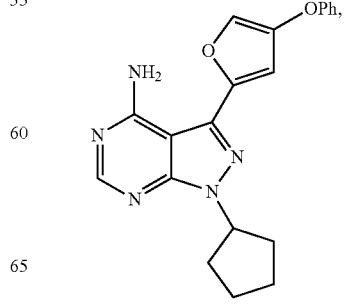

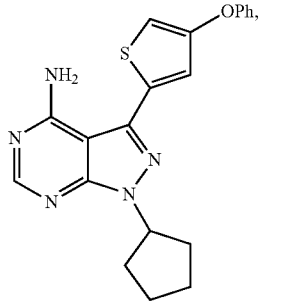
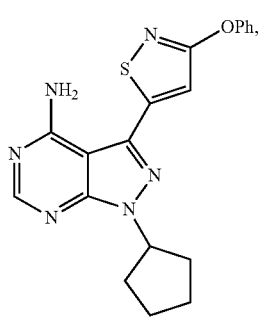
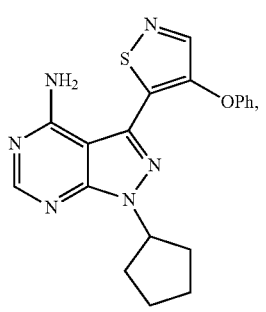
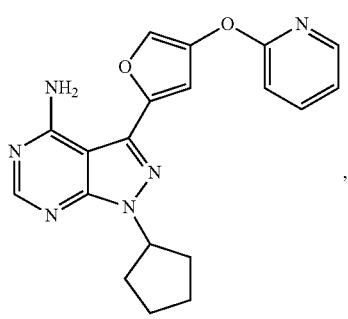
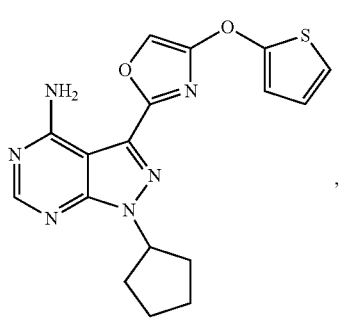
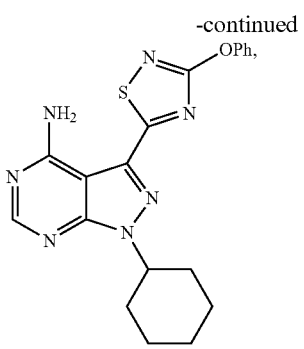
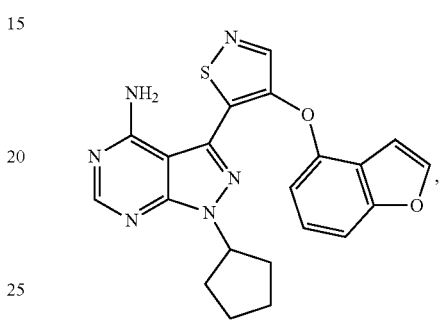
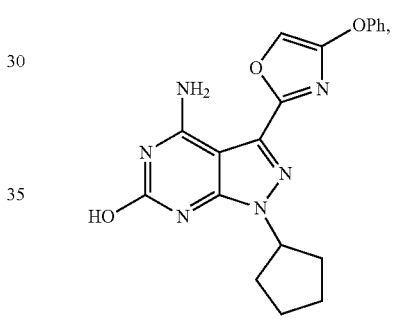
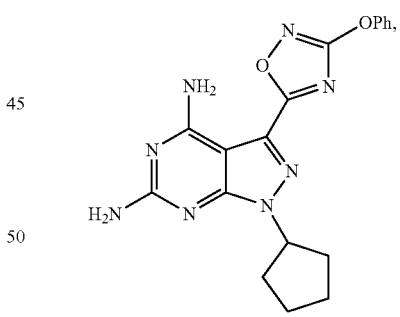
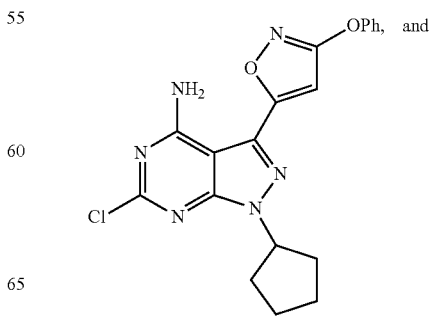

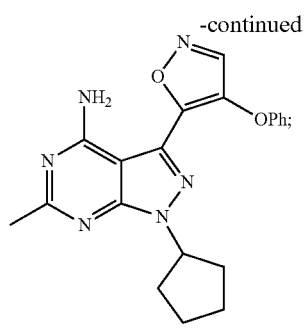
or a pharmaceutically acceptable salt, solvate, N-oxide, or prodrug thereof.
In another embodiments, provided herein is a compound selected from
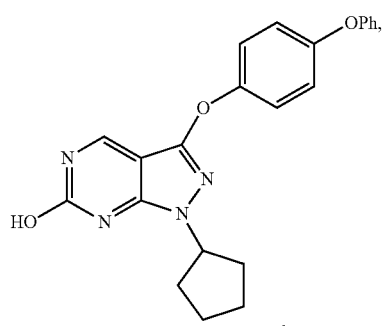
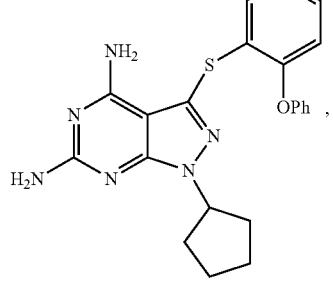
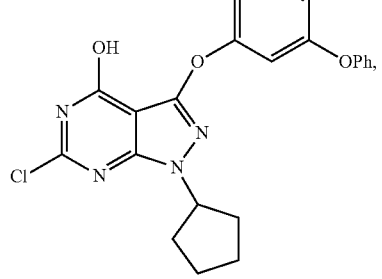
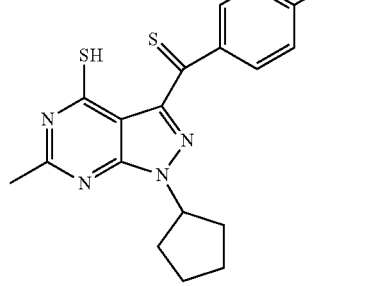
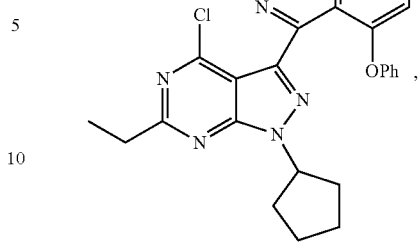
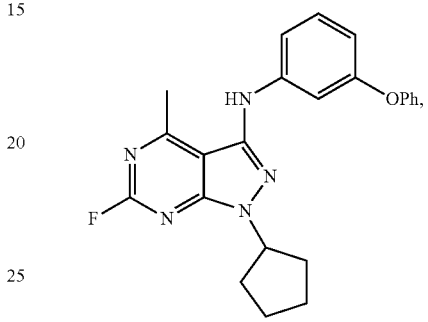
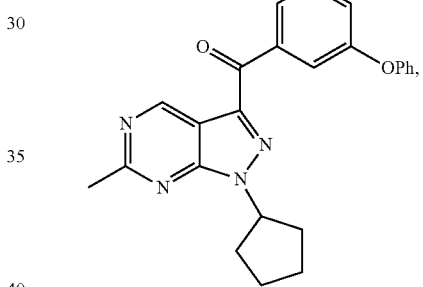
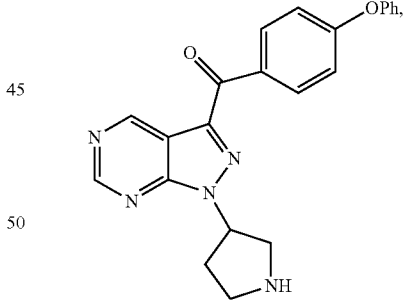
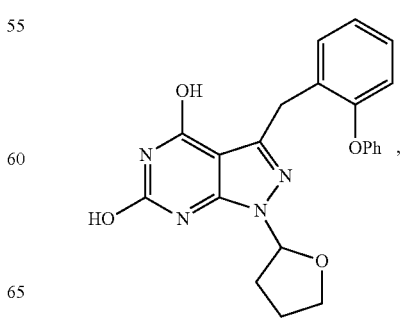

75
-continued
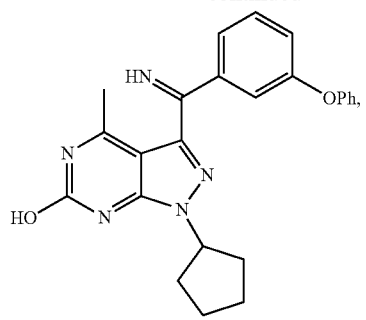
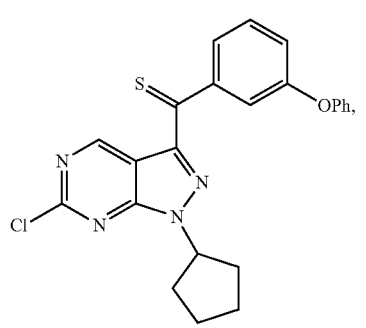
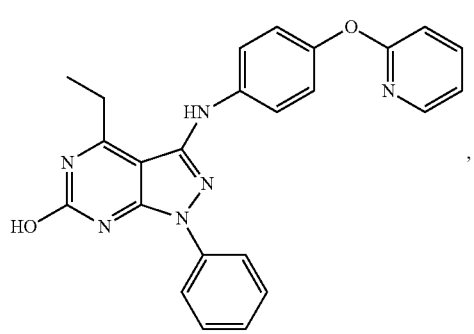
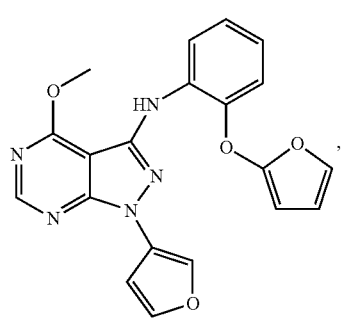
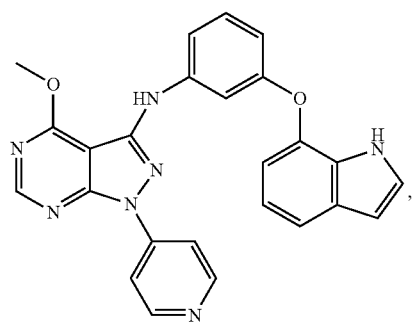
76
-continued
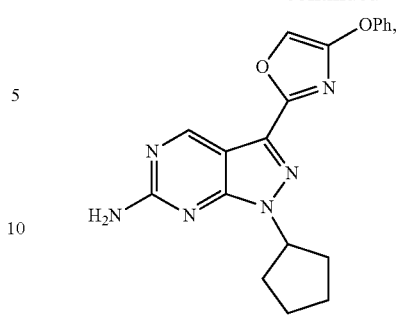
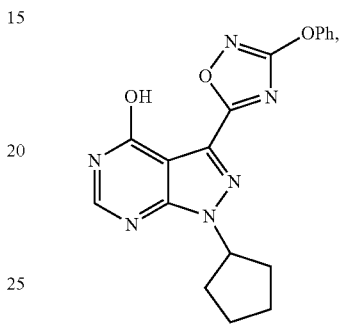
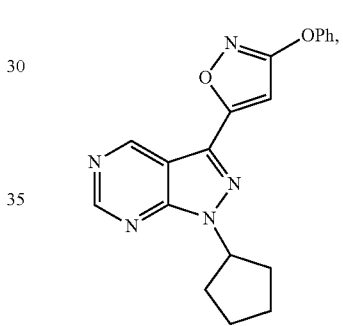
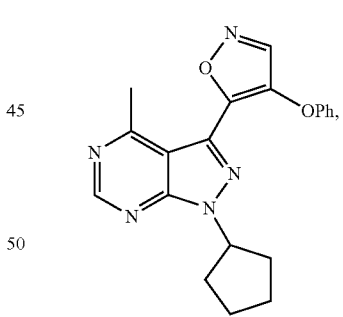
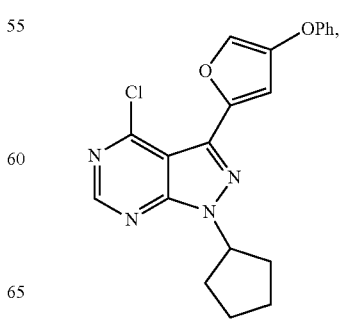

77
-continued
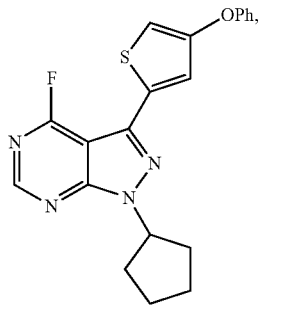
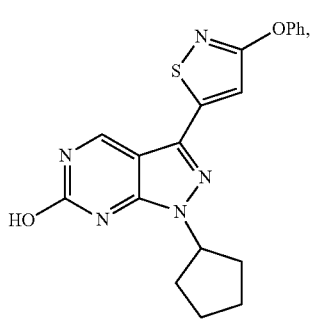
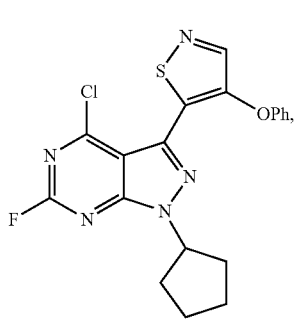
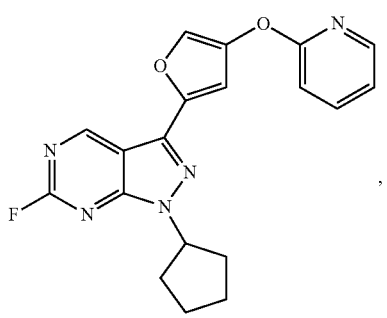
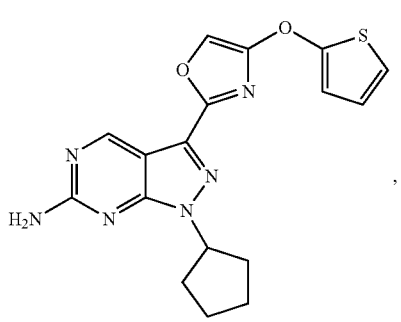
78
-continued
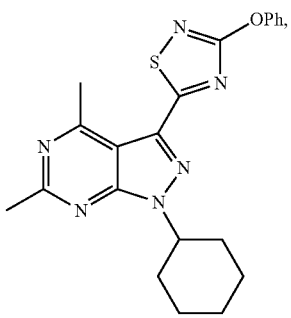
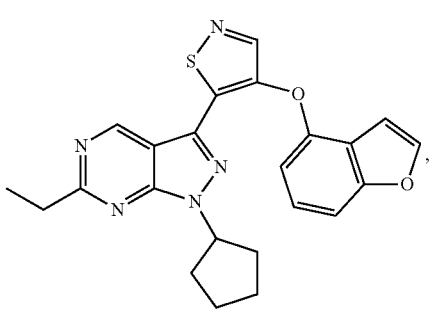
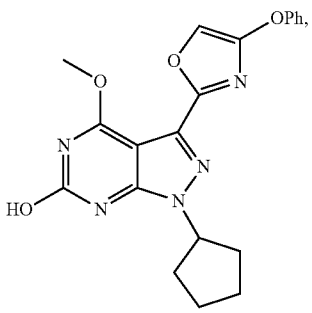
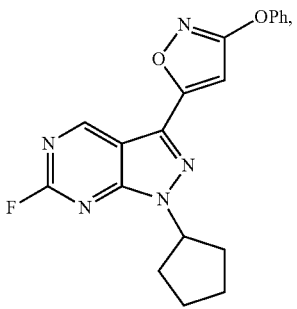

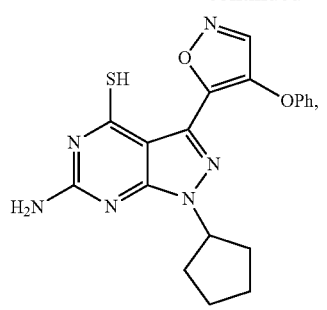
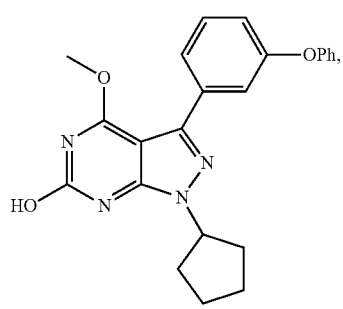
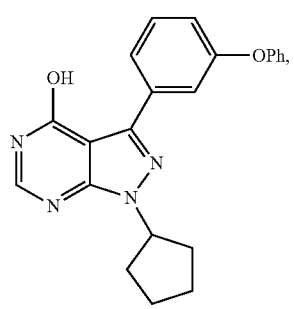
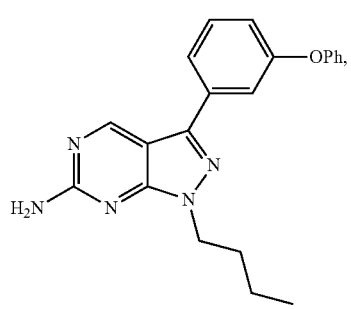
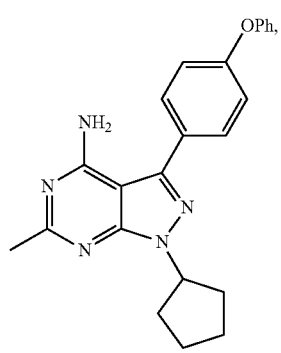
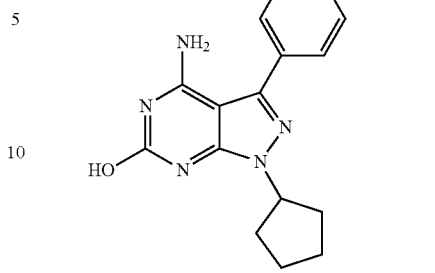
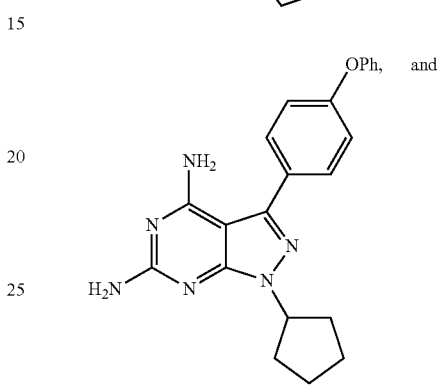
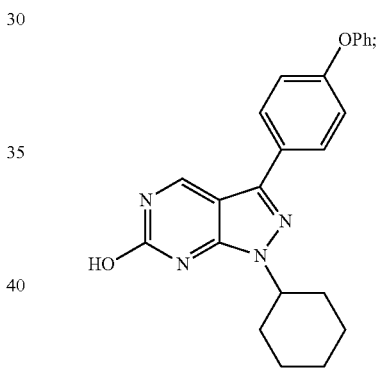
or a pharmaceutically acceptable salt, solvate, N-oxide, or prodrug thereof.
In another embodiment, provided herein is a compound selected from
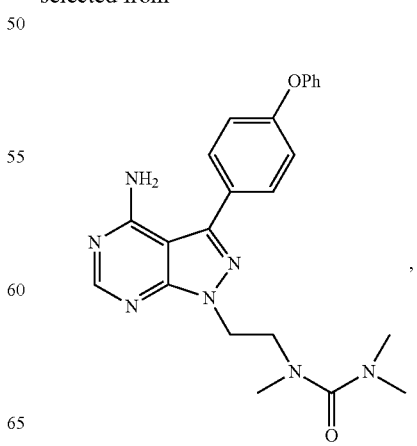

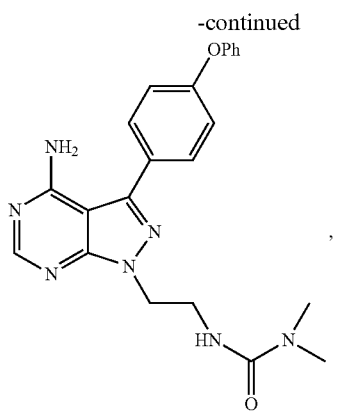
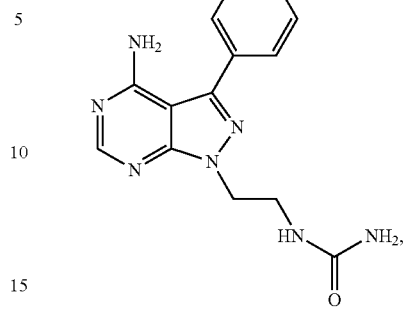
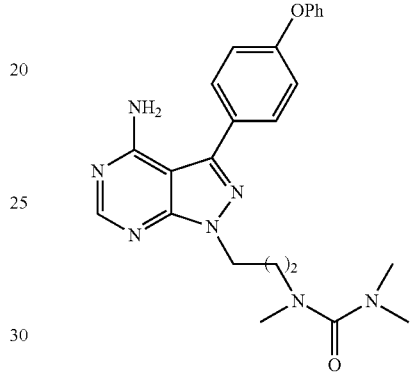
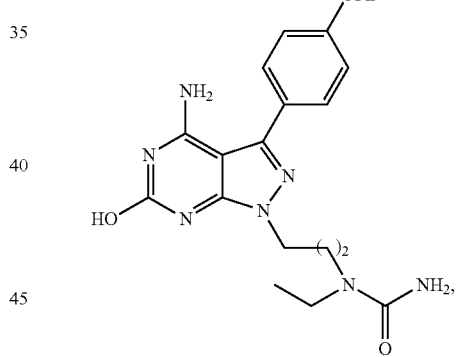
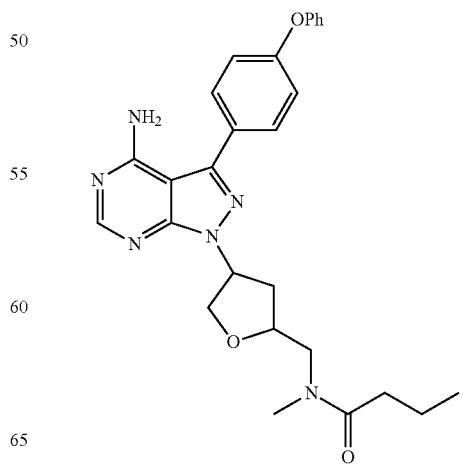

83
-continued
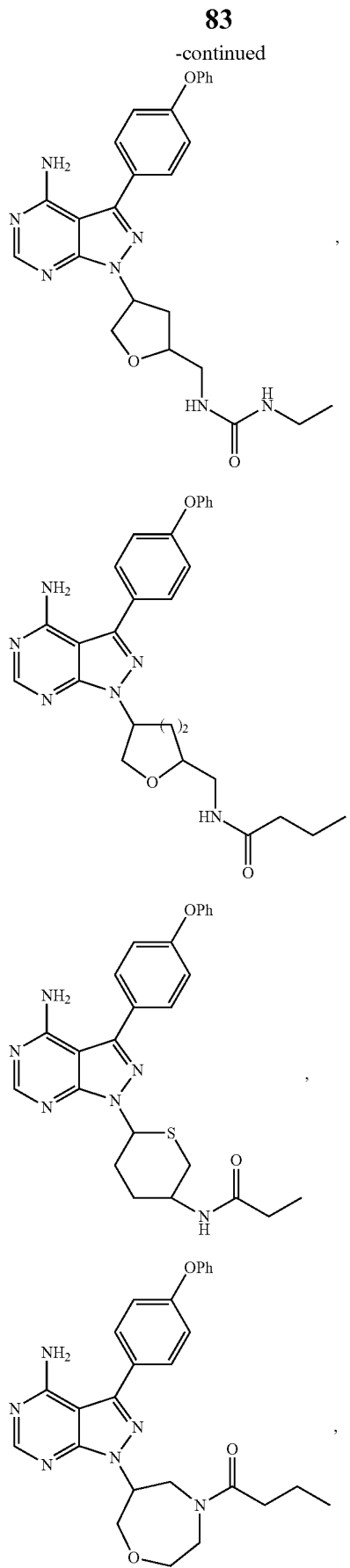
84
-continued
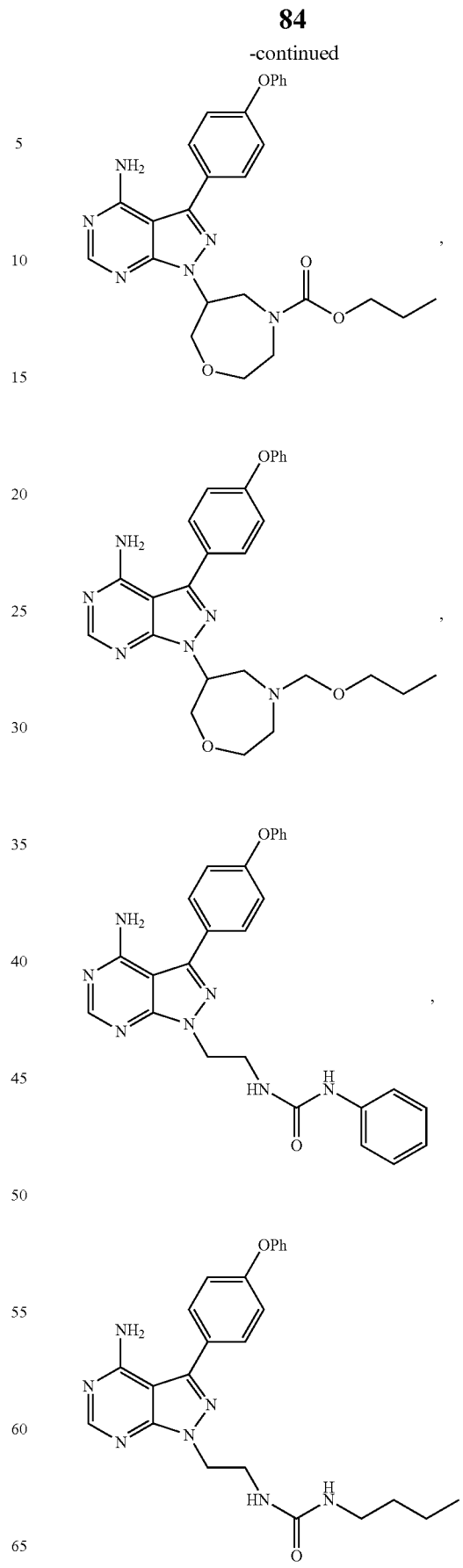

85
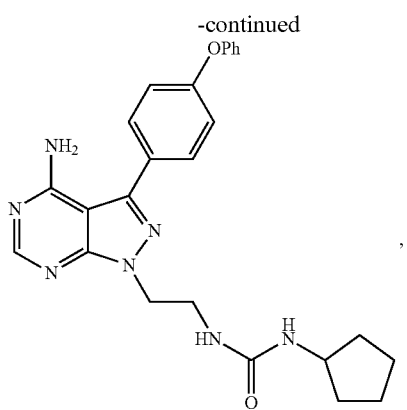
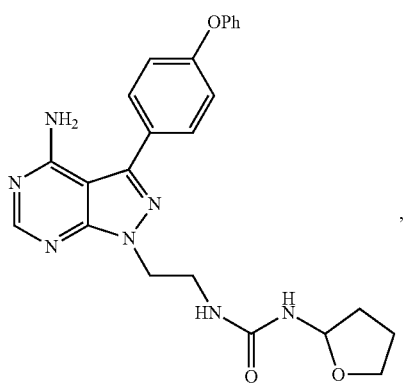
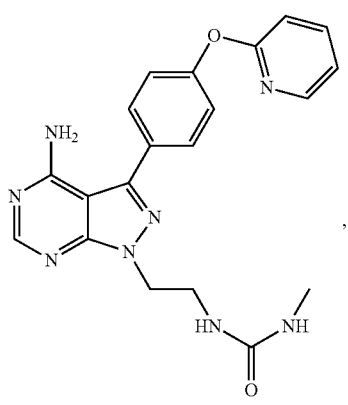
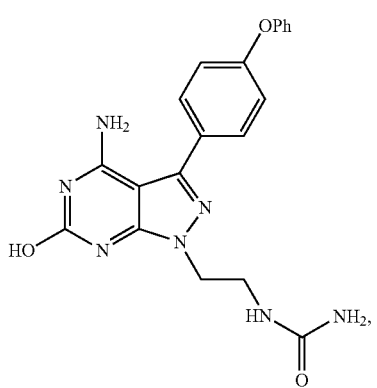
86
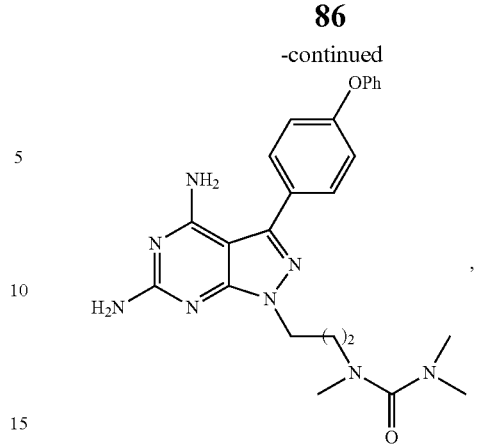
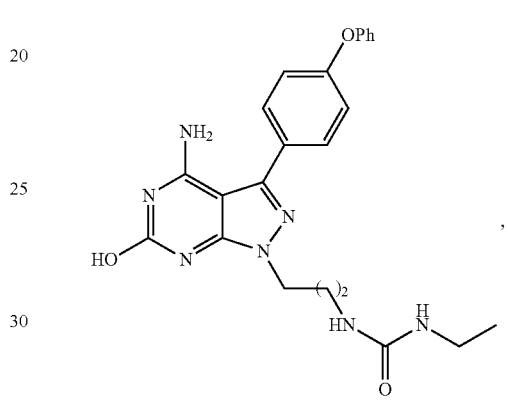
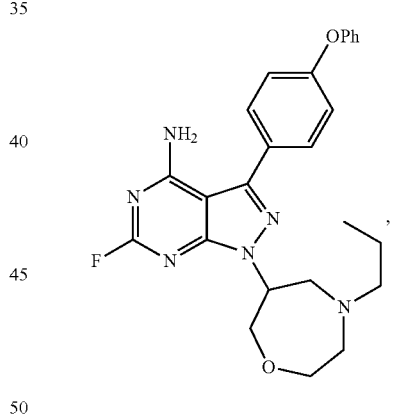
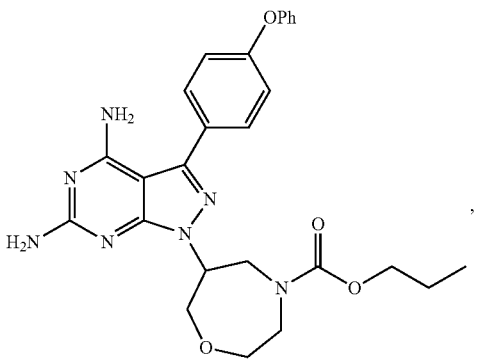

-continued
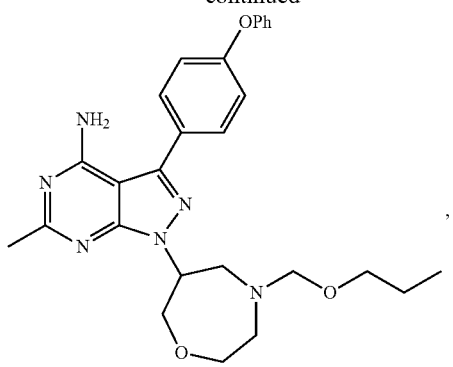
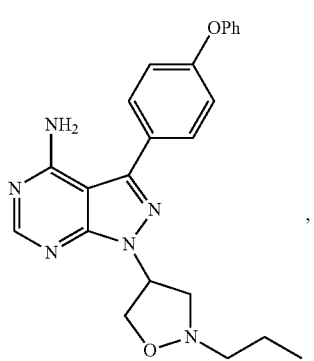
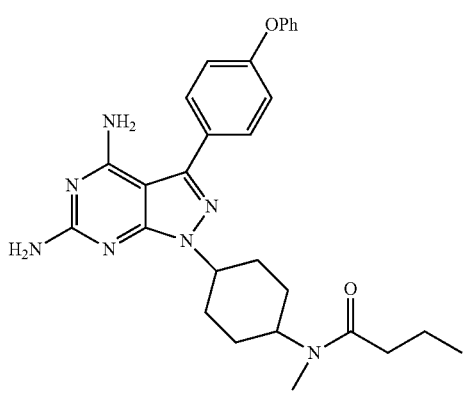
and
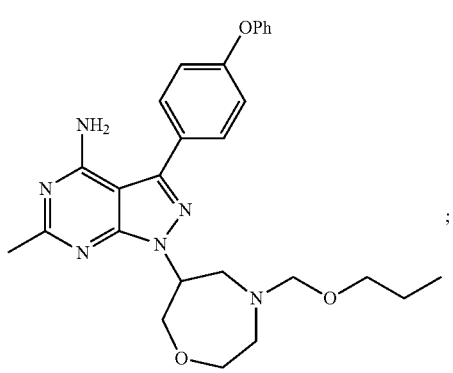
or a pharmaceutically acceptable salt, solvate, N-oxide, or prodrug thereof.
In another embodiment is a compound selected from:
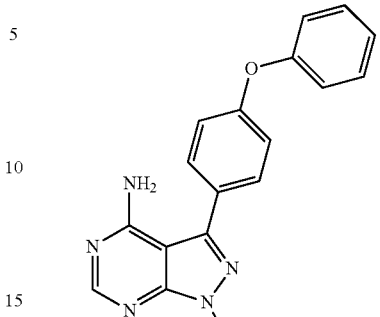
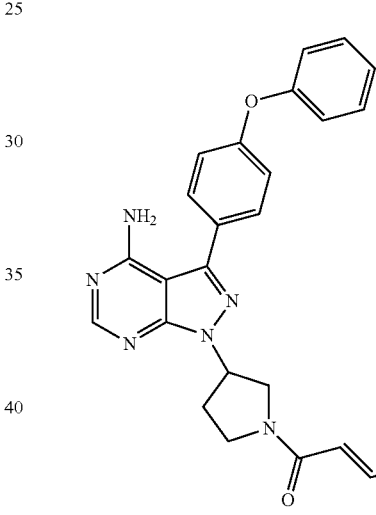
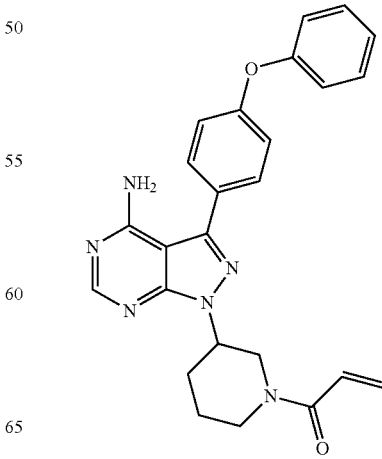

89
-continued
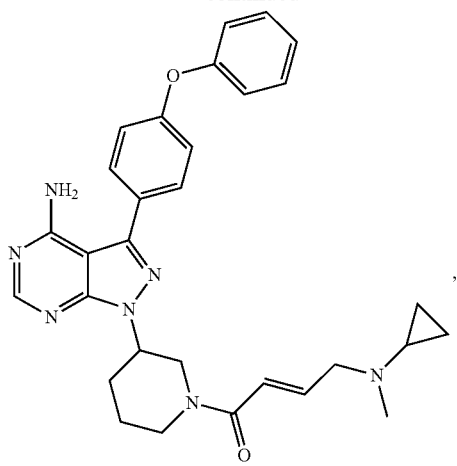,
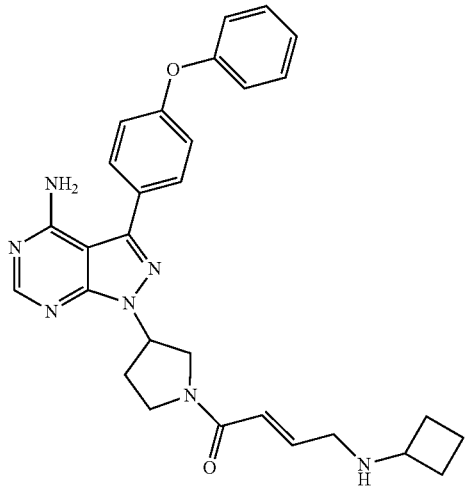,
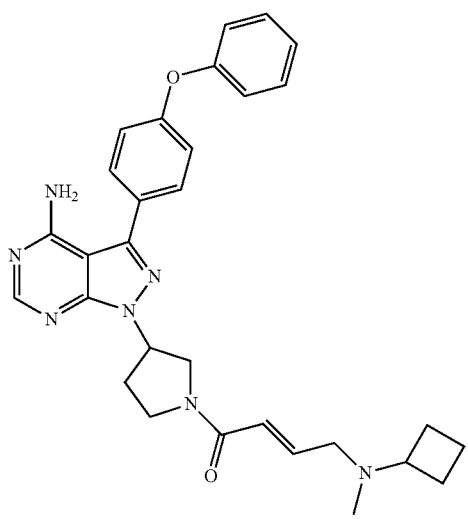,
90
-continued
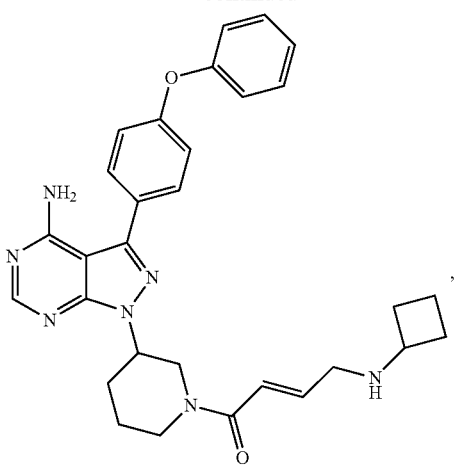,
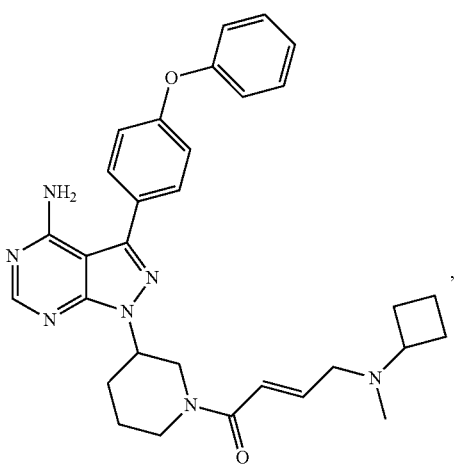,
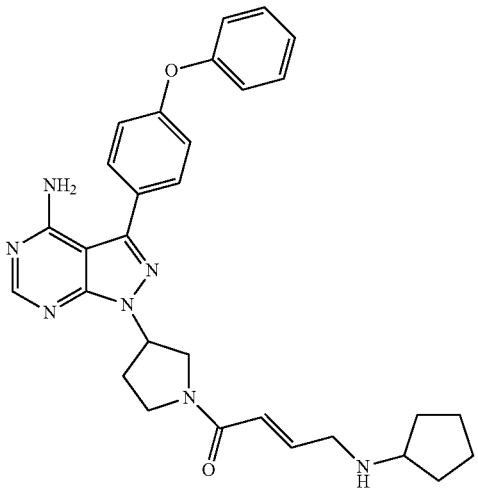,

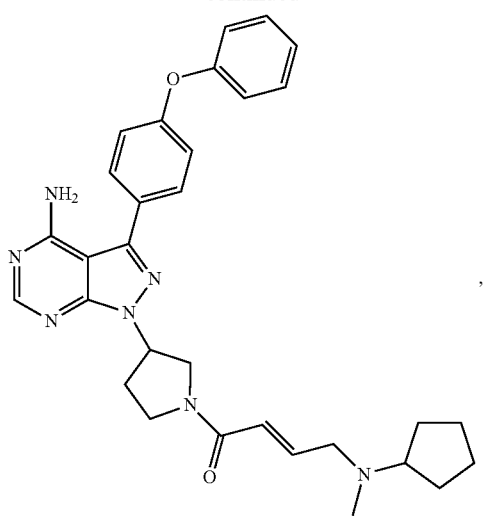
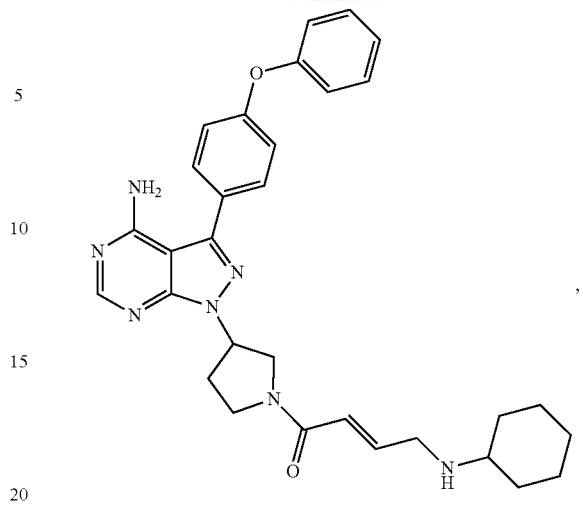

93
-continued
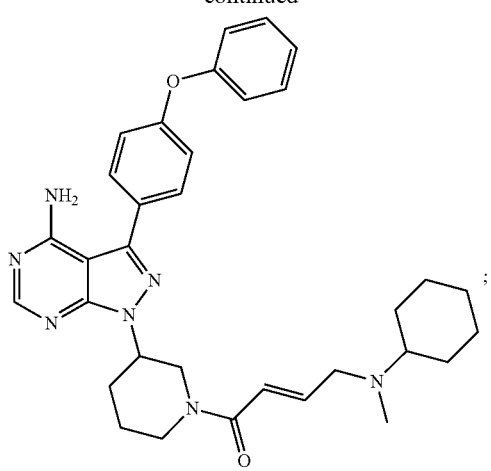
or a pharmaceutically acceptable salt, solvate, N-oxide, or prodrug thereof.
In another embodiment is a compound selected from:
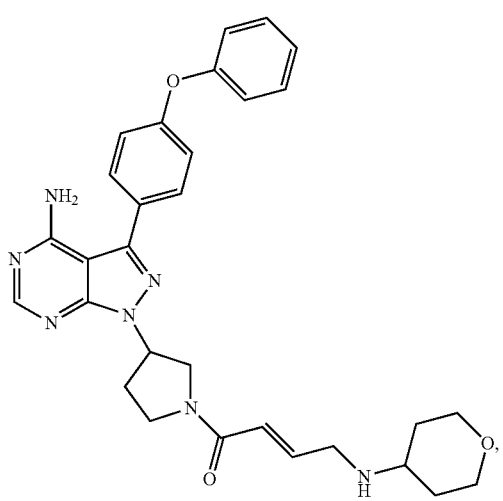
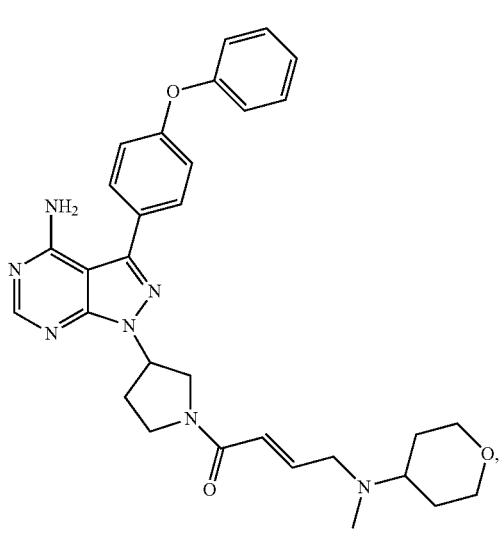
94
-continued
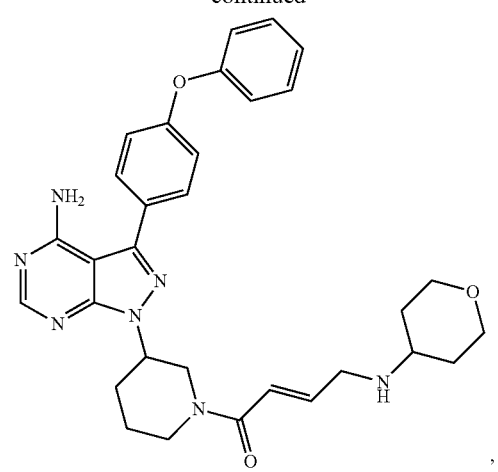
,
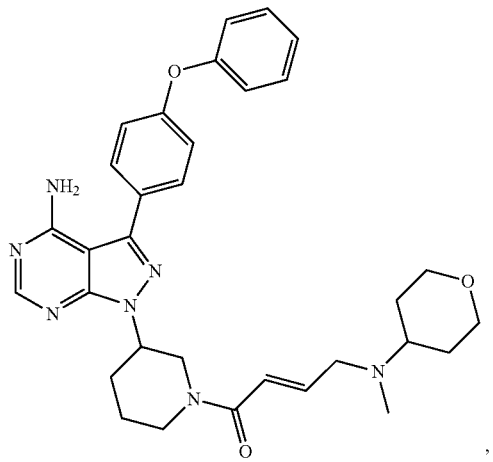
,
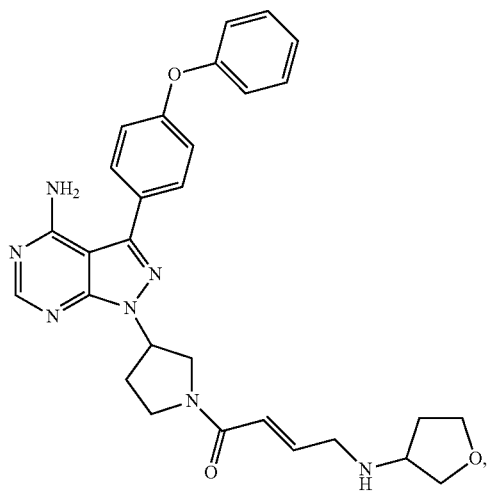

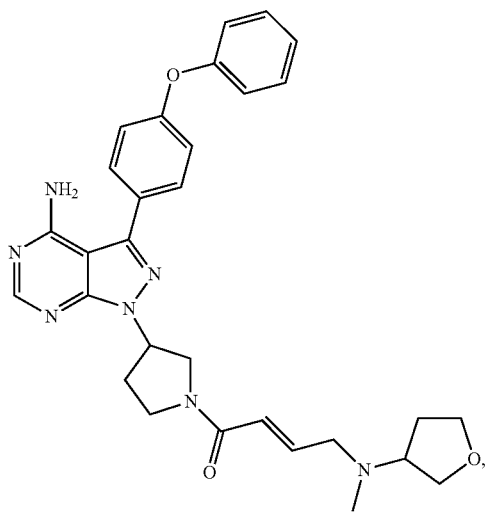
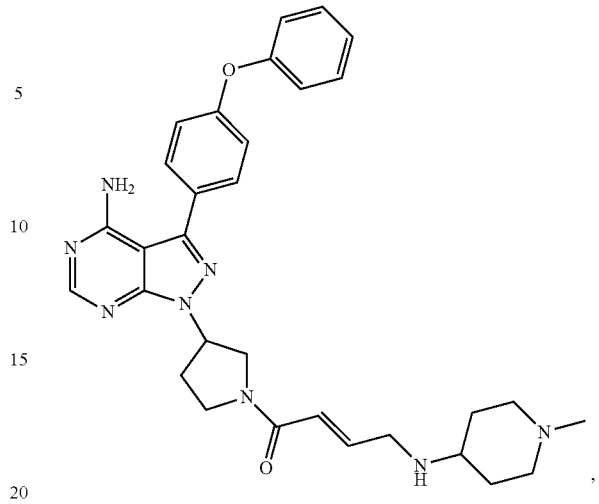

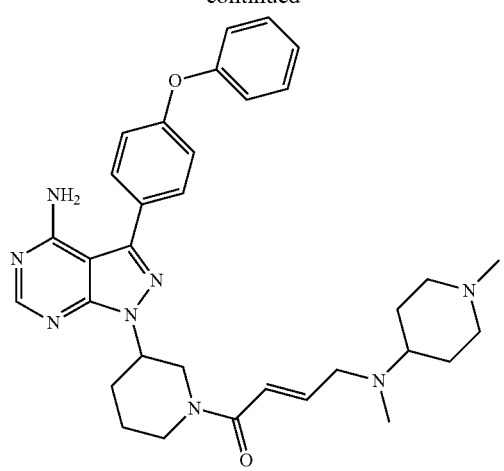
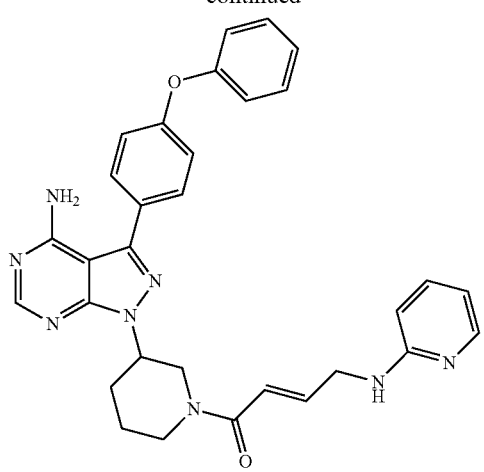
or a pharmaceutically acceptable salt, solvate, N-oxide, or prodrug thereof.
In another embodiment is a compound selected from:
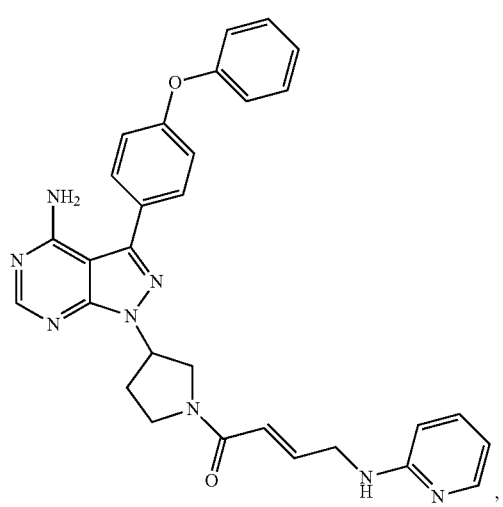
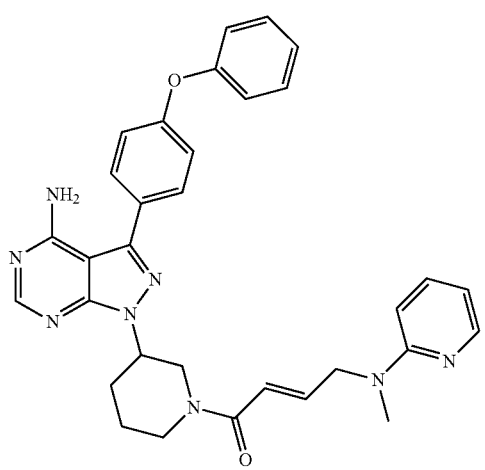
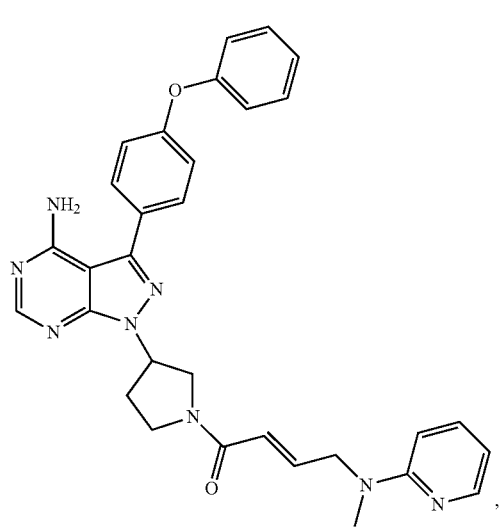
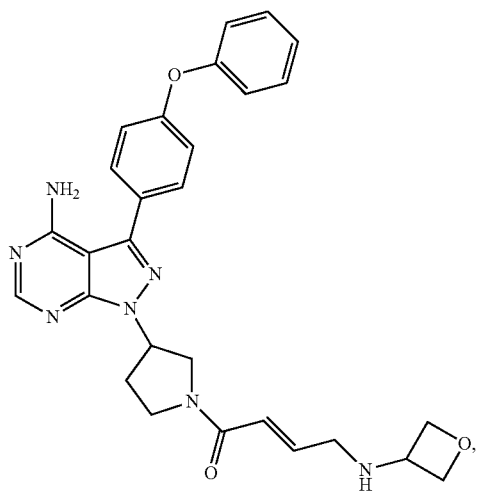

99
-continued
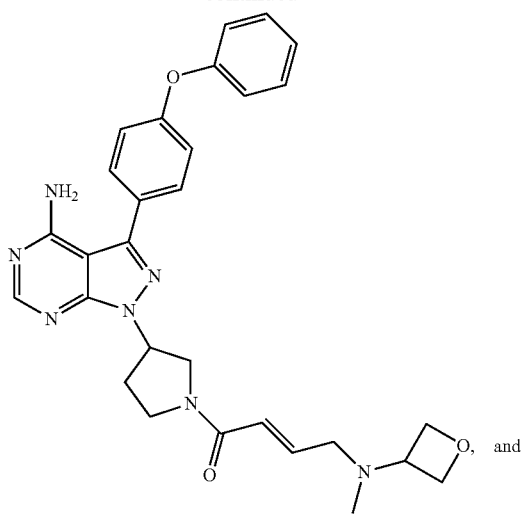
and
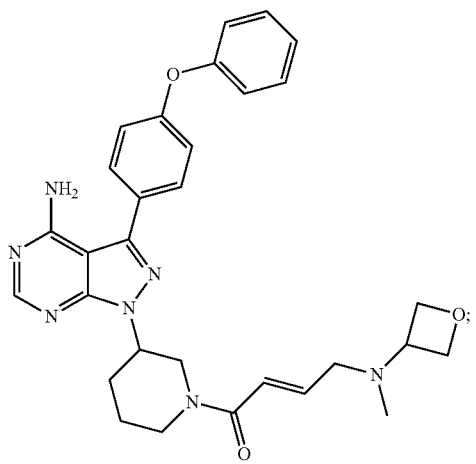 [SMILES: CN(C/C=C/C(=O)N1CCCC(n2nc(-c3ccc(Oc4ccccc4)cc3)c3c(N)ncnc32)C1)C1COC1]
or a pharmaceutically acceptable salt, solvate, N-oxide, or prodrug thereof.
In another embodiment is a compound selected from:
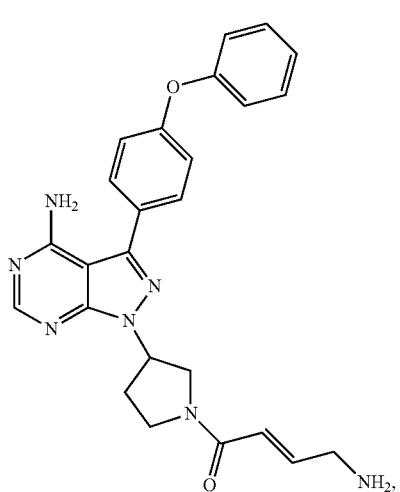
100
-continued
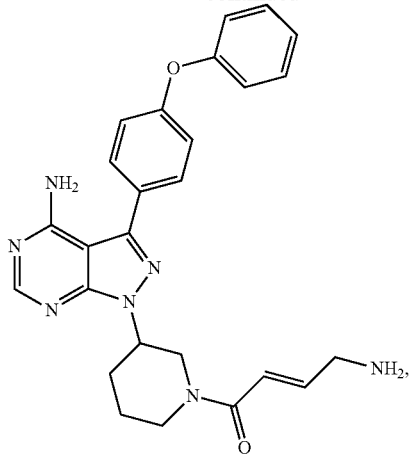
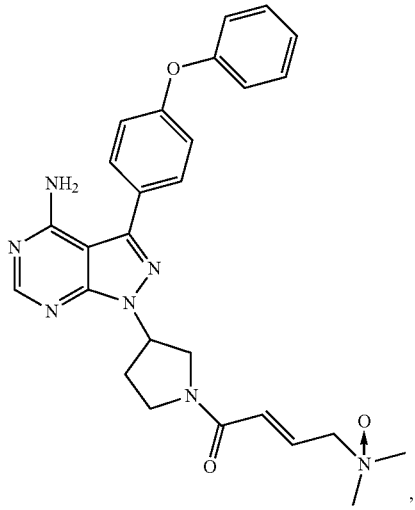
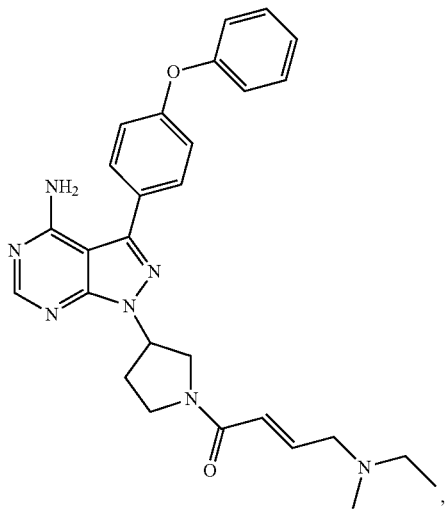

101
-continued
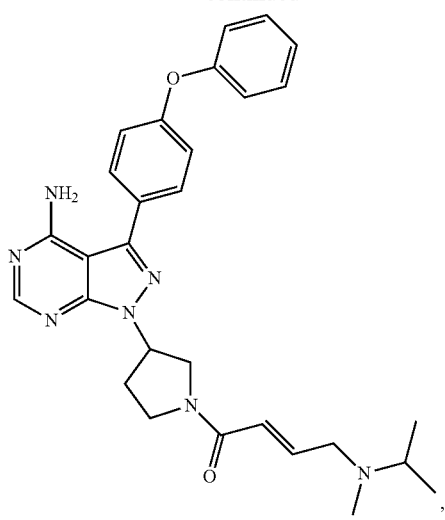
102
-continued
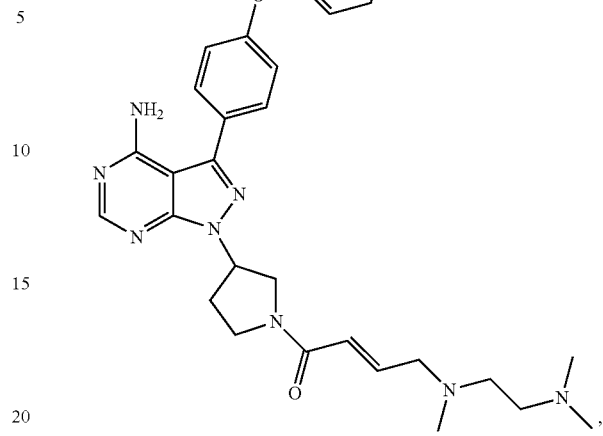
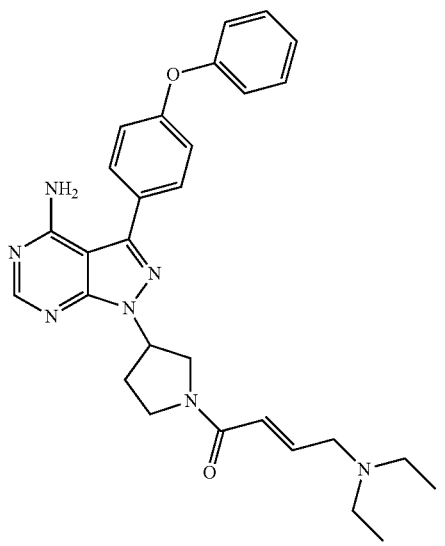
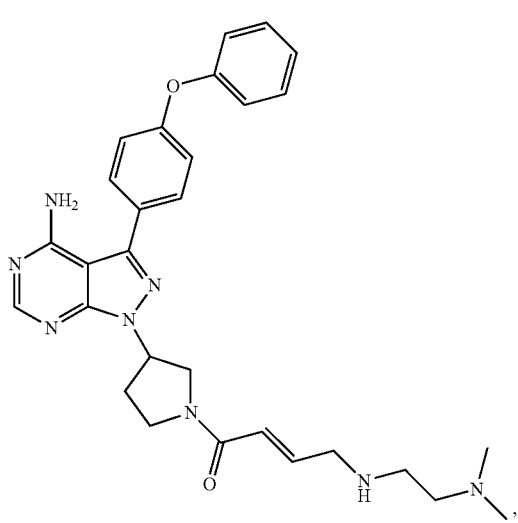
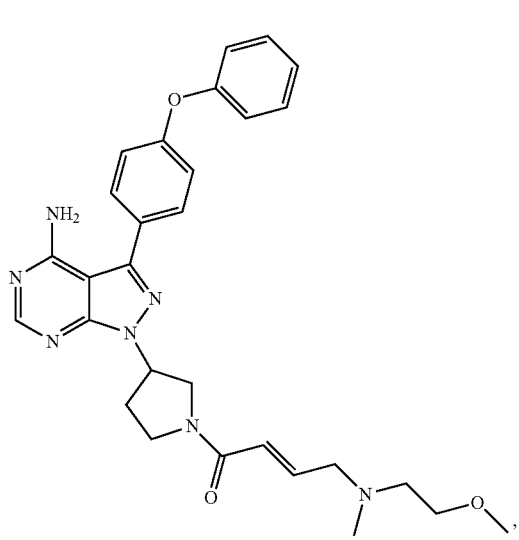

103
-continued
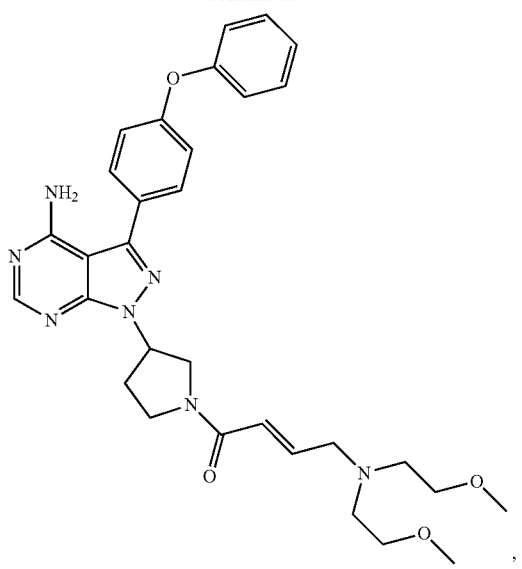
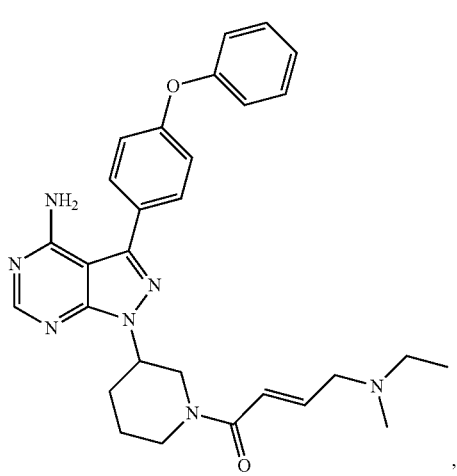
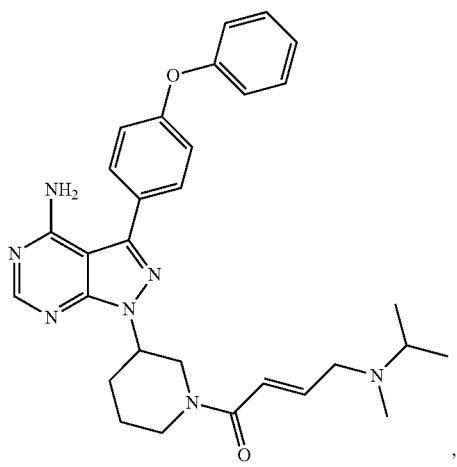
104
-continued
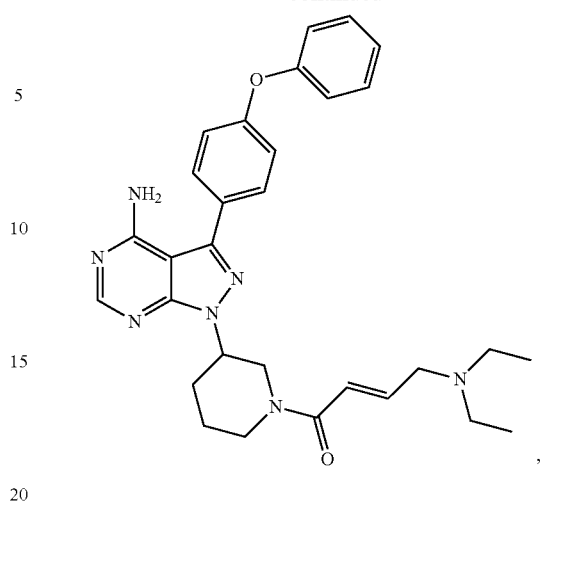
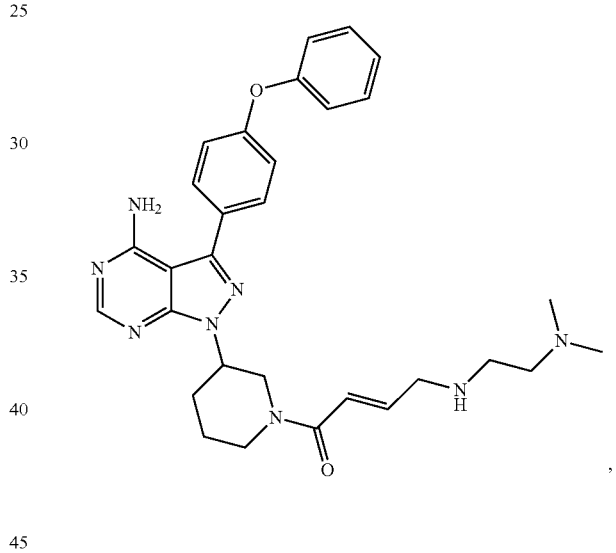
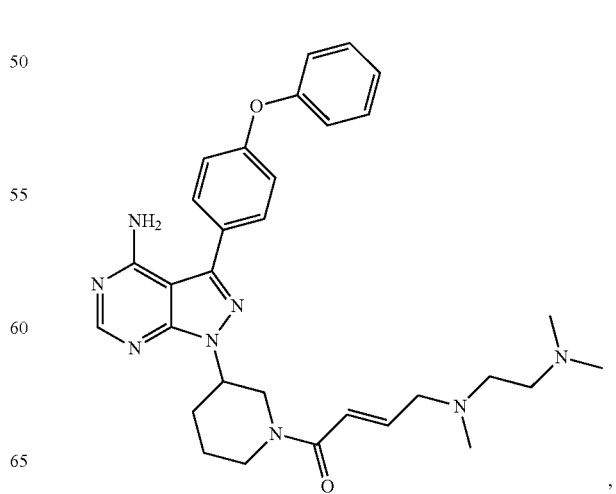

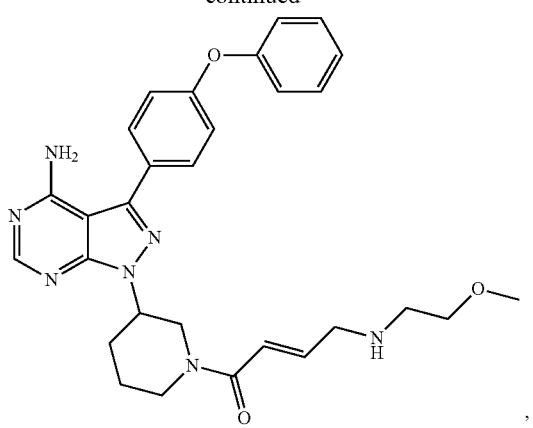
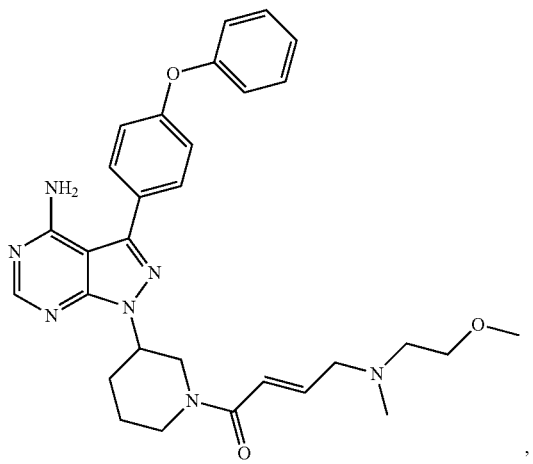
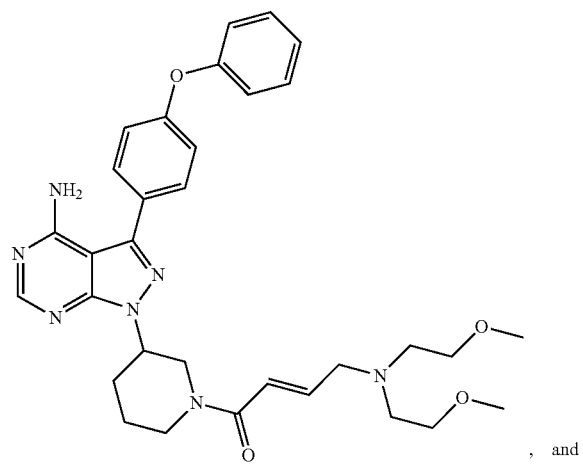
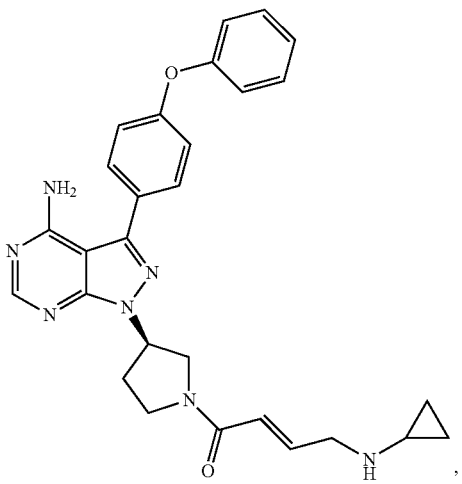
or a pharmaceutically acceptable salt, solvate, N-oxide, or prodrug thereof.
In another embodiment is a compound selected from:
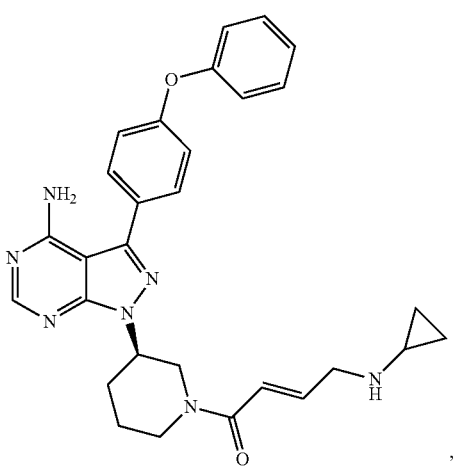

107
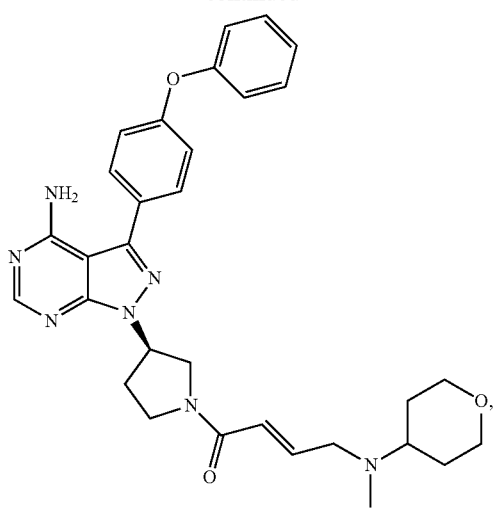
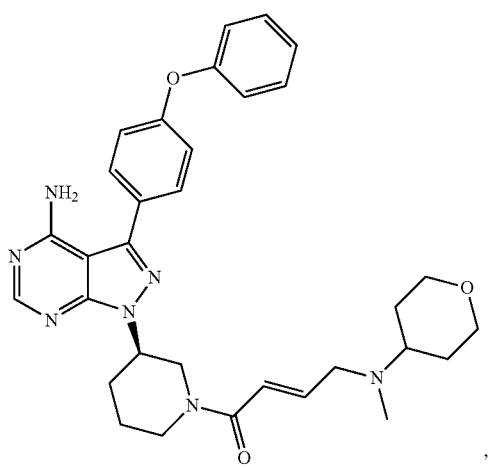
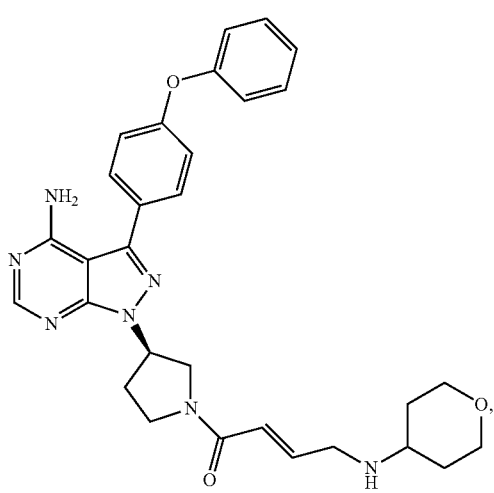
108
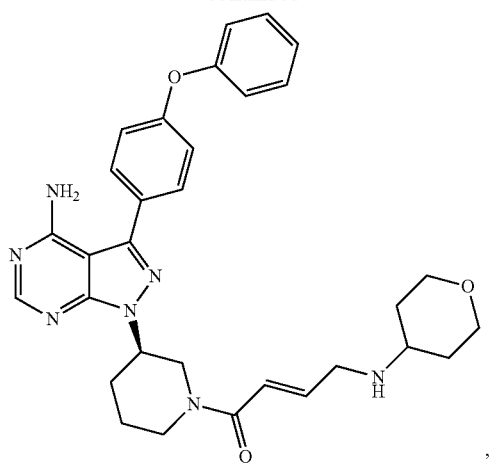
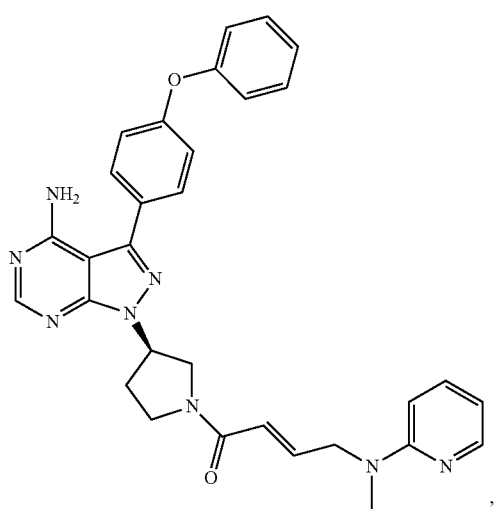
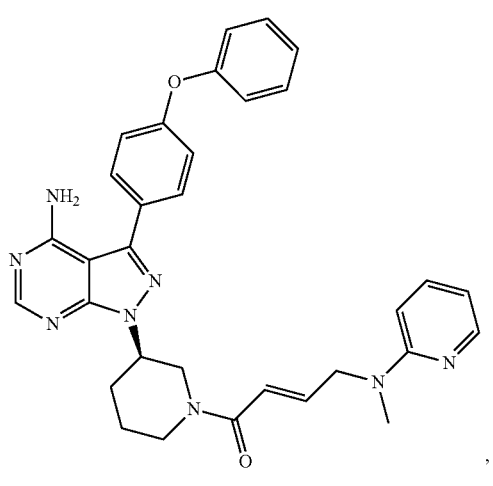

109
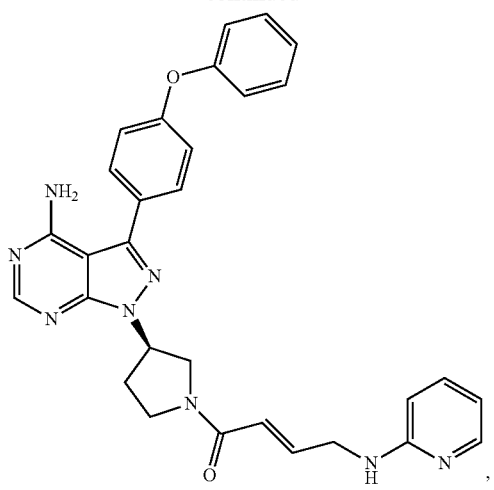
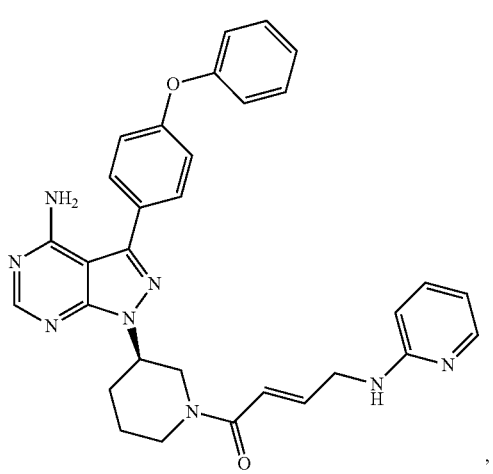
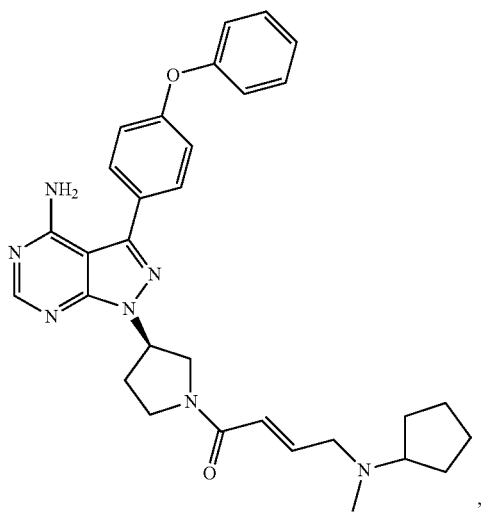
110
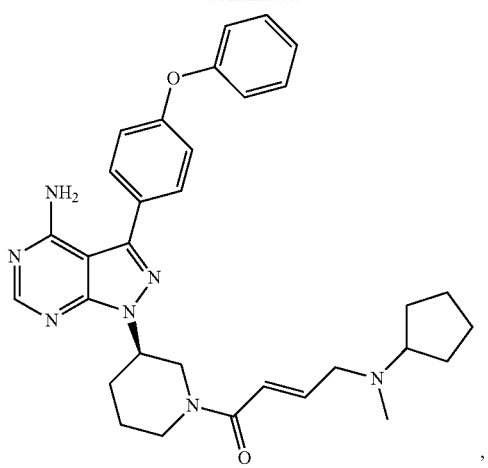
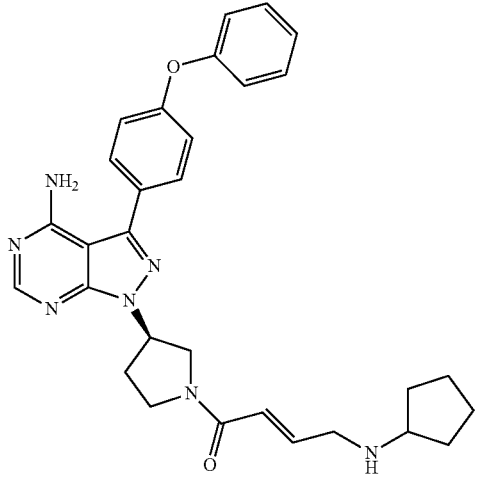
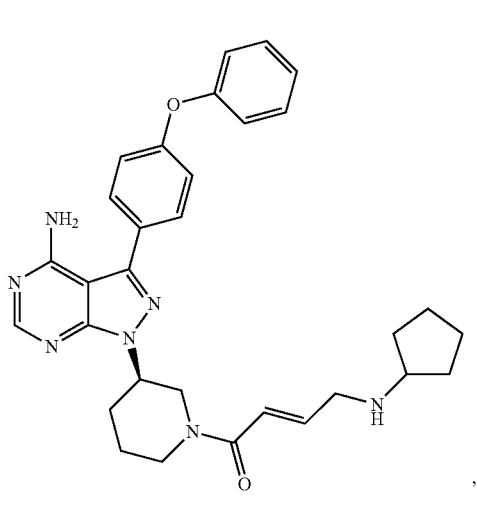

111
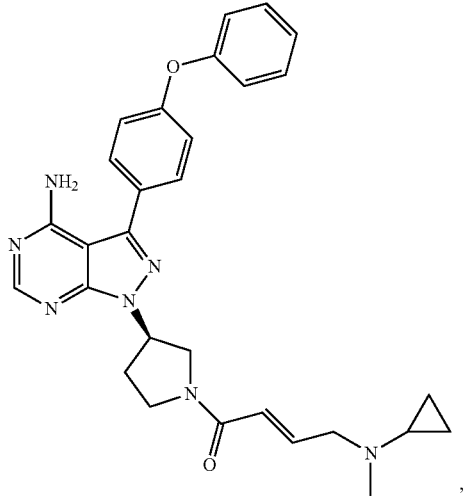
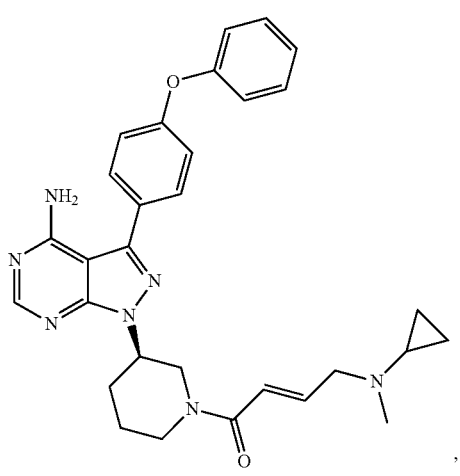
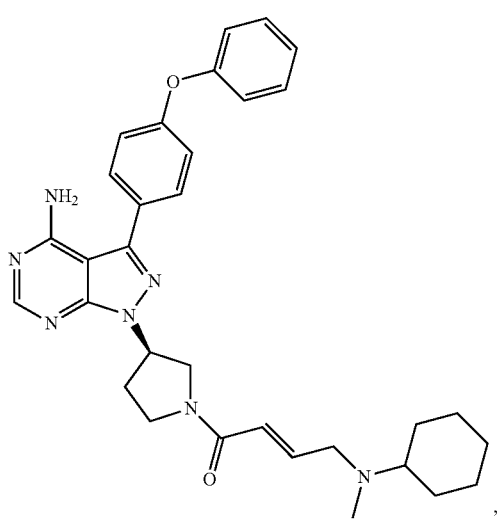
112
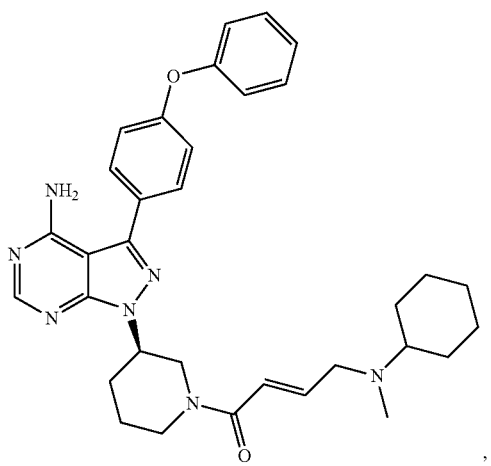
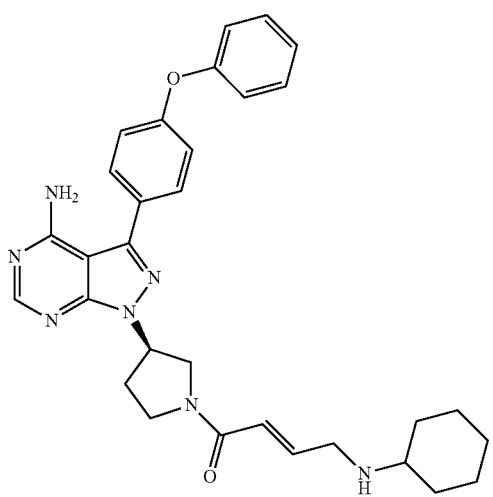
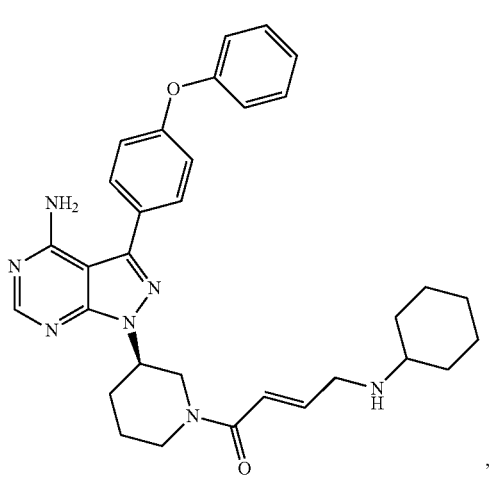

113
-continued
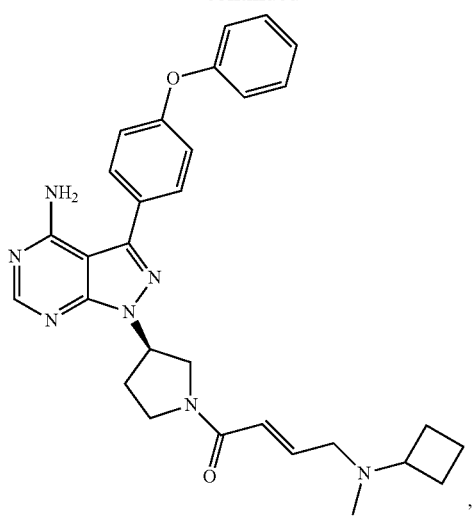
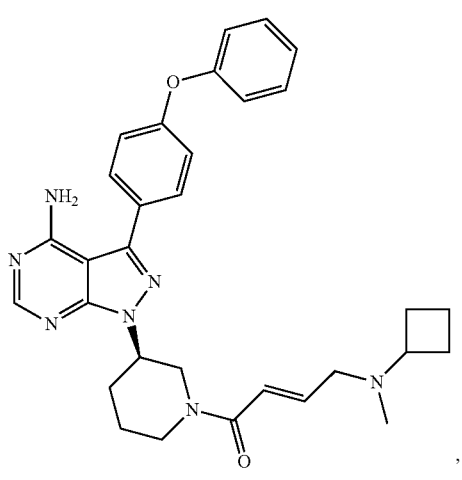
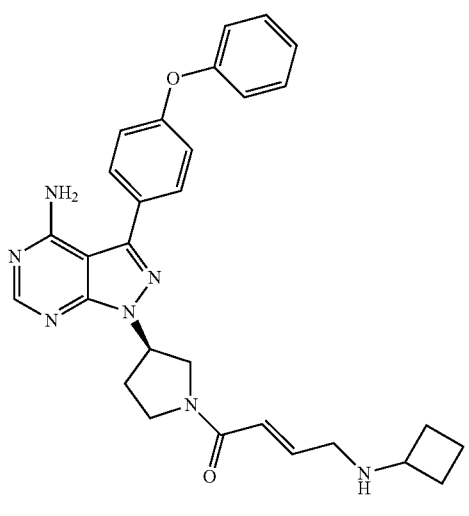
114
-continued
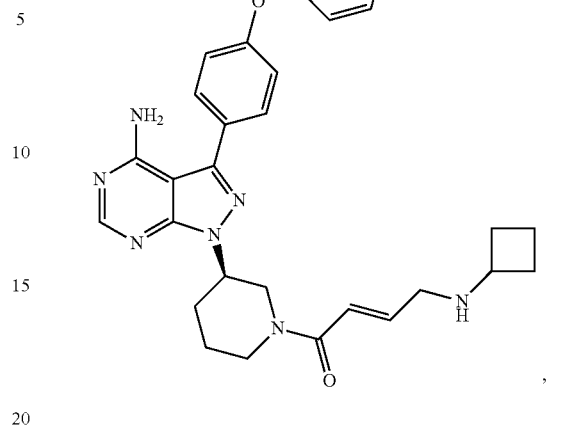
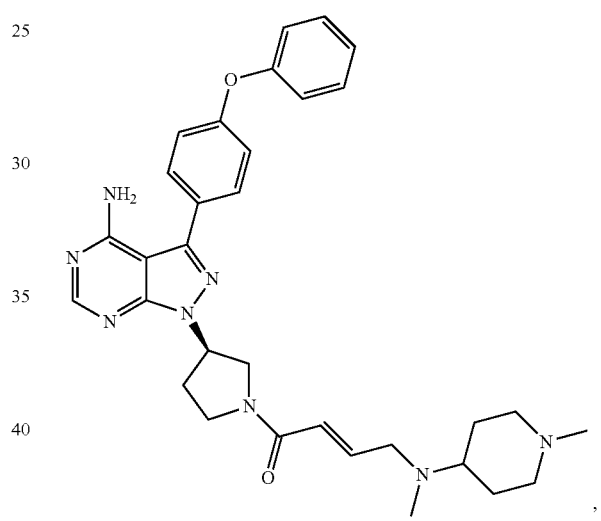
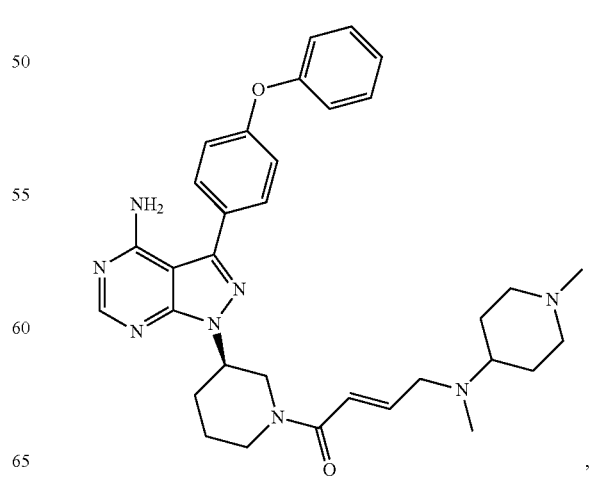

115
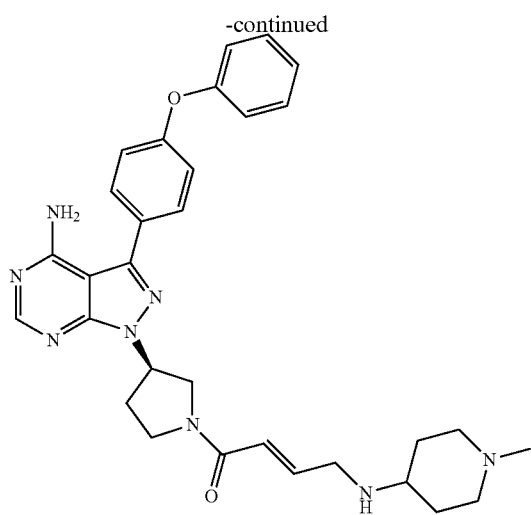
,
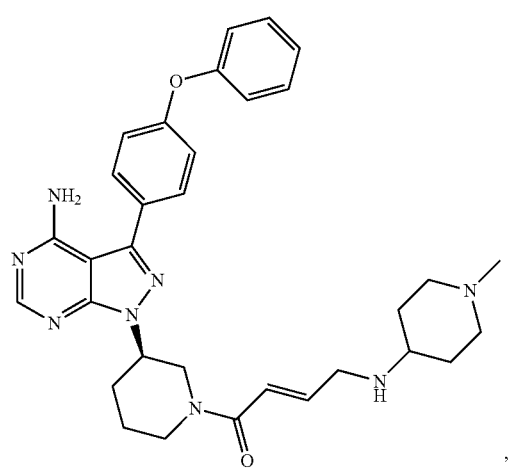
,
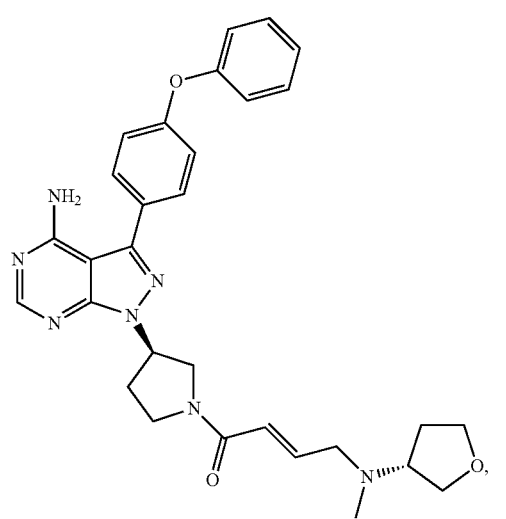
,
116
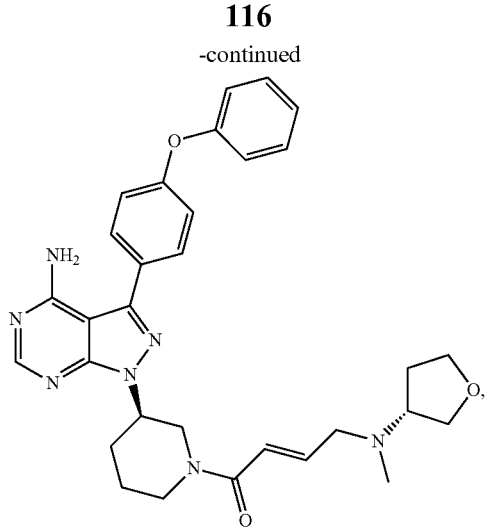
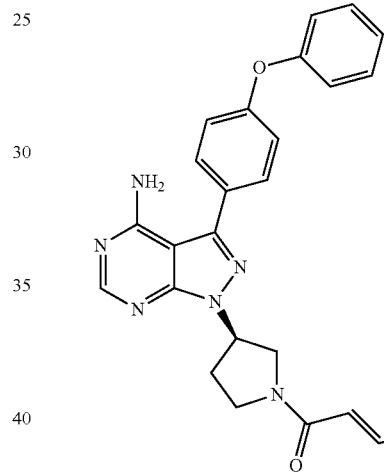
,
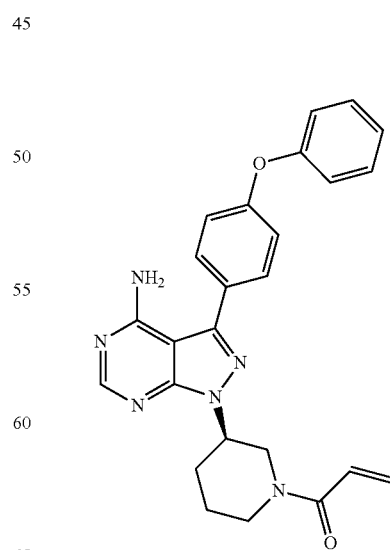
,

117
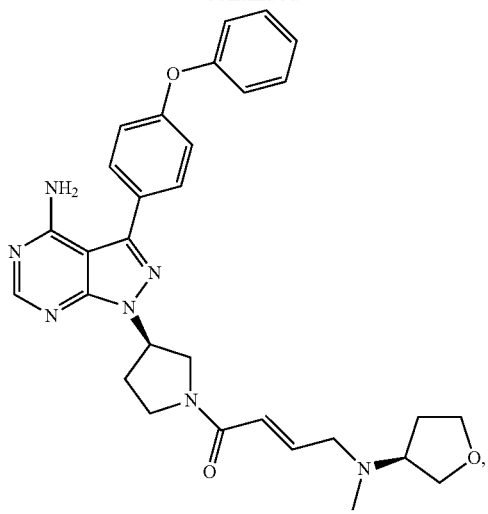
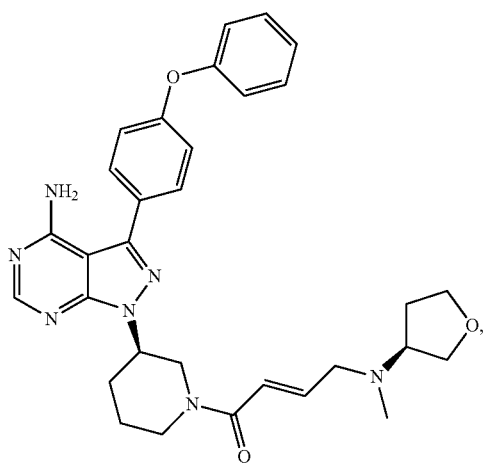
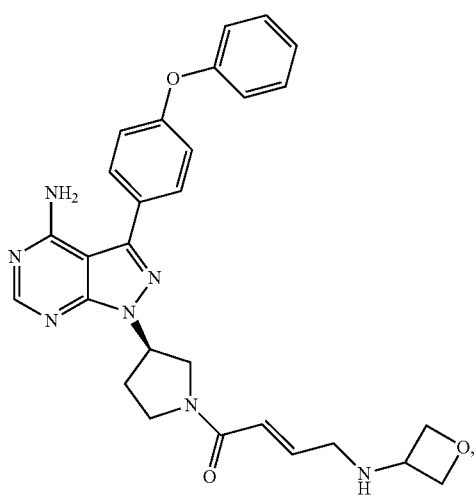
118
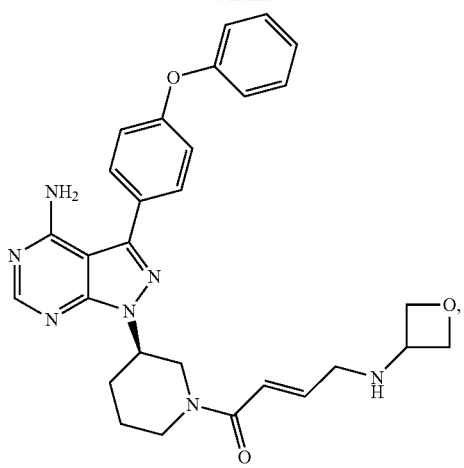
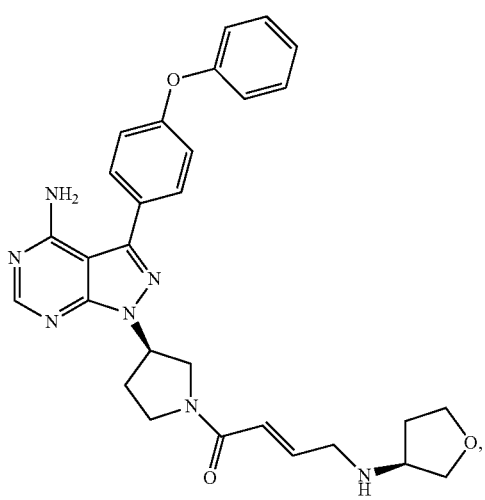
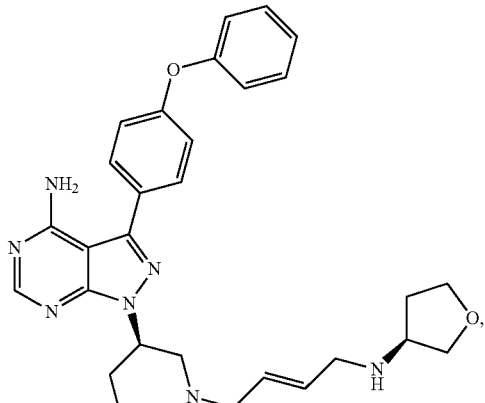

119
-continued
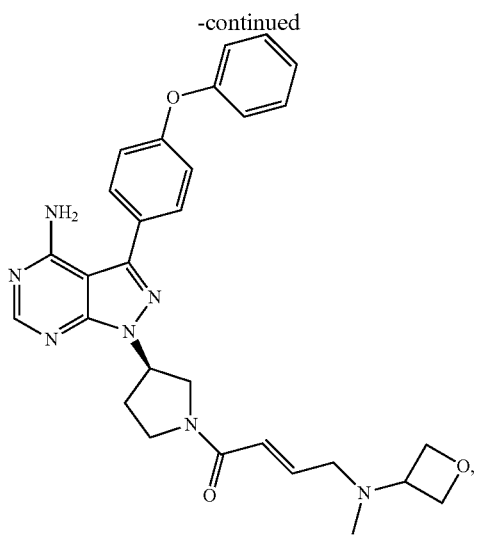
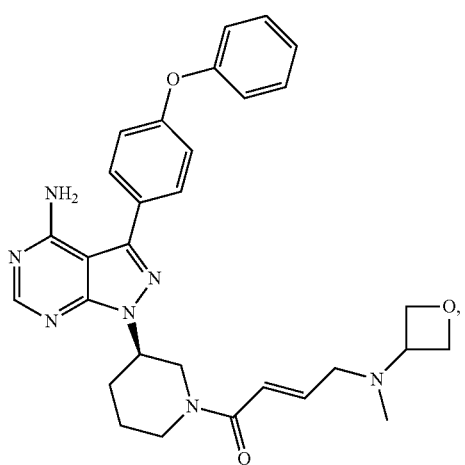
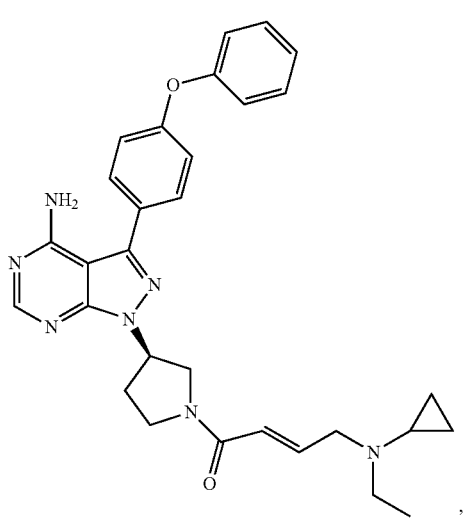
120
-continued
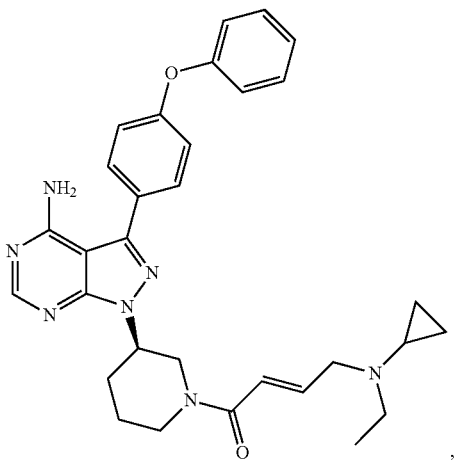
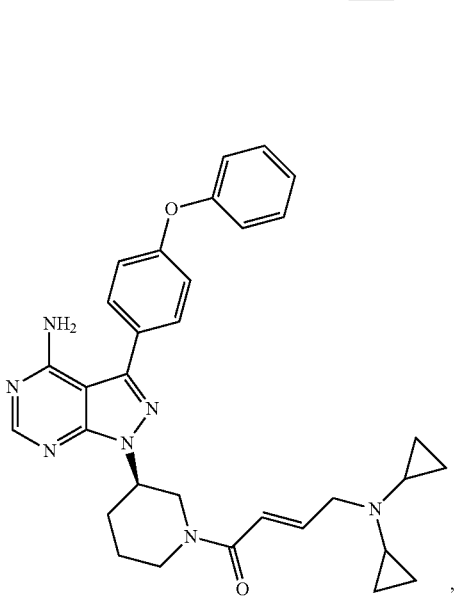

121 -continued
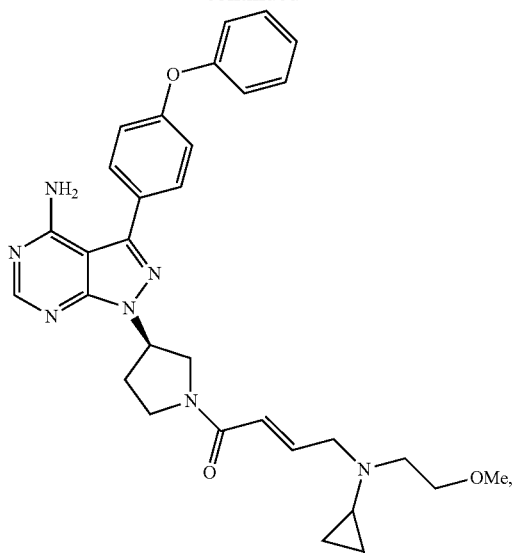
122 -continued
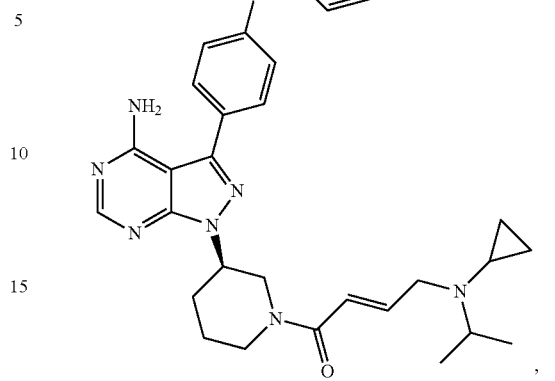
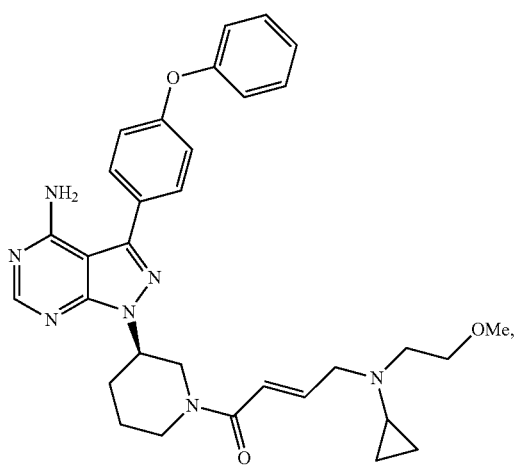
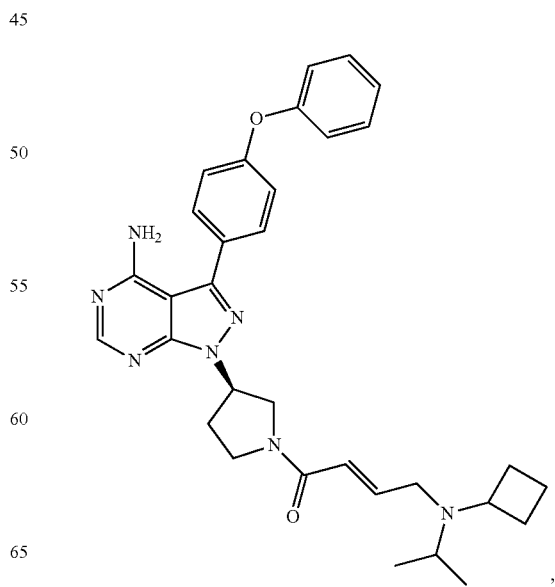

123
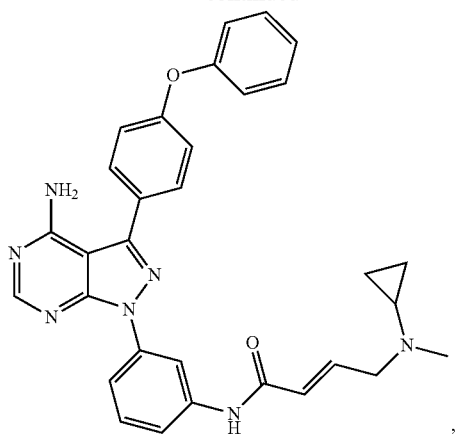
,
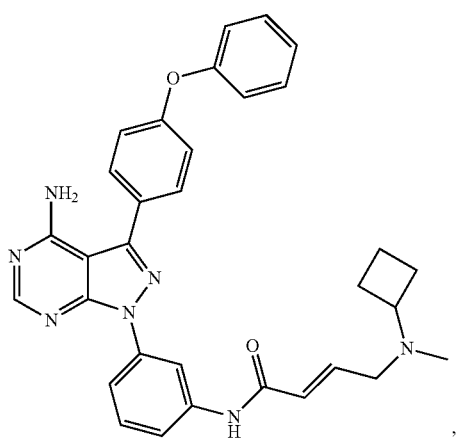
,
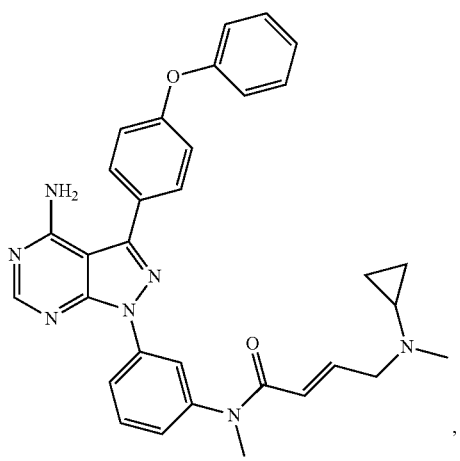
,
124
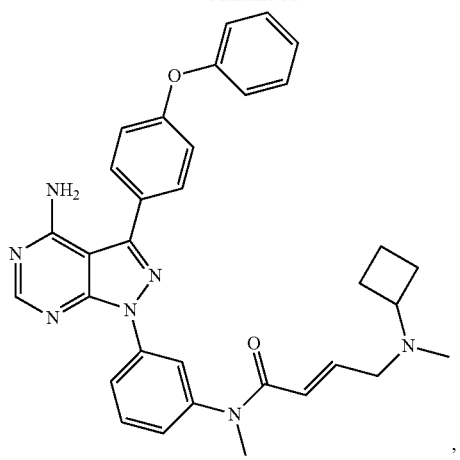
,
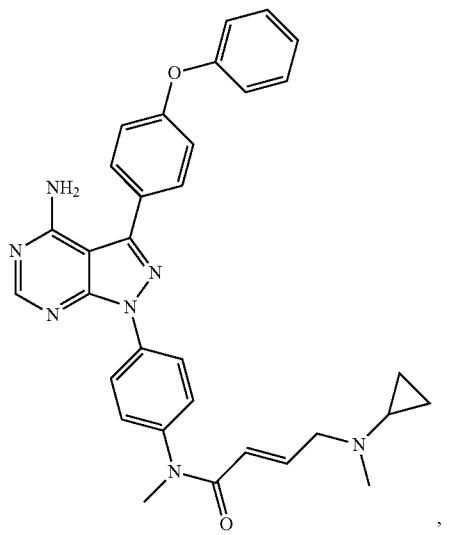
,
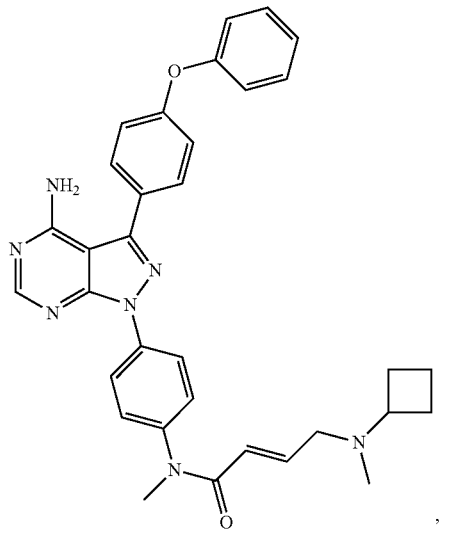
, 125
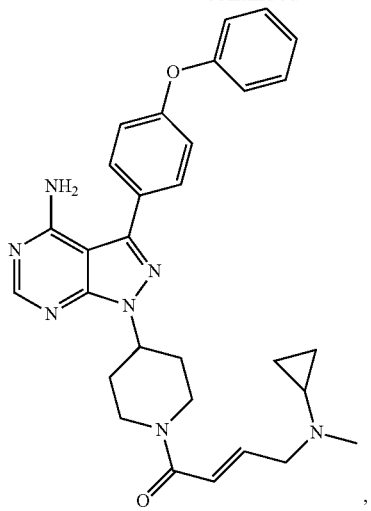
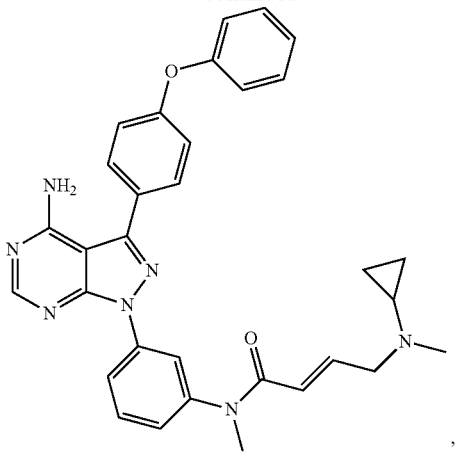
126
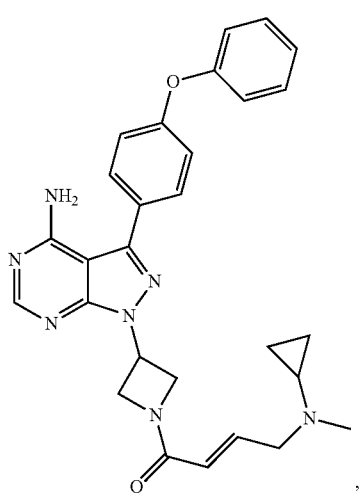
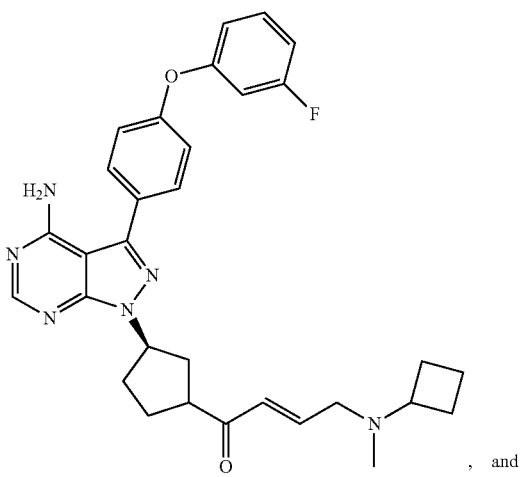
, and
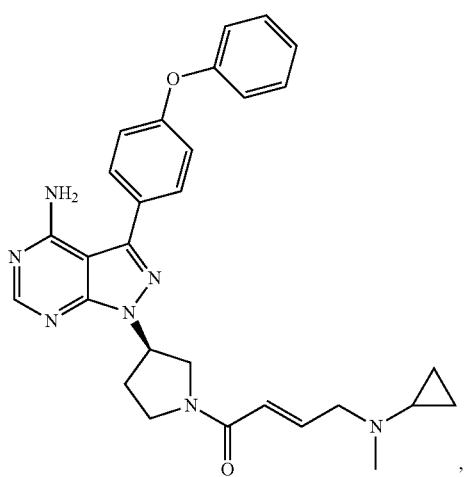
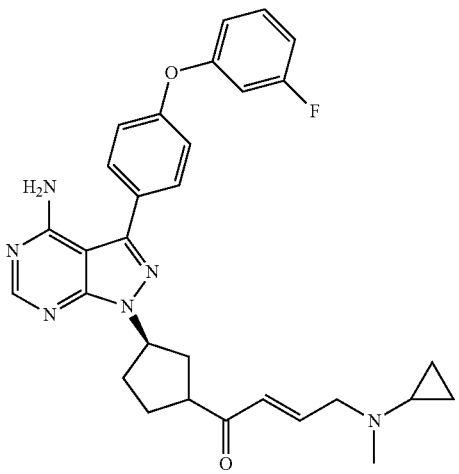
or a pharmaceutically acceptable salt, solvate, N-oxide, or prodrug thereof.

In another embodiment is a compound selected from:
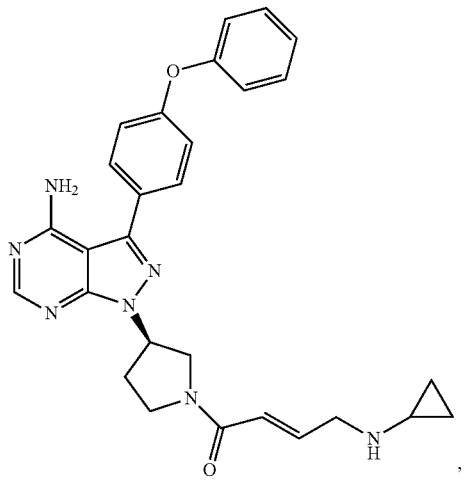
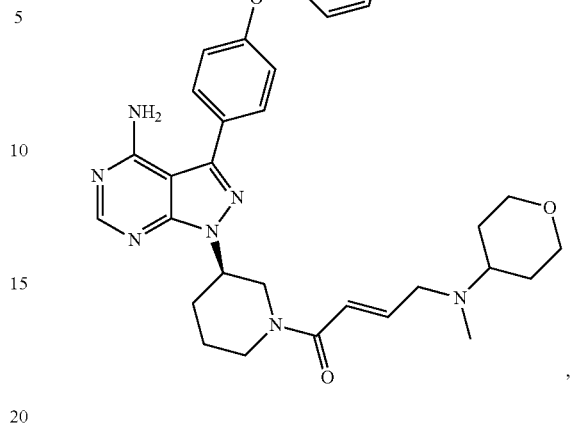
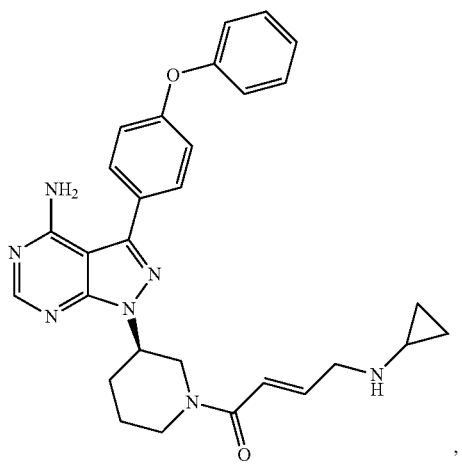
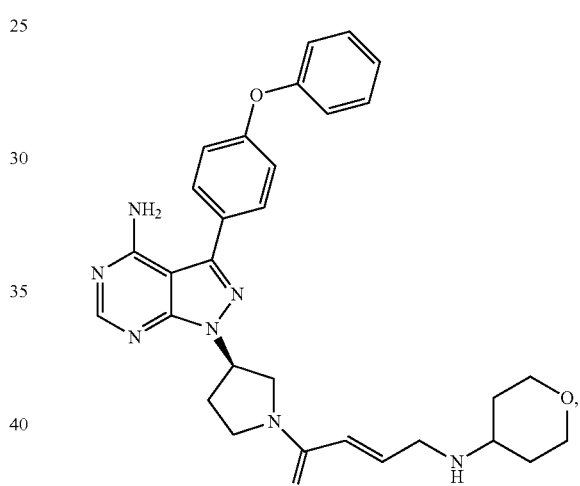
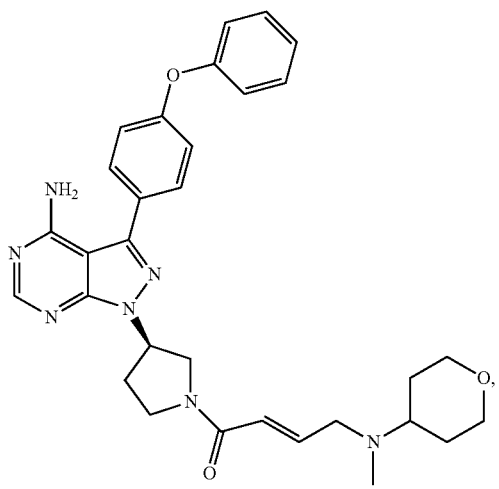
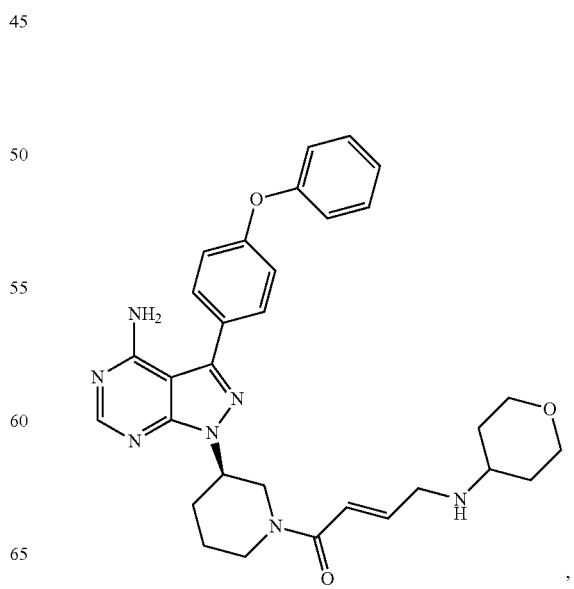

129
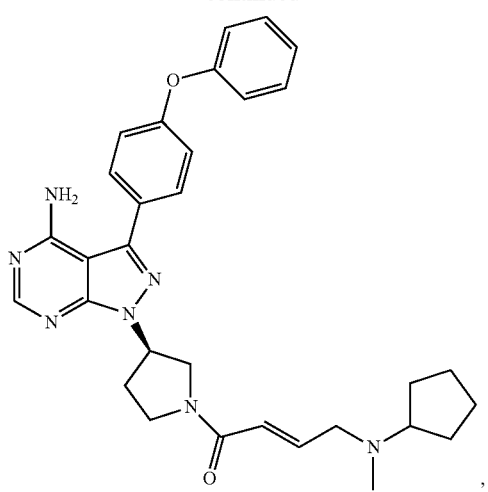
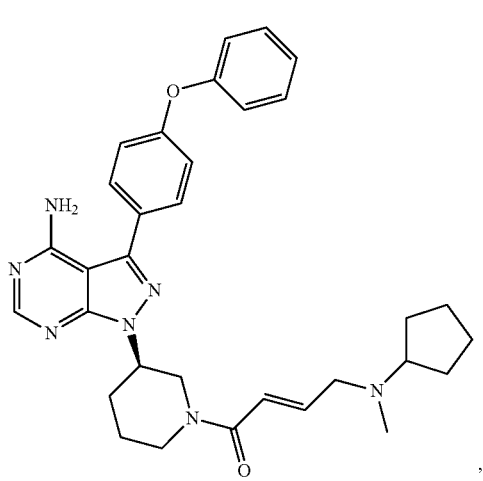
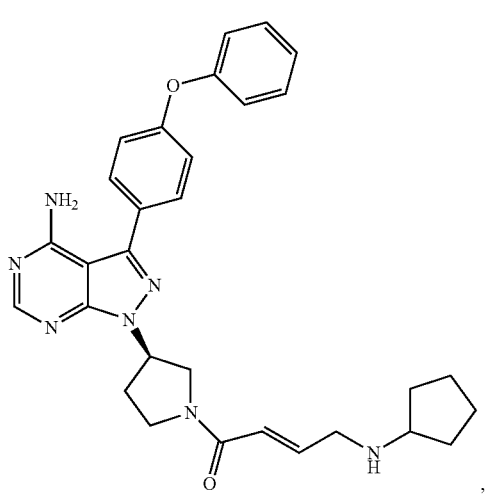
130
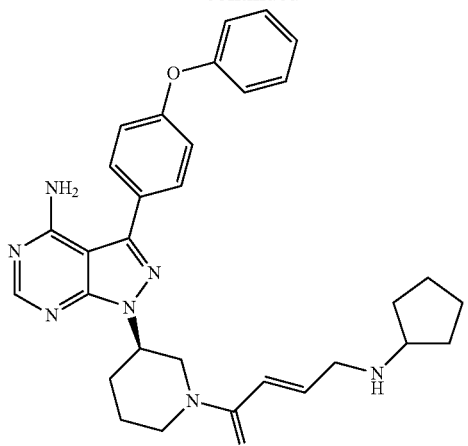
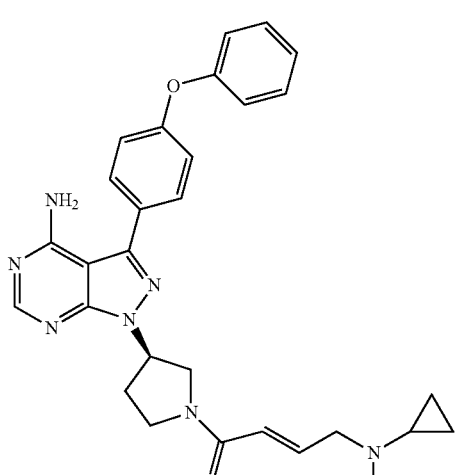
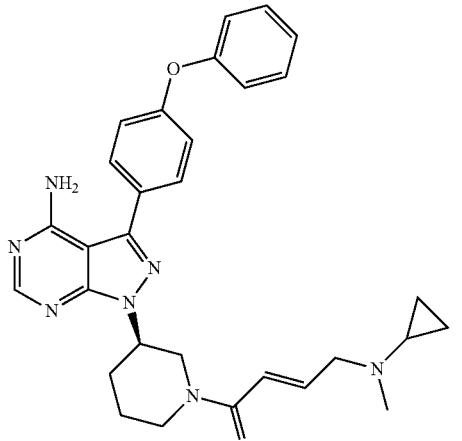

131
-continued
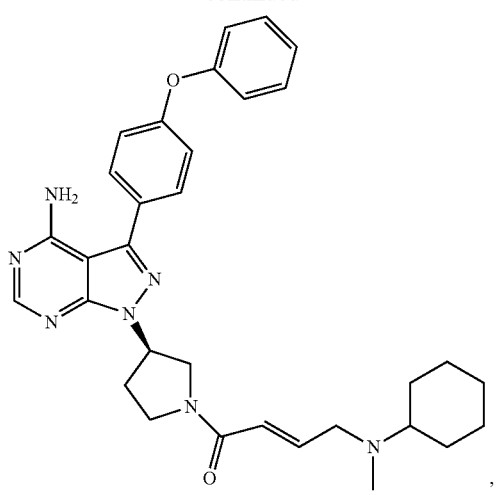
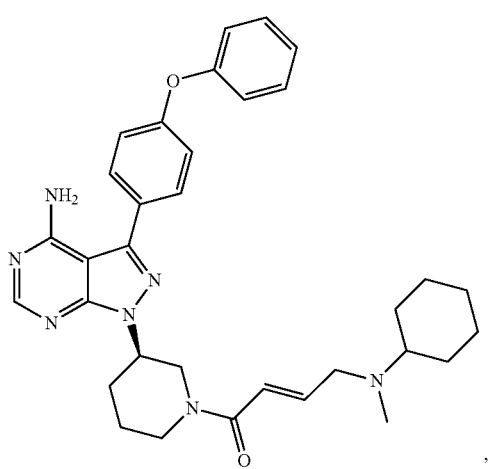
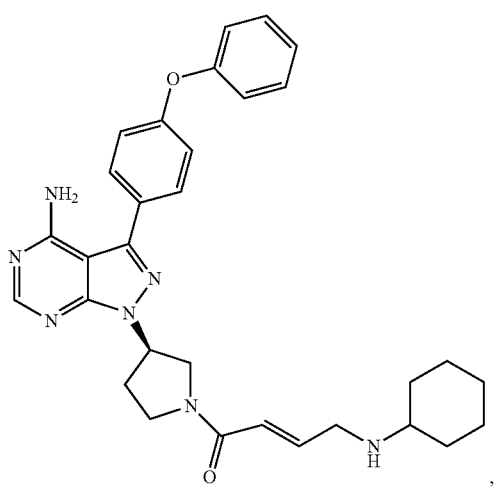
132
-continued
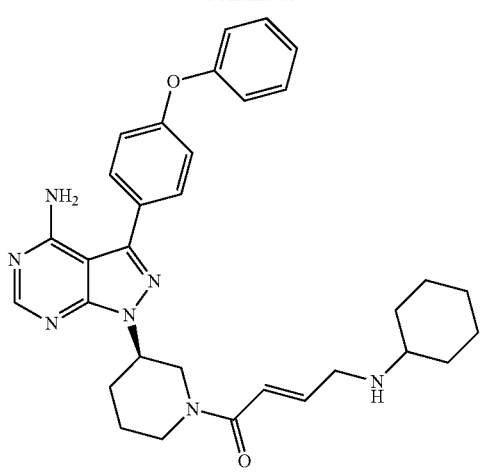
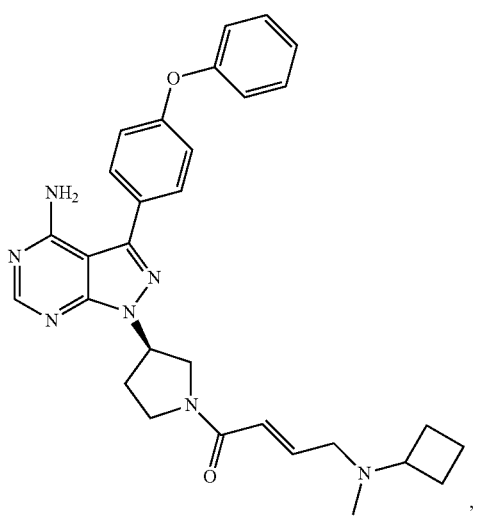
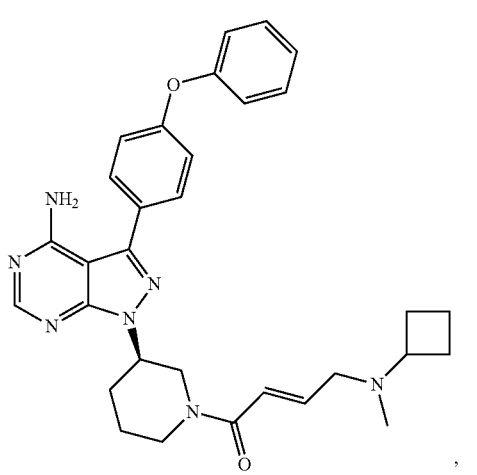

133
-continued
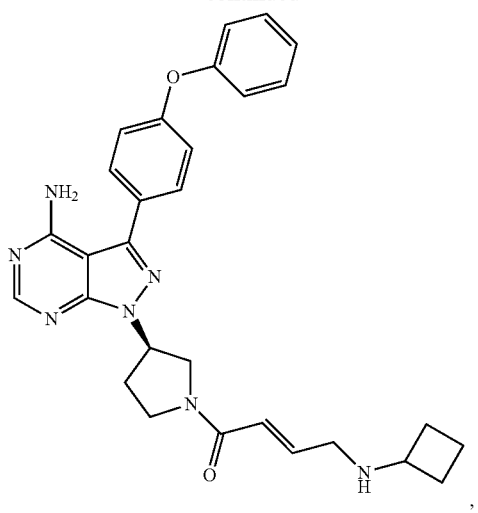
,
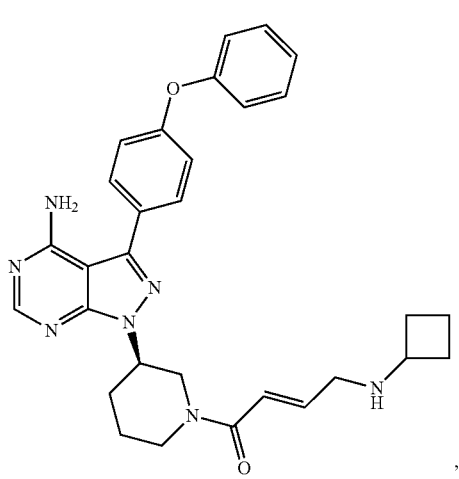
,
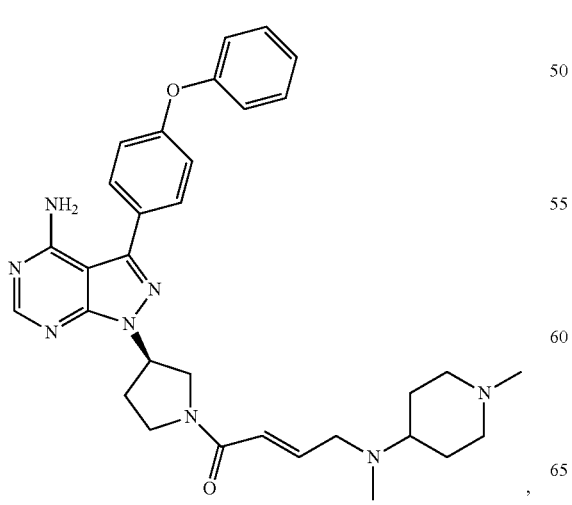
,
134
-continued
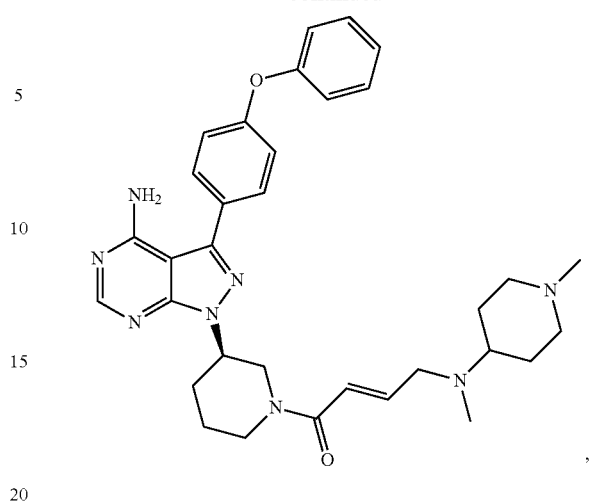
,
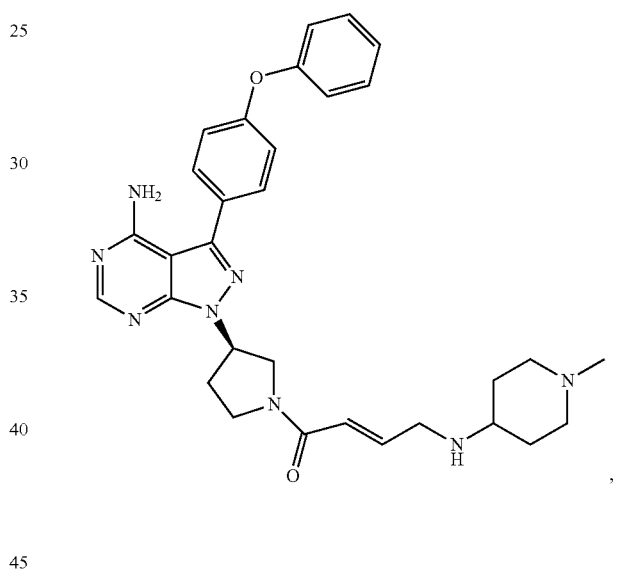
,
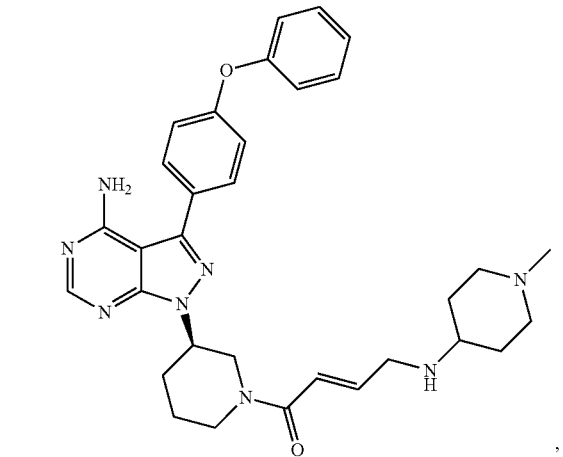
,

135
-continued
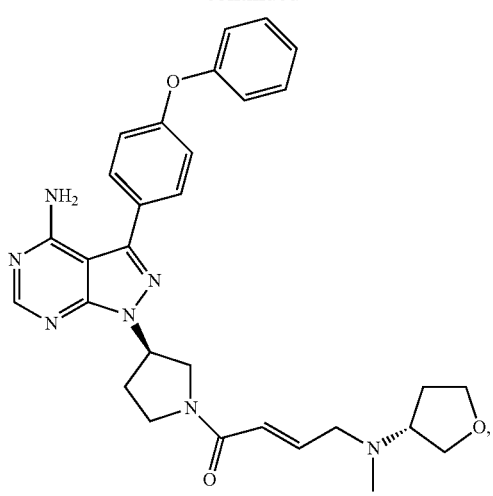
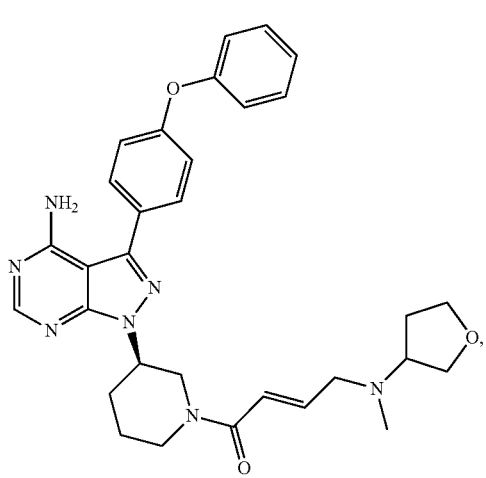
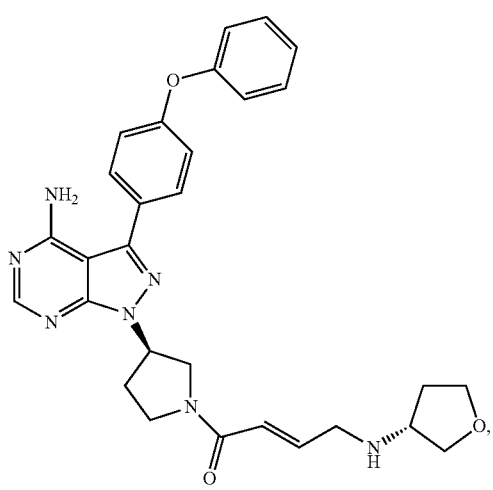
136
-continued
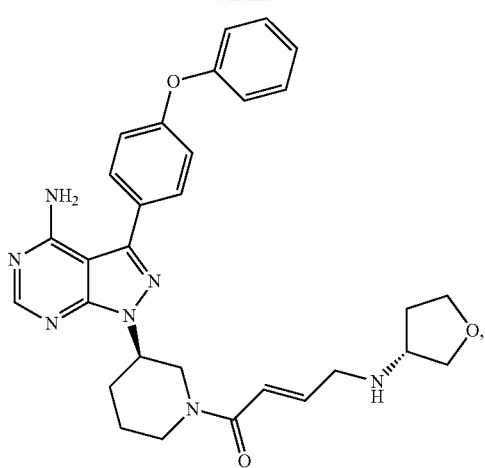
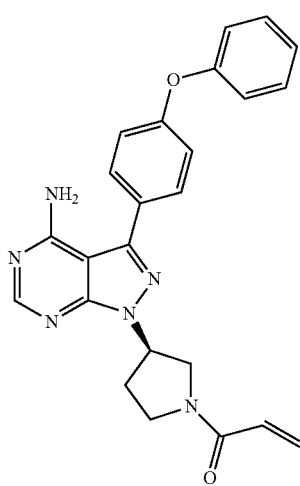
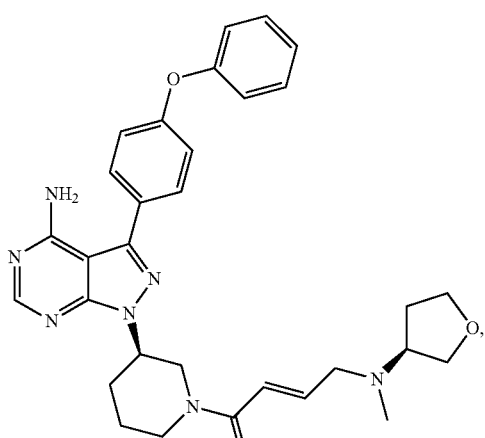

137
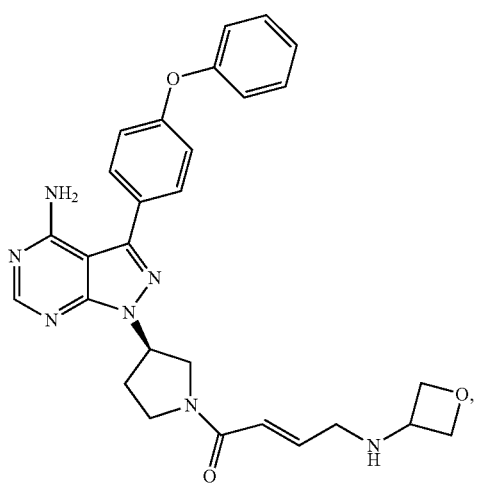
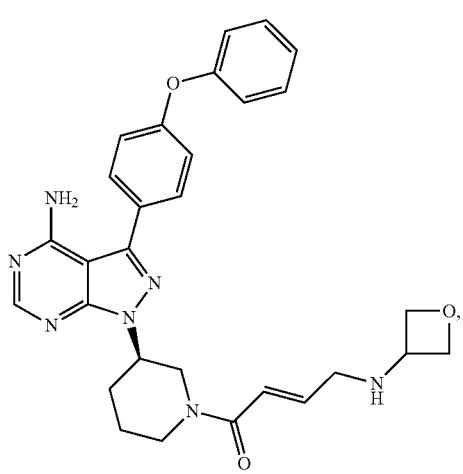
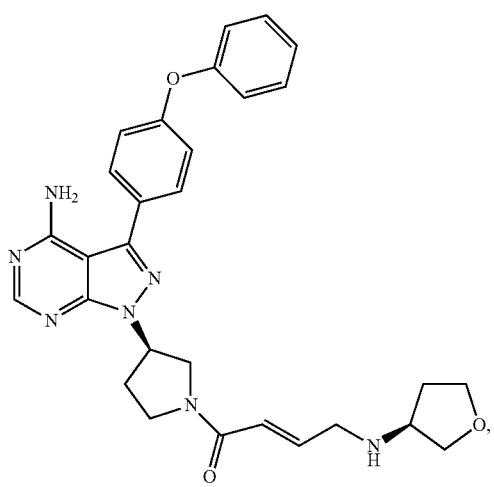
138
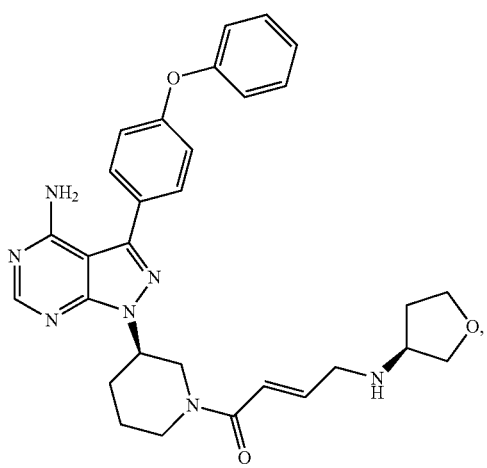
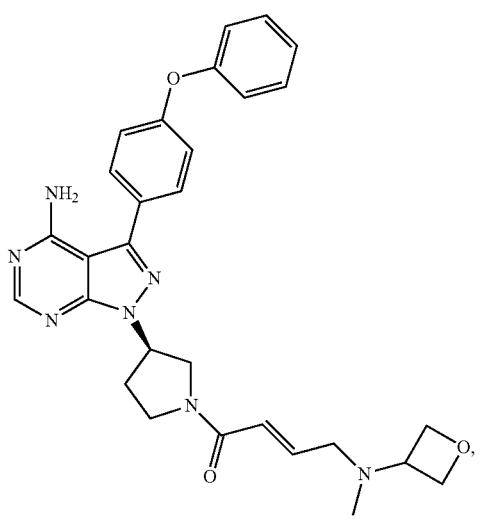
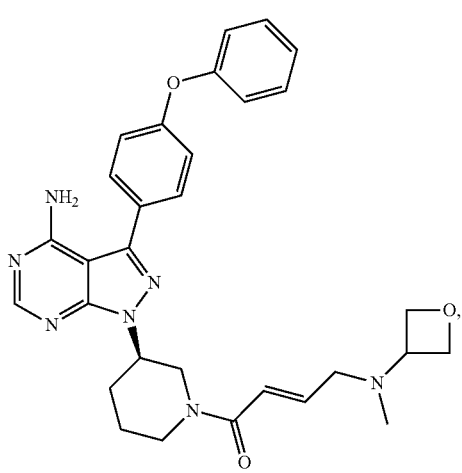

139
-continued
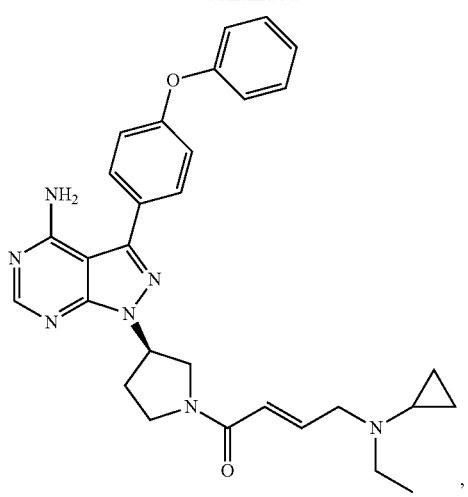
,
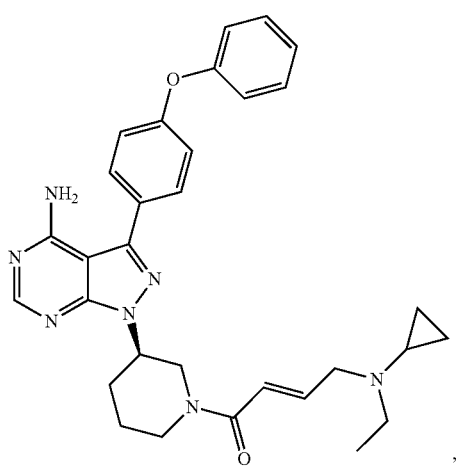
,
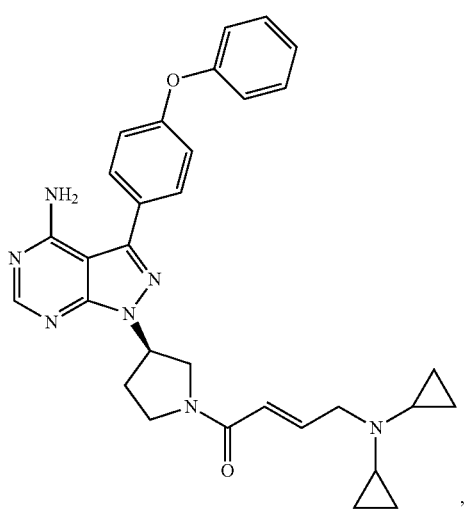
,
140
-continued
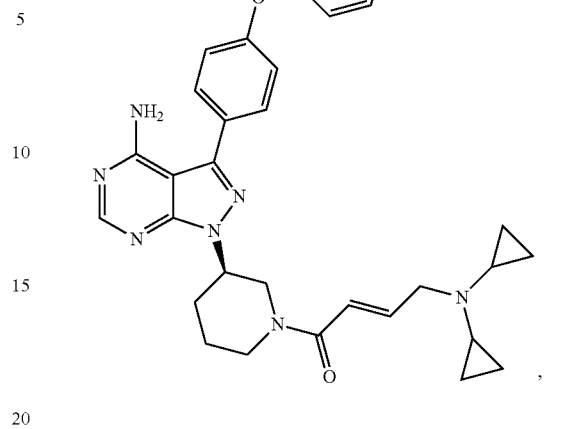
,
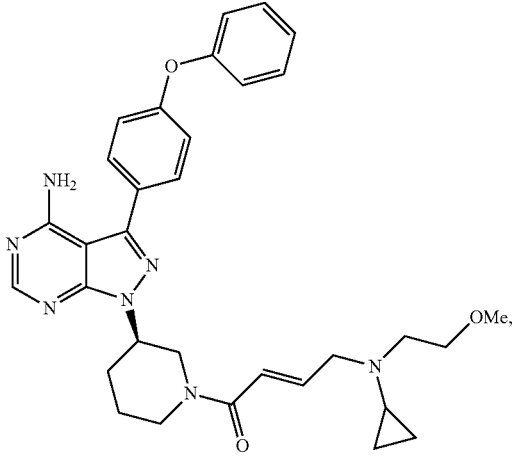
,

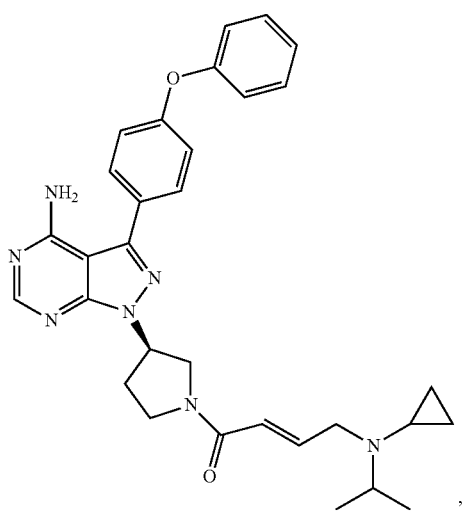
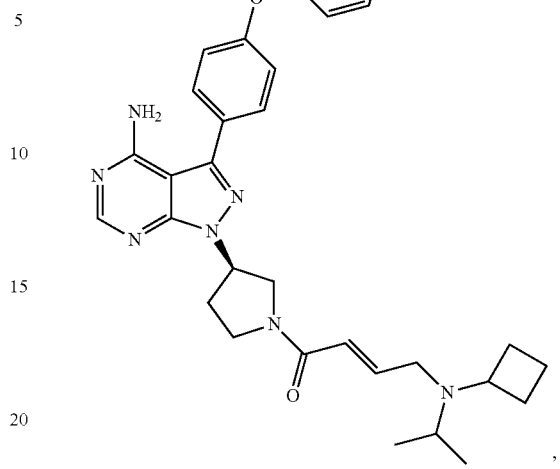

143
-continued
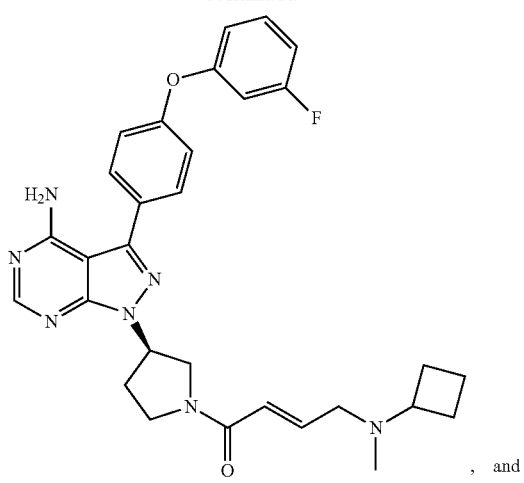
, and
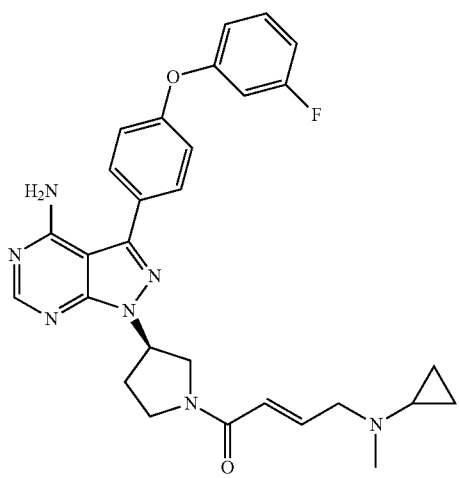
or a pharmaceutically acceptable salt, solvate, N-oxide, or prodrug thereof.
In another embodiment is a compound selected from:
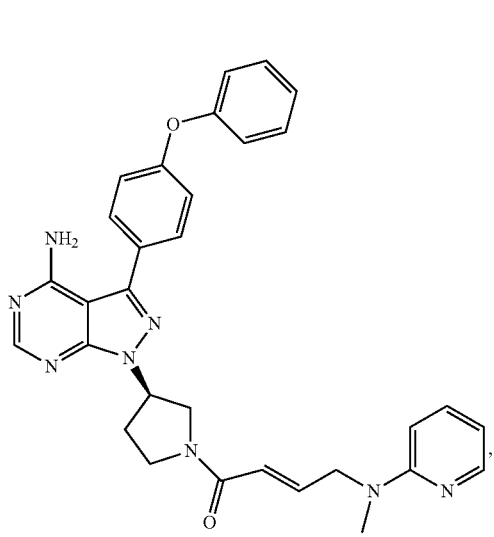
,
144
-continued
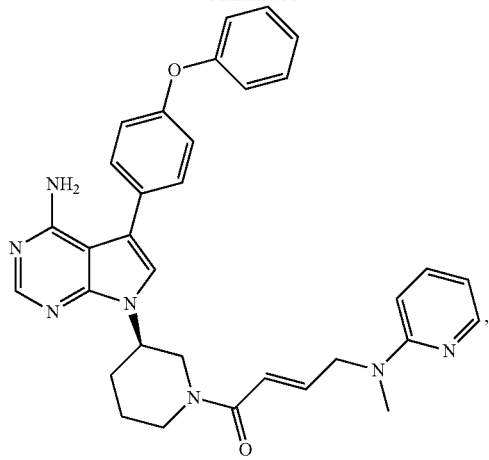
,
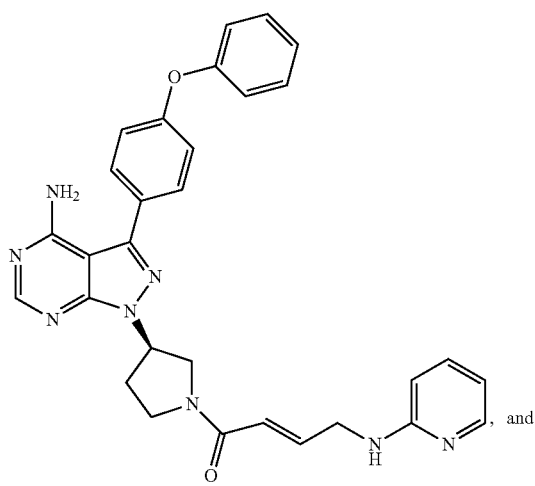
, and
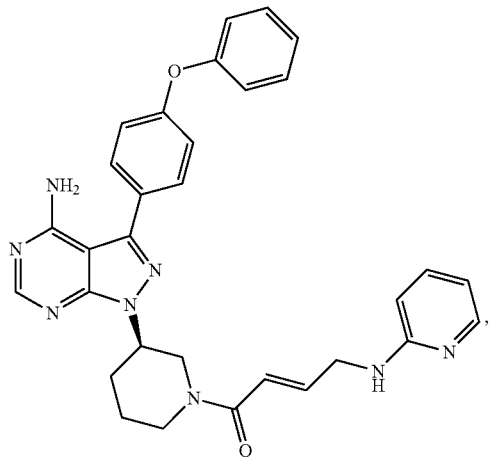 [SMILES: Nc1ncnc2c1c(-c1ccc(Oc3ccccc3)cc1)nn2[C@@H]1CCCN(C(=O)/C=C/CNc2ccccn2)C1 ; ","]
or a pharmaceutically acceptable salt, solvate, N-oxide, or prodrug thereof.

In another embodiment is a compound selected from:
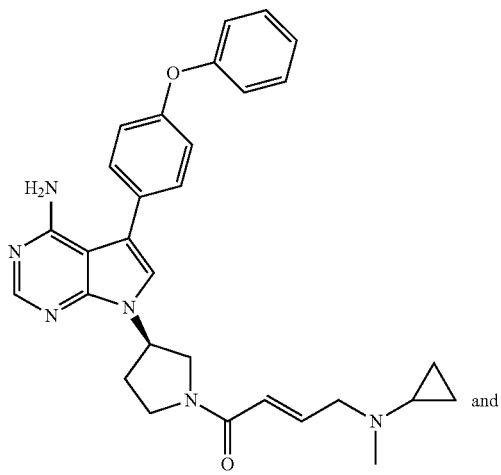
and
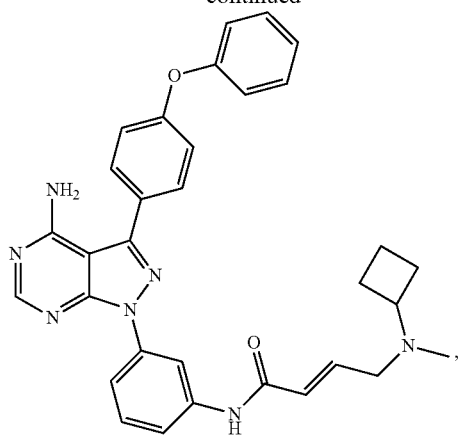
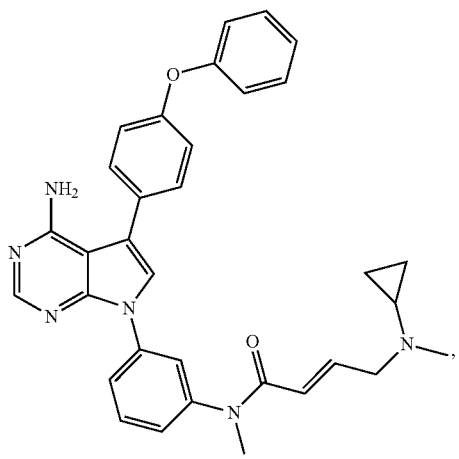
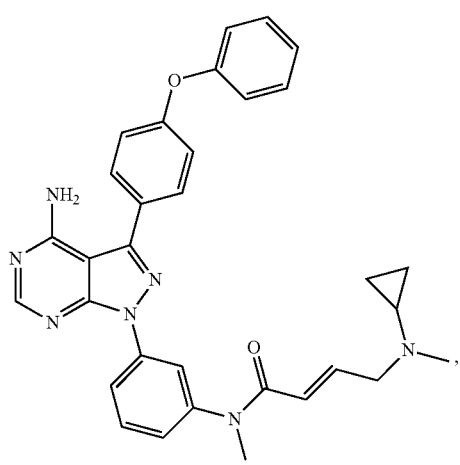
or a pharmaceutically acceptable salt, solvate, N-oxide, or prodrug thereof.
In another embodiment is a compound selected from:
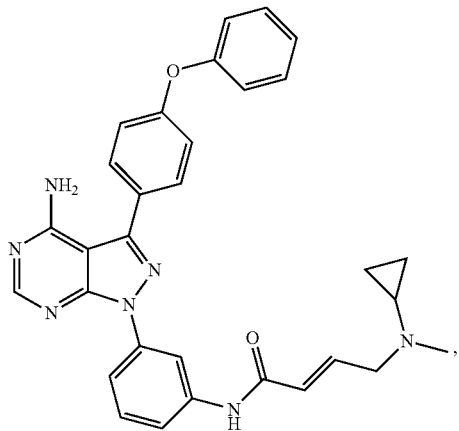
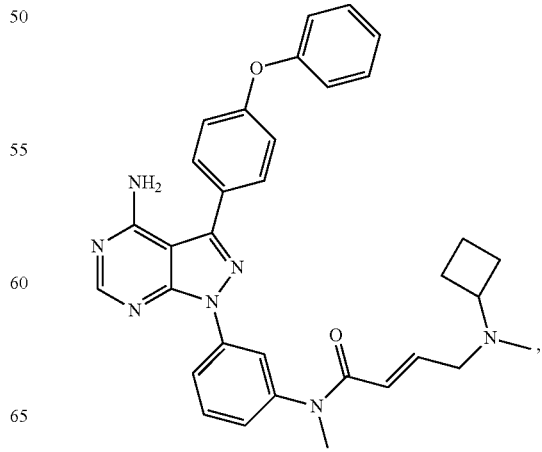

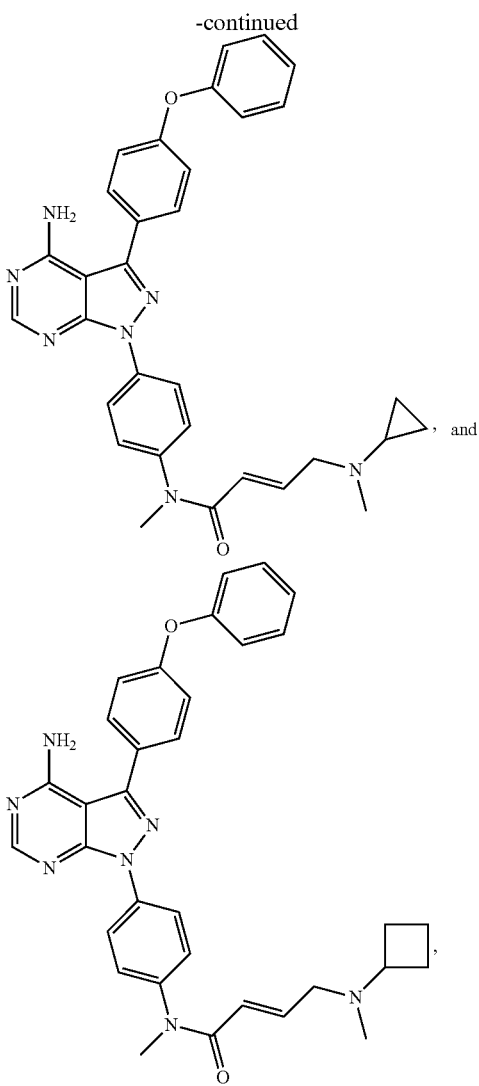

or a pharmaceutically acceptable salt, solvate, N-oxide, or prodrug thereof.

In one aspect is a pharmaceutical composition comprising a compound having the structure of Formula (I), (IA), (II), (III), (IV), (V), (VI), (VIA), (VIB), (VII), (VIII), (IX), (X), (XI), (XII), (XIII), (XIV), or a pharmaceutically acceptable salt or solvate thereof; and a pharmaceutically acceptable excipient, binder or carrier. In one aspect is a pharmaceutical composition comprising a compound having the structure of Formula (I), (IA), (II), (III), (IV), (V), (VI), (VIA), (VIB), (VII), (VIII), (IX), (X), or a pharmaceutically acceptable salt or solvate thereof; and a pharmaceutically acceptable excipient, binder or carrier. In another aspect is a pharmaceutical composition comprising a compound having the structure of Formula (I), (II), (III), (IV), (V), (VI), (VII), (VIII), (IX), or (X), or a pharmaceutically acceptable salt, solvate, or prodrug thereof; and a pharmaceutically acceptable excipient, binder or carrier. In another aspect is a pharmaceutical composition comprising a compound having the structure of Formula (VI) or a pharmaceutically acceptable salt, solvate, N-oxide, or prodrug thereof; and a pharmaceutically acceptable excipient, binder or carrier. In another aspect is a pharmaceutical composition comprising a compound having the structure of Formula (VII) or a pharmaceutically acceptable salt, solvate, N-oxide, or prodrug thereof; and a pharmaceutically acceptable excipient, binder or carrier. In another aspect is a pharmaceutical composition comprising a compound having the structure of Formula (VIII) or a pharmaceutically acceptable salt, solvate, N-oxide, or prodrug thereof; and a pharmaceutically acceptable excipient, binder or carrier. In another aspect is a pharmaceutical composition comprising a compound having the structure of Formula (X) or a pharmaceutically acceptable salt, solvate, N-oxide, or prodrug thereof; and a pharmaceutically acceptable excipient, binder or carrier.

In certain embodiments, provided herein is a pharmaceutical composition containing: i) a physiologically acceptable carrier, diluent, and/or excipient; and ii) one or more compounds provided herein.

In some embodiments, the inhibitors described herein are used for the manufacture of a medicament for treating any of the foregoing conditions (e.g., autoimmune diseases, inflammatory diseases, allergy disorders, B-cell proliferative disorders, or thromboembolic disorders).

In some embodiments, the inhibitor compound used for the methods described herein inhibits a Kinase activity with an in vitro $IC_{50}$ of less than about 10 μM. (e.g., less than about 1 μM, less than about 0.5 μM, less than about 0.4 μM, less than about 0.3 μM, less than about 0.1, less than about 0.08 μM, less than about 0.06 μM, less than about 0.05 μM, less than about 0.04 μM, less than about 0.03 μM, less than about 0.02 μM, less than about 0.01, less than about 0.008 μM, less than about 0.006 μM, less than about 0.005 μM, less than about 0.004 μM, less than about 0.003 μM, less than about 0.002 μM, less than about 0.001, less than about 0.00099 μM, less than about 0.00098 μM, less than about 0.00097 μM, less than about 0.00096 μM, less than about 0.00095 μM, less than about 0.00094 μM, less than about 0.00093 μM, less than about 0.00092, or less than about 0.00090 μM).

In one embodiment, the inhibitor compound selectively inhibits an activated form of its target tyrosine kinase (e.g., a phosphorylated form of the tyrosine kinase). For example, activated Btk is transphosphorylated at tyrosine 551. Thus, in these embodiments the Btk inhibitor inhibits the target kinase in cells only once the target kinase is activated by the signaling events.

Preparation of Compounds

Compounds of any of Formula (I), (IA), (II), (III), (IV), (V), (VI), (VIA), (VIB), (VII), (VIII), (IX), (X), (XI), (XII), (XIII), or (XIV) are optionally synthesized using standard synthetic techniques or using such methods known in combination with methods described herein. In additions, solvents, temperatures and other reaction conditions are presented herein for illustration only, and not to limit the scope of the methods and compositions described herein. As a further guide the following synthetic methods may also be utilized.

The reactions are optionally employed in a linear sequence to provide the compounds described herein or used to synthesize fragments which are subsequently joined by the methods described herein and/or documented elsewhere.

Formation of Covalent Linkages by Reaction of an Electrophile with a Nucleophile The compounds described herein can be modified using various electrophiles or nucleophiles to form new functional groups or substituents. Table 1 entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |
| Alkyl thiol | α,β-unsaturated ester | thiols |
| Alkyl ethers | α,β-unsaturated ester | alcohols |
| Alkyl amines | α,β-unsaturated ester | amines |
| Alkyl thiol | Vinyl sulfone | thiols |
| Alkyl ethers | Vinyl sulfone | alcohols |
| Alkyl amines | Vinyl sulfone | amines |
| Vinyl sulfide | Propargyl amide | thiol |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a $Pd^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

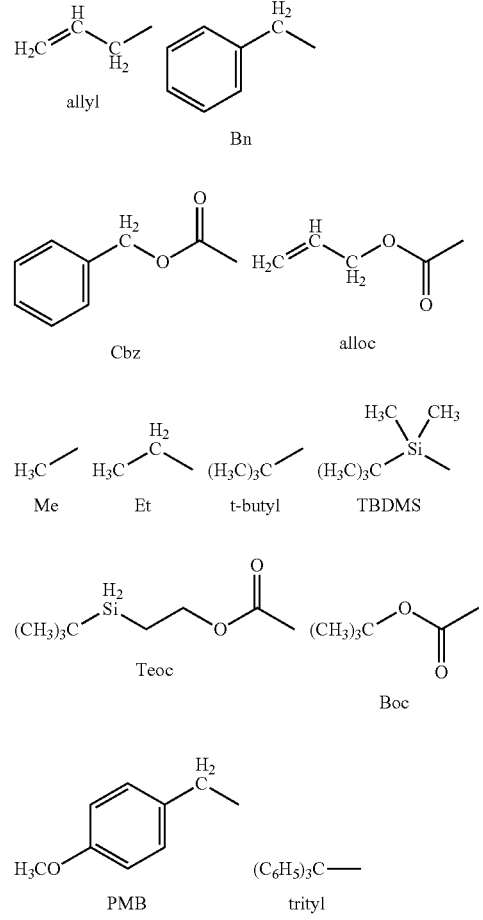

-continued

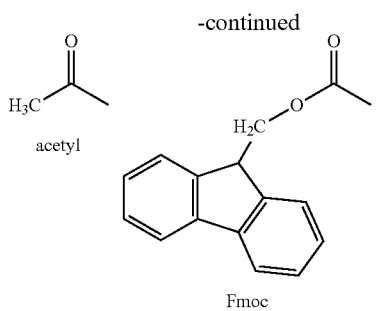

acetyl

Fmoc

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Synthesis of Compounds

In certain embodiments, provided herein are methods of making the tyrosine kinase inhibitor compounds described herein. In certain embodiments, compounds described herein are synthesized using the following synthetic schemes. In other embodiments, compounds are synthesized using methodologies analogous to those described below by the use of appropriate alternative starting materials.

The starting material used for the synthesis of the compounds described herein is either synthesized or obtained from commercial sources, such as, but not limited to, Bachem (Torrance, Calif.), or Sigma-Aldrich Chemical Co. (St. Louis, Mo.). The compounds described herein, and other related compounds having different substituents are optionally synthesized using techniques and materials, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001); Green and Wuts, PROTECTIVE GROUPS IN ORGANIC SYNTHESIS 3rd Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). Other methods for the synthesis of compounds described herein may be found in International Patent Publication No. WO 01/01982901, Arnold et al. Bioorganic & Medicinal Chemistry Letters 10 (2000) 2167-2170; Burchat et al. Bioorganic & Medicinal Chemistry Letters 12 (2002) 1687-1690. As a guide the following synthetic methods may be utilized.

The products of the reactions are optionally isolated and purified, if desired, using conventional techniques, including, but not limited to, filtration, distillation, crystallization, chromatography and the like. Such materials are optionally characterized using conventional means, including physical constants and spectral data.

Compounds described herein are optionally prepared using the synthetic methods described herein as a single isomer or a mixture of isomers.

A non-limiting example of a synthetic approach towards the preparation of compounds of Formula (I), (IA), (II), (III), (IV), (V), (VI), (VIA), (VIB), and (VII), focusing on the core ring preparation is shown in Scheme 1.

Scheme 1.

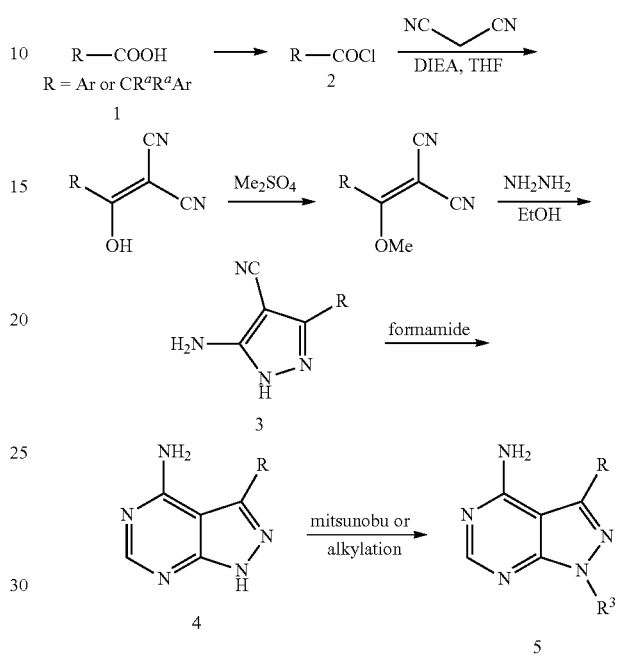

Referring to Scheme 1, the carboxylic acid 1 is converted to acid chloride by the known procedures, for example, using reagents such as oxalyl chloride or thionyl chloride in an inert solvent such as dichloromethane. The acid chloride intermediate 2 is then converted to the corresponding pyrazole 3 by, for example, reacting with malononitrile and methane sulfate followed by hydrazine. The formation of pyrimidine ring (e.g. compound 4) is accomplished, in one embodiment, by heating the pyrazole with formamide as a solvent. One of skilled in the art would readily find other suitable conditions to prepare pyrimidine ring. Derivatization at ring nitrogen of compound 4, e.g. alkylation, is completed using standard Mitsunobu condition with the corresponding alcohol or under standard alkylation conditions with corresponding electrophile such as alkyl mesylate or alkyl halide. (All of the name reactions referenced here could be found in Li, "Name Reactions: A Collection of Detailed Reaction Mechanisms" (Springer, 2003))

A non-limiting example of a synthetic approach towards the preparation of compounds of Formula (II) is shown in Scheme 2. The 3-iodo-1H-pyrazolo[3,4-d]pyrimidine intermediates 5a are versatile under a variety of known conditions for the installation of aromatic groups or aromatic groups with linker at C-3 position. Specific designed heteroaryl derivative at C-3 position are prepared in on embodiment via Mitsunobu reaction. In some embodiments, the heteroaryl groups are derivatized via its aldehyde precursors. In other embodiments, the heteroaryl groups are derivatized via its carboxylic acid precursors.

Scheme 2.

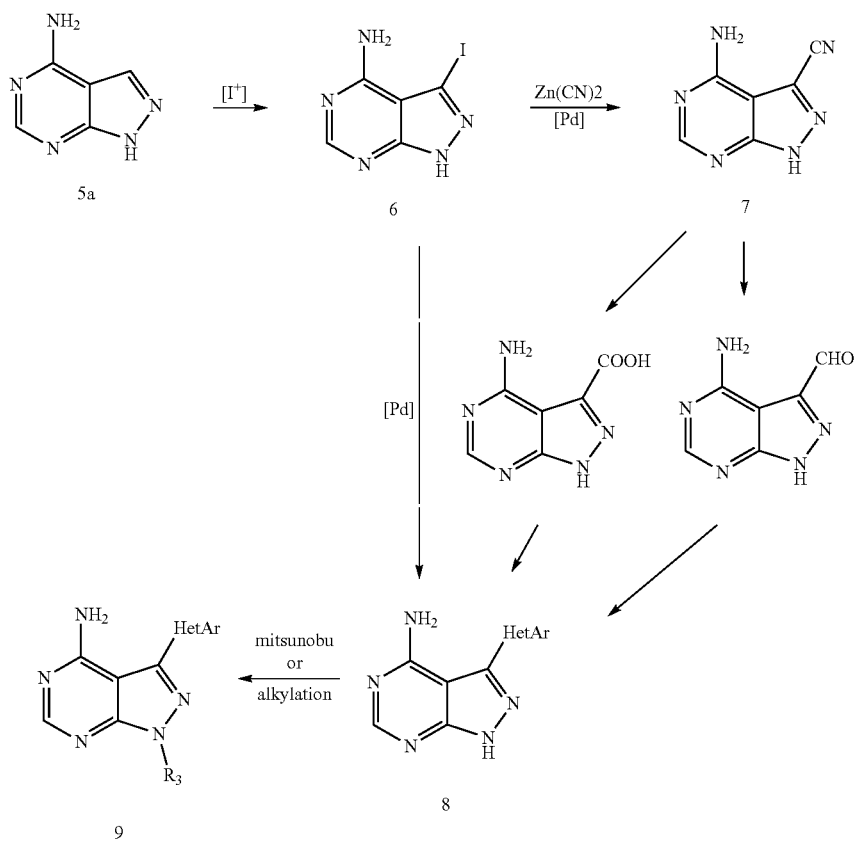

Referring to Scheme 2, in one embodiment, commercially available 1H-pyrazolo[3,4-d]pyrimidin-4-amine ($R^2$=H) is reacted with N-iodosuccinamide to give 3-iodo-1H-pyrazolo [3,4-d]pyrimidin-4-amine. In some embodiments, the 3-iodo-1H-pyrazolo[3,4-d]pyrimidine intermediates 6 are converted to nitrile compounds 7 using palladium catalyst under known procedures. The nitrile group is converted to aldehyde by, for example, reducing reagent such as DIBAL or it is converted to acid by hydrolysis in basic or acid media. In some embodiments, the 3-iodo-1H-pyrazolo[3,4-d]pyrimi- dine intermediates 6 are derivatized by conversion of iodo to heteroaromatic substituents using palladium catalyzed cross- coupling condition such as Suzuki reaction. In other embodi- ments, the acid or aldehyde group is converted to heteroaro- matic group using procedures/methods outlined in Joule and Mills, "Heterocyclic Chemistry" (Wiley-Blackwell, 2010).

A non-limiting example of a synthetic approach towards the preparation of compounds of Formula (I) is shown in Scheme 3. In some embodiments, after converting the nitrile precursor 7 to a carboxylic acids (11 or 12), the corresponding acids are converted to acylaromatic compounds (13 or 14) by Friedel-Krafts reaction. The resulting compounds 14 serve as precursor to the corresponding thionyl, or iminyl analogs.

Scheme 3.

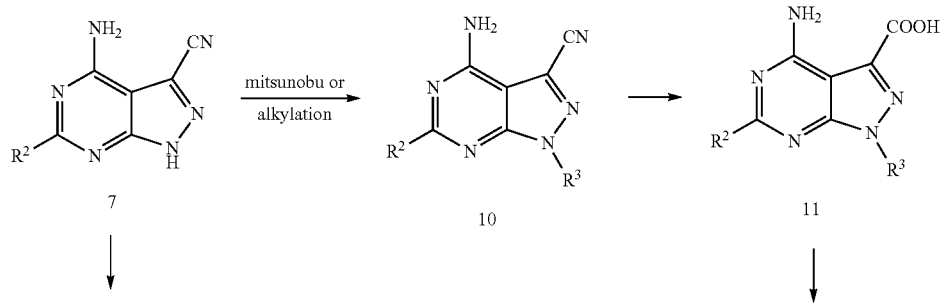

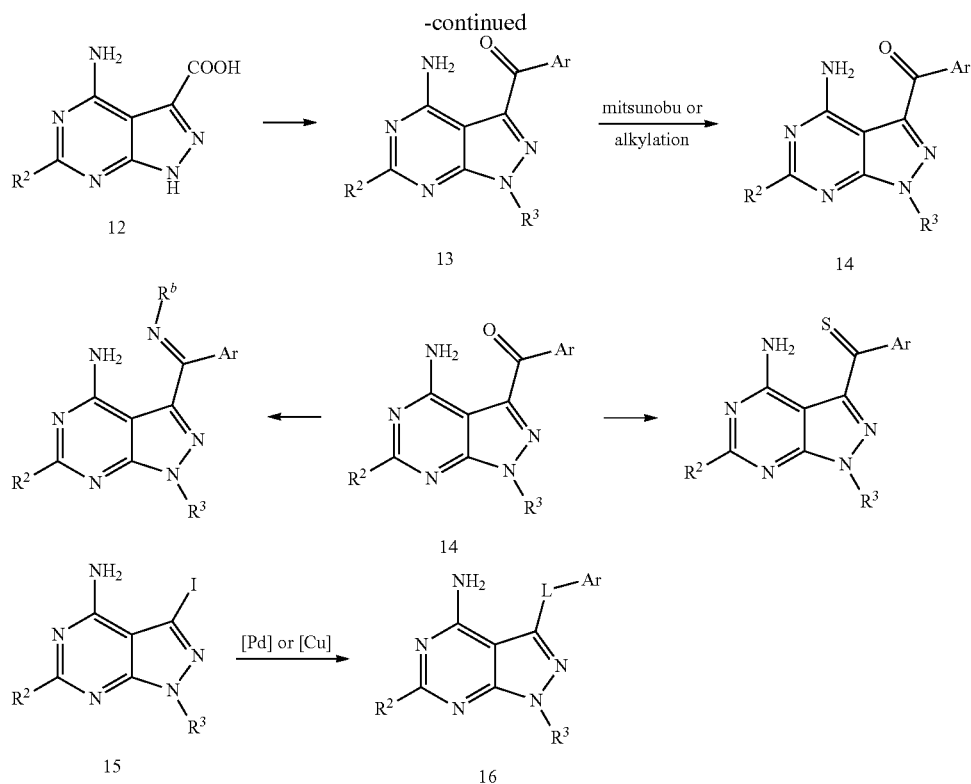

In some embodiments, the 3-iodo-1H-pyrazolo[3,4-jd]pyrimidine intermediates 15 undergo Suzuki and Stille coupling reaction to provide compounds 16 with L=CR$^a$R$^a$ (palladium catalyst); compounds with L=O or S (copper(I) catalyst). The intermediates undergo Buchwald-Hartwig coupling reaction with palladium catalyst to provide compounds with L=NR$^b$. (Scheme 3)

A non-limiting example of a synthetic approach towards the preparation of compounds of Formula (III) is shown in Scheme 4. In some embodiments, R$^2$ group is installed after derivatization at C-3 and at N-1.

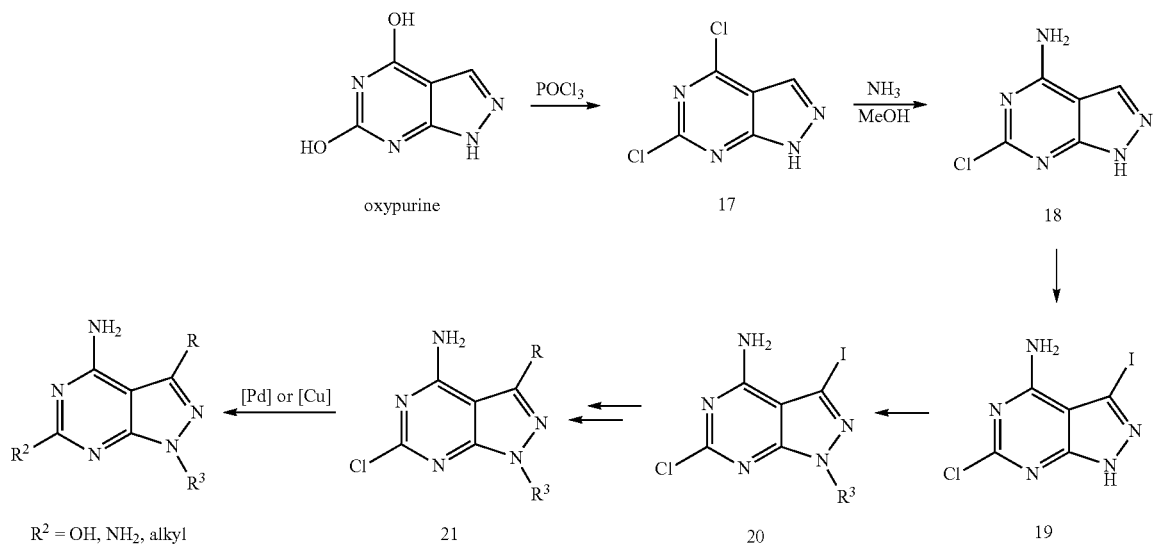

In some embodiments, starting from commercially available oxypurine followed by known procedures provide compounds 21 with 6-halide moiety (i.e. 6-chloro-1H-pyrazolo [3,4-d]pyrimidine analogs). In some embodiments, palladium catalyst coupling reaction such as Suzuki reaction converts the 6-halide to alkyl group. Copper (I) catalyst coupling reaction converts the 6-halide to OH or $NH_2$ group (Scheme 4).

A non-limiting example of a synthetic approach towards the preparation of certain compounds of Formula (IV) is shown in Scheme 5.

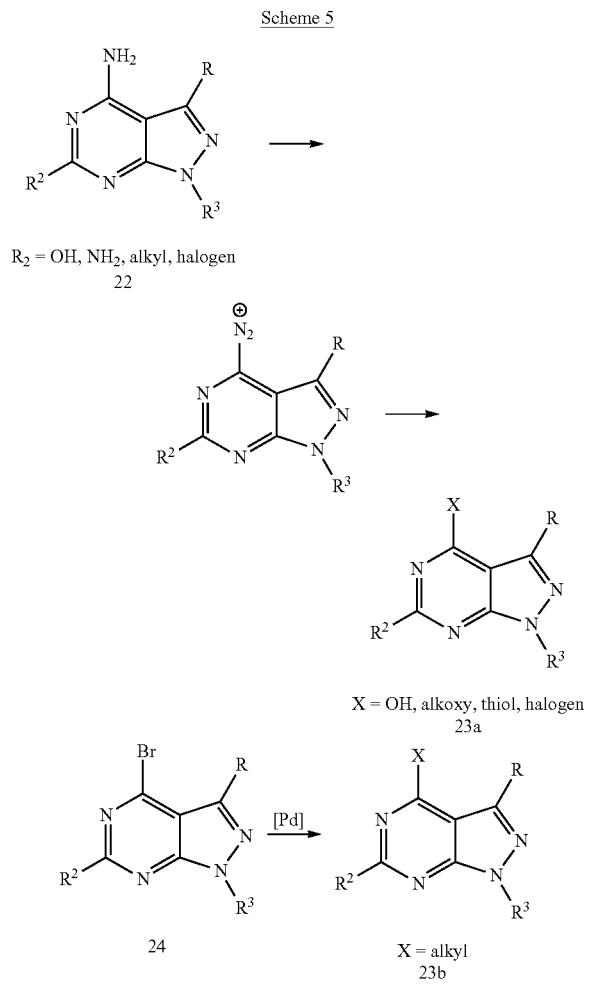

In some embodiments, 4-amino precursors 22 are converted to halide, hydroxy, alkoxy, thiol compounds by Sandmeyer reaction (22 to 23a). In other embodiments, Suziki reaction with the 4-bromide precursors 24 provide the corresponding alkyl compounds 23b.

The compounds prepared by the methods disclosed herein are purified by conventional means, such as, for example, filtration, recrystallization, chromatography, distillation, and combinations thereof.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further Forms of Compounds

Compounds disclosed herein have a structure of Formula (I), (IA), (II), (III), (IV), (V), (VI), (VIA), (VIB), (VII), (VIII), (IX), (X), (XI), (XII), (XIII), or (XIV). It is understood that when reference is made to compounds described herein, it is meant to include compounds of any of Formula (I), (IA), (II), (III), (IV), (V), (VI), (VIA), (VIB), (VII), (VIII), (IX), (X), (XI), (XII), (XIII), or (XIV), as well as to all of the specific compounds that fall within the scope of these generic formulae, unless otherwise indicated.

In some embodiments, the compounds described herein possess one or more stereocenters and in further embodiments, each center exists in the R or S configuration. The compounds presented herein include all diastereomeric, enantiomeric, and epimeric forms as well as the appropriate mixtures thereof. In other embodiments, stereoisomers are obtained, if desired, by methods such as, for example, the separation of stereoisomers by chiral chromatographic columns.

In further embodiments, diasteromeric mixtures are separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The methods and formulations described herein include the use of N-oxides, crystalline forms (also known as polymorphs), or pharmaceutically acceptable salts of compounds described herein. In some situations, compounds exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

In further embodiments, compounds of any of Formula (I), (IA), (II), (III), (IV), (V), (VI), (VIA), (VIB), (VII), (VIII), (IX), (X), (XI), (XII), (XIII), or (XIV) in unoxidized form are prepared from N-oxides of compounds of any of Formula (I), (IA), (II), (III), (IV), (V), (VI), (VIA), (VIB), (VII), (VIII), (IX), (X), (XI), (XII), (XIII), or (XIV) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$, $^{36}Cl$ respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

In one embodiment is an isolated and/or pure form of a compound of Formula (I), (IA), (II), (III), (IV), (V), (VI), (VIA), (VIB), (VII), (VIII), (IX), (X), (XI), (XII), (XIII), or (XIV). In another embodiment, is a compound of Formula (I), (IA), (II), (III), (IV), (V), (VI), (VIA), (VIB), (VII), (VIII), (IX), (X), (XI), (XII), (XIII), or (XIV) wherein the compound is at least about 40% pure. In another embodiment, is a compound of Formula (I), (IA), (II), (III), (IV), (V), (VI), (VIA), (VIB), (VII), (VIII), (IX), (X), (XI), (XII), (XIII), or (XIV) wherein the compound is at least about 50%, about 60%, about 70%, about 80%, about 90%, about 95% pure. In yet another embodiment is a compound of Formula (I), (IA), (II), (III), (IV), (V), (VI), (VIA), (VIB), (VII), (VIII), (IX), (X), (XI), (XII), (XIII), or (XIV) in an isolated form. In yet another embodiment, is a compound of Formula (I), (IA), (II), (III), (IV), (V), (VI), (VIA), (VIB), (VII), (VIII), (IX), (X), (XI), (XII), (XIII), or (XIV) wherein the compound is purified by chromatography.

Compounds described herein (for example, compounds of Formula (I), (IA), (II), (III), (IV), (V), (VI), (VIA), (VIB), (VII), (VIII), (IX), (X), (XI), (XII), (XIII), or (XIV)) are optionally in the form of, and/or used as, pharmaceutically acceptable salts. The type of pharmaceutical acceptable salts, include, but are not limited to: (1) acid addition salts, formed) by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts are optionally analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein are optionally in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Therapeutic Uses of Inhibitor Compounds

In one aspect, provided herein are methods for treating a patient by administering a compound provided herein. In some embodiments, provided herein is a method of inhibiting the activity of tyrosine kinase(s), such as Btk, or of treating a disease, disorder, or condition, which benefit from inhibition of tyrosine kinase(s), such as Btk, in a patient, which includes administering to the patient a therapeutically effective amount of at least one of any of the compounds described herein, or pharmaceutically acceptable salt, pharmaceutically acceptable tautomer, pharmaceutically acceptable prodrug, or pharmaceutically acceptable solvate.

In another aspect, provided herein is the use of a compound disclosed herein for inhibiting Bruton's tyrosine kinase (Btk) activity or for the treatment of a disease, disorder, or condition, which benefit from inhibition of Bruton's tyrosine kinase (Btk) activity.

In one aspect, provided herein is the use of a compound of Formula (I), (IA), (II), (III), (IV), (V), (VI), (VIA), (VIB), (VII), (VIII), (IX), (X), (XI), (XII), (XIII), or (XIV) in the manufacture of a medicament for the treatment of an autoimmune disease. In another aspect, provided herein is the use of a compound of Formula (I), (IA), (II), (III), (IV), (V), (VI), (VIA), (VIB), (VII), (VIII), (IX), (X), (XI), (XII), (XIII), or (XIV) in the manufacture of a medicament for the treatment of a heteroimmune disease. In another aspect, provided herein is the use of a compound of Formula (I), (IA), (II), (III), (IV), (V), (VI), (VIA), (VIB), (VII), (VIII), (IX), (X), (XI), (XII), (XIII), or (XIV) in the manufacture of a medicament for the treatment of an inflammatory disease. In another aspect, provided herein is the use of a compound of Formula (I), (IA), (II), (III), (IV), (V), (VI), (VIA), (VIB), (VII), (VIII), (IX), (X), (XI), (XII), (XIII), or (XIV) in the manufacture of a medicament for the treatment of a cancer. In another aspect, provided herein is the use of a compound of Formula (I), (IA), (II), (III), (IV), (V), (VI), (VIA), (VIB), (VII), (VIII), (IX), (X), (XI), (XII), (XIII), or (XIV) in the manufacture of a medicament for the treatment of a thromboembolic disorder. In another aspect, provided herein is the use of a compound of Formula (I), (IA), (II), (III), (IV), (V), (VI), (VIA), (VIB), (VII), (VIII), (IX), (X), (XI), (XII), (XIII), or (XIV) in the manufacture of a medicament for the treatment of mastocytosis. In another aspect, provided herein is the use of a compound of Formula (I), (IA), (II), (III), (IV), (V), (VI), (VIA), (VIB), (VII), (VIII), (IX), (X), (XI), (XII), (XIII), or (XIV) in the manufacture of a medicament for the treatment of a bone resorption disorder. In another aspect, provided herein is the use of a compound of Formula (I), (IA), (II), (III), (IV), (V), (VI), (VIA), (VIB), (VII), (VIII), (IX), (X), (XI), (XII), (XIII), or (XIV) in the manufacture of a medicament for the treatment of osteoporosis. In another aspect, provided herein is the use of a compound of Formula (I), (IA), (II), (III), (IV), (V), (VI), (VIA), (VIB), (VII), (VIII), (IX), (X), (XI), (XII), (XIII), or (XIV) in the manufacture of a medicament for the treatment of a hematological malignancy.

In some embodiments, compounds provided herein are administered to a human. In some embodiments, compounds provided herein are orally administered. In other embodiments, the pharmaceutical formulation that is formulated for a route of administration is selected from oral administration, parenteral administration, buccal administration, nasal administration, topical administration, or rectal administration.

In other embodiments, compounds provided herein are used for the formulation of a medicament for the inhibition of tyrosine kinase activity. In some other embodiments, compounds provided herein are used for the formulation of a medicament for the inhibition of Bruton's tyrosine kinase (Btk) activity.

In a further aspect, provided herein is a method for treating an autoimmune disease by administering to a subject in need thereof a composition containing a therapeutically effective amount of at least one compound having the structure of Formula (I), (IA), (II), (III), (IV), (V), (VI), (VIA), (VIB), (VII), (VIII), (IX), (X), (XI), (XII), (XIII), or (XIV). In one embodiment, the autoimmune disease is arthritis. In another embodiment, the autoimmune disease is lupus. In some embodiments, the autoimmune disease is inflammatory bowel disease (including Crohn's disease and ulcerative colitis), rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In a further aspect, provided herein is a method for treating a heteroimmune condition or disease by administering to a subject in need thereof a composition containing a therapeutically effective amount of at least one compound having the structure of Formula (I), (IA), (II), (III), (IV), (V), (VI), (VIA), (VIB), (VII), (VIII), (IX), (X), (XI), (XII), (XIII), or (XIV). In some embodiments, the heteroimmune condition or disease is graft versus host disease, transplantation, transfusion, anaphylaxis, allergy, type I hypersensitivity, allergic conjunctivitis, allergic rhinitis, or atopic dermatitis.

In a further aspect, provided herein is a method for treating an inflammatory disease by administering to a subject in need thereof a composition containing a therapeutically effective amount of at least one compound having the structure of Formula (I), (IA), (II), (III), (IV), (V), (VI), (VIA), (VIB), (VII), (VIII), (IX), (X), (XI), (XII), (XIII), or (XIV). In some embodiments, the inflammatory disease is asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect, provided herein is a method for treating a cancer by administering to a subject in need thereof a composition containing a therapeutically effective amount of at least one compound having the structure of Formula (I), (IA), (II), (III), (IV), (V), (VI), (VIA), (VIB), (VII), (VIII), (IX), (X), (XI), (XII), (XIII), or (XIV). In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt's lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one compound having the structure of Formula (I), (IA), (II), (III), (IV), (V), (VI), (VIA), (VIB), (VII), (VIII), (IX), (X), (XI), (XII), (XIII), or (XIV). In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In another aspect, provided herein is a method for treating a mastocytosis by administering to a subject in need thereof a composition containing a therapeutically effective amount of at least one compound having the structure of Formula (I), (IA), (II), (III), (IV), (V), (VI), (VIA), (VIB), (VII), (VIII), (IX), (X), (XI), (XII), (XIII), or (XIV).

In yet another aspect, provided herein is a method for treating an osteoporosis or bone resorption disorders by administering to a subject in need thereof a composition containing a therapeutically effective amount of at least one compound having the structure of Formula (I), (IA), (II), (III), (IV), (V), (VI), (VIA), (VIB), (VII), (VIII), (IX), (X), (XI), (XII), (XIII), or (XIV).

In another aspect, provided herein is a method for treating a hematological malignancy by administering to a subject in need thereof a composition containing a therapeutically effective amount of at least one compound having the structure of Formula (I), (IA), (II), (III), (IV), (V), (VI), (VIA), (VIB), (VII), (VIII), (IX), (X), (XI), (XII), (XIII), or (XIV). In some embodiments, the hematological malignancy is a chronic lymphocytic leukemia (CLL), small lymphocytic lymphoma (SLL), high risk CLL, a non-CLL/SLL lymphoma, follicular lymphoma, diffuse large B-cell lymphoma (DLBCL), mantle cell lymphoma, Waldenstrom's macroglobulinemia, multiple myeloma, marginal zone lymphoma, Burkitt's lymphoma, non-Burkitt high grade B cell lymphoma, extranodal marginal zone B cell lymphoma, acute or chronic myelogenous (or myeloid) leukemia, myelodysplastic syndrome, acute lymphoblastic leukemia, relapsed or refractory diffuse large B-cell lymphoma (DLBCL), relapsed or refractory mantle cell lymphoma, relapsed or refractory follicular lymphoma, relapsed or refractory CLL, relapsed or refractory SLL, relapsed or refractory multiple myeloma, Hodgkin's lymphoma or non-Hodgkin's lymphoma (NHL).

In further embodiments, the compound inhibits the Bruton's tyrosine kinase.

Also described herein are kinase inhibitors that selectively bind to a protein tyrosine kinase selected from Btk, a Btk homolog, and a Btk kinase cysteine homolog, in which the kinase inhibitor reversibly and non-selectively binds to a multiplicity of protein tyrosine kinases. In one embodiment the plasma half life of the kinase inhibitor is less than about 4 hours. In another embodiment the plasma half life of the kinase inhibitor is less than about 3 hours.

In a further embodiment are kinase inhibitors that selectively bind to at least one of Btk, Jak3, Blk, Bmx, Tec, and Itk. In another embodiment are kinase inhibitors that selectively bind to Btk. In another embodiment are kinase inhibitors that selectively bind to Jak3. In another embodiment are kinase inhibitors that selectively bind to Tec. In another embodiment are kinase inhibitors that selectively bind to Itk. In another embodiment are kinase inhibitors that selectively bind to Btk and Tec. In another embodiment are kinase inhibitors that selectively bind to Blk. In yet a further embodiment are kinase inhibitors that reversibly and non-selectively bind to a multiplicity of src-family protein kinase inhibitors.

Also described herein are inhibitors that are identified using such methods, assays and systems. In some embodiments, the inhibitor is a selective inhibitor, including selectivity for a particular Btk kinase cysteine homolog over other Btk kinase cysteine homologs.

Further described herein are pharmaceutical formulations comprising the kinase inhibitors of any kinase inhibitor compound previously listed. In one embodiment the pharmaceutical formulation includes a pharmaceutical acceptable excipient. In some embodiments, pharmaceutical formulations provided herein are administered to a human. In some embodiments, the selective kinase inhibitors provided herein are orally administered. In other embodiments, the selective kinase inhibitors provided herein are used for the formulation of a medicament for the inhibition of tyrosine kinase activity. In some other embodiments, the selective kinase inhibitors provided herein are used for the formulation of a medicament for the inhibition of a kinase activity, including a tyrosine kinase activity, including a Btk activity, including a Btk homolog activity, including a Btk kinase cysteine homolog activity.

In any of the aforementioned aspects are further embodiments in which administration is enteral, parenteral, or both, and wherein (a) the effective amount of the compound is systemically administered to the mammal; (b) the effective amount of the compound is administered orally to the mammal; (c) the effective amount of the compound is intravenously administered to the mammal; (d) the effective amount of the compound administered by inhalation; (e) the effective amount of the compound is administered by nasal administration; or (f) the effective amount of the compound is administered by injection to the mammal; (g) the effective amount of the compound is administered topically (dermal) to the mammal; (h) the effective amount of the compound is administered by ophthalmic administration; or (i) the effective amount of the compound is administered rectally to the mammal. In further embodiments the pharmaceutical formulation is formulated for a route of administration selected from oral administration, parenteral administration, buccal administration, nasal administration, topical administration, or rectal administration.

In any of the aforementioned aspects are further embodiments comprising single administrations of the effective amount of the pharmaceutical formulation, including further embodiments in which (i) the pharmaceutical formulations is administered once; (ii) the pharmaceutical formulations is administered to the mammal once a day; (iii) the pharmaceutical formulations is administered to the mammal multiple times over the span of one day; (iv) continually; or (v) continuously.

In any of the aforementioned aspects are further embodiments comprising multiple administrations of the effective amount of the pharmaceutical formulations, including further embodiments in which (i) the pharmaceutical formulations is administered in a single dose; (ii) the time between multiple administrations is every 6 hours; (iii) the pharmaceutical formulations is administered to the mammal every 8 hours. In further or alternative embodiments, the method comprises a drug holiday, wherein the administration of the pharmaceutical formulations is temporarily suspended or the dose of the pharmaceutical formulations being administered is temporarily reduced; at the end of the drug holiday, dosing of the pharmaceutical formulations is resumed. The length of the drug holiday varies from 2 days to 1 year.

In some aspects described herein the inhibitor is selective for one kinase selected from Btk, a Btk homolog, and a Btk kinase cysteine homolog over at least one other kinase selected from Btk, a Btk homolog, and a Btk kinase cysteine homolog. In other aspects described herein the inhibitor is selective for at least one kinase selected from Btk, a Btk homolog, and a Btk kinase cysteine homolog over at least one other non-kinase molecule having an accessible SH group.

Described herein are methods, compositions, uses and medicaments for the treatment of disorders comprising administering to a patient in need an inhibitor of an ACK. In some embodiments, the ACK is Btk or a Btk homolog. In further embodiments, the ACK is Blk or a Blk homolog. In yet further embodiments, the ACK is tyrosine kinases that share homology with Btk by having a cysteine residue (including a Cys 481 residue) that can form a covalent bond with the inhibitor.

The methods described herein (which includes uses of a pharmaceutical composition to treat a disease or disorder, or uses of a compound to form a medicament for treating a disease or disorder) include administering to a subject in need a composition containing a therapeutically effective amount of one or more Btk inhibitor compounds described herein. Without being bound by theory, the diverse roles played by Btk signaling in various hematopoietic cell functions, e.g., B-cell receptor activation, show that small molecule Btk inhibitors are useful for reducing the risk of or treating a variety of diseases affected by or affecting many cell types of the hematopoietic lineage including, e.g., autoimmune diseases, heteroimmune conditions or diseases, inflammatory diseases, cancer (e.g., B-cell proliferative disorders), and thromboembolic disorders.

In some embodiments, are methods for treating an autoimmune disease or condition comprising administering to a patient in need a pharmaceutical formulation of any inhibitor of Btk (or a Btk homolog) of Formula (I), (IA), (II), (III), (IV), (V), (VI), (VIA), (VIB), (VII), (VIII), (IX), (X), (XI), (XII), (XIII), or (XIV). Such an autoimmune disease or condition includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia. In some embodiments, the autoimmune disease is selected from rheumatoid arthritis or lupus.

In some embodiments, are methods for treating a heteroimmune disease or condition comprising administering to a patient in need a pharmaceutical formulation of any inhibitor of Btk (or a Btk homolog) of Formula (I), (IA), (II), (III), (IV), (V), (VI), (VIA), (VIB), (VII), (VIII), (IX), (X), (XI), (XII), (XIII), or (XIV). Such a heteroimmune condition or disease includes, but is not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, are methods for treating a cancer comprising administering to a patient in need a pharmaceutical formulation of any inhibitor of Btk (or a Btk homolog) of Formula (I), (IA), (II), (III), (IV), (V), (VI), (VIA), (VIB), (VII), (VIII), (IX), (X), (XI), (XII), (XIII), or (XIV). Such a cancer, e.g., B-cell proliferative disorders, includes but is not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In some embodiments, are methods for treating mastocytosis comprising administering to a patient in need a pharmaceutical formulation of any inhibitor of Btk (or a Btk homolog) of Formula (I), (IA), (II), (III), (IV), (V), (VI), (VIA), (VIB), (VII), (VIII), (IX), (X), (XI), (XII), (XIII), or (XIV). Mastocytosis includes but is not limited to diseases characterized by hyperactive mast cells.

In some embodiments, are methods for treating osteoporosis or bone resorption disorders comprising administering to a patient in need a pharmaceutical formulation of any inhibitor of Btk (or a Btk homolog) of Formula (I), (IA), (II), (III), (IV), (V), (VI), (VIA), (VIB), (VII), (VIII), (IX), (X), (XI), (XII), (XIII), or (XIV). Bone resorption disorders include but are not limted to Paget's disease of bone, osteoporosis, and the bone changes secondary to cancer, such as occur in myeloma and metastases from breast cancer.

In some embodiments, are methods for treating inflammatory diseases comprising administering to a patient in need a pharmaceutical formulation of any inhibitor of Btk (or a Btk homolog) of Formula (I), (IA), (II), (III), (IV), (V), (VI), (VIA), (VIB), (VII), (VIII), (IX), (X), (XI), (XII), (XIII), or (XIV). Inflammatory diseases include but are not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In another aspect, are methods for treating hematological malignancies by administering to a patient in need a pharmaceutical formulation of any inhibitor of Btk (or a Btk homolog) of Formula (I), (IA), (II), (III), (IV), (V), (VI), (VIA), (VIB), (VII), (VIII), (IX), (X), (XI), (XII), (XIII), or (XIV). The hematological malignancies include but are not limited to chronic lymphocytic leukemia (CLL), small lymphocytic lymphoma (SLL), high risk CLL, non-CLL/SLL lymphoma, follicular lymphoma, diffuse large B-cell lymphoma (DLBCL), mantle cell lymphoma, Waldenstrom's macroglobulinemia, multiple myeloma, marginal zone lymphoma, Burkitt's lymphoma, non-Burkitt high grade B cell lymphoma, extranodal marginal zone B cell lymphoma, acute or chronic myelogenous (or myeloid) leukemia, myelodysplastic syndrome, acute lymphoblastic leukemia, relapsed or refractory diffuse large B-cell lymphoma (DLBCL), relapsed or refractory mantle cell lymphoma, relapsed or refractory follicular lymphoma, relapsed or refractory CLL, relapsed or refractory SLL, relapsed or refractory multiple myeloma, Hodgkin's lymphoma and non-Hodgkin's lymphoma (NHL).

A subset of tyrosine kinases other than Btk are also expected to be useful as therapeutic targets in a number of health conditions, including:

autoimmune diseases, which include, but are not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

inflammatory diseases, which include, but are not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

mastocytosis, which include but are not limited to diseases characterized by hyperactive mast cells.

bone resorption disorders, which include but are not limted to Paget's disease of bone, osteoporosis, and the bone changes secondary to cancer, such as occur in myeloma and metastases from breast cancer.

Symptoms, diagnostic tests, and prognostic tests for each of the above-mentioned conditions include, e.g., *Harrison's Principles of Internal Medicine®,*" 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models are useful for establishing a range of therapeutically effective doses of inhibitors, including Btk inhibitor compounds for treating any of the foregoing diseases. Also, for example, dosing of inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), *Am. J. Pathol* 163:1827-1837. In another example, dosing of inhibitors for the treatment of B-cell proliferative disorders can be examined in, e.g., a human-to-mouse xenograft model in which human B-cell lymphoma cells (e.g. Ramos cells) are implanted into immunodefficient mice (e.g., "nude" mice) as described in, e.g., Pagel et al. (2005), Clin Cancer Res 11(13):4857-4866. Animal models for treatment of thromboembolic disorders are also known.

In one embodiment, the therapeutic efficacy of the compound for one of the foregoing diseases is optimized during a course of treatment. For example, a subject being treated optionally undergoes a diagnostic evaluation to correlate the relief of disease symptoms or pathologies to inhibition of in vivo Btk activity achieved by administering a given dose of a Btk inhibitor. Cellular assays are used to determine in vivo activity of Btk in the presence or absence of an Btk inhibitor. For example, since activated Btk is phosphorylated at tyrosine 223 (Y223) and tyrosine 551 (Y551), phospho-specific immunocytochemical staining of P-Y223 or P-Y551-positive cells are used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor inhibitor compound that is administered to a subject is optionally increased or decreased as needed so as to maintain a level of Btk inhibition optimal for treating the subject's disease state.

Combination Treatments

In some embodiments, the Btk inhibitor compositions described herein are used in combination with other well known therapeutic reagents that are selected for their therapeutic value for the condition to be treated. In general, the compositions described herein and, in embodiments where combinational therapy is employed, other agents do not have to be administered in the same pharmaceutical composition, and are optionally, because of different physical and chemical characteristics, have to be administered by different routes. The initial administration is made, for example, according to established protocols, and then, based upon the observed effects, the dosage, modes of administration and times of administration are modified.

In certain instances, it is appropriate to administer at least one Btk inhibitor compound described herein in combination with another therapeutic agent. By way of example only, if one of the side effects experienced by a patient upon receiving one of the Btk inhibitor compounds described herein is nausea, then it is appropriate to administer an anti-nausea agent in combination with the initial therapeutic agent. Or, by way of example only, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by a patient is increased by administering one of the compounds described herein with another therapeutic agent (which also includes a therapeutic regimen) that also has therapeutic benefit. In any case, regardless of the disease, disorder or condition being treated, the overall benefit experienced by the patient is in some embodiments simply additive of the two therapeutic agents or in other embodiments, the patient experiences a synergistic benefit.

The particular choice of compounds used will depend upon the diagnosis of the attending physicians and their judgment of the condition of the patient and the appropriate treatment protocol. The compounds are optionally administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is based on an evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I) described herein) are optionally administered in any order or even simultaneously. If simultaneously, the multiple therapeutic agents are optionally provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also are optionally used in combination with procedures that provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

In some embodiments, the compounds described herein and combination therapies are administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

Therapeutic Agents for Use in Combination with an Inhibitor Compound

In some embodiments, where the subject is suffering from or at risk of suffering from an autoimmune disease, an inflammatory disease, or an allergy disease, a Btk inhibitor compound is used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), nonsteroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, anticholinergics or other selective kinase inhibitors (e.g p38 inhibitors, Syk inhibitors, PKC inhibitors).

In yet other embodiments, where the subject is suffering from or at risk of suffering from a B-cell proliferative disorder (e.g., plasma cell myeloma), the subjected is treated with a Btk inhibitor compound in any combination with one or more other anti-cancer agents. In some embodiments, one or more of the anti-cancer agents are proapoptotic agents. Examples of anti-cancer agents include, but are not limited to, any of the following: gossyphol, Genasense®, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with an Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

In further embodiments, other anti-cancer agents are employed in combination with an Btk inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometerxol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimeterxate; trimeterxate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In yet other embodiments, other anti-cancer agents are employed in combination with an Btk inhibitor compound include: 20-epi-1,25 dihydroxyvitamin D3; 5-ethynyl uracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron;

azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometerxol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimeterxate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a Btk inhibitor compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that are employed in combination a Btk inhibitor compound in some embodiments, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin).

Examples of hormones and antagonists useful in combination with a Btk inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which are used in some embodiments, in combination with a Btk inhibitor compound include without limitation marketed drugs and drugs in development.

Where the subject is suffering from or at risk of suffering from a thromboembolic disorder (e.g., stroke), the subject, in some embodiments is treated with a Btk inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), factor VIIa inhibitors, ticlopidine, clopidogrel, CS-747 (prasugrel, LY640315), ximelagatran, or BIBR 1048.

Pharmaceutical Composition/Formulation

In a further aspect are provided pharmaceutical compositions, which include a therapeutically effective amount of at least one of any of the compounds described herein, or a pharmaceutically acceptable salt, pharmaceutically acceptable tautomer, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by tyrosine kinase activity, or in which tyrosine kinase activity is implicated, are provided. The effective amounts and concentrations are effective for ameliorating any of the symptoms of any of the diseases, disorders or conditions disclosed herein.

Pharmaceutical compositions are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999).

A pharmaceutical composition, as used herein, refers to a mixture of a compound described herein, such as, for example, compounds of any of Formula (I), (IA), (II), (III), (IV), (V), (VI), (VIA), (VIB), (VII), (VIII), (IX), (X), (XI), (XII), (XIII), or (XIV), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. The compounds, in some embodiments, are used singly or in combination with one or more therapeutic agents as components of mixtures.

The pharmaceutical formulations described herein in some embodiments, is administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein are optionally manufactured in a conventional manner, such as, by way of example only, by means of conventional mixing, dissolving, granulating, dragee-making, levigating, emulsifying, encapsulating, entrapping or compression processes.

A "carrier" or "carrier materials" includes excipients in pharmaceutics and is selected on the basis of compatibility with compounds disclosed herein, such as, compounds of Formula (I), (IA), (II), (III), (IV), (V), (VI), (VIA), (VIB), (VII), (VIII), (IX), (X), (XI), (XII), (XIII), or (XIV), and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999).

A "measurable serum concentration" or "measurable plasma concentration" describes the blood serum or blood plasma concentration, typically measured in mg, µg, or ng of therapeutic agent per ml, dl, or l of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action. "Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

Dosage Forms

Moreover, the pharmaceutical compositions described herein, which include a compound of Formula (I), (IA), (II), (III), (IV), (V), (VI), (VIA), (VIB), (VII), (VIII), (IX), (X), (XI), (XII), (XIII), or (XIV) are, in some embodiments, formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound of Formula (I), (IA), (II), (III), (IV), (V), (VI), (VIA), (VIB), (VII), (VIII), (IX), (X), (XI), (XII), (XIII), or (XIV). In one embodiment, some or all of the particles of the compound of Formula (I), (IA), (II), (III), (IV), (V), (VI), (VIA), (VIB), (VII), (VIII), (IX), (X), (XI), (XII), (XIII), or (XIV), are coated. In another embodiment, some or all of the particles of the compound of Formula (I), (IA), (II), (III), (IV), (V), (VI), (VIA), (VIB), (VII), (VIII), (IX), (X), (XI), (XII), (XIII), or (XIV), are microencapsulated. In still another embodiment, the particles of the compound of Formula (I), (IA), (II), (III), (IV), (V), (VI), (VIA), (VIB), (VII), (VIII), (IX), (X), (XI), (XII), (XIII), or (XIV), are not microencapsulated and are uncoated.

Examples of Methods of Dosing and Treatment Regimens

The compounds described herein, in some embodiments, is used in the preparation of medicaments for the inhibition of Btk or a homolog thereof, or for the treatment of diseases or conditions that benefit, at least in part, from inhibition of Btk or a homolog thereof. In addition, a method for treating any of the diseases or conditions described herein in a subject in need of such treatment, involves administration of pharmaceutical compositions containing at least one compound of any of Formula (I), (IA), (II), (III), (IV), (V), (VI), (VIA), (VIB), (VII), (VIII), (IX), (X), (XI), (XII), (XIII), or (XIV), described herein, or a pharmaceutically acceptable salt, pharmaceutically acceptable N-oxide, pharmaceutically acceptable solvate, or pharmaceutically acceptable prodrug thereof, in therapeutically effective amounts to said subject.

The compositions containing the compound(s) described herein, in other embodiments, are administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In some embodiments, the kinase inhibitor is administered to the patient on a regular basis, e.g., three times a day, two times a day, once a day, every other day or every 3 days. In other embodiments, the kinase inhibitor is administered to the patient on an intermittent basis, e.g., twice a day followed by once a day followed by three times a day; or the first two days of every week; or the first, second and third day of a week. In some embodiments, intermittent dosing is as effective as regular dosing. In further or alternative embodiments, the kinase inhibitor is administered only when the patient exhibits a particular symptom, e.g., the onset of pain, or the onset of a fever, or the onset of an inflammation, or the onset of a skin disorder.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10%-about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, and is determined according to the particular circumstances surrounding the case, including, e.g., the specific agent being administered, the route of administration, the condition being treated, and the subject or host being treated. In general, however, doses employed for adult human treatment will typically be in the range of about 0.02—about 5000 mg per day, or from about 1—about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to, ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Kits/Articles of Manufacture

Articles of manufacture including packaging material, a compound or composition or pharmaceutically acceptable derivative thereof provided herein, which is effective for inhibiting the activity of tyrosine kinase(s), such as Btk, within the packaging material, and a label that indicates that the compound or composition, or pharmaceutically acceptable salt, pharmaceutically acceptable tautomer, pharmaceutically acceptable prodrug, or pharmaceutically acceptable solvate thereof, is used for inhibiting the activity of tyrosine kinase(s), such as Btk, are provided.

EXAMPLES

The following specific and non-limiting examples are to be construed as merely illustrative, and do not limit the present disclosure in any way whatsoever.

Synthesis of Compounds

Example 1

Preparation of 4-Amino-3-(4-phenoxyphenyl)-1H-pyrazolo[3,4-d]pyrimidine

4-Amino-3-(4-phenoxyphenyl)-1H-pyrazolo[3,4-d]pyrimidine is prepared as disclosed in International Patent Publication No. WO 01/019829. Briefly, 4-phenoxybenzoic acid (48 g) is added to thionyl chloride (100 mL) and heated under gentle reflux for 1 h. Thionyl chloride is removed by distillation, the residual oil dissolved in toluene and volatile material removed at 80° C./20 mbar. The resulting acid chloride is dissolved in toluene (200 mL) and tetrahydrofuran (35 mL). Malononitrile (14.8 g) is added and the solution and stirred at −10° C. while adding diisopropylethylethylamine (57.9 g) in toluene (150 mL), while maintaining the temperature below 0° C. After 1 h at 0° C., the mixture is stirred at 20° C. overnight. Amine hydrochloride is removed by filtration and the filtrate evaporated in vacuo. The residue is taken up in ethyl acetate (EA) and washed with 1.25 M sulphuric acid, then with brine and dried over sodium sulfate. Evaporation of the solvents gives a semisolid residue which is treated with a little EA to give 4.1 g of 1,1-dicyano-2-hydroxy-2-(4-phenoxyphenyl)ethene as a white solid (m.p. 160-162° C.). The filtrate on evaporation gives 56.58 (96%) of 1,1-dicyano-2-hydroxy-2-(4-phenoxyphenyl)ethene as a grey-brown solid, which is sufficiently pure for further use.

1,1-Dicyano-2-hydroxy-2-(4-phenoxyphenyl)ethene (56.5 g) in acetonitrile (780 mL) and methanol (85 mL) is stirred under nitrogen at 0° C. while adding diisopropylethylamine (52.5 mL) followed by 2M trimethylsilyldiazomethane (150 mL) in THF. The reaction is stirred for 2 days at 20° C., and then 2 g of silica is added (for chromatography). The brown-red solution is evaporated in vacuo, the residue dissolved in EA and washed well with water then brine, dried and evaporated. The residue is extracted with diethyl ether (3×250 mL), decanting from insoluble oil. Evaporation of the ether extracts gives 22.5 g of 1,1-dicyano-2-methoxy-2-(4-phenoxyphenyl)ethene as a pale orange solid. The insoluble oil is purified by flash chromatography to give 15.0 g of a red-orange oil.

1,1-Dicyano-2-methoxy-2-(4-phenoxyphenyl)ethene (22.5 g) and 1,1-dicyano-2-methoxy-2-(4-phenoxyphenyl) ethene oil (15 g) are treated with a solution of hydrazine hydrate (18 mL) in ethanol (25 mL) and heated on the steambath for 1 h. Ethanol (15 mL) is added followed by water (10 mL). The precipitated solid is collected and washed with ethanol:water (4:1) and then dried in air to give 3-amino-4-cyano-5-(4-phenoxyphenyl)pyrazole as a pale orange solid.

3-Amino-4-cyano-5-(4-phenoxyphenyl)pyrazole (29.5 g) is suspended in formamide (300 mL) and heated under nitrogen at 180° C. for 4 h. The reaction mixture is cooled to 30° C. and water (300 mL) is added. The solid is collected, washed well with water, then with methanol and dried in air to give of 4-amino-3-(4-phenoxyphenyl)-1H-pyrazolo[3,4-d]pyrimidine.

Example 1-1

Preparation of (R)-3-(4-phenoxyphenyl)-1-(pyrrolidin-3-yl)-1H-pyrazolo[3,4-d]pyrimidin-4-amine (Compound A)

To a mixture of 4-amino-3-(4-phenoxyphenyl)-1H-pyrazolo[3,4-d]pyrimidine (45.50 g, 150 mmol, 1.0 eq), (S)-pyrrolidin-3-ol (bought from CNH, 51.95 g, 277.5 mmol, 1.85 eq) and $Ph_3P$ (72.79 g, 277.5 mmol, 1.85 eq) in THF (400 mL)

at rt was added DIAD (57.6 mL, 292.5 mmol, 1.95 eq) dropwise over 1.5 h. The mixture was stirred another 30 min and concentrated HCl solution (100 mL) was added dropwise over 30 min. The mixture was stirred overnight at rt. The mixture was then heated to 50° C. for 1 h to push the de-Boc to completion. THF was removed by rotavap. The crude was diluted with toluene and water. The aqueous solution was further washed with EtOAc and toluene. MeOH (70 mL, 10% v/v to the aqueous solution) was added followed by KOH solution (100 g in 100 ml, water). The mixture became warm and precipitate immediately formed. The mixture was cooled in a 4° C. fridge for 2 h and filtered. The solid was washed with water, air-dried and then dried under high-vac for 3 days. Yield 49.45 g (89%), HPLC purity 95%.

Example 1-2

Preparation of (R)-3-(4-phenoxyphenyl)-1-(piperidine-3-yl)-1H-pyrazolo[3,4-d]pyrimidin-4-amine (Compound B)

The title compound was made in the similar fashion as Compound A.

Example 1a

Synthesis of N-((4-(4-amino-3-(4-phenoxyphenyl)-1H-pyrazolo[3,4-d]pyrimidin-1-yl)tetrahydrofuran-2-yl)methyl)-N-methylpropionamide

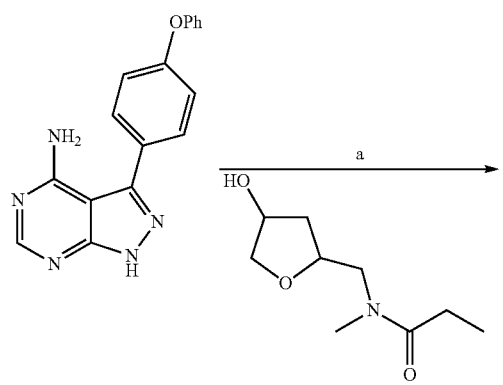

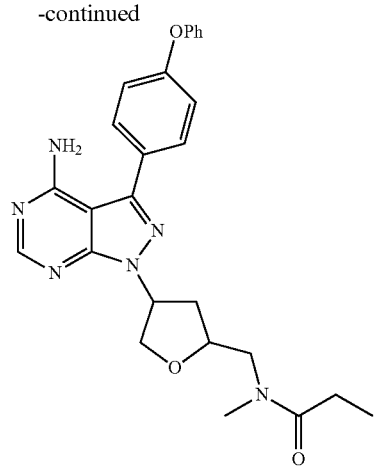

a) polymer-bound triphenylphosphine (TPP), diisopropyl diazodicarboxylate (DIAD), tetrahydrofuran (THF)

4-amino-3-(4-phenoxyphenyl)-1H-pyrazolo[3,4-d]pyrimidine and polymer-bound triphenylphosphine(TPP) (polymerlab) are mixed together with 5 mL of tetrahydrofuran (THF). N-((4-(4-amino-3-(4-phenoxyphenyl)-1H-pyrazolo[3,4-d]pyrimidin-1-yl)tetrahydrofuran-2-yl)methyl)-N-methylpropionamide is added to the mixture followed by the addition of diisopropyl diazodicarboxylate. The reaction mixture is stirred at room temperature overnight. The reaction mixture is filtered to remove the resins and the reaction mixture is concentrated and purified by flash chromatography (pentane/ethyl acetate=1/1) to give the title compound.

Example 1b

Synthesis of 1-(6-(4-amino-3-(4-phenoxyphenyl)-1H-pyrazolo[3,4-d]pyrimidin-1-yl)-4,4-oxazepan-4-yl)butan-1-one

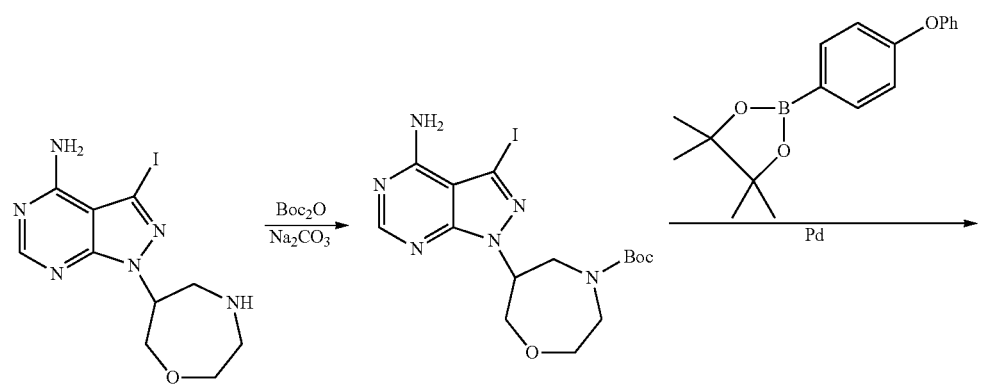

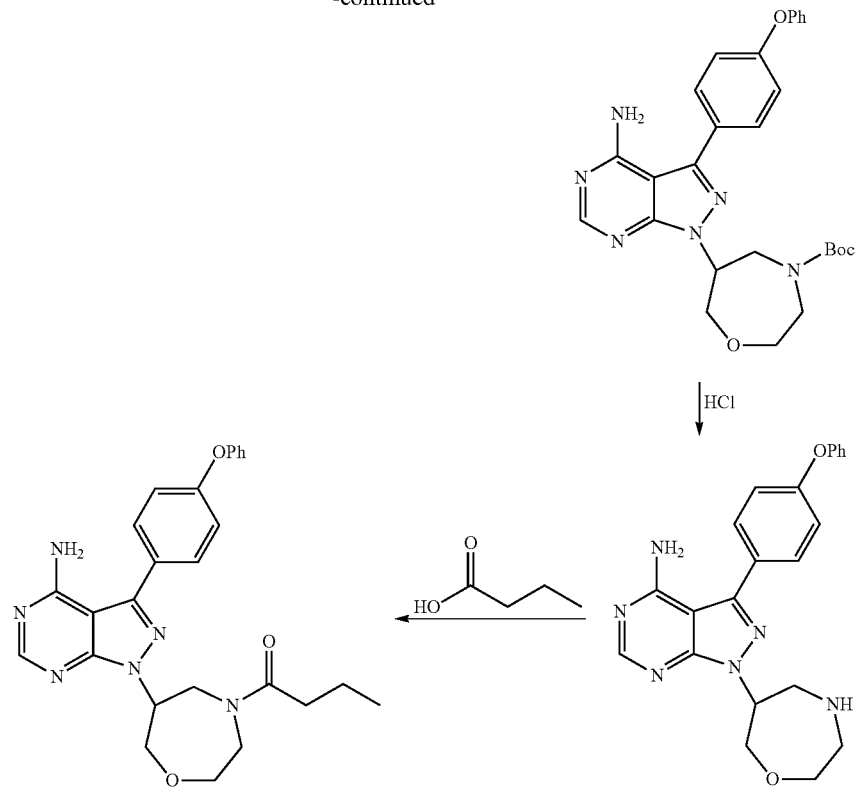

a) tert-butyl 6-(4-amino-3-iodo-1H-pyrazolo[3,4-d]pyrimidin-1-yl)-1,4-oxazepane-4-carboxylate Di-tert-butyl dicarbonate (1.32 mmol) is added to a mixture of 3-iodo-1-(1,4-oxazepan-6-yl)-1H-pyrazolo[3,4-d]pyrimidin-4-amine (1.20 mmol) and sodium carbonate (4.20 mmol) in dioxane (10 mL) and water (10 mL) and the reaction is stirred for 18 h. Dichloromethane (100 mL) is added and the organic layer is washed with water (30 mL) and brine (30 mL), dried ($Na_2SO_4$) and concentrated in vacuo to afford the title compound.

b) tert-butyl 6-(4-amino-3-(4-phenoxyphenyl)-1H-pyrazolo[3,4-d]pyrimidin-1-yl)-1,4-oxazepane-4-carboxylate tert-butyl 6-(4-amino-3-iodo-1H-pyrazolo[3,4-d]pyrimidin-1-yl)-1,4-oxazepane-4-carboxylate (1.18 mmol) is dissolved in ethylene glycol dimethylether (50 mL) and water (10 mL). 4,4,5,5-tetramethyl-2-(4-phenoxyphenyl)-1,3,2-dioxaborolane (1.47 mmol), palladium tetrakistriphenylphosphine (0.059 mmol) and sodium carbonate (2.95 mmol) are added and the reaction is heated for 12-20 hours. Additional boronate and palladium tetrakistriphenylphosphine are added and the reaction is heated at 60-90° C. for a further 20-24 hours. The reaction is concentrated under reduced pressure. The remaining residue was partitioned between dichloromethane and water. The organic layer is dried then concentrated under reduced pressure to yield the title compound.

c). 1-(1,4-oxazepan-6-yl)-3-(4-phenoxyphenyl)-1H-pyrazolo[3,4-d]pyrimidin-4-amine tert-butyl 6-(4-amino-3-(4-phenoxyphenyl)-1H-pyrazolo[3,4-d]pyrimidin-1-yl)-1,4-oxazepane-4-carboxylate is dissolved in acetone and 6N aqueous hydrochloric acid. The reaction is then heated at 45° C. which yielded a precipitate. After 2.5 hours, the precipitate is collected by vacuum filtration, washed with a minimal amount of acetone and dried on the lyophilizer to afford title compound.

d). 1-(6-(4-amino-3-(4-phenoxyphenyl)-1H-pyrazolo[3,4-d]pyrimidin-1-yl)-1,4-oxazepan-4-yl)butan-1-one 1-(1,4-oxazepan-6-yl)-3-(4-phenoxyphenyl)-1H-pyrazolo[3,4-d]pyrimidin-4-amine is coupled with butyric acid under basic condition to afford title compound in good yield.

Example 1c

Synthesis of (R,E)-1-(3-(4-amino-3-(4-phenoxyphenyl)-1H-pyrazolo[3,4-d]pyrimidin-1-yl)pyrrolidin-1-yl)-4-(2-methoxyethylamino)but-2-en-1-one (1c)

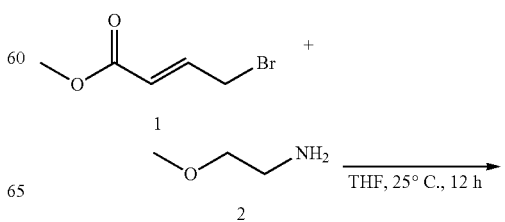

-continued

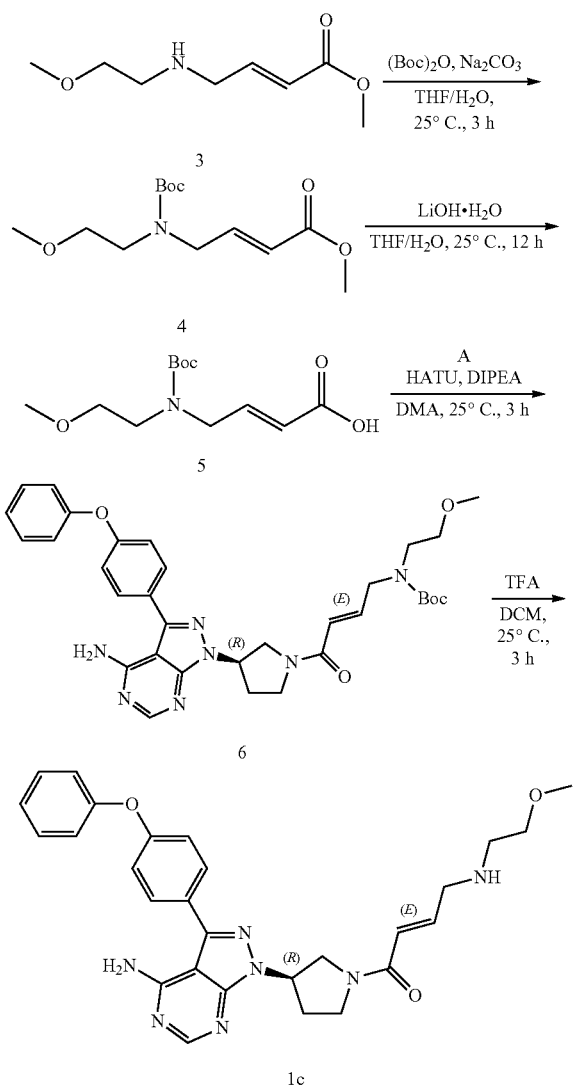

Step 1

To a solution of compound 2 (1.9 g, 25 mmol) in 20 mL of THF was added 4-bromo-methyl-crotonate 1 (450 mg, 2.5 mmol), and the mixture was stirred at 25° C. for 12 h. The reaction was monitored by TLC. After the reaction was complete, the reaction mixture was diluted with 20 mL of ethyl acetate. Then it was washed with brine several times, dried over MgSO₄ and concentrated under reduced pressure to give 150 mg of 3 as a crude product, which was used directly in the next step without further purification.

Step 2

To a solution of compound 3 (150 mg, 0.87 mmol) and Na₂CO₃ (180 mg, 1.74 mmol) in THF/H₂O (10 mL/10 mL) was added (Boc)₂O (375 mg, 1.74 mmol), and the mixture was stirred at 25° C. for 3 h. Then the mixture was diluted with dichloromethane (20 mL), washed with brine several times, dried over MgSO4 and concentrated under reduced pressure to give 202 mg of 4 as a crude product, which was used directly in the next step without further purification.

Step 3

To a solution of compound 4 (200 mg, 0.73 mmol) in THF/H₂O was added LiOH.H₂O (60 mg, 1.47 mmol), and the mixture was stirred at 25° C. for 12 h. Then the pH value of the mixture was adjusted to about 7, and the solvent was removed under reduced pressure to give 189 mg of 5 as a crude product, which was used directly in the next step without further purification.

Step 4

A solution of compound 5 (100 mg, 0.38 mmol) and HATU (146 mg, 0.38 mmol) in DMA (5 mL) was stirred at 25° C. for 10 min. Then it was added to a solution of (R)-3-(4-phenoxyphenyl)-1-(pyrrolidin-3-yl)-1H-pyrazolo[3,4-d]pyrimidin-4-amine (compound A) (144 mg, 0.38 mmol, prepared as disclosed in U.S. Pat. No. 7,514,444) and DIPEA (100 mg, 0.76 mmol) in DMA (5 mL), and the mixture was stirred at 25° C. for 3 h. The reaction was monitored by LC-MS, and purified by prep-HPLC to give 110 mg of 6.

Step 5

Compound 6 (110 mg, 0.18 mmol) was dissolved in 10 mL of DCM, and then TFA (1 mL) was added. After stirring at 25° C. for 3 h, the solvent was removed under reduced pressure. The residue was dissolved by DCM again, and treated with aqueous NaHCO₃. The organic phase separated and was dried over MgSO₄, concentrated under reduced pressure to give 80 mg of the title compound (1c). MS (ESI) m/e (M+1H)⁺: 514.1.

Example 1d

Synthesis of (R,E)-1-(3-(4-amino-3-(4-phenoxyphenyl)-1H-pyrazolo[3,4-d]pyrimidin-1-yl)pyrrolidin-1-yl)-4-(tetrahydro-2H-pyran-4-ylamino)but-2-en-1-one (1d)

Similarly, compound 1d was prepared by substituting tetrahydro-2H-pyran-4-amine for compound 2 in Step 1 of Example 1c. MS (ESI) m/e (M+1H)⁺: 540.1.

Example 1e

Synthesis of (R,E)-1-(3-(4-amino-3-(4-phenoxyphenyl)-1H-pyrazolo[3,4-d]pyrimidin-1-yl)piperidin-1-yl)-4-(2-methoxyethylamino)but-2-en-1-one (1e)

Similarly, compound 1e was prepared by substituting (R)-3-(4-phenoxyphenyl)-1-(piperidin-3-yl)-1H-pyrazolo[3,4-d]pyrimidin-4-amine (compound B, prepared as disclosed in U.S. Pat. No. 7,514,444) for compound A in Step 4 of Example 1c. MS (ESI) m/e (M+1H)⁺: 528.1.

Example 1f

Synthesis of (R,E)-1-(3-(4-amino-3-(4-phenoxyphenyl)-1H-pyrazolo[3,4-d]pyrimidin-1-yl)piperidin-1-yl)-4-(tetrahydro-2H-pyran-4-ylamino)but-2-en-1-one (1f)

Similarly, compound 1f was prepared by substituting tetrahydro-2H-pyran-4-amine for compound 2 in Step 1 of Example 1c and by substituting compound B for compound A in Step 4 of Example 1c. MS (ESI) m/e (M+1H)⁺: 554.1.

Example 1g

Synthesis of (R,E)-1-(3-(4-amino-3-(4-phenoxyphenyl)-1H-pyrazolo[3,4-d]pyrimidin-1-yl)pyrrolidin-1-yl)-4-((2-methoxyethyl)(methyl)amino)but-2-en-1-one (1g)

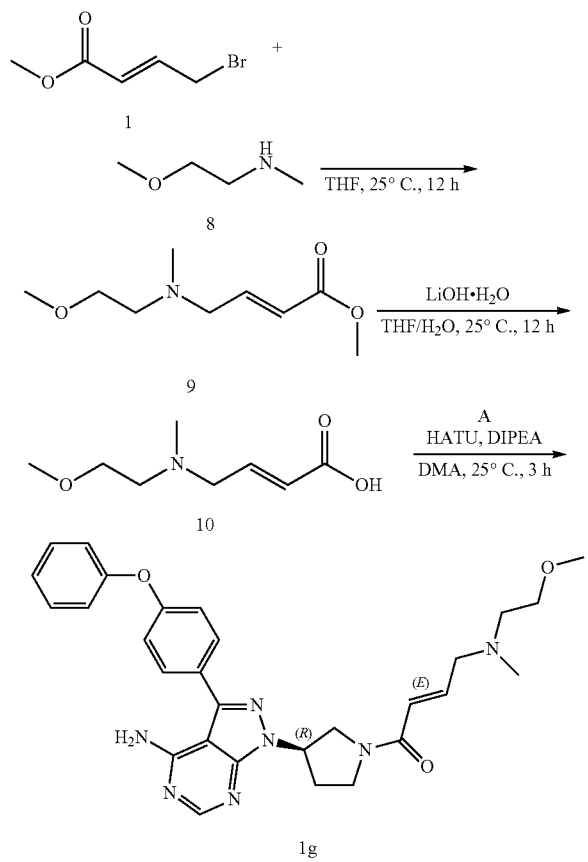

Step 1
To a solution of compound 8 (765 mg, 8.6 mmol) in 20 mL of THF was added 4-bromo-methyl-crotonate 1 (700 mg, 3.9 mmol), and the mixture was stirred at 25° C. for 12 h. The reaction was monitored by TLC. After the reaction finished, it was diluted by ethyl acetate (20 mL). Then it was washed with brine several times, dried over MgSO₄ and concentrated under reduced pressure to give 500 mg of 9 as a crude product, which was used directly in the next step without further purification.

Step 2
To a solution of compound 9 (400 mg, 2.1 mmol) in THF/H₂O (10 mL/10 mL) was added LiOH.H₂O (175 mg, 4.3 mmol), and the mixture was stirred at 25° C. for 12 h. Then the pH value of the mixture was adjusted to about 7. The solvent was removed under reduced pressure to give 360 mg of 10 as a crude product, which was used for the next step directly without further purification.

Step 3
The solution of compound 10 (200 mg, 1.1 mmol) and HATU (439 mg, 1.1 mmol) in 10 mL of DMA was stirred at 25° C. for 10 mins. Then it was added to the solution of compound A (400 mg, 1.1 mmol) and DIPEA (298 mg, 2.3 mmol) in 10 mL of DMA, and the mixture was stirred at 25° C. for 3 h. The reaction was monitored by LC-MS, and purified by prep-HPLC to give 76 mg of the title compound (1g). MS (ESI) m/e (M+1H)⁺: 528.3.

Example 1h

Synthesis of (R,E)-1-(3-(4-amino-3-(4-phenoxyphenyl)-1H-pyrazolo[3,4-d]pyrimidin-1-yl)pyrrolidin-1-yl)-4-(ethyl(methyl)amino)but-2-en-1-one (1h)

Similarly, compound 1h was prepared by substituting ethyl(methyl)amine for compound 8 in Step 1 of Example 1g. MS (ESI) m/e (M+1H)⁺: 498.1.

Example 1i

Synthesis of (R,E)-1-(3-(4-amino-3-(4-phenoxyphenyl)-1H-pyrazolo[3,4-d]pyrimidin-1-yl)pyrrolidin-1-yl)-4-(isopropyl(methyl)amino)but-2-en-1-one (1i)

Similarly, compound 1i was prepared by substituting isopropyl(methyl)amine for compound 8 in Step 1 of Example 1g. MS (ESI) m/e (M+1H)⁺: 512.3.

Example 1j

Synthesis of (R,E)-1-(3-(4-amino-3-(4-phenoxyphenyl)-1H-pyrazolo[3,4-d]pyrimidin-1-yl)pyrrolidin-1-yl)-4-(diethylamino)but-2-en-1-one (1j)

Similarly, compound 1j was prepared by substituting diethylamine for compound 8 in Step 1 of Example 1g. MS (ESI) m/e (M+1H)⁺: 512.1.

Example 1k

Synthesis of (R,E)-1-(3-(4-amino-3-(4-phenoxyphenyl)-1H-pyrazolo[3,4-d]pyrimidin-1-yl)pyrrolidin-1-yl)-4-(methyl(tetrahydro-2H-pyran-4-yl)amino)but-2-en-1-one (1k)

Similarly, compound 1k was prepared by substituting N-methyltetrahydro-2H-pyran-4-amine for compound 8 in Step 1 of Example 1g. MS (ESI) m/e (M+1H)⁺: 554.1.

Example 1m

Synthesis of (R,E)-1-(3-(4-amino-3-(4-phenoxyphenyl)-1H-pyrazolo[3,4-d]pyrimidin-1-yl)piperidin-1-yl)-4-((2-methoxyethyl)(methyl)amino)but-2-en-1-one (1m)

Similarly, compound 1m was prepared by substituting compound B for compound A in Step 3 of Example 1g. MS (ESI) m/e (M+1H)⁺: 542.3.

Example 1n

Synthesis of (R,E)-1-(3-(4-amino-3-(4-phenoxyphenyl)-1H-pyrazolo[3,4-d]pyrimidin-1-yl)piperidin-1-yl)-4-(ethyl(methyl)amino)but-2-en-1-one (1n)

Similarly, compound 1n was prepared by substituting ethyl(methyl)amine for compound 8 in Step 1 of Example 1g and by substituting compound B for compound A in Step 3 of Example 1g. MS (ESI) m/e (M+1H)⁺: 512.1.

Example 1o

Synthesis of (R,E)-1-(3-(4-amino-3-(4-phenoxyphenyl)-1H-pyrazolo[3,4-d]pyrimidin-1-yl)piperidin-1-yl)-4-(isopropyl(methyl)amino)but-2-en-1-one (1o)

Similarly, compound 1o was prepared by substituting isopropyl(methyl)amine for compound 8 in Step 1 of Example 1g and by substituting compound B for compound A in Step 3 of Example 1g. MS (ESI) m/e (M+1H)$^+$: 526.2.

Example 1p

Synthesis of (R,E)-1-(3-(4-amino-3-(4-phenoxyphenyl)-1H-pyrazolo[3,4-d]pyrimidin-1-yl)piperidin-1-yl)-4-(diethylamino)but-2-en-1-one (1p)

Similarly, compound 1p was prepared by substituting diethylamine for compound 8 in Step 1 of Example 1g and by substituting compound B for compound A in Step 3 of Example 1g. MS (ESI) m/e (M+1H)$^+$: 526.3.

Example 1q

Synthesis of (R,E)-1-(3-(4-amino-3-(4-phenoxyphenyl)-1H-pyrazolo[3,4-d]pyrimidin-1-yl)piperidin-1-yl)-4-(methyl(tetrahydro-2H-pyran-4-yl)amino)but-2-en-1-one (1q)

Similarly, compound 1q was prepared by substituting N-methyltetrahydro-2H-pyran-4-amine for compound 8 in Step 1 of Example 1g and by substituting compound B for compound A in Step 3 of Example 1g. MS (ESI) m/e (M+1H)$^+$: 568.3.

Example 1r

Synthesis of (R,E)-1-(3-(4-amino-3-(4-phenoxyphenyl)-1H-pyrazolo[3,4-d]pyrimidin-1-yl)pyrrolidin-1-yl)-4-(methyl(pyridin-2-yl)amino)but-2-en-1-one (1r)

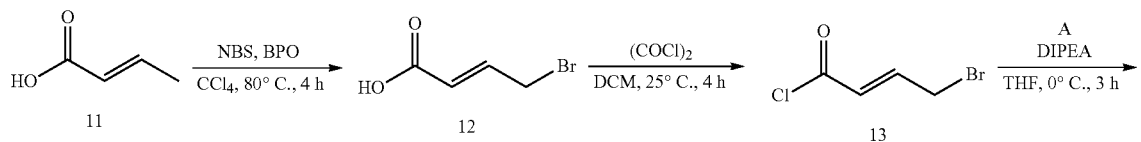

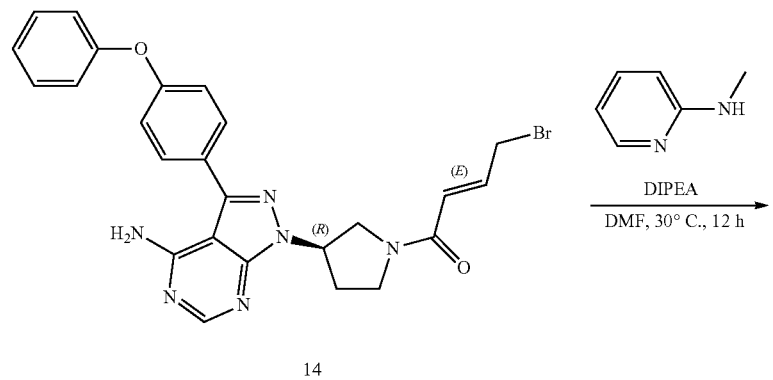

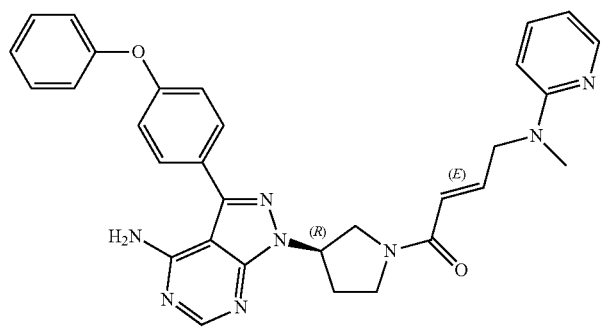

Step 1

To a solution of compound 11 (10 g, 116 mmol) and bromosuccinimide (13.7 g, 116 mmol) in 200 mL of CCl$_4$ was added benzoyl peroxide (3.37 g, 13.9 mmol), and the mixture was stirred at 100° C. for 4 h. Then the solvent was removed under reduced pressure to give a crude product, which was purified by silica gel column (Eluent: EA) to give 4.2 g of 12.

Steps 2 and 3

To a solution of compound 12 (652 mg, 4 mmol) in 10 mL of DCM was added oxalyl chloride (10 mL), and the mixture was stirred at 25° C. for 4 h. Then the solvent and excess oxalyl chloride was removed under reduced pressure to give the crude product. One-sixteenth of the crude product was added to a solution of compound A (110 mg, 0.25 mmol) in THF (10 mL) in the presence of DIPEA (129 mg, 1 mmol) at 0° C. After stirring for 3 h, the mixture was diluted with EA (20 mL), washed with brine, dried over MgSO$_4$ and concentrated under reduced pressure to give the crude 110 mg of 14, which was used in the next step directly without further purification.

Step 4

To a solution of compound 14 (110 mg, 0.21 mmol) and DIPEA (55 mg, 0.43 mmol) in DMF (3 mL) was added N-methylpyridin-2-amine (45 mg, 0.43 mmol), and the mixture was stirred at 30° C. for 12 h. The mixture was purified by prep-HPLC to give 49 mg of the title compound (1r). MS (ESI) m/e (M+1H)$^+$: 547.1.

Example 1s

Synthesis of (R,E)-1-(3-(4-amino-3-(4-phenoxyphenyl)-1H-pyrazolo[3,4-d]pyrimidin-1-yl)pyrrolidin-1-yl)-4-(pyridin-2-ylamino)but-2-en-1-one (1s)

Similarly, compound is was prepared by substituting pyridin-2-amine for N-methylpyridin-2-amine in Step 4 of Example 1r. MS (ESI) m/e (M+1H)$^+$: 533.1.

Example 1t

Synthesis of (R,E)-1-(3-(4-amino-3-(4-phenoxyphenyl)-1H-pyrazolo[3,4-d]pyrimidin-1-yl)piperidin-1-yl)-4-(methyl(pyridin-2-yl)amino)but-2-en-1-one (10

Similarly, compound 1t was prepared by substituting compound B for compound A in Step 3 of Example 1r. MS (ESI) m/e (M+1H)$^+$: 561.0.

Example 1u

Synthesis of (R,E)-1-(3-(4-amino-3-(4-phenoxyphenyl)-1H-pyrazolo[3,4-d]pyrimidin-1-yl)piperidin-1-yl)-4-(pyridin-2-ylamino)but-2-en-1-one (1u)

Similarly, compound 1u was prepared by substituting compound B for compound A in Step 3 of Example 1r and substituting pyridin-2-amine for N-methylpyridin-2-amine in Step 4 of Example 1r. MS (ESI) m/e (M+1H)$^+$: 547.0.

Example 2a

Synthesis of (R,E)-1-(3-(4-amino-3-(4-phenoxyphenyl)-1H-pyrazolo[3,4-d]pyrimidin-1-yl)pyrrolidin-1-yl)-4-(dicyclopropylamino)but-2-en-1-one (2a)

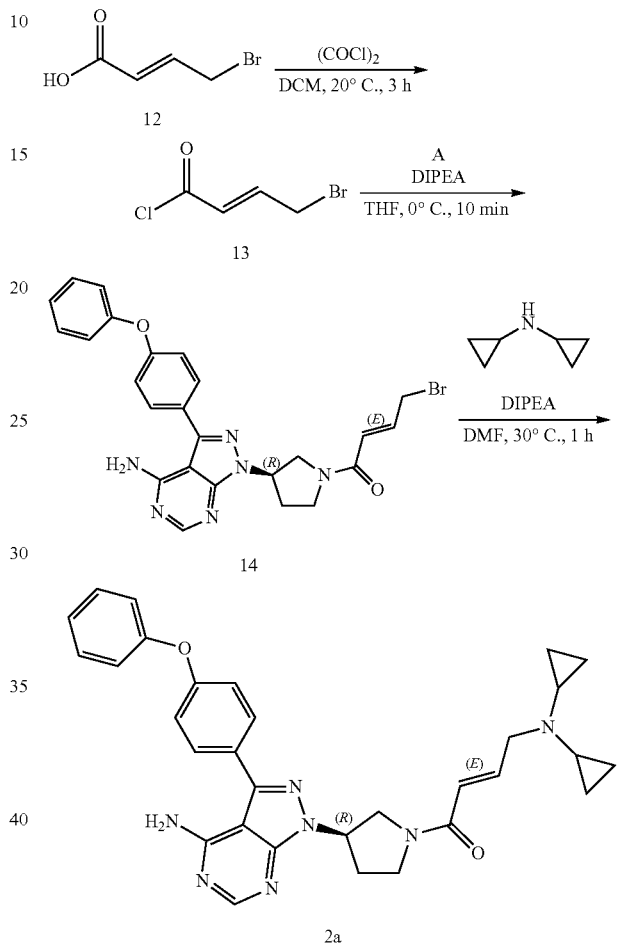

Steps 1 and 2

To a solution of compound 12 (2.0 g, 7.9 mmol) in DCM (10 mL), oxalyl chloride (20 ml) was added, and the mixture was stirred at 20° C. for 3 h. Excess oxalyl chloride and solvent were removed in vacuo to give the crude product 13. Half of crude 13 was added to a solution of compound A (1.2 g, 2.6 mmol) in THF (10 ml) in the presence of DIPEA (1 g, 7.8 mmol) at 0° C. After stirring for 10 min, the mixture was diluted with EA (20 mL), washed with brine, dried over Na$_2$SO$_4$, concentrated in vacuo to give 0.65 g of the crude compound 14, which was used in the next step directly without further purification.

Step 3

To a solution of 14 (100 mg, 0.19 mmol) and DIPEA (49 mg, 0.38 mmol) in DMF (2 ml) was added dicyclopropylamine (37 mg, 0.38 mmol). The mixture was stirred at 30° C. for 1 h and then purified by prep-HPLC to give 24 mg of the title compound (2a). MS (ESI) m/e (M+1H)$^+$: 536.3.

Example 2b

Synthesis of (E)-1-((R)-3-(4-amino-3-(4-phenoxyphenyl)-1H-pyrazolo[3,4-d]pyrimidin-1-yl)pyrrolidin-1-yl)-4-(methyl((R)-tetrahydrofuran-3-yl)amino)but-2-en-1-one (2b)

Similarly, compound 2b was prepared by substituting (R)—N-methyltetrahydrofuran-3-amine for dicyclopropylamine in Step 3 of Example 2a. MS (ESI) m/e (M+1H)$^+$: 540.1.

Example 2c

Synthesis of (E)-1-((R)-3-(4-amino-3-(4-phenoxyphenyl)-1H-pyrazolo[3,4-d]pyrimidin-1-yl)pyrrolidin-1-yl)-4-((R)-tetrahydrofuran-3-ylamino)but-2-en-1-one (2c)

Similarly, compound 2c was prepared by substituting (R)-tetrahydrofuran-3-amine for dicyclopropylamine in Step 3 of Example 2a. MS (ESI) m/e (M+1H)$^+$: 526.1.

Example 2d

Synthesis of (E)-1-((R)-3-(4-amino-3-(4-phenoxyphenyl)-1H-pyrazolo[3,4-d]pyrimidin-1-yl)pyrrolidin-1-yl)-4-(methyl((S)-tetrahydrofuran-3-yl)amino)but-2-en-1-one (2d)

Similarly, compound 2d was prepared by substituting (S)—N-methyltetrahydrofuran-3-amine for dicyclopropylamine in Step 3 of Example 2a. MS (ESI) m/e (M+1H)$^+$: 540.3.

Example 2e

Synthesis of (E)-1-((R)-3-(4-amino-3-(4-phenoxyphenyl)-1H-pyrazolo[3,4-d]pyrimidin-1-yl)pyrrolidin-1-yl)-4-((S)-tetrahydrofuran-3-ylamino)but-2-en-1-one (2e)

Similarly, compound 2e was prepared by substituting (S)-tetrahydrofuran-3-amine for dicyclopropylamine in Step 3 of Example 2a. MS (ESI) m/e (M+1H)$^+$: 526.0.

Example 2f

Synthesis of (R,E)-1-(3-(4-amino-3-(4-phenoxyphenyl)-1H-pyrazolo[3,4-d]pyrimidin-1-yl)pyrrolidin-1-yl)-4-(methyl(oxetan-3-yl)amino)but-2-en-1-one (2f)

Similarly, compound 2f was prepared by substituting N-methyloxetan-3-amine for dicyclopropylamine in Step 3 of Example 2a. MS (ESI) m/e (M+1H)$^+$: 526.1.

Example 2g

Synthesis of (R,E)-1-(3-(4-amino-3-(4-phenoxyphenyl)-1H-pyrazolo[3,4-d]pyrimidin-1-yl)pyrrolidin-1-yl)-4-(oxetan-3-ylamino)but-2-en-1-one (2g)

Similarly, compound 2g was prepared by substituting oxetan-3-amine for dicyclopropylamine in Step 3 of Example 2a. MS (ESI) m/e (M+1H)$^+$: 512.1.

Example 2h

Synthesis of (E)-1-((R)-3-(4-amino-3-(4-phenoxyphenyl)-1H-pyrazolo[3,4-d]pyrimidin-1-yl)piperidin-1-yl)-4-(methyl((R)-tetrahydrofuran-3-yl)amino)but-2-en-1-one (2h)

Similarly, compound 2h was prepared by substituting compound B for compound A in Step 2 of Example 2a and substituting (R)—N-methyltetrahydrofuran-3-amine for dicyclopropylamine in Step 3 of Example 2a. MS (ESI) m/e (M+1H)$^+$: 554.1.

Example 2i

Synthesis of (E)-1-((R)-3-(4-amino-3-(4-phenoxyphenyl)-1H-pyrazolo[3,4-d]pyrimidin-1-yl)piperidin-1-yl)-4-((R)-tetrahydrofuran-3-ylamino)but-2-en-1-one (2i)

Similarly, compound 2i was prepared by substituting compound B for compound A in Step 2 of Example 2a and substituting (R)-tetrahydrofuran-3-amine for dicyclopropylamine in Step 3 of Example 2a. MS (ESI) m/e (M+1H)$^+$: 540.1.

Example 2j

Synthesis of (E)-1-((R)-3-(4-amino-3-(4-phenoxyphenyl)-1H-pyrazolo[3,4-d]pyrimidin-1-yl)piperidin-1-yl)-4-(methyl((S)-tetrahydrofuran-3-yl)amino)but-2-en-1-one (2j)

Similarly, compound 2j was prepared by substituting compound B for compound A in Step 2 of Example 2a and substituting (S)—N-methyltetrahydrofuran-3-amine for dicyclopropylamine in Step 3 of Example 2a. MS (ESI) m/e (M+1H)$^+$: 554.1.

Example 2k

Synthesis of (E)-1-((R)-3-(4-amino-3-(4-phenoxyphenyl)-1H-pyrazolo[3,4-d]pyrimidin-1-yl)piperidin-1-yl)-4-((S)-tetrahydrofuran-3-ylamino)but-2-en-1-one (2k)

Similarly, compound 2k was prepared by substituting compound B for compound A in Step 2 of Example 2a and substituting (S)-tetrahydrofuran-3-amine for dicyclopropylamine in Step 3 of Example 2a. MS (ESI) m/e (M+1H)$^+$: 540.1.

Example 2m

Synthesis of (R,E)-1-(3-(4-amino-3-(4-phenoxyphenyl)-1H-pyrazolo[3,4-d]pyrimidin-1-yl)piperidin-1-yl)-4-(methyl(oxetan-3-yl)amino)but-2-en-1-one (2m)

Similarly, compound 2m was prepared by substituting compound B for compound A in Step 2 of Example 2a and substituting N-methyloxetan-3-amine for dicyclopropylamine in Step 3 of Example 2a. MS (ESI) m/e (M+1H)$^+$: 540.1.

Example 2n

Synthesis of (R,E)-1-(3-(4-amino-3-(4-phenoxyphenyl)-1H-pyrazolo[3,4-d]pyrimidin-1-yl)piperidin-1-yl)-4-(oxetan-3-ylamino)but-2-en-1-one (2n)

Similarly, compound 2n was prepared by substituting compound B for compound A in Step 2 of Example 2a and substituting oxetan-3-amine for dicyclopropylamine in Step 3 of Example 2a. MS (ESI) m/e (M+1H)$^+$: 526.1.

Example 2o

Synthesis of (R,E)-1-(3-(4-amino-3-(4-phenoxyphenyl)-1H-pyrazolo[3,4-d]pyrimidin-1-yl)pyrrolidin-1-yl)-4-(ethyl(2-methoxyethyl)amino)but-2-en-1-one (2o)

Similarly, compound 2o was prepared by substituting ethyl-(2-methoxyethyl)-amine for dicyclopropylamine in Step 3 of Example 2a. MS (ESI) m/e (M+1H)$^+$: 542.1. $^1$H NMR (CDCl$_3$, 400 MHz): 8.43 (s, 1H), 7.67 (dd, J$_1$=2.0 Hz, J$_2$=6.8 Hz, 2H), 7.43 (t, J=8.0 Hz, 2H), 7.21-7.09 (m, 5H), 6.88-6.77 (m, 2H), 5.71 (m, 1H), 4.22 (d, J=5.6 Hz, 1H), 4.23-3.67 (m, 7H), 3.41-3.25 (m, 7H), 2.65-2.54 (m, 2H), 1.35-1.29 (m, 3H).

Example 2p

Synthesis of (R,E)-1-(3-(4-amino-3-(4-phenoxyphenyl)-1H-pyrazolo[3,4-d]pyrimidin-1-yl)pyrrolidin-1-yl)-4-(cyclopropyl(2-methoxyethyl)amino)but-2-en-1-one (2p)

Similarly, compound 2p was prepared by substituting N-(2-methoxyethyl)cyclopropanamine for dicyclopropylamine in Step 3 of Example 2a. MS (ESI) m/e (M+1H)$^+$: 554.3.

Example 2q

Synthesis of (R,E)-1-(3-(4-amino-3-(4-phenoxyphenyl)-1H-pyrazolo[3,4-d]pyrimidin-1-yl)pyrrolidin-1-yl)-4-(cyclopropyl(isopropyl)amino)but-2-en-1-one (2q)

Similarly, compound 2q was prepared by substituting N-isopropylcyclopropanamine for dicyclopropylamine in Step 3 of Example 2a. MS (ESI) m/e (M+1H)$^+$: 538.2.

Example 2r

Synthesis of (R,E)-1-(3-(4-amino-3-(4-phenoxyphenyl)-1H-pyrazolo[3,4-d]pyrimidin-1-yl)piperidin-1-yl)-4-(dicyclopropylamino)but-2-en-1-one (2r)

Similarly, compound 2r was prepared by substituting compound B for compound A in Step 2 of Example 2a. MS (ESI) m/e (M+1H)$^+$: 550.4.

Example 2s

Synthesis of (R,E)-1-(3-(4-amino-3-(4-phenoxyphenyl)-1H-pyrazolo[3,4-d]pyrimidin-1-yl)piperidin-1-yl)-4-(cyclopropyl(2-methoxyethyl)amino)but-2-en-1-one (2s)

Similarly, compound 2s was prepared by substituting compound B for compound A in Step 2 of Example 2a and substituting N-(2-methoxyethyl)cyclopropanamine for dicyclopropylamine in Step 3 of Example 2a. MS (ESI) m/e (M+1H)$^+$: 568.3.

Example 2t

Synthesis of (R,E)-1-(3-(4-amino-3-(4-phenoxyphenyl)-1H-pyrazolo[3,4-d]pyrimidin-1-yl)piperidin-1-yl)-4-(cyclopropyl(isopropyl)amino)but-2-en-1-one (2t)

Similarly, compound 2t was prepared by substituting compound B for compound A in Step 2 of Example 2a and substituting N-isopropylcyclopropanamine for dicyclopropylamine in Step 3 of Example 2a. MS (ESI) m/e (M+1H)$^+$: 552.3.

Example 2u

Synthesis of (R,E)-1-(3-(4-amino-3-(4-phenoxyphenyl)-1H-pyrazolo[3,4-d]pyrimidin-1-yl)pyrrolidin-1-yl)-4-(cyclopropyl(methyl)amino)but-2-en-1-one (2u)

Similarly, compound 2u was prepared by substituting N-methylcyclopropanamine for dicyclopropylamine in Step 3 of Example 2a. MS (ESI) m/e (M+1H)$^+$: 510.1.

Example 2v

Synthesis of (R,E)-1-(3-(4-amino-3-(4-phenoxyphenyl)-1H-pyrazolo[3,4-d]pyrimidin-1-yl)pyrrolidin-1-yl)-4-(cyclopropyl(ethyl)amino)but-2-en-1-one (2v)

Similarly, compound 2v was prepared by substituting N-ethylcyclopropanamine for dicyclopropylamine in Step 3 of Example 2a. MS (ESI) m/e (M+1H)$^+$: 524.1.

Example 2w

Synthesis of (R,E)-1-(3-(4-amino-3-(4-phenoxyphenyl)-1H-pyrazolo[3,4-d]pyrimidin-1-yl)pyrrolidin-1-yl)-4-(cyclohexyl(methyl)amino)but-2-en-1-one (2w)

Similarly, compound 2w was prepared by substituting N-methylcyclohexanamine for dicyclopropylamine in Step 3 of Example 2a. MS (ESI) m/e (M+1H)$^+$: 552.1.

Example 2x

Synthesis of (R,E)-1-(3-(4-amino-3-(4-phenoxyphenyl)-1H-pyrazolo[3,4-d]pyrimidin-1-yl)pyrrolidin-1-yl)-4-(cyclohexylamino)but-2-en-1-one (2x)

Similarly, compound 2x was prepared by substituting cyclohexanamine for dicyclopropylamine in Step 3 of Example 2a. MS (ESI) m/e (M+1H)$^+$: 538.1.

Example 2y

Synthesis of (R,E)-1-(3-(4-amino-3-(4-phenoxyphenyl)-1H-pyrazolo[3,4-d]pyrimidin-1-yl)pyrrolidin-1-yl)-4-(cyclopentyl(methyl)amino)but-2-en-1-one (2y)

Similarly, compound 2y was prepared by substituting N-methylcyclopentanamine for dicyclopropylamine in Step 3 of Example 2a. MS (ESI) m/e (M+1H)$^+$: 538.4.

Example 2z

Synthesis of (R,E)-1-(3-(4-amino-3-(4-phenoxyphenyl)-1H-pyrazolo[3,4-d]pyrimidin-1-yl)pyrrolidin-1-yl)-4-(cyclopentylamino)but-2-en-1-one (2z)

Similarly, compound 2z was prepared by substituting cyclopentanamine for dicyclopropylamine in Step 3 of Example 2a. MS (ESI) m/e (M+1H)$^+$: 524.2.

Example 2aa

Synthesis of (R,E)-1-(3-(4-amino-3-(4-phenoxyphenyl)-1H-pyrazolo[3,4-d]pyrimidin-1-yl)pyrrolidin-1-yl)-4-(cyclobutyl(methyl)amino)but-2-en-1-one (2aa)

Similarly, compound 2aa was prepared by substituting N-methylcyclobutanamine for dicyclopropylamine in Step 3 of Example 2a. MS (ESI) m/e (M+1H)$^+$: 524.1.

Example 2ab

Synthesis of (R,E)-1-(3-(4-amino-3-(4-phenoxyphenyl)-1H-pyrazolo[3,4-d]pyrimidin-1-yl)pyrrolidin-1-yl)-4-(cyclobutylamino)but-2-en-1-one (2ab)

Similarly, compound 2ab was prepared by substituting cyclobutanamine for dicyclopropylamine in Step 3 of Example 2a. MS (ESI) m/e (M+1H)$^+$: 510.1.

Example 2ac

Synthesis of (R,E)-1-(3-(4-amino-3-(4-phenoxyphenyl)-1H-pyrazolo[3,4-d]pyrimidin-1-yl)pyrrolidin-1-yl)-4-(methyl(1-methylpiperidin-4-yl)amino)but-2-en-1-one (2ac)

Similarly, compound 2ac was prepared by substituting N,1-dimethylpiperidin-4-amine for dicyclopropylamine in Step 3 of Example 2a. MS (ESI) m/e (M+1H)$^+$: 567.3.

Example 2ad

Synthesis of (R,E)-1-(3-(4-amino-3-(4-phenoxyphenyl)-1H-pyrazolo[3,4-d]pyrimidin-1-yl)pyrrolidin-1-yl)-4-(1-methylpiperidin-4-ylamino)but-2-en-1-one (2ad)

Similarly, compound 2ad was prepared by substituting 1-methylpiperidin-4-amine for dicyclopropylamine in Step 3 of Example 2a. MS (ESI) m/e (M+1H)$^+$: 553.1.

Example 2ae

Synthesis of (R,E)-1-(3-(4-amino-3-(4-phenoxyphenyl)-1H-pyrazolo[3,4-d]pyrimidin-1-yl)piperidin-1-yl)-4-(cyclopropyl(methyl)amino)but-2-en-1-one (2ae)

Similarly, compound 2ae was prepared by substituting compound B for compound A in Step 2 of Example 2a and substituting N-methylcyclopropanamine for dicyclopropylamine in Step 3 of Example 2a. MS (ESI) m/e (M+1H)$^+$: 524.3.

Example 2af

Synthesis of (R,E)-1-(3-(4-amino-3-(4-phenoxyphenyl)-1H-pyrazolo[3,4-d]pyrimidin-1-yl)piperidin-1-yl)-4-(cyclopropylamino)but-2-en-1-one (2af)

Similarly, compound 2af was prepared by substituting compound B for compound A in Step 2 of Example 2a and substituting cyclopropanamine for dicyclopropylamine in Step 3 of Example 2a. MS (ESI) m/e (M+1H)$^+$: 509.4.

Example 2ag

Synthesis of (R,E)-1-(3-(4-amino-3-(4-phenoxyphenyl)-1H-pyrazolo[3,4-d]pyrimidin-1-yl)piperidin-1-yl)-4-(cyclohexyl(methyl)amino)but-2-en-1-one (2ag)

Similarly, compound 2ag was prepared by substituting compound B for compound A in Step 2 of Example 2a and substituting N-methylcyclohexanamine for dicyclopropylamine in Step 3 of Example 2a. MS (ESI) m/e (M+1H)$^+$: 566.1.

Example 2ah

Synthesis of (R,E)-1-(3-(4-amino-3-(4-phenoxyphenyl)-1H-pyrazolo[3,4-d]pyrimidin-1-yl)piperidin-1-yl)-4-(cyclohexylamino)but-2-en-1-one (2ah)

Similarly, compound 2ah was prepared by substituting compound B for compound A in Step 2 of Example 2a and substituting cyclohexanamine for dicyclopropylamine in Step 3 of Example 2a. MS (ESI) m/e (M+1H)$^+$: 552.4.

Example 2ai

Synthesis of (R,E)-1-(3-(4-amino-3-(4-phenoxyphenyl)-1H-pyrazolo[3,4-d]pyrimidin-1-yl)piperidin-1-yl)-4-(cyclopentyl(methyl)amino)but-2-en-1-one (2ai)

Similarly, compound 2ai was prepared by substituting compound B for compound A in Step 2 of Example 2a and substituting N-methylcyclopentanamine for dicyclopropylamine in Step 3 of Example 2a. MS (ESI) m/e (M+1H)$^+$: 552.1.

Example 2aj

Synthesis of (R,E)-1-(3-(4-amino-3-(4-phenoxyphenyl)-1H-pyrazolo[3,4-d]pyrimidin-1-yl)piperidin-1-yl)-4-(cyclopentylamino)but-2-en-1-one (2aj)

Similarly, compound 2aj was prepared by substituting compound B for compound A in Step 2 of Example 2a and substituting cyclopentanamine for dicyclopropylamine in Step 3 of Example 2a. MS (ESI) m/e (M+1H)$^+$: 538.4.

Example 2ak

Synthesis of (R,E)-1-(3-(4-amino-3-(4-phenoxyphenyl)-1H-pyrazolo[3,4-d]pyrimidin-1-yl)piperidin-1-yl)-4-(cyclobutyl(methyl)amino)but-2-en-1-one (2ak)

Similarly, compound 2ak was prepared by substituting compound B for compound A in Step 2 of Example 2a and substituting N-methylcyclobutanamine for dicyclopropylamine in Step 3 of Example 2a. MS (ESI) m/e (M+1H)$^+$: 538.1.

Example 2am

Synthesis of (R,E)-1-(3-(4-amino-3-(4-phenoxyphenyl)-1H-pyrazolo[3,4-d]pyrimidin-1-yl)piperidin-1-yl)-4-(cyclobutylamino)but-2-en-1-one (2am)

Similarly, compound 2am was prepared by substituting compound B for compound A in Step 2 of Example 2a and substituting cyclobutanamine for dicyclopropylamine in Step 3 of Example 2a. MS (ESI) m/e (M+1H)$^+$: 524.1.

Example 2an

Synthesis of (R,E)-1-(3-(4-amino-3-(4-phenoxyphenyl)-1H-pyrazolo[3,4-d]pyrimidin-1-yl)piperidin-1-yl)-4-(methyl(1-methylpiperidin-4-yl)amino)but-2-en-1-one (2an)

Similarly, compound 2an was prepared by substituting compound B for compound A in Step 2 of Example 2a and substituting N,1-dimethylpiperidin-4-amine for dicyclopropylamine in Step 3 of Example 2a. MS (ESI) m/e (M+1H)$^+$: 581.1.

Example 2ao

Synthesis of (R,E)-1-(3-(4-amino-3-(4-phenoxyphenyl)-1H-pyrazolo[3,4-d]pyrimidin-1-yl)piperidin-1-yl)-4-(1-methylpiperidin-4-ylamino)but-2-en-1-one (2ao)

Similarly, compound 2ao was prepared by substituting compound B for compound A in Step 2 of Example 2a and substituting 1-methylpiperidin-4-amine for dicyclopropylamine in Step 3 of Example 2a. MS (ESI) m/e (M+1H)$^+$: 567.2.

Example 2ap

Synthesis of (R,E)-1-(3-(4-amino-3-(4-phenoxyphenyl)-1H-pyrazolo[3,4-d]pyrimidin-1-yl)pyrrolidin-1-yl)-4-(cyclobutyl(ethyl)amino)but-2-en-1-one (2ap)

Similarly, compound 2ap was prepared by substituting N-ethylcyclobutanamine for dicyclopropylamine in Step 3 of Example 2a. MS (ESI) m/e (M+1H)$^+$: 538.2.

Example 2aq

Synthesis of (R,E)-1-(3-(4-amino-3-(4-phenoxyphenyl)-1H-pyrazolo[3,4-d]pyrimidin-1-yl)pyrrolidin-1-yl)-4-(cyclobutyl(isopropyl)amino)but-2-en-1-one (2aq)

Similarly, compound 2aq was prepared by substituting N-isopropylcyclobutanamine for dicyclopropylamine in Step 3 of Example 2a. MS (ESI) m/e (M+1H)$^+$: 552.4.

Example 2ar

Synthesis of (R,E)-1-(3-(4-amino-3-(4-phenoxyphenyl)-1H-pyrazolo[3,4-d]pyrimidin-1-yl)pyrrolidin-1-yl)-4-(isopropyl(2-methoxyethyl)amino)but-2-en-1-one (2ar)

Similarly, compound 2ar was prepared by substituting N-(2-methoxyethyl)propan-2-amine for dicyclopropylamine in Step 3 of Example 2a.

Example 2 as

Synthesis of (R,E)-1-(3-(4-amino-3-(4-phenoxyphenyl)-1H-pyrazolo[3,4-d]pyrimidin-1-yl)piperidin-1-yl)-4-(isopropyl(2-methoxyethyl)amino)but-2-en-1-one (2 as)

Similarly, compound 2 as was prepared by substituting compound B for compound A in Step 2 of Example 2a and substituting N-(2-methoxyethyl)propan-2-amine for dicyclopropylamine in Step 3 of Example 2a.

Example 2 at

Synthesis of (R,E)-1-(3-(4-amino-3-(4-phenoxyphenyl)-1H-pyrazolo[3,4-d]pyrimidin-1-yl)pyrrolidin-1-yl)-4-(bis(2-methoxyethyl)amino)but-2-en-1-one (2 at)

Similarly, compound 2 at was prepared by substituting bis(2-methoxyethyl)amine for dicyclopropylamine in Step 3 of Example 2a.

Example 2au

Synthesis of (R,E)-1-(3-(4-amino-3-(4-phenoxyphenyl)-1H-pyrazolo[3,4-d]pyrimidin-1-yl)piperidin-1-yl)-4-(bis(2-methoxyethyl)amino)but-2-en-1-one (2au)

Similarly, compound 2au was prepared by substituting compound B for compound A in Step 2 of Example 2a and substituting bis(2-methoxyethyl)amine for dicyclopropylamine in Step 3 of Example 2a.

Example 3a

Synthesis of (R,E)-1-(3-(4-amino-3-(4-phenoxyphenyl)-1H-pyrazolo[3,4-d]pyrimidin-1-yl)pyrrolidin-1-yl)-4-(cyclopropylamino)but-2-en-1-one (3a)

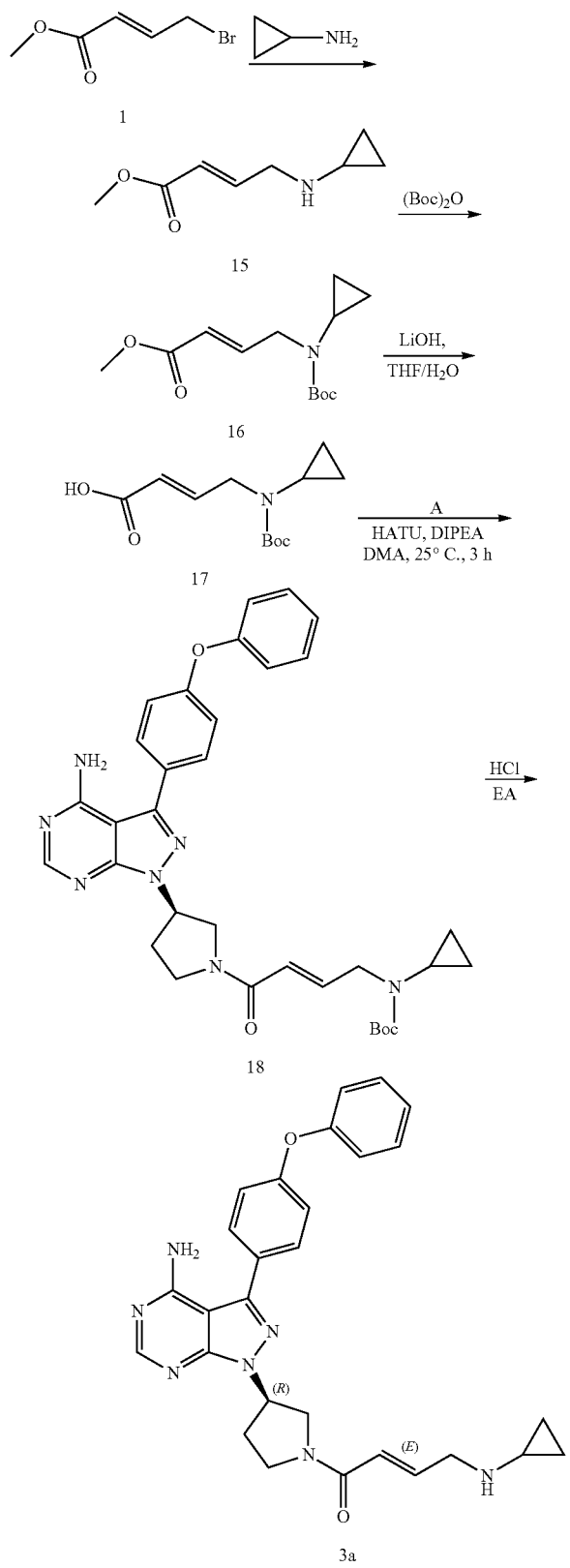

Step 1

To a solution of cyclopropylamine (12.8 g, 0.22 mol) in THF (20 mL) was added 1 (20 g, 0.11 mol), and the mixture was stirred at 25° C. for 12 h. The reaction was monitored by LCMS. Upon reaction completion, the solvent was removed under reduced pressure, re-dissolved in DCM, washed with brine several times, dried over $Na_2SO_4$ and concentrated under reduced pressure to give 10 g of 15 as a crude product, which was used directly in the next step without further purification. MS (ESI) m/e $(M+1H)^+$: 156.0.

Step 2

To a solution of 15 (10 g, 64.5 mmol) and $Na_2CO_3$ (13.6 g, 129 mmol) in $THF/H_2O$ (30 mL/30 mL) was added $(Boc)_2O$ (28.1 g, 129 mmol), and the mixture was stirred at 25° C. for 3 h. Upon reaction completion, the mixture was diluted with DCM (50 mL), washed with brine several times, dried over $Na_2SO_4$ and concentrated under reduced pressure to give 15 g of 16 as a crude product, which was used directly in the next step without further purification.

Step 3

To a solution of 16 (15 g, 58 mmol) in $THF/H_2O$ (15 mL/15 mL) was added $LiO.H_2O$ (4.9 g, 117 mmol), and the mixture was stirred at 25° C. for 12 h. Upon reaction completion, the pH of the mixture was adjusted to about pH=7, and the solvent was removed under reduced pressure to give 8.0 g of 17 as a crude product, which was used directly in the next step without further purification.

Step 4

A solution of 17 (8.0 g, 33.2 mmol) and HATU (17.1 g, 45 mmol) in DMA (5 mL) was stirred at 25° C. for 10 min. To this solution was added a solution of compound A (10 g, 22.5 mmol) and DIPEA (5.8 g, 45 mmol) in DMA (5 mL). The mixture was stirred at 25° C. for 3 h and monitored by LC-MS. Upon reaction completion, the reaction mixture was poured into water and extracted with EA three times, dried over $Na_2SO_4$ and concentrated under reduced pressure to give 8.0 g of 18 as a crude product. MS (ESI) m/e $(M+1H)^+$: 596.1.

Step 5

To a solution of 18 (8.0 g, 13.4 mmol) in EA (20 mL), was added HCl/EA (10 mL). After stirring at 25° C. for 3 h, the solvent was removed under reduced pressure. The residue was purified by prep-HPLC to give 2.6 g of 3a. MS (ESI) m/e $(M+1H)^+$: 496.1.

Example 3b

Synthesis of (R,E)-1-(3-(4-amino-3-(4-phenoxyphenyl)-1H-pyrazolo[3,4-d]pyrimidin-1-yl)pyrrolidin-1-yl)-4-((2-methoxyethyl)(methyl)amino)but-2-en-1-one (3b)

Similarly, compound 3b was prepared in an analogous manner as Example 3a.

Example 4a

Synthesis of (R)-3-(4-(3-fluorophenoxy)phenyl)-1-(pyrrolidin-3-yl)-1H-pyrazolo[3,4-d]pyrimidin-4-amine (4a)

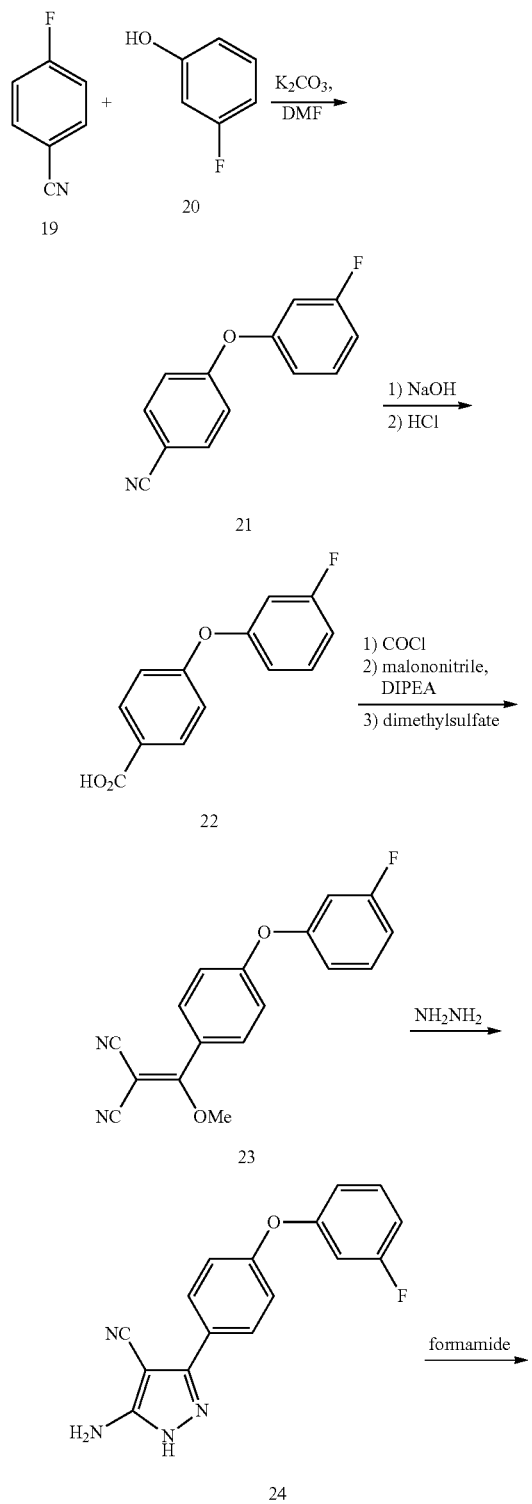

-continued

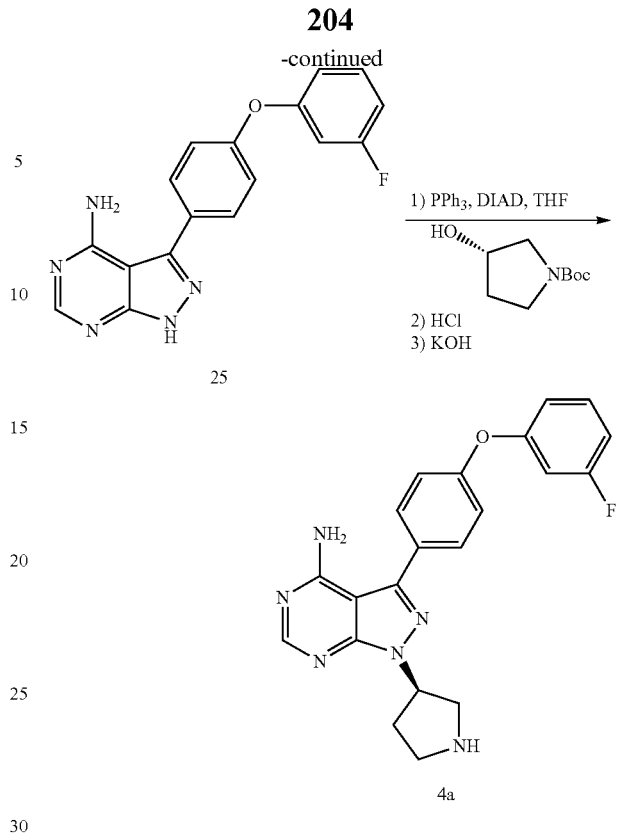

Step 1

A mixture of 19 (25.0 g, 206.4 mmol), 20 (20.4 mL, 227.0 mmol) and $K_2CO_3$ (31.38 g, 227.0 mmol) in DMF (200 mL) was heated to 150° C. for 3 h. The mixture was cooled to rt and water (800 mL) was added with stirring. White precipitate was formed during this exothermic process. The mixture was cooled to rt and filtered. The solid was washed with water (500 mL) and air-dried. After further drying under reduced pressure, 44.4 g of 21 was obtained and used without additional purification.

Step 2

A mixture of 21 (10.66 g, 50.0 mmol) and aq. NaOH solution (60 mL) was heated to reflux for 2.5 h. HPLC monitoring of the reaction revealed a large amount of unreacted starting material. Additional aq. NaOH solution (80 mL) was added, and the reaction mixture was heated to reflux for another 2.5 h. The mixture became a homogeneous clear solution. HPLC monitoring indicated complete consumption of the starting material but also showed two major peaks likely corresponding to the amide intermediate and the desired product. Heating was continued for another 5 h before the mixture was cooled to rt, during which the mixture remained a homogeneous clear solution. HPLC analysis indicated complete conversion to final carboxylic acid. Concentrated HCl solution was added to the mixture to adjust the pH to approximately pH=0. The mixture was cooled to rt and filtered. The solid was further washed with water (150 mL) and air dried. The solid was further dried under reduced pressure to provide 11.61 g of 22 as a white solid.

Steps 3 and 4

To a mixture of 22 (44.31 g, 190.8 mmol) and DMF (0.20 mL) in THF (300 mL) stirring in an ice bath was slowly added oxalyl chloride (19.4 mL, 229.0 mmol) over 10 min. The reaction mixture was warmed up to rt and stirred for 2 h. An additional amount of DMF (0.20 mL) was added and the mixture was heated to 40° C. for 2 h. The solvent was removed under reduced pressure, and the residue was mixed with THF (200 mL) and malononitrile (13.2 mL, 209.9 mmol) and cooled in an ice bath. DIPEA (83.1 mL, 477.0 mmol) was added slowly over 1 h. The mixture was warmed up to rt and stirred for 2 h. After dimethylsulfate (54.2 mL, 572.5 mmol) was added in one portion, the mixture was heated to 70° C. for 2 h, cooled to rt and stirred overnight (note: stirring overnight is not necessary). Ethanol (100 mL) was added in one portion to the mixture. The mixture was cooled in an ice bath followed by the addition of hydrazine hydrate (27.8 mL, 572.5 mmol) in one portion. The mixture was warmed up to rt and stirred for 2 h after which more hydrazine hydrate (9.0 mL, 190.0 mmol) was added and the mixture was stirred for an additional 2 h. Water (300 mL) was added in one portion to the mixture and an additional amount of water (300 mL) was added dropwise over 2 h. The mixture was stirred at rt overnight. More water (500 mL) was added and the precipitate was filtered. The solid was washed with MeOH/H$_2$O (1:1, 200 mL) and water (100 mL), air-dried and then dried in a vacuum oven at 50° C. overnight to provide 38.77 g of 24, which was used without additional purification.
Step 5

A mixture of 24 (35.30 g, 120.0 mmol) and formamide (250 mL) was heated to 175° C. for 3.5 h. Some precipitate was formed at the end of the heating. The mixture was cooled to 80° C., and water (75 mL) was added. The mixture was stirred at 80° C. for 3 h, cooled to rt and stirred overnight. The mixture was filtered and the solid collected was washed with water (100 mL), MTBE (100 mL) and ether (100 mL). The solid was air-dried and then dried in a vacuum oven at 50° C. overnight to provide 33.55 g of 25, which was used without additional purification.
Step 6

To a mixture of 25 (30.51 g, 95.0 mmol), Ph$_3$P (44.83 g, 170.9 mmol) and (S)-tert-butyl 3-hydroxypyrrolidine-1-carboxylate (32.0 g, 170.9 mmol) in THF (500 mL) stirring at rt was added dropwise DIAD (37.0 mL, 188.0 mmol) over 2 h. The mixture became a homogeneous solution and was stirred an additional 1 h at rt followed by the addition of HCl in dioxane (4 M, 250 mL, 1.0 mol) and MeOH (20 mL). The solution was stirred at rt overnight and became a cloudy mixture. The mixture was filtered. The solid collected was washed with EA (50 mL) and ether (50 mL). The solid was then dissolved in a mixture of water (300 mL) and MeOH (30 mL) and the resulting solution was filtered. KOH (15 g) was added in one portion to the filtrate with stirring, resulting in a cloudy mixture (pH~11). The mixture was cooled in an ice bath for 1 h and filtered. The solid was washed with water, air-dried and then dried in a vacuum oven at 50° C. overnight to provide 26.14 g of 4a, which was used without additional purification.

Example 4b

Synthesis of (R,E)-1-(3-(4-amino-3-(4-(3-fluorophenoxy)phenyl)-1H-pyrazolo[3,4-d]pyrimidin-1-yl) pyrrolidin-1-yl)-4-(cyclobutyl(methyl)amino)but-2-en-1-one (4b)

To a solution of 4a (134 mg, 0.344 mmol), (E)-4-(cyclobutyl(methyl)amino)but-2-enoic acid hydrochloride (0.344 mmol) and HATU (122 mg, 0.38 mmol) in DMF (1.5 ml) was dropwise added DIPEA (134 mg, 1.032 mmol) at rt. Stirring was continued for 30 min at rt (monitored by HPLC). The reaction mixture was diluted with EA, washed with water and brine, and dried over sodium sulfate. Filtration followed by concentration under reduced pressure provided a residue which was purified by flash chromatography using silica gel (1-12% MeOH/DCM) to give 32 mg of the title compound (4b). MS (ESI) m/e (M+1H)$^+$: 542.1.

Example 4c

Synthesis of (R,E)-1-(3-(4-amino-3-(4-(3-fluorophenoxy)phenyl)-1H-pyrazolo[3,4-d]pyrimidin-1-yl) pyrrolidin-1-yl)-4-(cyclopropyl(methyl)amino)but-2-en-1-one (4c)

Similarly, compound 4c was prepared by substituting (E)-4-(cyclopropyl(methyl)amino)but-2-enoic acid for (E)-4-(cyclobutyl(methyl)amino)but-2-enoic acid hydrochloride in Example 4b. MS (ESI) m/e (M+1H)$^+$: 528.3.

Example 5a

Synthesis of (R,E)-1-(3-(4-amino-3-(4-phenoxyphenyl)-1H-pyrazolo[3,4-d]pyrimidin-1-yl)piperidin-1-yl)-4-(cyclopropyl(ethyl)amino)but-2-en-1-one (5a)

Example 5a was prepared using analogous methods of the preceding examples. MS (ESI) m/e (M+1H)$^+$: 538.1.

Example 5b

Synthesis of (E)-1-(4-(4-amino-3-(4-phenoxyphenyl)-1H-pyrazolo[3,4-d]pyrimidin-1-yl)piperidin-1-yl)-4-(cyclopropyl(methyl)amino)but-2-en-1-one (5b)

Example 5b was prepared using analogous methods of the preceding examples. MS (ESI) m/e (M+1H)$^+$: 524.3.

Example 5c

Synthesis of (E)-1-(3-(4-amino-3-(4-phenoxyphenyl)-1H-pyrazolo[3,4-d]pyrimidin-1-yl)azetidin-1-yl)-4-(cyclopropyl(methyl)amino)but-2-en-1-one (5c)

Example 5c was prepared using analogous methods of the preceding examples. MS (ESI) m/e (M+1H)$^+$: 496.2.

Example 6a

Synthesis of (R,E)-1-(3-(4-amino-5-(4-phenoxyphenyl)-7H-pyrrolo[2,3-d]pyrimidin-7-yl)pyrrolidin-1-yl)-4-(dimethylamino)but-2-en-1-one (6a)

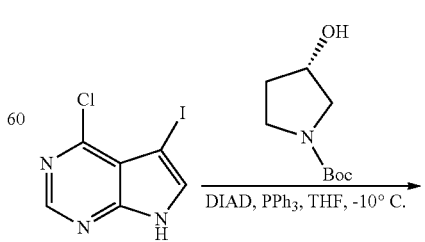

26

-continued

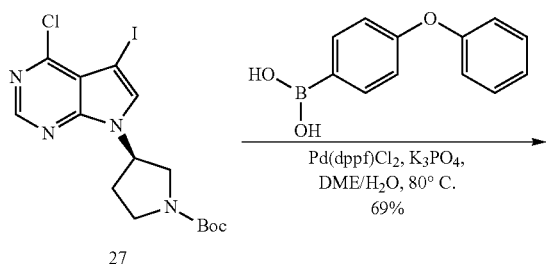

27

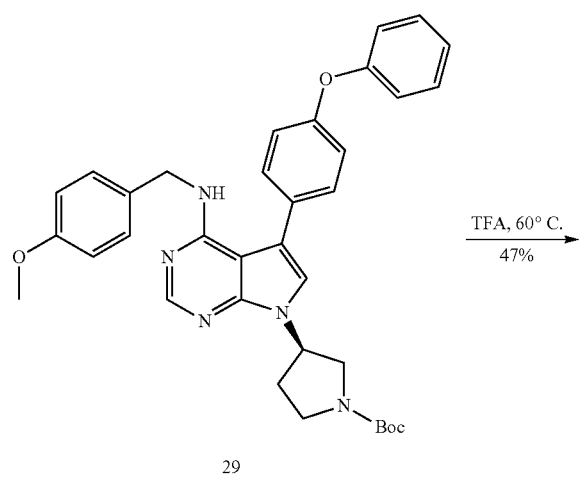

28

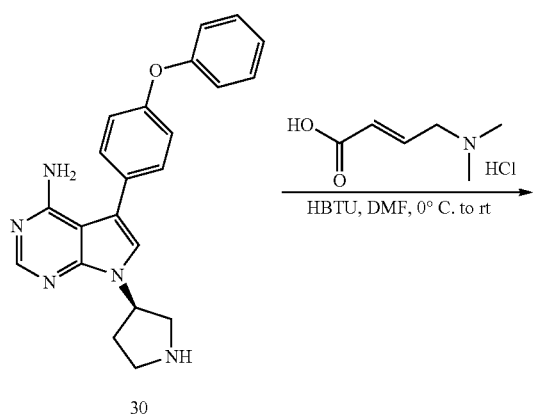

29

30

-continued

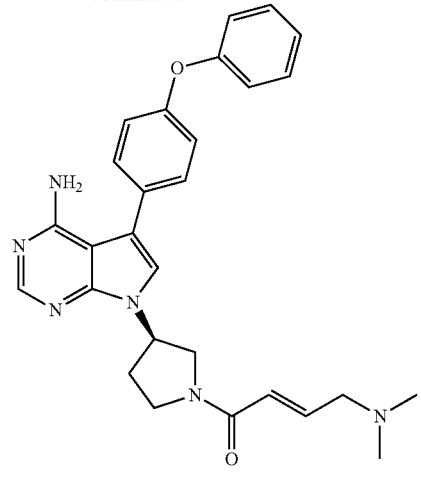

6a

Step 1

To a stirred solution of 26 (20 g, 71.6 mmol), (S)-tert-butyl 3-hydroxypyrrolidine-1-carboxylate (20.1 g, 107.4 mmol) and PPh$_3$ (33.8 g, 128.8 mmol) in anhydrous THF (350 mL) was slowly added DIAD (18.8 g, 93.03 mmol) over 1 h at −10° C. and under N$_2$ atmosphere. The resulting reaction mixture was subsequently warmed up to rt and stirred for additional 2 h. Once yellow precipitation was generated, the reaction mixture was cooled back to −5° C. and stirred overnight. While the solution was still cold, the yellow precipitation was quickly filtered and washed with cold THF (30 mL) to afford 22.7 g of 27 as light yellow powder. MS (ESI) m/e (M+2H)$^+$: 451.0.

Step 2

To a suspension of 27 (22.6 g, 50.4 mmol), 4-phenoxyphenylboronic acid (11.3 g. 53 mmol), K$_3$PO$_4$.3H$_2$O (40.2 g, 151.2 mmol) in DME (240 mL) and water (60 mL) was added Pd(dppf)Cl$_2$ (1.24 g, 1.51 mmol). The resulting mixture was purged with N$_2$ (3×) before heated to 80° C. overnight under N$_2$ atmosphere. The mixture was cooled down to rt. The organic layer was separated and the aqueous layer was extracted with EA (20 mL×2). The combined organic phase was dried over Na$_2$SO$_4$ and concentrated in vacuo. The residue was purified flash chromatography using silica gel (15% to 59% EA in petroleum ether) to give 17.0 g of 28 as a white solid. MS (ESI) m/e (M+2H)$^+$: 493.1.

Step 3

A solution of 28 (11.2 g, 22.8 mmol), (4-methoxyphenyl)methanamine (4 g, 29.6 g) and Et$_3$N (6.4 mL, 45.6 mmol) in dioxane (150 mL) was stirred at 140° C. for 16 h in a 350-mL sealed tube. After the reaction mixture was cooled down to rt, the precipitation was filtered and the filtrate was concentrated in vacuo. The residue was purified by flash chromatography using silica gel (30% to 50% EA in petroleum ether) to give 11.0 g of 29 as a white solid. MS (ESI) m/e (M+H)$^+$: 592.3.

Step 4

Compound 29 (16 g, 27.1 mmol) was dissolved in TFA (100 mL). The mixture was stirred at 60° C. for 6 h before the solvent was removed under reduced pressure. The residue was dissoved in EA (200 mL), adjusted pH to >7 with sat'd. aq. NaHCO$_3$ and extracted with EA (50 mL×3). The combined organic phase was dried over Na$_2$SO$_4$ and concentrated in vacuo. The residue was purified by flash chromatography using silica gel (5% MeOH in DCM with 0.3% Et$_3$N) to obtain 4.65 g of 30 as a white solid. MS (ESI) m/e (M+H)$^+$: 372.3.

Step 5

To a solution of 30 (7.4 g, 19.9 mmol), (E)-4-(dimethylamino)but-2-enoic acid hydrochloride (3.5 g, 20.9 mmol) and DIPEA (18 mL, 99.5 mmol) in DMF (70 mL) was added HBTU (11.6 g, 29.9 mmol) portionwise at −10° C. The mixture was stirred at rt for 3 h before the addition of water (200 mL) and EA (80 mL). The organic layer was separated, and the aqueous layer was extracted with EA (80 mL×4). The combined organic phase was washed with brine and dried over Na$_2$SO$_4$. The solvent was removed in vacuo and the residue was pre-purified by flash chromatography using silica gel (15:1 to 10:1 DCM/MeOH) followed by HPLC(C18, 40-60 μm, 60 Å, on CombiFlash, 40% to 100% MeOH in water (0.2% NH$_3$/H$_2$O)) to give 5.1 g of 6a as a light yellow solid. MS (ESI) m/e (M+H)$^+$: 483.2. $^1$H NMR (DMSO-d$_6$, 400 MHz,) 8.15 (s, 1H), 7.47-7.33 (m, 5 H), 7.16-7.04 (m, 5 H), 6.62 (dd, J=14.3, 6.2 Hz, 1H), 6.38 (dd, J=23.5, 15.2 Hz, 1H), 6.15 (br, 2 H), 5.34 (dt, J=13.2, 6.9 Hz, 1 H), 4.11-3.45 (m, 4 H), 3.00 (dd, J=17.1, 6.0 Hz, 2 H), 2.39 (dd, J=33.6, 7.1 Hz, 2 H), 2.13 (s, 3 H), 2.10 (s, 3 H).

Example 6b

Synthesis of (R,E)-1-(3-(4-amino-5-(4-phenoxyphenyl)-7H-pyrrolo[2,3-d]pyrimidin-7-yl)pyrrolidin-1-yl)-4-(cyclopropyl(methyl)amino)but-2-en-1-one (6b)

Similarly, compound 6b was prepared by substituting (E)-4-(cyclopropyl(methyl)amino)but-2-enoic acid for (E)-4-(dimethylamino)but-2-enoic acid hydrochloride in Step 5 of Example 6a. MS (ESI) m/e (M+1H)$^+$: 509.3.

Example 7a

Synthesis of (E)-N-(4-(4-amino-3-(4-phenoxyphenyl)-1H-pyrazolo[3,4-d]pyrimidin-1-yl)phenyl)-4-(dimethylamino)-N-methylbut-2-enamide (7a)

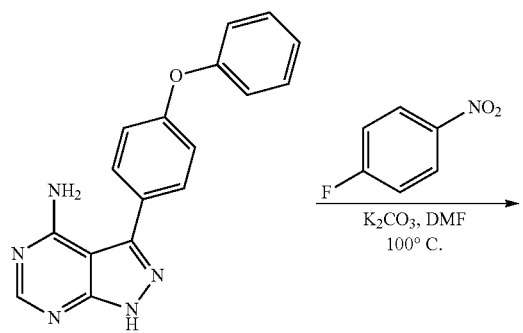

31

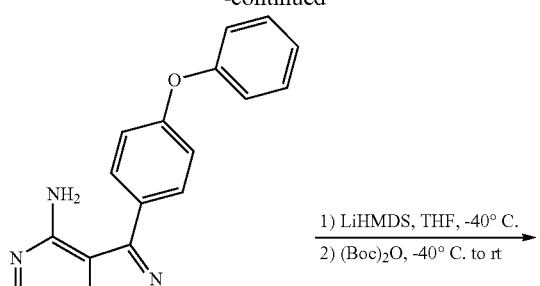

32

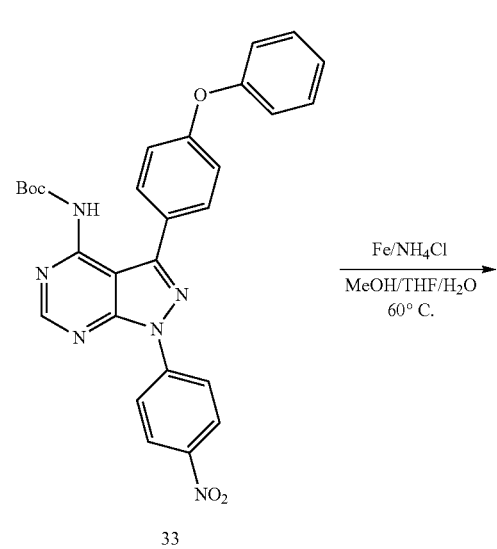

33

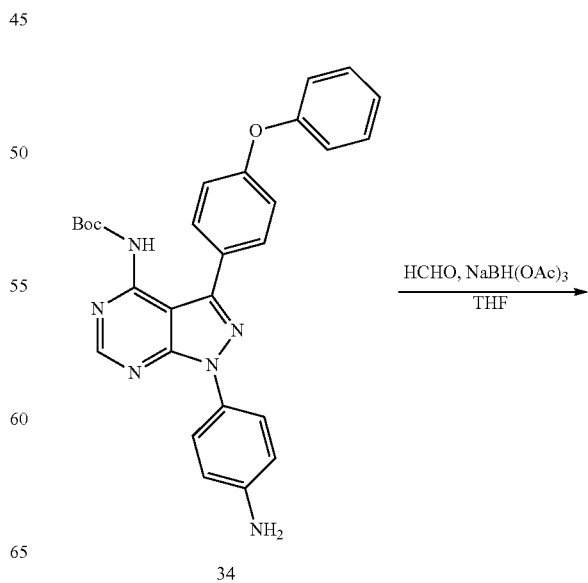

34

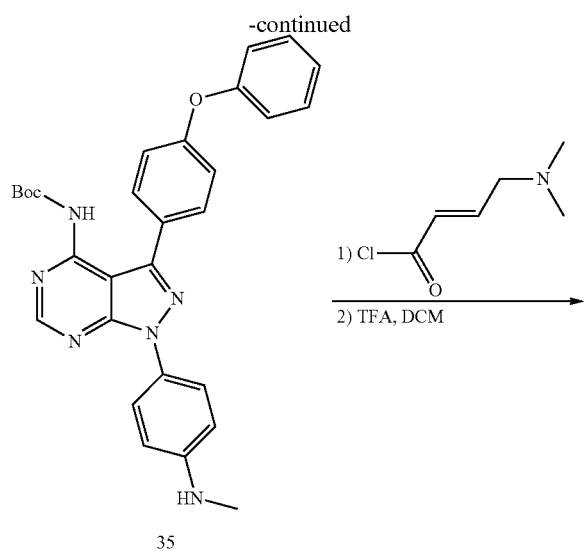

Step 1

To a solution of 31 (15 g, 49.45 mmol) and 1-fluoro-4-nitrobenzene (7.33 g, 51.9 mmol) in DMF (200 mL) was added $K_2CO_3$ (20.5 g, 148.4 mmol). After the mixture was stirred at 120° C. under a $N_2$ atmosphere for 48 h, the mixture was slowly poured into stirred water (1 L). The resulting precipitate was collected by filtration, washed with MeOH (200 mL×5), and dried in vacuo to afford 16 g of 32 as a gray solid. MS (ESI) m/e (M+H)$^+$: 425.2.

Step 2

To a stirred solution of 32 (16 g, 37.7 mmol) in THF (300 mL) under a $N_2$ atmosphere was added LiHMDS (1M, 76 mL, 76 mmol) dropwise at −40° C. The resulting mixture was stirred at −40° C. for 30 min before the addition of (Boc)$_2$O (12.33 g, 56.55 mmol). The reaction mixture was warmed up to rt and was stirred at rt for 1 h before a quench with sat'd. aq. NH$_4$Cl (30 mL). EA (200 mL) was added to the mixture and a precipitate was generated. The resulting precipitate was collected by filtration, washed with EA (50 mL), and dried in vacuo to afford 18.5 g of 33 as a gray solid that was used without further purification. MS (ESI) m/e (M+H)$^+$: 525.3.

Step 3

To a solution of 33 (18.5 g, 35.3 mmol) in a mixture of MeOH/THF/H$_2$O (5/10/1, 350 mL) was added Fe (9.9 g, 176.5 mmol) and NH$_4$Cl (18.9 g, 353 mmol). The mixture was stirred at 60° C. under a $N_2$ atmosphere for 3 h and then filtered through a Celite pad. The filtrate was concentrated in vacuo. The residue was purified by flash chromatography using silica gel (0 to 25% EA in DCM) to give 14 g of 34 as a light yellow solid. MS (ESI) m/e (M+H)$^+$: 495.2.

Step 4

To a solution of 34 (14 g, 28.3 mmol) in DCM (150 mL) was added HCHO (38% aqueous, 3.4 g, 42.45 mmol). The mixture was stirred at rt overnight before NaBH(OAc)$_3$ (18 g, 84.9 mmol) was added in several portions. Stirring was continued at rt for 5 h before a quench with water (10 mL). Solvents were removed in vacuo. The residue was purified by flash chromatography using silica gel (0 to 10% EA in DCM) to provide 6 g of 35 as a yellow solid. MS (ESI) m/e (M+H)$^+$: 509.3.

Step 5

To a suspension of (E)-4-(dimethylamino)but-2-enoic acid (2.35 g, 14.2 mmol) and a drop of DMF in dry DCM (20 mL) was added oxalyl dichloride (4.5 g, 35.4 mmol) slowly. The mixture was stirred at rt for 2 h before the solvent was removed in vacuo. The freshly generated acid chloride was dissolved in dry DCM (50 mL) and was added dropwise into a solution of 35 (6 g, 11.8 mmol) in DCM (50 mL) at 0° C. The resulting mixture was stirred at rt for 3 h. TFA (20 mL) was added and the mixture was stirred at rt for 5 h. The solvent was removed under reduced pressure. The resulting residue was partitioned between DCM (100 mL) and water (50 mL), and the pH was adjusted to pH=8-9 with sat'd. aq. NaHCO$_3$. The aqueous layer was extracted with DCM (100 mL×5). The combined organic phase was washed with brine, dried over Na$_2$SO$_4$, and concentrated in vacuo. The residue was purified by flash chromatography using silca gel (0 to 7% MeOH in DCM) to provide 5.4 g of the title compound (7a) as a white solid. MS (ESI) m/e (M+H)$^+$: 520.3. $^1$H NMR (DMSO, 400 MHz) 9.77 (s, 1H), 8.38 (d, J=1.8 Hz, 1H), 8.33 (d, J=7.2 Hz, 2H), 7.74 (dd, J=8.5, 1.8 Hz, 2H), 7.50 (dd, J=8.7, 1.8 Hz, 2H), 7.44 (t, J=7.0 Hz, 2H), 7.24-7.09 (m, 5H), 6.64 (dd, J=14.4, 6.3 Hz, 1H), 6.30-6.10 (m, 1H), 3.77 (d, J=6.0 Hz, 2H), 3.30 (s, 3H), 2.68 (s, 6H).

Example 7b

Synthesis of (E)-N-(4-(4-amino-3-(4-phenoxyphenyl)-1H-pyrazolo[3,4-d]pyrimidin-1-yl)phenyl)-4-(cyclopropyl(methyl)amino)-N-methylbut-2-enamide (7b)

Similarly, compound 7b was prepared by substituting (E)-4-(cyclopropyl(methyl)amino)but-2-enoic acid for (E)-4-(dimethylamino)but-2-enoic acid in Step 5 of Example 7a. MS (ESI) m/e (M+1H)$^+$: 546.2.

Example 7c

Synthesis of (E)-N-(4-(4-amino-3-(4-phenoxyphenyl)-1H-pyrazolo[3,4-d]pyrimidin-1-yl)phenyl)-4-(cyclobutyl(methyl)amino)-N-methylbut-2-enamide (7c)

Similarly, compound 7c was prepared by substituting (E)-4-(cyclobutyl(methyl)amino)but-2-enoic acid for (E)-4-(dimethylamino)but-2-enoic acid in Step 5 of Example 7a. MS (ESI) m/e (M+1H)$^+$: 560.2.

Example 7d

Synthesis of (E)-N-(3-(4-amino-3-(4-phenoxyphenyl)-1H-pyrazolo[3,4-d]pyrimidin-1-yl)phenyl)-4-(cyclopropyl(methyl)amino)-N-methylbut-2-enamide (7d)

Similarly, compound 7d was prepared by substituting 1-fluoro-3-nitrobenzene for 1-fluoro-4-nitrobenzene in Step 1 and (E)-4-(cyclopropyl(methyl)amino)but-2-enoic acid for (E)-4-(dimethylamino)but-2-enoic acid in Step 5 of Example 7a. MS (ESI) m/e (M+1H)$^+$: 546.2.

Example 7e

Synthesis of (E)-N-(3-(4-amino-3-(4-phenoxyphenyl)-1H-pyrazolo[3,4-d]pyrimidin-1-yl)phenyl)-4-(cyclobutyl(methyl)amino)-N-methylbut-2-enamide (7e)

Similarly, compound 7e was prepared by substituting 1-fluoro-3-nitrobenzene for 1-fluoro-4-nitrobenzene in Step 1 and (E)-4-(cyclobutyl(methyl)amino)but-2-enoic acid for (E)-4-(dimethylamino)but-2-enoic acid in Step 5 of Example 7a. MS (ESI) m/e (M+1H)$^+$: 560.2.

Example 7f

Synthesis of (E)-N-(3-(4-amino-3-(4-phenoxyphenyl)-1H-pyrazolo[3,4-d]pyrimidin-1-yl)phenyl)-4-(cyclopropyl(methyl)amino)but-2-enamide (7f)

Compound 7f was prepared in an analogous manner as Example 7d, but Step 4 was omitted. MS (ESI) m/e (M+1H)$^+$: 532.2.

Example 7g

Synthesis of (E)-N-(3-(4-amino-3-(4-phenoxyphenyl)-1H-pyrazolo[3,4-d]pyrimidin-1-yl)phenyl)-4-(cyclobutyl(methyl)amino)but-2-enamide (7g)

Compound 7g was prepared in an analogous manner as Example 7e, but Step 4 was omitted. MS (ESI) m/e (M+1H)$^+$: 546.5.

Example 8a

Synthesis of 1-cyclopentyl-N$^3$-phenyl-1H-pyrazolo[3,4-d]pyrimidine-3,4-diamine (8a)

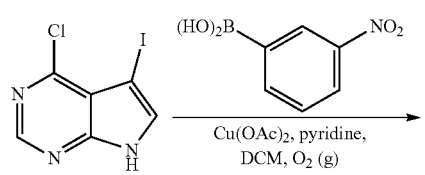

26

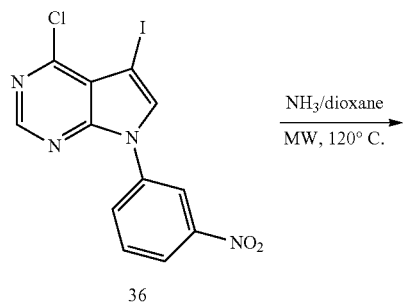

36

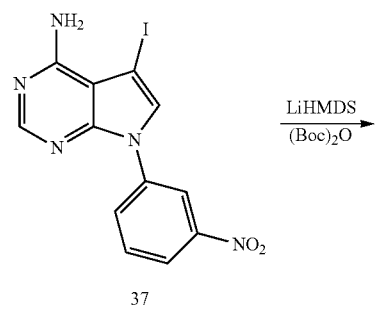

37

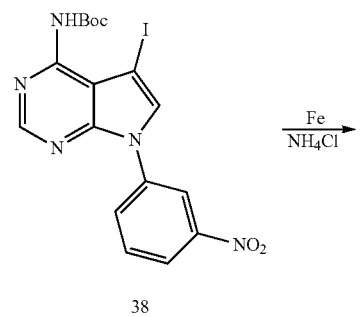

38

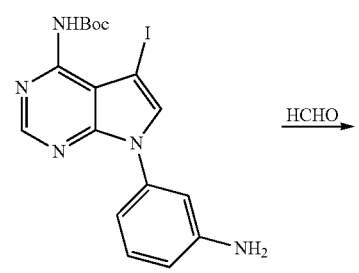

39

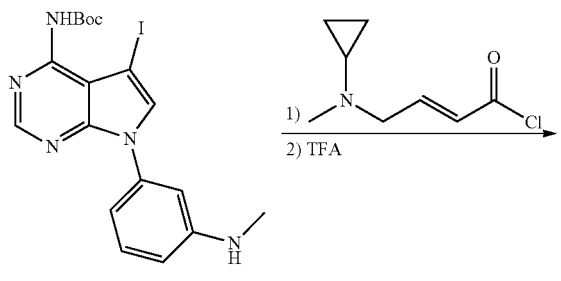

40

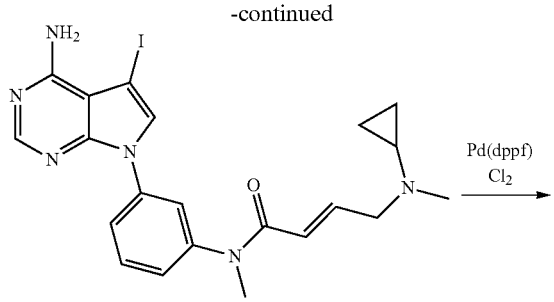

41

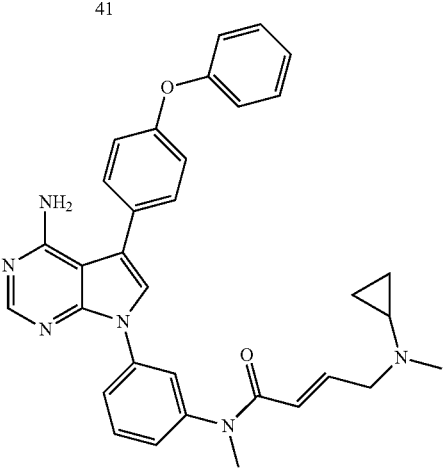

8a

Step 1

To a solution of 26 (5.58 g, 20 mmol) in DCM (200 mL) were added 3-nitrophenylboronic acid (5 g, 30 mmol), pyridine (9.49 g, 120 mmol), anhydrous Cu(OAc)$_2$ (3.64 g, 20 mmol) and 4 Å MS (20 g). The resulting suspension was stirred at rt overnight under O$_2$ atmosphere. After quenching with water, the mixture was filtered through a Celite pad. The filtrate was concentrated down under vacuum. The crude product was purified by flash chromatography using silica gel (0-30% EA in petroleum ether) to provide 5.9 g of 36. MS (ESI) m/e (M+1H)$^+$: 401.

Step 2

A solution of 36 (500 mg, 1.25 mmol), NH$_3$.H$_2$O (3 mL) and dioxane (6 mL) in a sealed tube was heated to 120° C. in a microwave reactor for 40 min. The yellow precipitate was collected by filtration to provide 460 mg of 37. MS (ESI) m/e (M+1H)$^+$: 382.

Step 3

Compound 38 was prepared in an analogous manner as compound 33 in Step 2 of Example 7a. MS (ESI) m/e (M+1H)$^+$: 482.

Step 4

Compound 39 was prepared in an analogous manner as compound 34 in Step 3 of Example 7a. MS (ESI) m/e (M+1H)$^+$: 453.

Step 5

Compound 40 was prepared in an analogous manner as compound 35 in Step 4 of Example 7a. MS (ESI) m/e (M+1H)$^+$: 467.

Step 6

Compound 41 was prepared in an analogous manner as Example 7a. MS (ESI) m/e (M+1H)$^+$: 503.

Step 7

Compound 8a was prepared in an analogous manner as compound 28 in Step 2 of Example 6a. MS (ESI) m/e (M+1H)$^+$: 545.3. $^1$H NMR (DMSO, 400 MHz) 9.61 (br, 1H), 8.40 (s, 1H), 7.95 (m, 2H), 7.88 (s, 1H), 7.65 (t, J=8.1 Hz, 1H), 7.56 (d, J=8.4 Hz, 1H), 7.46-7.34 (m, 3H), 7.20-7.07 (m, 5H), 6.70 (dt, J=14.6, 7.2 Hz, 1H), 6.32 (m, 1H), 3.94 (s, 2H), 3.33 (s, 3H), 2.74 (s, 4H), 0.93-0.63 (m, 4H).

Therapeutic Uses of Inhibitor Compounds

Example 9

Inhibition of Btk

The properties of the compounds disclosed herein are further characterized by assaying a number of cellular biochemical and functional endpoints. In particular, we sought to assess the selectivity of these compounds for inhibition of Btk versus the closely related protein kinases Lck, Lyn, and Syk. In anti-IgM-stimulated Ramos cells (a human B cell line), are assayed Btk-dependent phosphorylation of PLC-γ1; Lyn and Syk-dependent phosphorylation of tyrosine 551 on Btk; and BCR-activated calcium flux. The effect of compounds disclosed herein on Jurkat cells are measured wherein a human T cell line in which Lck and Itk, but not Btk are required for T cell receptor mediated Ca$^{2+}$ flux.

Example 9a

Btk In vitro Inhibitory Activity

The Btk IC$_{50}$s of compounds disclosed herein is determined in both an acellular kinase assay and in a cellular functional assay of BCR-induced calcium flux as described below.

Btk kinase activity is determined using a time-resolved fluorescence resonance energy transfer (TR-FRET) methodology. Measurements are performed in a reaction volume of 50 μL using 96-well assay plates. Kinase enzyme, inhibitor, ATP (at the K$_m$ for the kinase), and 1 μM peptide substrate (Biotin-AVLESEEELYSSARQ-NH$_2$) are incubated in a reaction buffer composed of 20 mM Tris, 50 mM NaCl, MgCl$_2$ (5-25 mM depending on the kinase), MnCl$_2$ (0-10 mM), 1 mM DTT, 0.1 mM EDTA, 0.01% bovine serum albumin, 0.005% Tween-20, and 10% DMSO at pH 7.4 for one hour. The reaction is quenched by the addition of 1.2 equivalents of EDTA (relative to divalent cation) in 25 μL of 1× Lance buffer (Perkin-Elmer). Streptavidin-APC (Perkin-Elmer) and Eu-labeled p-Tyr100 antibody (Perkin-Elmer) in 1× Lance buffer are added in a 25 μL volume to give final concentrations of 100 nM and 2.5 nM, respectively, and the mixture is allowed to incubate for one hour. The TR-FRET signal is measured on a multimode plate reader with an excitation wavelength ($\lambda_{Ex}$) of 330 nm and detection wavelengths ($\lambda_{Em}$) of 615 and 665 nm. Activity is determined by the ratio of the fluorescence at 665 nm to that at 615 nm. For each compound, enzyme activity is measured at various concentrations of compound. Negative control reactions are performed in the absence of inhibitor in replicates of six, and two no-enzyme controls were used to determine baseline fluorescence levels. Inhibition constants, K$_i$(app), are obtained using the program BatchK$_i$ (Kuzmic et al. (2000), *Anal. Biochem.* 286:45-50). IC$_{50}$s are obtained according to the equation:

$$IC_{50} = \{Ki(app)/(1+[ATP]/K_m^{ATP})\} + [E]_{total}/2;$$

For all kinases, [ATP]=K$_m^{ATP}$, [Btk]$_{total}$=0.5 nM and [Lck]$_{total}$=6 nM.

Calcium flux fluoresence-based assays are performed in a FlexStation II384 fluorometric imaging plate reader (Molecular Devices) according to manufacturer instructions. In brief, actively growing Ramos cells (ATCC) in RPM1 medium supplemented with 10% FBS (Invitrogen) are washed and re-plated in low serum medium at approximately $5 \times 10^5$ cells per 100 µl per well in a 96-well plate. Compounds to be assayed are dissolved in DMSO and then diluted in low serum medium to final concentrations ranging from 0 to 10 µM (at a dilution factor of 0.3). The diluted compounds are then added to each well (final DMSO concentration is 0.01%) and incubate at 37 degree in 5% $CO_2$ incubator for one hour. Afterwards, 100 µl of a calcium-sensitive dye (from the Calcium 3 assay kit, Molecular Devices) is added to each well and incubated for an additional hour. The compound-treated cells are stimulated with a goat anti-human IgM antibody (80 ug/ml; Jackson ImmunoResearch) and read in the FlexStation 11384 using a $\lambda_{Ex}$=485 nm and $\lambda_{Em}$=538 nm for 200 seconds. The relative fluorescence unit (RFU) and the $IC_{50}$ are recorded and analyzed using a built-in SoftMax program (Molecular devices).

TABLE 2

| Example | Btk $IC_{50}$* |
|---|---|
| 1d | A |
| 1f | A |
| 1k | A |
| 1q | A |
| 1r | A |
| 1s | A |
| 1t | A |
| 1u | A |
| 2a | A |
| 2b | A |
| 2c | A |
| 2d | A |
| 2e | A |
| 2f | A |
| 2g | A |
| 2h | A |
| 2i | A |
| 2j | A |
| 2k | A |
| 2m | A |
| 2n | A |
| 2p | A |
| 2q | A |
| 2r | A |
| 2s | A |
| 2t | A |
| 2u | A |
| 2v | A |
| 2w | A |
| 2x | A |
| 2y | A |
| 2z | A |
| 2aa | A |
| 2ab | A |
| 2ac | A |
| 2ad | A |
| 2ae | A |
| 2af | A |
| 2ag | A |
| 2ah | A |
| 2ai | A |
| 2aj | A |
| 2ak | A |
| 2am | A |
| 2an | A |
| 2ao | A |
| 2ap | A |
| 2aq | A |
| 3a | A |
| 4b | A |
| 4c | A |
| 5a | A |
| 5b | A |
| 5c | A |
| 6b | A |
| 7b | A |
| 7c | A |
| 7d | A |
| 7e | A |
| 7f | A |
| 7g | A |
| 8a | A |

*A: <100 nM

Example 10

Use of a Compound of Formula (I), (IA), (II), (III), (IV), (V), (VI), (VIA), (VIB), (VII), (VIII), (IX), (X), (XI), (XII), (XIII), or (XIV) to Treat Rheumatoid Arthritis The in vivo efficacy of the compounds described herein are evaluated in a mouse model of rheumatoid arthritis. Arthritis is induced in Balb/c mice by administration of anti-collagen antibodies and lipopolysaccharide (LPS). See Nandakumar et al. (2003), *Am. J. Pathol.* 163:1827-1837. Female Balb/c mice are treated with 100 mg/kg of Chemicon mAb cocktail to Type II collagen intravenously on Day 0 and 1.25 mg/kg of LPS intraperitoneally on Day 1. A test compound is administered orally in a methylcellulose-based aqueous suspension formulation at 1, 3, 10 and 30 mg/kg once daily starting on Day 2 through Day 12. Blood samples are collected at 0.5 and 2 hours post dose of the test compound administration on Day 12. The serum concentrations of the test compound are quantified by LC/MS/MS. Twenty four hours post dose, levels of the test compound below the level of quantitation.

Example 11

Inhibition of Mast Cell Degranulation

Human CD34+ cells differentiated to mast cells by 9 weeks in culture in the presence of 1 ng/ml IL-3, 50 ng/ml IL-6, 100 ng/ml SCF. Cells are incubated with IgE+IL-4 for 4 days and then degranulation is induced by cross-linking with anti-IgE. Degranulation quantitated using hexosaminidase assay. The $IC_{50}$ in MC degranulation of the compounds are determined. Compounds with desired $IC_{50}$ values are used for the treatment of inflammatory diseases, such as asthma.

Example 12

Inhibition of Lyphoma Tumor Cell Growth

An inhibitor disclosed herein is evaluated for inhibition of lymphoma tumor cell growth. A variety of lymphoma cell lines are incubated with a range of concentrations of an inhibitor disclosed herein to determine the GI50, the concentration that results in 50% decrease in cell proliferation.

For in vitro cell proliferation assays, cells are seeded in 96-well plates in standard growth media (in most cases RPMI+10% fetal calf serum) and an inhibitor disclosed herein is added in a 9-point dilution series ranging from 10 uM to 0.04 uM with DMSO at 0.1% final concentration in all wells. After 72 hours, cell number is measured using Alamar Blue using manufacturer's protocol. A dilution series of untreated cells is run in parallel to verify that the Alamar Blue assay reliably reflected cell number and that growth conditions are not limiting. The GI50, the concentration that results in a 50% decrease in cell number, is calculated using Calcusyn to fit the dose-response curve. GI50 values are confirmed in two or more separate experiments for each cell line.

For in vivo lymphoma xenograft studies, 5E6 DOHH2 or DLCL2 cells in 50% matrigel are implanted subcutaneously in SCID mice and dosed orally with an inhibitor disclosed herein beginning when tumor size reaches 100 mm2.

Example 13

Inhibition of Collagen-Induced Arthritis in a Mouse

An inhibitor disclosed herein is evaluated for inhibition of collagen-induced arthritis in the mouse. Male DBA/1OlaHsd mice are injected intradermally with 150 microliters of 2 mg/mL Type II collagen in Freund's complete adjuvant with supplemental *M. tuberculosis,* 4 mg/mL and boosted with the same injection 21 days later. After paw inflammation is established, animals are randomized and an inhibitor disclosed herein or vehicle is dosed orally once per day starting at day 1. Paw inflammation is scored from 0-5 and averaged across all paws from all animals for each group in the study. Examples of doses to be used in this study are 3.125 mg/kg, 12.5 mg/kg and 50 mg/kg. Dexamethasone is included as a positive control.

In another study, an inhibitor disclosed herein is dosed at 12.5 mg/kg or 50 mg/kg to such mice over: (a) each day of an 11-day period; (b) days 1, 2, and 3 of an 11-day period; or (c) days 9, 10, and 11 of an 11-day period.

Example 14

Inhibition of Lupus in a Mouse Model

An inhibitor disclosed herein is evaluated for inhibition of disease progression in the mouse MRL/lpr model of lupus. Paw inflammation is scored from 0-5 and averaged across all paws from all animals for each group in the study. Examples of doses to be used in this study are 3.125 mg/kg, 12.5 mg/kg and 50 mg/kg. MRL/lpr mice (Jax strain 000485) are dosed orally once per day from 12 weeks of age until 20 weeks of age and urine protein levels are measured weekly using Clinitech Multistick dipstick.

Example 15

Pharmaceutical Compositions

The compositions described below are presented with a compound of Formula (I), (IA), (II), (III), (IV), (V), (VI), (VIA), (VIB), (VII), (VIII), (IX), (X), (XI), (XII), (XIII), or (XIV) for illustrative purposes; any of the compounds of any of Formula (I), (IA), (II), (III), (IV), (V), (VI), (VIA), (VIB), (VII), (VIII), (IX), (X), (XI), (XII), (XIII), or (XIV) are optionally used in such pharmaceutical compositions.

Example 15a

Parenteral Composition

To prepare a parenteral pharmaceutical composition suitable for administration by injection, 100 mg of a water-soluble salt of a compound of Formula (I), (IA), (II), (III), (IV), (V), (VI), (VIA), (VIB), (VII), (VIII), (IX), (X), (XI), (XII), (XIII), or (XIV) is dissolved in DMSO and then mixed with 10 mL of 0.9% sterile saline. The mixture is incorporated into a dosage unit form suitable for administration by injection.

Example 15b

Oral Composition

To prepare a pharmaceutical composition for oral delivery, 100 mg of a compound of Formula (I), (IA), (II), (III), (IV), (V), (VI), (VIA), (VIB), (VII), (VIII), (IX), (X), (XI), (XII), (XIII), or (XIV) is mixed with 750 mg of starch. The mixture is incorporated into an oral dosage unit for, such as a hard gelatin capsule, which is suitable for oral administration.

Example 15c

Sublingual (Hard Lozenge) Composition

To prepare a pharmaceutical composition for buccal delivery, such as a hard lozenge, mix 100 mg of a compound of Formula (I), (IA), (II), (III), (IV), (V), (VI), (VIA), (VIB), (VII), (VIII), (IX), (X), (XI), (XII), (XIII), or (XIV), with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 15d

Inhalation Composition

To prepare a pharmaceutical composition for inhalation delivery, 20 mg of a compound of Formula (I), (IA), (II), (III), (IV), (V), (VI), (VIA), (VIB), (VII), (VIII), (IX), (X), (XI), (XII), (XIII), or (XIV) is mixed with 50 mg of anhydrous citric acid and 100 mL of 0.9% sodium chloride solution. The mixture is incorporated into an inhalation delivery unit, such as a nebulizer, which is suitable for inhalation administration.

Example 15e

Rectal Gel Composition

To prepare a pharmaceutical composition for rectal delivery, 100 mg of a compound of Formula (I), (IA), (II), (III), (IV), (V), (VI), (VIA), (VIB), (VII), (VIII), (IX), (X), (XI), (XII), (XIII), or (XIV) is mixed with 2.5 g of methylcellulose (1500 mPa), 100 mg of methylparaben, 5 g of glycerin and 100 ml, of purified water. The resulting gel mixture is then incorporated into rectal delivery units, such as syringes, which are suitable for rectal administration.

Example 15f

Topical Gel Composition

To prepare a pharmaceutical topical gel composition, 100 mg of a compound of Formula (I), (IA), (II), (III), (IV), (V), (VI), (VIA), (VIB), (VII), (VIII), (IX), (X), (XI), (XII), (XIII), or (XIV) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 15g

Ophthalmic Solution Composition

To prepare a pharmaceutical ophthalmic solution composition, 100 mg of a compound of Formula (I), (IA), (II), (III), (IV), (V), (VI), (VIA), (VIB), (VII), (VIII), (IX), (X), (XI), (XII), (XIII), or (XIV) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 16

Clinical Trial to Determine Safety and Efficacy of an Inhibitor Disclosed Herein The purpose of this clinical trial is to study the side effects and best dose of a compound of Formula (I), (IA), (II), (III), (IV), (V), (VI), (VIA), (VIB), (VII), (VIII), (IX), (X), (XI), (XII), (XIII), or (XIV) and to determine its efficacy in the treatment of patients diagnosed with recurrent B-cell lymphoma.

Study Design

Cohorts of 6 patients each receive a compound of Formula (I), (IA), (II), (III), (IV), (V), (VI), (VIA), (VIB), (VII), (VIII), (IX), (X), (XI), (XII), (XIII), or (XIV) at 1.25, 2.5, 5.0, 8.3, 12.5, 17.5 mg/kg/d until the MTD is established. In cases where MTD is not reached, dosing levels are increased beyond 17.5 mg/kg/d by 33% increments. Patients receive daily treatment for 28 days followed by a 7 day rest period (one cycle). Tests for Btk occupancy by the compound of Formula (I), (IA), (II), (III), (IV), (V), (VI), (VIA), (VIB), (VII), (VIII), (IX), (X), (XI), (XII), (XIII), or (XIV) ("occupancy") are performed on Day 1, 2, 8, 15 and 29 during Cycle 1 and on Day 1 and 15 of Cycles 3, 5, 7, 9, and 11. If ≤1 DLT ("dose-limiting toxicity") is observed in the cohort during Cycle 1, escalation to the next cohort will proceed. Patients are enrolled in the next cohort if four of the six patients enrolled in the cohort completed Cycle 1 without experiencing a DLT, while the remaining two patients are completing evaluation. If ≥2 DLTs are observed during Cycle 1, dosing at that dose and higher is suspended and the MTD is established as the previous cohort. Patients are allowed to continue dosing at the MTD. If ≥2 DLTs are seen at the 5.0 mg/kg/d cohort an additional cohort of 6 patients can be added at 3.75 mg/kg/d.

Upon determination of the MTD, a cohort of 6 patients is enrolled to receive a compound of Formula (I), (IA), (II), (III), (IV), (V), (VI), (VIA), (VIB), (VII), (VIII), (IX), (X), (XI), (XII), (XIII), or (XIV) at the MTD or "preferred occupying dose" continuously for 35 days with no rest period (one cycle).

Study Population

Up to 52 patients with recurrent surface immunoglobulin positive B cell non-Hodgkin's lymphoma according to WHO classification (including small lymphocytic lymphoma/chronic lymphocytic leukemia.

Study Objectives

1. Primary Objectives include:
A. Determine pharmacokinetics (PK) of an orally administered compound of Formula (I), (IA), (II), (III), (IV), (V), (VI), (VIA), (VIB), (VII), (VIII), (IX), (X), (XI), (XII), (XIII), or (XIV).

B. Evaluate tumor response. Patients have screening (i.e., baseline) disease assessments within 30 days before beginning treatment. Patients undergo follow-up disease assessments following specified dosing cycles. Patients without evidence of disease progression on treatment are followed for a maximum of 6 months off treatment for disease progression. At screening, a computed tomography (CT) (with contrast unless contraindicated) and positron-emission tomography (PET) or CT/PET scan of the chest, abdomen, and pelvis are required. At other visits, a CT (with contrast unless contraindicated) scan of the chest, abdomen, and pelvis are obtained. A CT/PET or PET is required to confirm a complete response. Bone marrow biopsy is optional. In patients known to have positive bone marrow before treatment with a compound of Formula (I), (IA), (II), (III), (IV), (V), (VI), (VIA), (VIB), (VII), (VIII), (IX), (X), (XI), (XII), (XIII), or (XIV), a repeat biopsy should be done to confirm a complete response following treatment. All patients are evaluated for response based on International Working Group Revised Response Criteria for Malignant Lymphoma, Guidelines for the diagnosis and treatment of chronic lymphocytic leukemia14, or Uniform Response Criteria in Waldenstrom's Macroglobulinemia.

C. Measure pharmacodynamic (PD) parameters to include drug occupancy of Btk, the target enzyme, and effect on biological markers of B cell function. Specifically, this study examines the pharmacodynamics (PD) of the compound of Formula (I), (IA), (II), (III), (IV), (V), (VI), (VIA), (VIB), (VII), (VIII), (IX), (X), (XI), (XII), (XIII), or (XIV) in peripheral blood mononuclear cells (PBMCs) using two PD assays. The first PD assay measures occupancy of the Btk active site by the compound of Formula (I), (IA), (II), (III), (IV), (V), (VI), (VIA), (VIB), (VII), (VIII), (IX), (X), (XI), (XII), (XIII), or (XIV) using a specially designed fluorescent probe. The second PD assay measures inhibition of B cell activation by stimulating the PBMCs ex vivo at the BCR with anti-IgM/IgG, and then assaying cell surface expression of the activation marker CD69 by flow cytometry. The PD biomarkers are measured in vitro from a blood sample removed from patients 4-6 hours following an oral dose of the compound of Formula (I), (IA), (II), (III), (IV), (V), (VI), (VIA), (VIB), (VII), (VIII), (IX), (X), (XI), (XII), (XIII), or (XIV). These assays determine what levels of a compound of Formula (I), (IA), (II), (III), (IV), (V), (VI), (VIA), (VIB), (VII), (VIII), (IX), (X), (XI), (XII), (XIII), or (XIV) are required to achieve maximal occupancy of Btk and maximal inhibition of BCR signaling. When possible, similar studies are conducted on circulating tumor cells isolated from blood of patients.

2. Secondary Objectives include:
A. To analyze tumor biopsy samples (when possible) for apoptotic biomarker expression analysis.

Inclusion Criteria

To be eligible to participate in this study, a patient must meet the following criteria:

Women and men ≥18 years of age

Body weight ≥40 kg

Recurrent surface immunoglobulin positive B cell non-Hodgkin's lymphoma (NHL) according to WHO classification, including small lymphocytic lymphoma/chronic lymphocytic leukemia (SLL/CLL) and lymphoplasmacytic lymphoma, including Waldenstrom's Macroglobulinemia (WM)

Measurable disease (for NHL, bidimensional disease ≥2 cm diameter in at least one dimension, for CLL ≥5000 leukemia cells/mm$^3$, and for WM presence of immunoglobulin M paraprotein with a minimum IgM level≥1000 mg/dL and infiltration of bone marrow by lymphoplasmacytic cells)

Have failed≥1 previous treatment for lymphoma and no standard therapy is available. Patients with diffuse large B cell lymphoma must have failed, refused or be ineligible for autologous stem cell transplant ECOG performance status of ≤1

Ability to swallow oral capsules without difficulty

Willing and able to sign a written informed consent

Exclusion Criteria

A patient meeting any of the following criteria will be excluded from this study:

More than four prior systemic therapies (not counting maintenance rituximab), except for CLL patients. Salvage therapy/conditioning regimen leading up to autologous bone marrow transplantation is considered to be one regimen Prior allogeneic bone marrow transplant Immunotherapy, chemotherapy, radiotherapy or experimental therapy within 4 weeks before first day of study drug dosing Major surgery within 4 weeks before first day of study drug dosing CNS involvement by lymphoma Active opportunistic infection or treatment for opportunistic infection within 4 weeks before first day of study drug dosing Uncontrolled illness including but not limited to: ongoing or active infection, symptomatic congestive heart failure (New York Heart Association Class III or IV heart failure), unstable angina pectoris, cardiac arrhythmia, and psychiatric illness that would limit compliance with study requirements History of myocardial infarction, acute coronary syndromes (including unstable angina), coronary angioplasty and/or stenting within the past 6 months Known HIV infection Hepatitis B sAg or Hepatitis C positive Other medical or psychiatric illness or organ dysfunction which, in the opinion of the investigator, would either compromise the patient's safety or interfere with the evaluation of the safety of the study agent Pregnant or lactating women (female patients of childbearing potential must have a negative serum pregnancy test within 14 days of first day of drug dosing, or, if positive, a pregnancy ruled out by ultrasound)

History of prior cancer<2 years ago, except for basal cell or squamous cell carcinoma of the skin, cervical cancer in situ or other in situ carcinomas Example 17

Safety and Tolerability Study of an Inhibitor Disclosed Herein in Chronic Lymphocytic Leukemia Purpose: The purpose of this study is to establish the safety and optimal dose of orally administered a compound of Formula (I), (IA), (II), (III), (IV), (V), (VI), (VIA), (VIB), (VII), (VIII), (IX), (X), (XI), (XII), (XIII), or (XIV) in patients with B-cell chronic lymphocytic leukemia/small lymphocytic lymphoma/diffuse well-differentiated lymphocytic lymphoma.

Primary Outcome Measures: Safety and tolerability of a compound of Formula (I), (IA), (II), (III), (IV), (V), (VI), (VIA), (VIB), (VII), (VIII), (IX), (X), (XI), (XII), (XIII), or (XIV) (frequency, severity, and relatedness of adverse events).

Secondary Outcome Measures: Pharmacokinetic/Pharmacodynamic assessments. Tumor response—overall response rate as defined by recent guidelines on CLL and SLL (B cell lymphoma) and duration of response.

Eligibility: 18 Years and older; both genders are eligible.

Inclusion Criteria: 1. For treatment-naive group only: Men and women≥65 years of age with confirmed diagnosis of CLL/SLL, who require treatment per NCI or International Working Group guidelines11-14. 2. For relapsed/refractory group only: Men and women≥18 years of age with a confirmed diagnosis of relapsed/refractory CLL/SLL unresponsive to therapy (ie, failed≥2 previous treatments for CLL/SLL and at least 1 regimen had to have had a purine analog [eg, fludarabine] for subjects with CLL). 3. Body weight≥40 kg. 4. ECOG performance status of ≤2. 5. Agreement to use contraception during the study and for 30 days after the last dose of study drug if sexually active and able to bear children. 6. Willing and able to participate in all required evaluations and procedures in this study protocol including swallowing capsules without difficulty. 7. Ability to understand the purpose and risks of the study and provide signed and dated informed consent and authorization to use protected health information (in accordance with national and local subject privacy regulations).

Exclusion Criteria: 1. A life-threatening illness, medical condition or organ system dysfunction which, in the investigator's opinion, could compromise the subject's safety, interfere with the absorption or metabolism of a compound of Formula (I), (IA), (II), (III), (IV), (V), (VI), (VIA), (VIB), (VII), (VIII), (IX), (X), (XI), (XII), (XIII), or (XIV) PO, or put the study outcomes at undue risk. 2. Any immunotherapy, chemotherapy, radiotherapy, or experimental therapy within 4 weeks before first dose of study drug (corticosteroids for disease-related symptoms allowed but require 1-week washout before study drug administration). 3. Central nervous system (CNS) involvement by lymphoma. 4. Major surgery within 4 weeks before first dose of study drug. 5. Creatinine>1.5×institutional upper limit of normal (ULN); total bilirubin>1.5×ULN (unless due to Gilbert's disease); and aspartate aminotransferase (AST) or alanine aminotransferase (ALT)>2.5×ULN unless disease related. 6. Concomitant use of medicines known to cause QT prolongation or torsades de pointes. 7. Significant screening electrocardiogram (ECG) abnormalities including left bundle branch block, 2nd degree AV block type II, 3rd degree block, bradycardia, and QTc>470 msec. 8. Lactating or pregnant.

Example 18

Safety and Efficacy of an Inhibitor Disclosed Herein in Subjects with Relapsed/Refractory Mantle Cell Lymphoma (MCL)

The primary objective of this trial is to evaluate the efficacy of a compound of Formula (I), (IA), (II), (III), (IV), (V), (VI), (VIA), (VIB), (VII), (VIII), (IX), (X), (XI), (XII), (XIII), or (XIV) in relapsed/refractory subjects with Mantle Cell Lymphoma (MCL). The secondary objective is to evaluate the safety of a fixed daily dosing regimen of a compound of Formula (I), (IA), (II), (III), (IV), (V), (VI), (VIA), (VIB), (VII), (VIII), (IX), (X), (XI), (XII), (XIII), or (XIV) in this population.

Primary Outcome Measures: To measure the number of participants with a response to a compound of Formula (I), (IA), (II), (III), (IV), (V), (VI), (VIA), (VIB), (VII), (VIII), (IX), (X), (XI), (XII), (XIII), or (XIV).

Secondary Outcome Measures: To measure the number of participants with adverse events as a measure of safety and tolerability. To measure pharmacokinetics to assist in determining how the body responds to the compound of Formula (I), (IA), (II), (III), (IV), (V), (VI), (VIA), (VIB), (VII), (VIII), (IX), (X), (XI), (XII), (XIII), or (XIV). Patient reported outcomes (to measure the number of participants reported outcomes in determining the health related quality of life).

Eligibility: 18 Years and older; both genders are eligible.

Inclusion Criteria: Men and women≥18 years of age. ECOG performance status of ≤2. Pathologically confirmed MCL, with documentation of either overexpression of cyclin D1 or t(11;14), and measurable disease on cross sectional imaging that is ≥2 cm in the longest diameter and measurable in 2 perpendicular dimensions. Documented failure to achieve at least partial response (PR) with, or documented disease progression disease after, the most recent treatment regimen. At least 1, but no more than 5, prior treatment regimens for MCL (Note: Subjects having received≥2 cycles of prior treatment with bortezomib, either as a single agent or as part of a combination therapy regimen, will be considered to be bortezomib-exposed.). Willing and able to participate in all required evaluations and procedures in this study protocol including swallowing capsules without difficulty. Ability to understand the purpose and risks of the study and provide signed and dated informed consent and authorization to use protected health information (in accordance with national and local subject privacy regulations).

Major exclusion criteria: Prior chemotherapy within 3 weeks, nitrosoureas within 6 weeks, therapeutic anticancer antibodies within 4 weeks, radio- or toxin-immunoconjugates within 10 weeks, radiation therapy within 3 weeks, or major surgery within 2 weeks of first dose of study drug. Any life-threatening illness, medical condition or organ system dysfunction which, in the investigator's opinion, could compromise the subject's safety, interfere with the absorption or metabolism of a compound of Formula (I), (IA), (II), (III), (IV), (V), (VI), (VIA), (VIB), (VII), (VIII), (IX), (X), (XI), (XII), (XIII), or (XIV), or put the study outcomes at undue risk. Clinically significant cardiovascular disease such as uncontrolled or symptomatic arrhythmias, congestive heart failure, or myocardial infarction within 6 months of screening, or any Class 3 or 4 cardiac disease as defined by the New York Heart Association Functional Classification. Malabsorption syndrome, disease significantly affecting gastrointestinal function, or resection of the stomach or small bowel or ulcerative colitis, symptomatic inflammatory bowel disease, or partial or complete bowel obstruction. Any of the following laboratory abnormalities: 1. Absolute neutrophil count (ANC)<750 cells/mm³ (0.75×109/L) unless there is documented bone marrow involvement. 2. Platelet count<50,000 cells/mm³ (50×109/L) independent of transfusion support unless there is documented bone marrow involvement. 3. Serum aspartate transaminase (AST/SGOT) or alanine transaminase (ALT/SGPT)≥3.0×upper limit of normal (ULN). 4. Creatinine>2.0×ULN.

What is claimed is:

1. A compound having the structure of Formula (VIA)

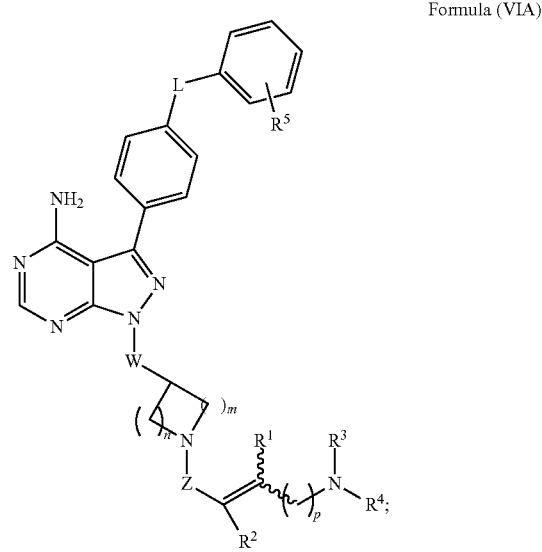

Formula (VIA)

wherein:

L is $CR^aR^a$, O, S, $NR^b$, N—$OR^b$, C=O, C=S, C=N—$R^b$ or C=N—$OR^b$;

W is a bond or optionally substituted $C_1$-$C_3$ alkyl;

Z is C=O, $SO_2$ or SO;

$R^1$ and $R^2$ are each independently H or $C_1$-$C_3$ alkyl, wherein $R^1$ and $R^2$ have a cis or trans relationship; or $R^1$ and $R^2$ join together to form a bond;

n and p are each independently an integer from 0 to 3;

m is an integer from 1 to 3;

$R^3$ is H, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;

$R^5$ is H, OH, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;

$R^a$ is each independently H, $C_1$-$C_6$ alkyl, $C_1$-$C_6$ heteroalkyl, halogen, $OR^b$, or $NR^bR^b$;

$R^b$ is each independently H, $C_1$-$C_6$ alkyl, $C_2$-$C_6$ heteroalkyl, $C_3$-$C_6$ cycloalkyl or $C_2$-$C_6$ heterocycloalkyl;

or a pharmaceutically acceptable salt, solvate, N-oxide, or prodrug thereof.

2. A compound having the structure of Formula (VII)

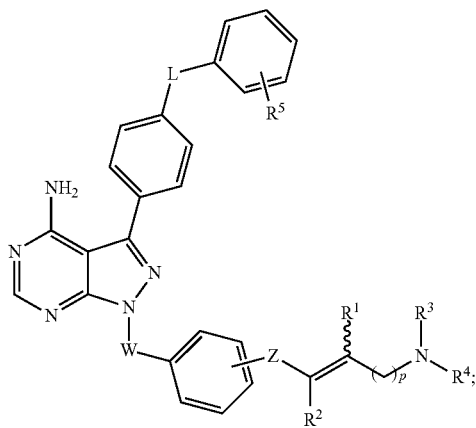

Formula (VII)

wherein:
L is $CR^aR^a$, O, S, $NR^b$, $N-OR^b$, C=O, C=S, C=N—$R^b$ or C=N—$OR^b$;
W is a bond or optionally substituted $C_1$-$C_3$ alkyl;
Z is $NR^cC$=O, $SO_2$ or SO;
$R^1$ and $R^2$ are each independently H or $C_1$-$C_3$ alkyl, wherein $R^1$ and $R^2$ have a cis or trans relationship; or $R^1$ and $R^2$ jointogether to form a bond;
p is an integer from 0 to 3;
$R^3$ is H, substituted or unsubstituted $C_1$-$C_3$ alkyl, substituted or unsubstituted $C_3$-$C_6$ cycloalkyl, substituted or unsubstituted $C_1$-$C_6$ heteroalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;
$R^4$ is substituted or unsubstituted $C_3$-$C_6$ cycloalkyl, substituted or unsubstituted $C_2$-$C_6$ heterocycloalkyl, substituted or unsubstituted $C_6$-$C_{12}$ aryl, or substituted or unsubstituted $C_5$-$C_{11}$ heteroaryl;
$R^5$ is H, OH, $OR^b$, $NR^bR^b$, halogen, $C_1$-$C_6$ alkyl, $C_1$-$C_6$ heteroalkyl, $C_3$-$C_6$ cycloalkyl or $C_2$-$C_6$ heterocycloalkyl;
$R^a$ is each independently H, $C_1$-$C_6$ alkyl, $C_1$-$C_6$ heteroalkyl, halogen, $OR^b$, or $NR^bR^b$;
$R^b$ is each independently H, $C_1$-$C_6$ alkyl, $C_2$-$C_6$ heteroalkyl, $C_3$-$C_6$ cycloalkyl or $C_2$-$C_6$ heterocycloalkyl;
$R^c$ is H or $C_1$-$C_6$ alkyl;
or a pharmaceutically acceptable salt, solvate, N-oxide, or prodrug thereof.
3. A compound selected from:

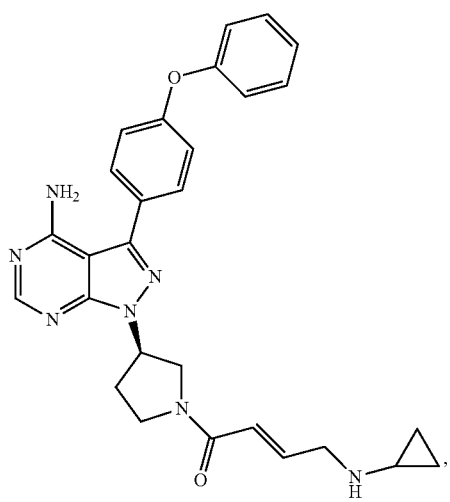

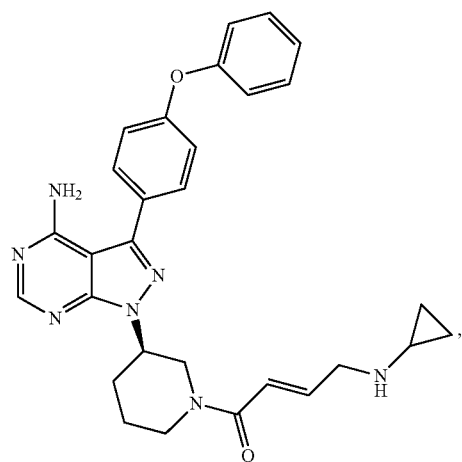

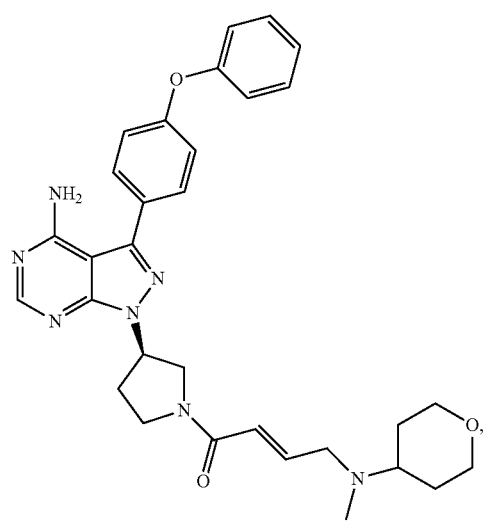

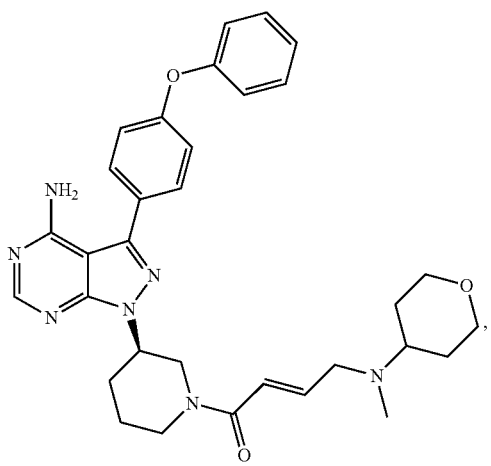

229
-continued
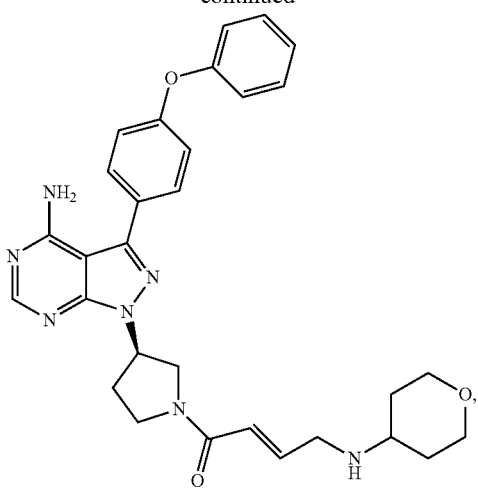
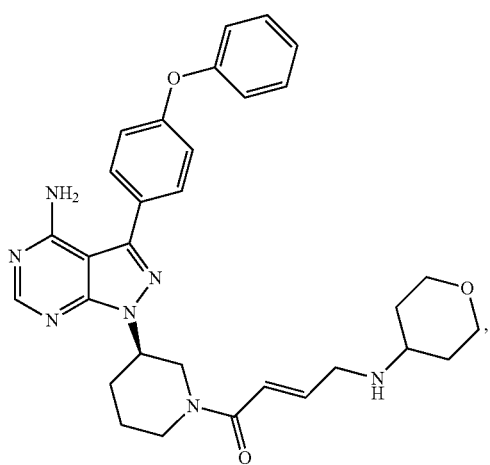
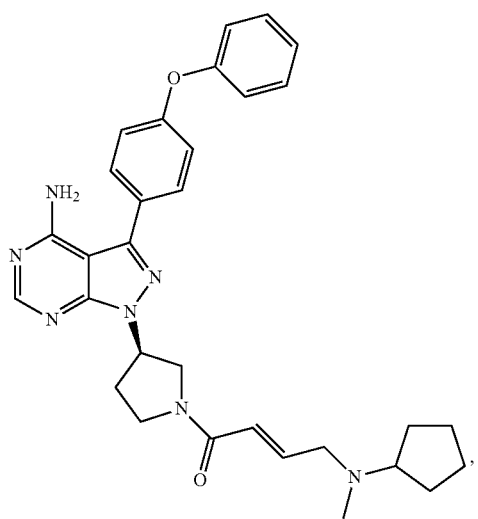
230
-continued
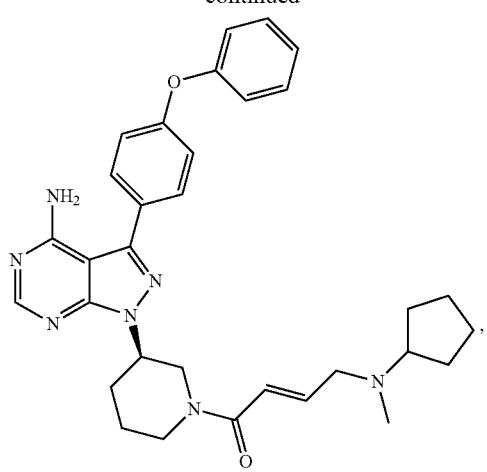
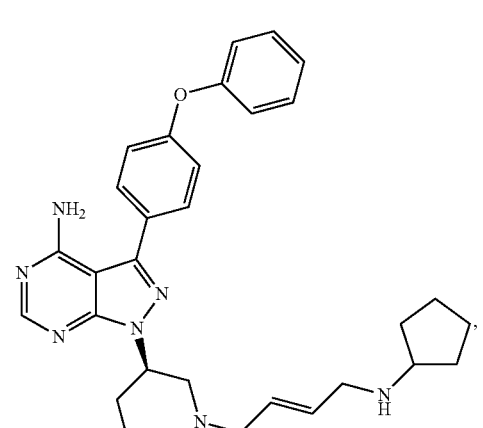

231
-continued
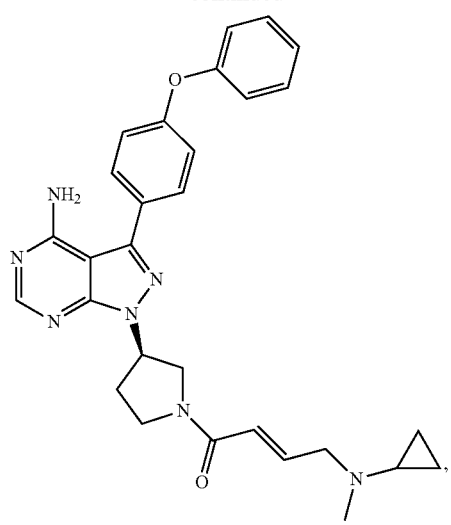
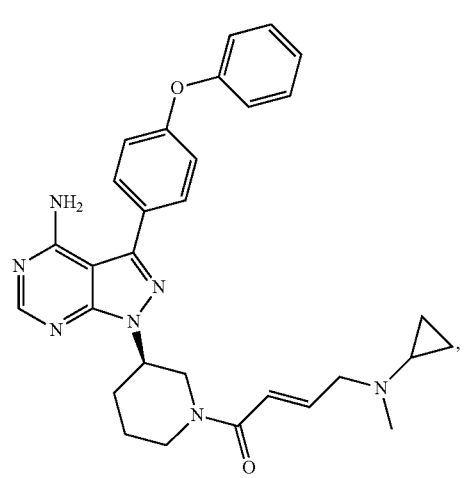
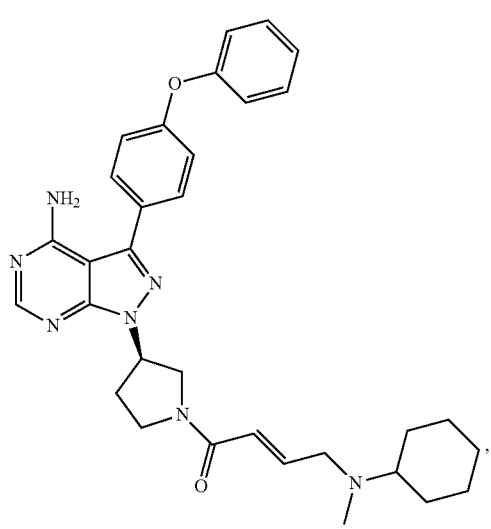
232
-continued
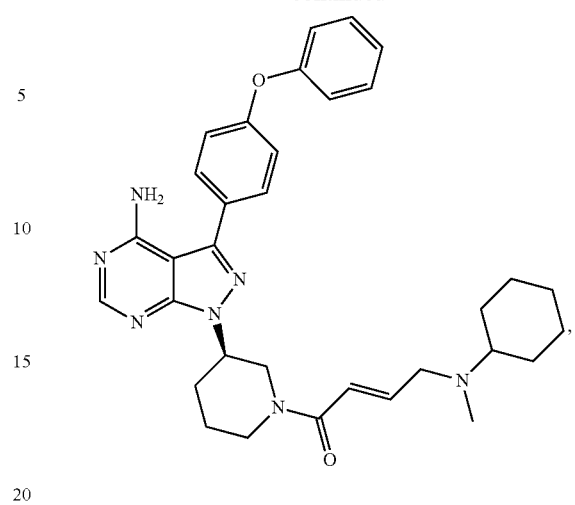

233
-continued
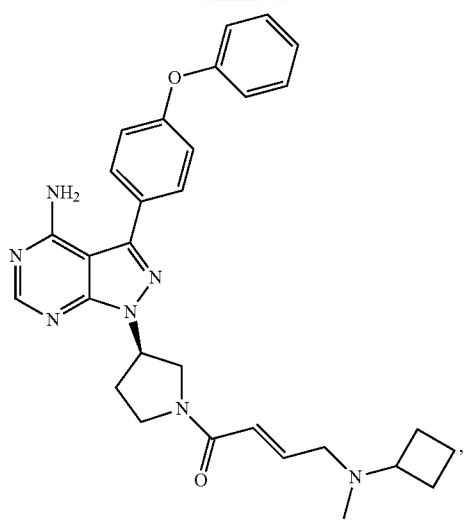
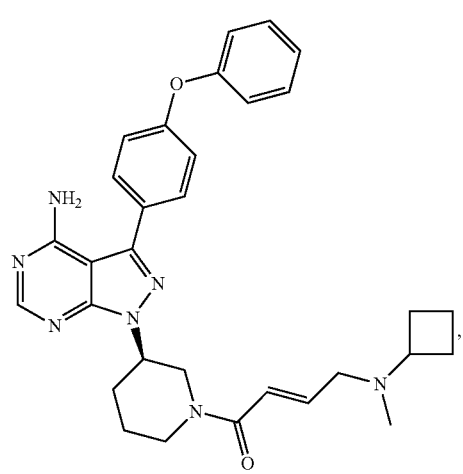
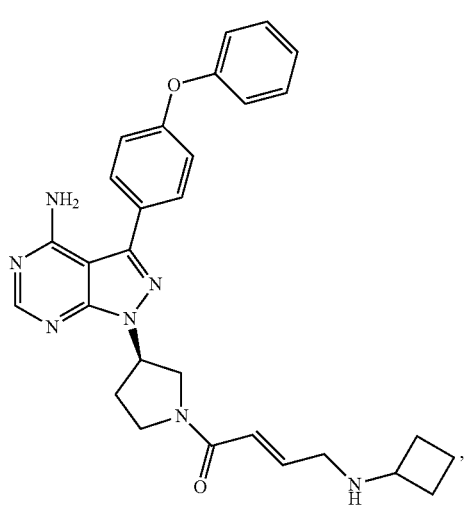
234
-continued
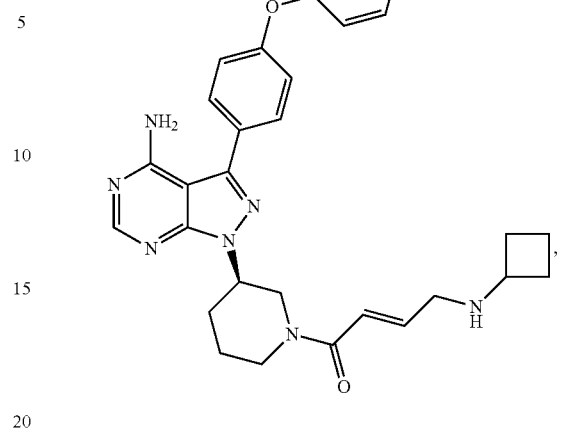
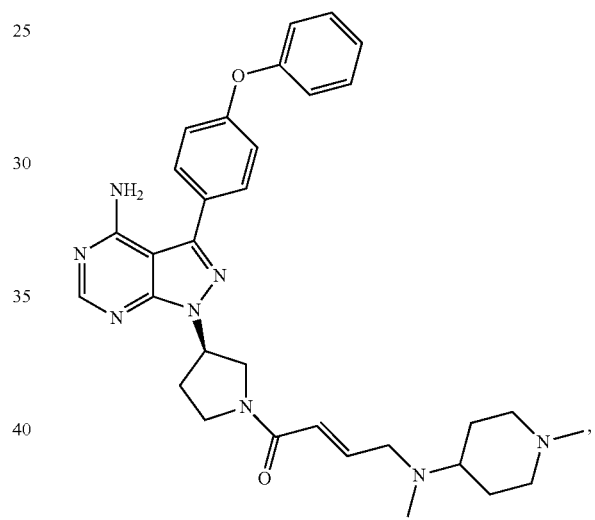
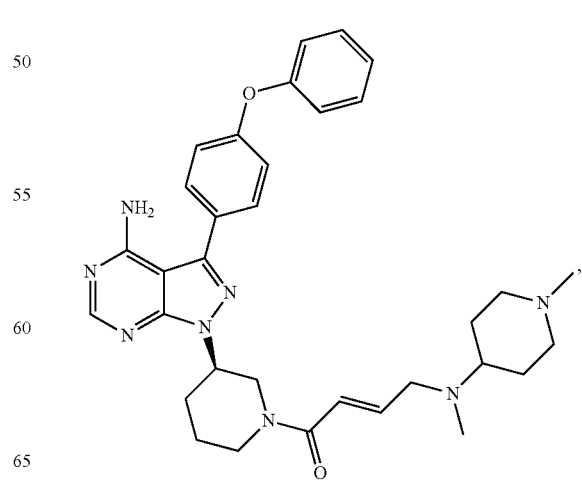

235
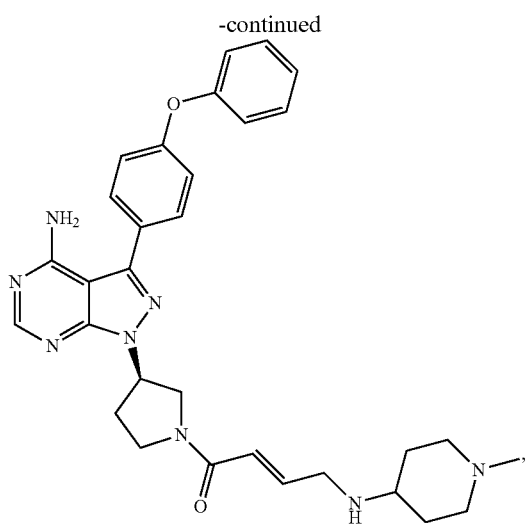
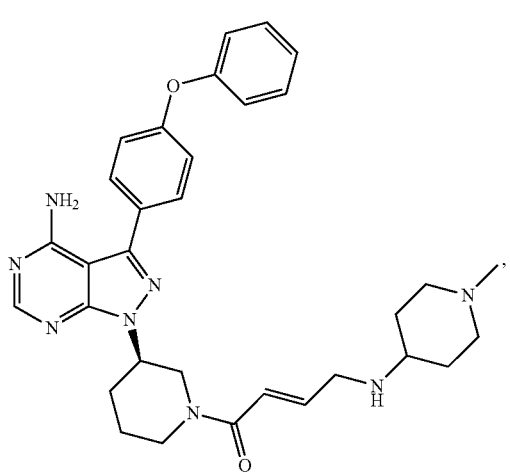
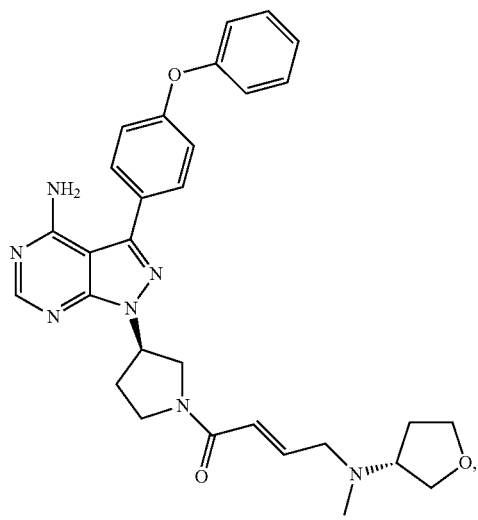
236
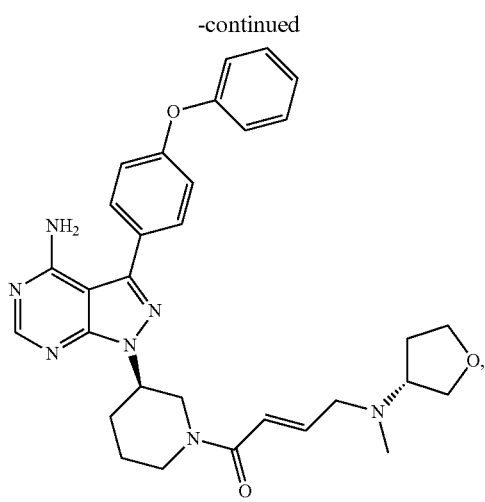
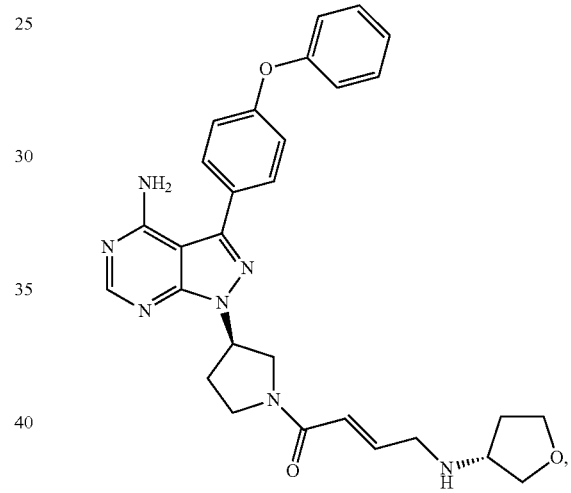
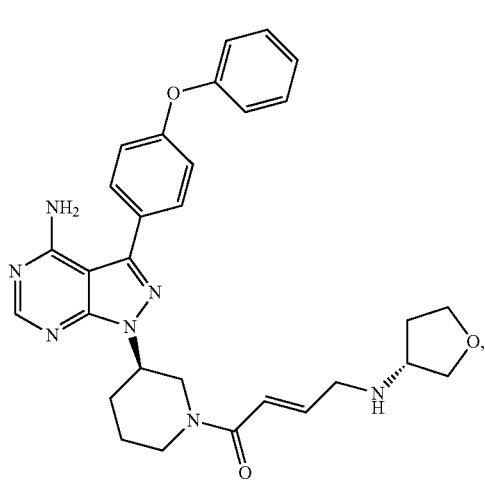

237
-continued
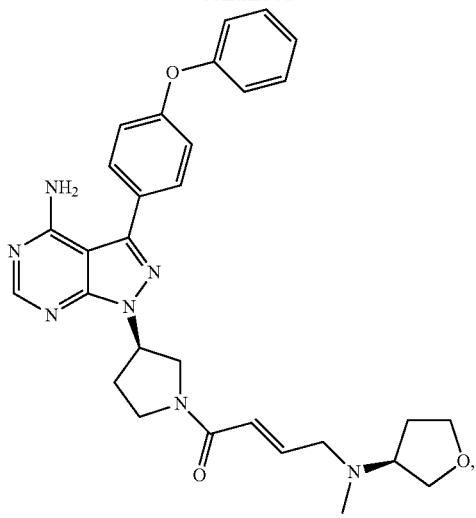
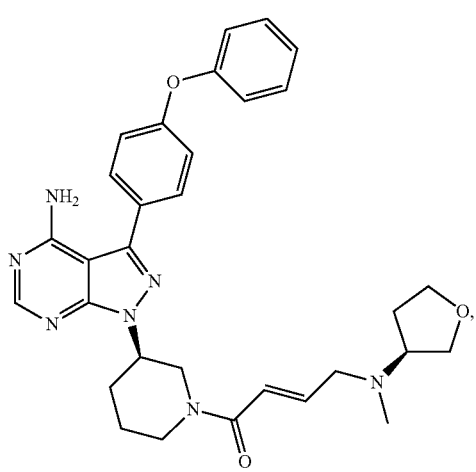
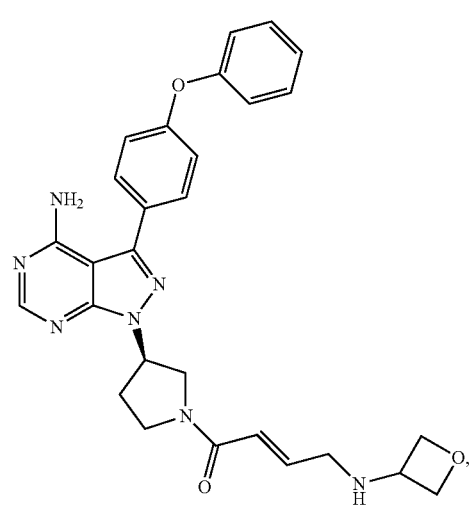
238
-continued
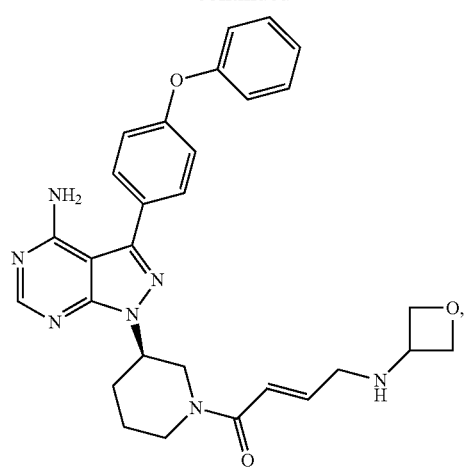
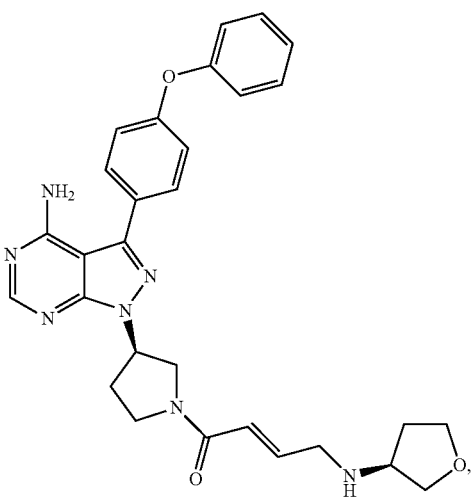
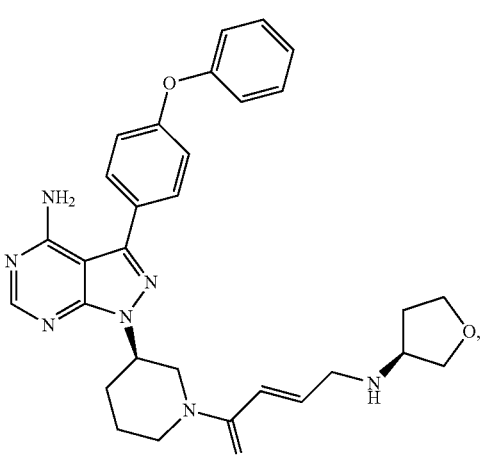

239
-continued
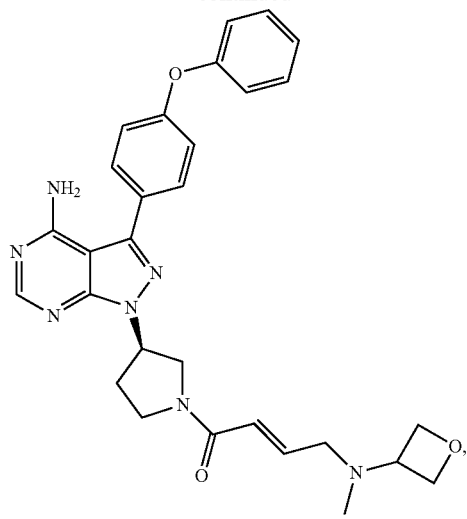
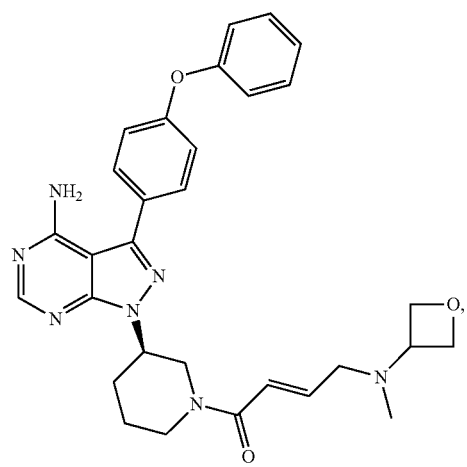
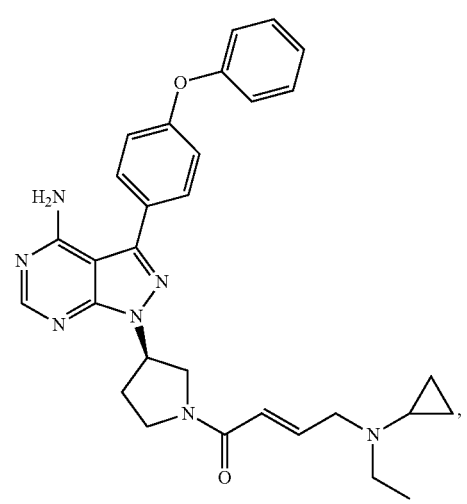
240
-continued
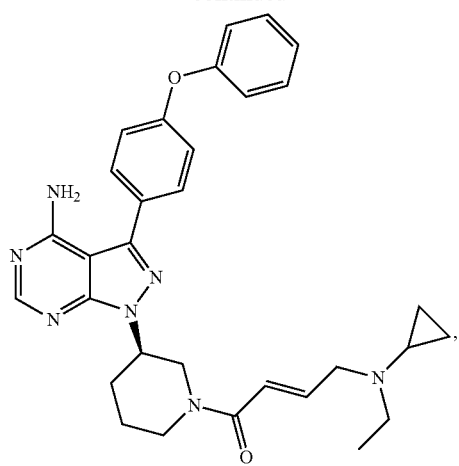
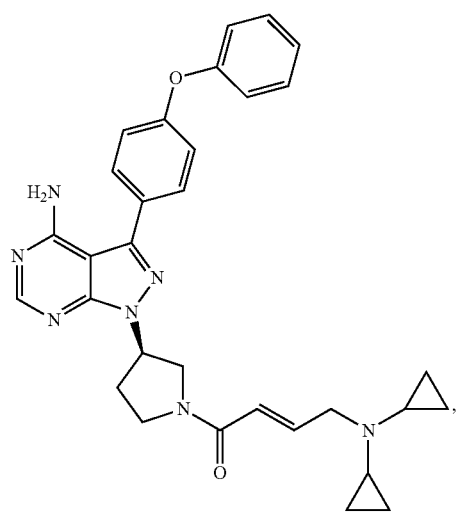
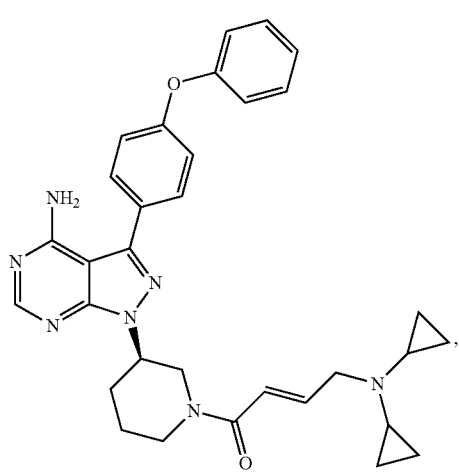

241
-continued
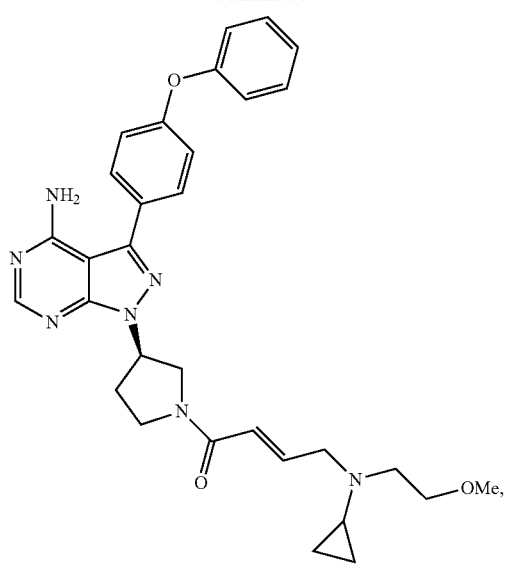
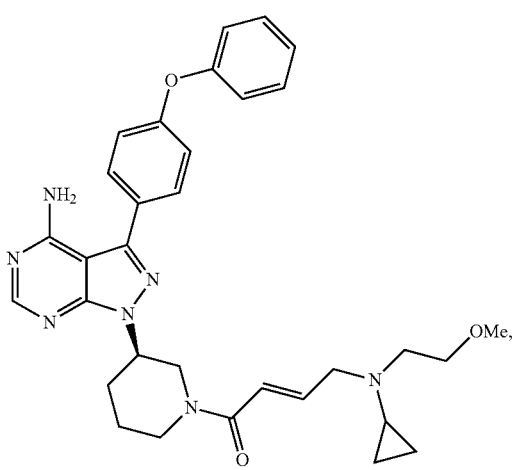
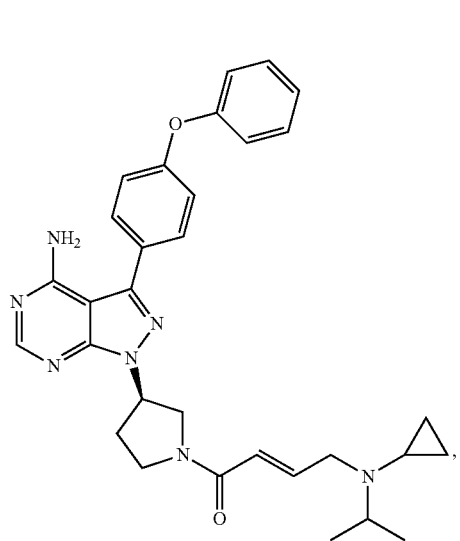
242
-continued
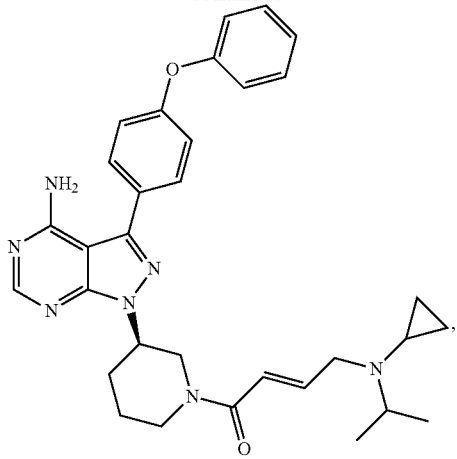
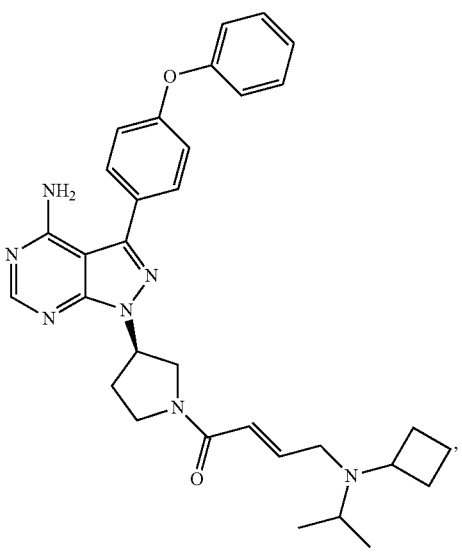

243
-continued
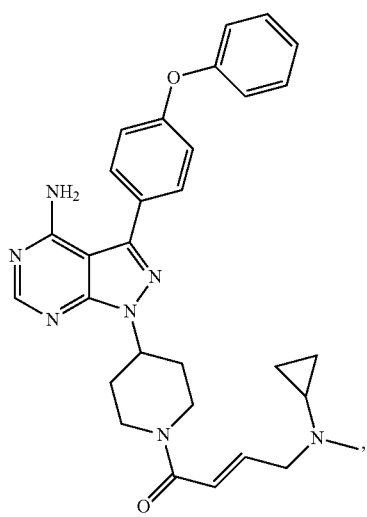
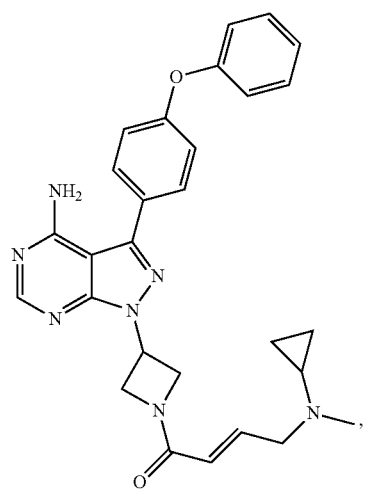
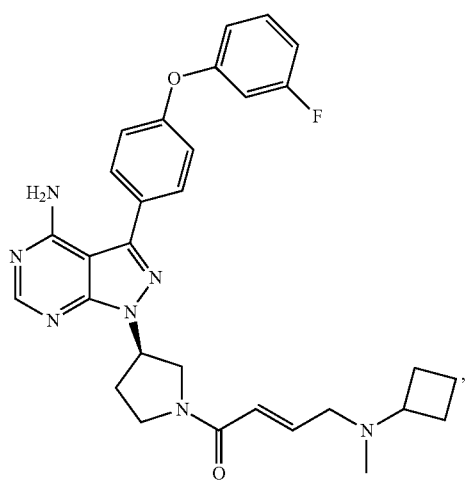
244
-continued
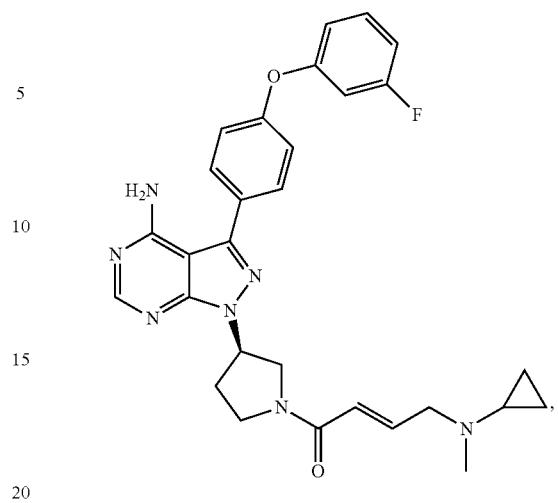
or a pharmaceutically acceptable salt, solvate, or N-oxide thereof.
4. A compound selected from:
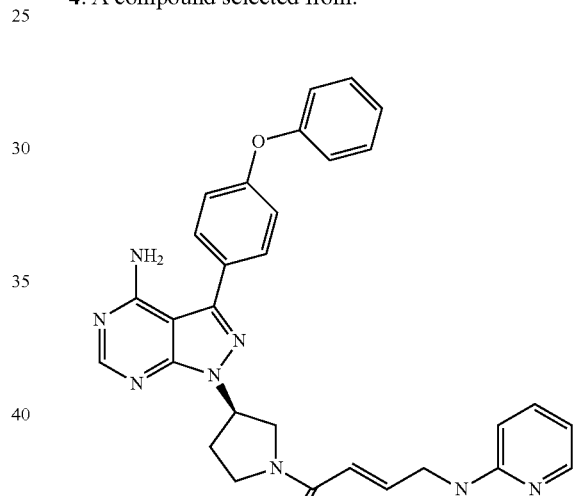
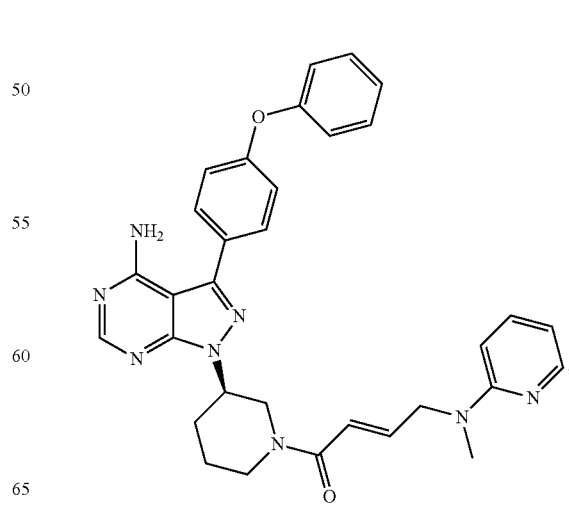
and 245
-continued
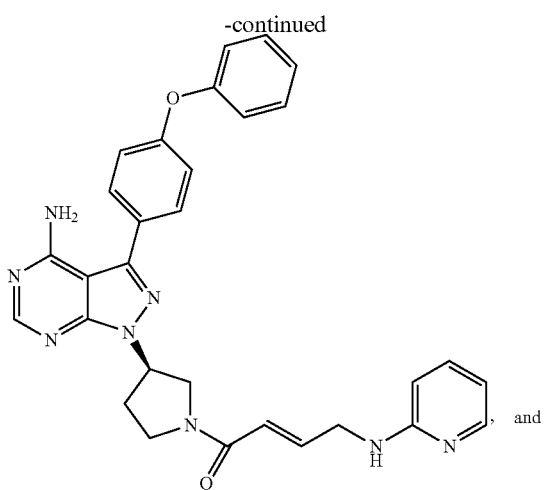
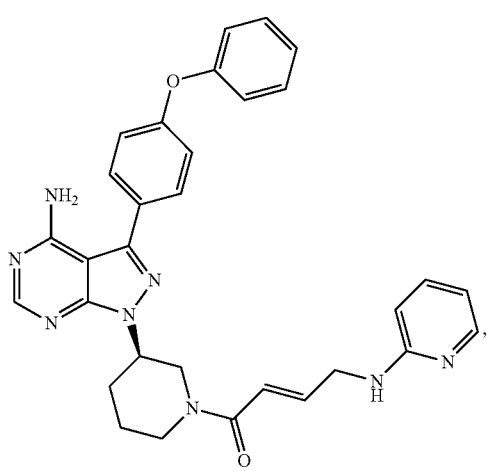 [SMILES: Nc1ncnc2c1c(-c1ccc(Oc3ccccc3)cc1)nn2[C@@H]1CCCN(C(=O)/C=C/CNc2ccccn2)C1]
or a pharmaceutically acceptable salt, solvate, or N-oxide thereof.
5. A compound selected from:
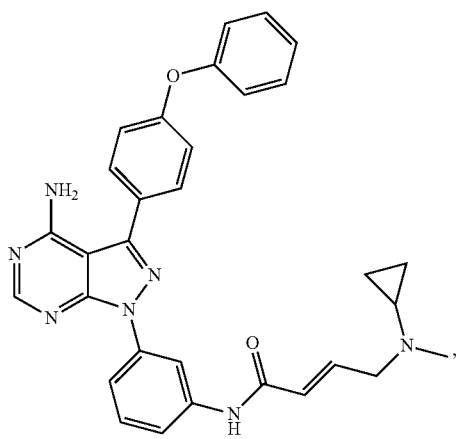
246
-continued
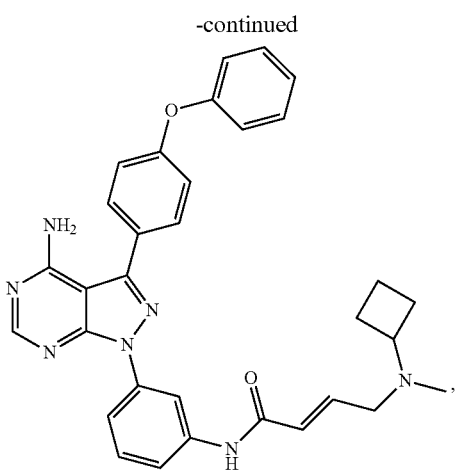, and
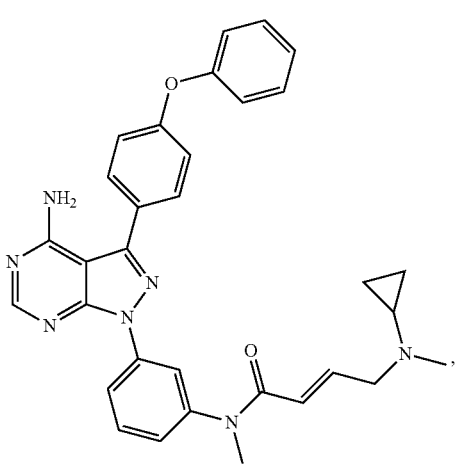
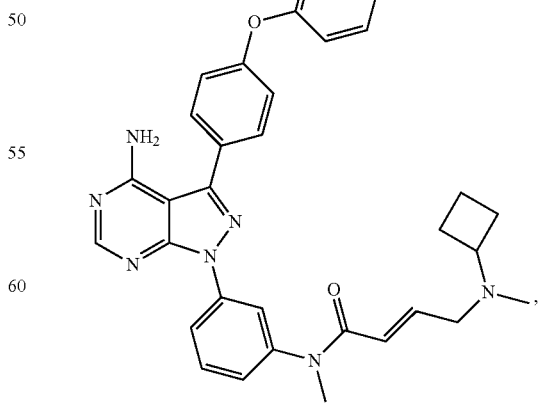

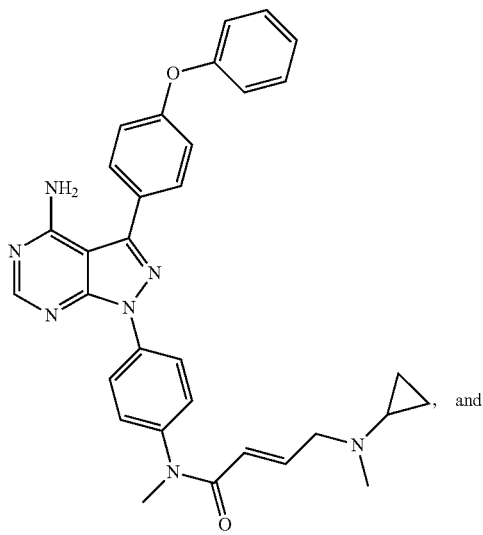, and
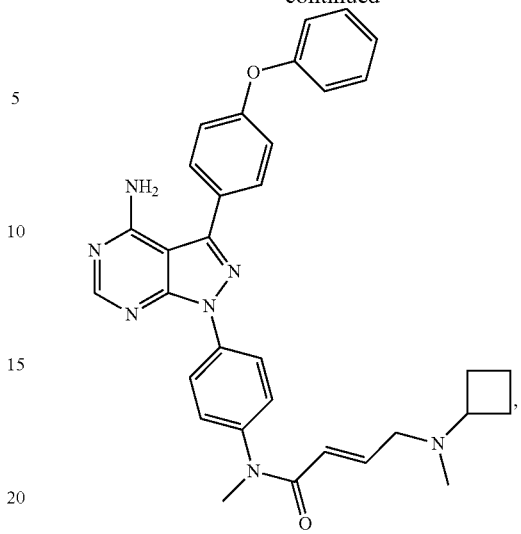
or a pharmaceutically acceptable salt, solvate, N-oxide, or prodrug thereof.
6. A pharmaceutical composition comprising a compound of claim 2, or a pharmaceutically acceptable salt, solvate, N-oxide, or prodrug thereof; and a pharmaceutically acceptable excipient, binder or carrier.
\* \* \* \* \*